(12) United States Patent
Oxford et al.

(10) Patent No.: US 7,528,157 B2
(45) Date of Patent: May 5, 2009

(54) EP₄ RECEPTOR ANTAGONISTS

(75) Inventors: Alexander W. Oxford, Royston (GB); Richard J. Davis, Hitchin (GB); Robert A. Coleman, Royston (GB); Kenneth L. Clark, Linton (GB); David E. Clark, Harlow (GB); Neil V. Harris, Harlow (GB); Garry Fenton, Harlow (GB); George Hynd, Harlow (GB); Keith A. J. Stuttle, Harlow (GB); Jonathan M. Sutton, Harlow (GB); Christopher G. Newton, Harlow (GB)

(73) Assignee: Asterand UK Limited, Hertfordshire (GB)

( * ) Notice: Subject to any disclaimer, the term of this patent is extended or adjusted under 35 U.S.C. 154(b) by 14 days.

(21) Appl. No.: 11/615,024

(22) Filed: Dec. 22, 2006

(65) Prior Publication Data

US 2007/0123575 A1 May 31, 2007

Related U.S. Application Data

(62) Division of application No. 10/766,030, filed on Jan. 29, 2004, now Pat. No. 7,196,089.

(60) Provisional application No. 60/443,872, filed on Jan. 31, 2003, provisional application No. 60/509,521, filed on Oct. 9, 2003.

(30) Foreign Application Priority Data

Jan. 29, 2003 (GB) ................................. 0302094.8

(51) Int. Cl.
*C07D 307/68* (2006.01)
*C07D 405/10* (2006.01)
*A61K 31/34* (2006.01)
*A61K 31/443* (2006.01)

(52) U.S. Cl. ........................ 514/336; 514/380; 514/471; 544/296; 544/333; 546/256; 546/284.7; 549/479; 549/483; 549/484; 549/487; 549/488; 549/494; 549/495

(58) Field of Classification Search .................. 549/479, 549/483, 484, 487, 488, 494, 495; 546/256, 546/283.4, 284.7; 544/296, 333; 514/336, 514/471, 380
See application file for complete search history.

(56) References Cited

U.S. PATENT DOCUMENTS 5,545,645 A 8/1996 Pascal et al.

(Continued)

FOREIGN PATENT DOCUMENTS

EP 661260 7/1995

(Continued)

OTHER PUBLICATIONS

Berge, et al., "Pharmaceutically Acceptable Salts", *J. Pharm. Sci.*, 1977, vol. 66, pp. 1-19.

(Continued)

*Primary Examiner*—Bernard Dentz
(74) *Attorney, Agent, or Firm*—Nixon & Vanderhye P.C.

(57) ABSTRACT

Compounds of formula (I):

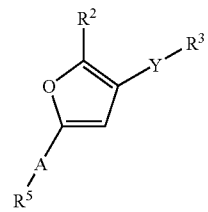

(I)

wherein: $R^2$ is H or an optionally substituted $C_{1-4}$ alkyl group; Y is either $-(CH_2)_n-X-$, where n is 1 or 2 and X is O, S, S(=O), S(=O)$_2$, or $NR^{N1}$, where $R^{N1}$ is selected from H or optionally substituted $C_{1-4}$ alkyl, or Y is $-C(=O)NR^{N2}-$, where $R^{N2}$ is selected from H, and optionally substituted $C_{1-7}$ alkyl or $C_{5-20}$ aryl; $R^3$ is an optionally substituted $C_6$ aryl group linked to a further optionally substituted $C_6$ aryl group, wherein if both $C_6$ aryl groups are benzene rings, there may be an oxygen bridge between the two rings, bound adjacent the link on both rings; A is a single bond or a $C_{1-3}$ alkylene group; and $R^5$ is either:
(i) carboxy;
(ii) a group of formula (II):

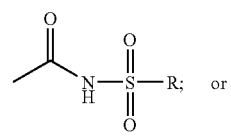

(II)

(iii) a group of formula (III):

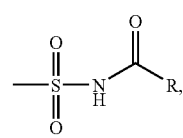

(III)

wherein R is optionally substituted $C_{1-7}$ alkyl, $C_{5-20}$ aryl or $NR^{N3}R^{N4}$, where $R^{N3}$ and $R^{N4}$ are independently selected from optionally substituted $C_{1-4}$ alkyl;
(iv) tetrazol-5-yl.

24 Claims, No Drawings

U.S. PATENT DOCUMENTS

| | | | |
|---|---|---|---|
| 5,602,136 A | 2/1997 | Ruhter et al. |
| 5,607,951 A | 3/1997 | Macor et al. |
| 5,645,566 A | 7/1997 | Brenneman et al. |
| 5,663,357 A | 9/1997 | Teng et al. |
| 5,679,692 A | 10/1997 | Friary et al. |
| 5,686,445 A | 11/1997 | Albright et al. |
| 5,834,468 A | 11/1998 | Breault et al. |
| 5,883,106 A | 3/1999 | Stevens et al. |
| 5,939,436 A | 8/1999 | Carling et al. |
| 5,977,170 A | 11/1999 | Commons et al. |
| 6,008,362 A | 12/1999 | Commons et al. |
| 6,121,671 A | 9/2000 | Ko et al. |
| 6,162,819 A | 12/2000 | Schindler et al. |
| 6,184,245 B1 | 2/2001 | Sugawara et al. |
| 6,211,197 B1 | 4/2001 | Belley |
| 6,291,677 B1 | 9/2001 | Vasudevan et al. |
| 6,380,218 B1 | 4/2002 | Moarfat et al. |
| 6,610,719 B2 | 8/2003 | Paralkar et al. |
| 6,716,864 B2 | 4/2004 | Burk et al. |
| 6,797,712 B2 | 9/2004 | Maul et al. |
| 6,835,212 B2 | 12/2004 | Rozzell et al. |
| 6,849,641 B1 | 2/2005 | Tang et al. |
| 6,861,441 B1 | 3/2005 | Clayton et al. |
| 6,878,740 B2 | 4/2005 | Sundermann et al. |
| 6,956,057 B2 | 10/2005 | Woodward et al. |
| 2002/0040024 A1 | 4/2002 | Apodaca et al. |
| 2002/0115671 A1 | 8/2002 | Goehring et al. |
| 2002/0137736 A1 | 9/2002 | Mattes et al. |
| 2003/0100583 A1 | 5/2003 | Bernardon |
| 2003/0119817 A1 | 6/2003 | Mehta et al. |
| 2003/0158240 A1 | 8/2003 | Baxter et al. |
| 2003/0195190 A1 | 10/2003 | Peschke et al. |
| 2004/0048889 A1 | 3/2004 | Peters et al. |
| 2004/0147559 A1 | 7/2004 | Taveras et al. |
| 2004/0152734 A1 | 8/2004 | Sundermann et al. |
| 2004/0192758 A1 | 9/2004 | Leban et al. |
| 2004/0235888 A1 | 11/2004 | Yamamori et al. |
| 2004/0259880 A1 | 12/2004 | Lockhart et al. |
| 2005/0004133 A1 | 1/2005 | Makings et al. |
| 2005/0043386 A1 | 2/2005 | Nishi et al. |
| 2005/0176987 A1 | 8/2005 | Goossen et al. |

FOREIGN PATENT DOCUMENTS

| | | |
|---|---|---|
| EP | 776885 | 6/1997 |
| EP | 1 067 109 A1 | 1/2001 |
| EP | 1108426 | 6/2001 |
| JP | 03-240066 | 10/1991 |
| JP | 04-253974 | 9/1992 |
| JP | 07-281440 | 10/1995 |
| JP | 09-311401 | 12/1997 |
| JP | 10-287654 | 10/1998 |
| JP | 11-209366 | 1/1999 |
| JP | 2001-139550 | 5/2001 |
| JP | 2004-051628 | 2/2004 |
| JP | 2005-41867 | 2/2005 |
| JP | 2005-046141 | 2/2005 |
| WO | WO9117163 | 11/1991 |
| WO | WO9118897 | 12/1991 |
| WO | WO9221644 | 12/1992 |
| WO | WO9303012 | 2/1993 |
| WO | WO9306118 | 4/1993 |
| WO | WO9402460 | 2/1994 |
| WO | WO9402483 | 2/1994 |
| WO | WO9406796 | 3/1994 |
| WO | WO9521171 | 8/1995 |
| WO | WO9601827 | 1/1996 |
| WO | WO9611911 | 4/1996 |
| WO | WO9807835 | 2/1998 |
| WO | WO9834909 | 8/1998 |
| WO | WO9847894 | 10/1998 |
| WO | WO9851662 | 11/1998 |
| WO | WO9856783 | 12/1998 |
| WO | WO9857925 | 12/1998 |
| WO | WO9857927 | 12/1998 |
| WO | WO9857928 | 12/1998 |
| WO | WO9910322 | 3/1999 |
| WO | WO9919300 | 4/1999 |
| WO | WO/00/06529 | 2/2000 |
| WO | WO/00/18405 | 4/2000 |
| WO | WO/00/24738 | 5/2000 |
| WO | WO/0040561 | 7/2000 |
| WO | WO/0069987 | 11/2000 |
| WO | WO/0157006 | 8/2001 |
| WO | WO/0164676 | 9/2001 |
| WO | WO/0206278 | 1/2002 |
| WO | WO02/18361 | 3/2002 |
| WO | WO02/26727 | 4/2002 |
| WO | WO02/40473 | 4/2002 |
| WO | WO/02058698 | 8/2002 |
| WO | WO/02060898 | 8/2002 |
| WO | WO/02067930 | 9/2002 |
| WO | WO/02067937 | 9/2002 |
| WO | WO02068412 | 9/2002 |
| WO | WO02/083624 | 10/2002 |
| WO | WO03/018585 | 3/2003 |
| WO | WO03/033503 | 4/2003 |
| WO | WO03044015 | 5/2003 |
| WO | WO03/053352 | 7/2003 |
| WO | WO03/055479 | 7/2003 |
| WO | WO03/059871 | 7/2003 |
| WO | WO03/097621 | 11/2003 |
| WO | WO03/097644 | 11/2003 |
| WO | WO03090869 | 11/2003 |
| WO | WO2004/002948 | 1/2004 |
| WO | WO2004/011418 | 2/2004 |
| WO | WO2004/019932 | 3/2004 |
| WO | WO2004/024663 | 3/2004 |
| WO | WO2004024738 | 3/2004 |
| WO | WO2004048349 | 6/2004 |
| WO | WO2004063194 | 7/2004 |
| WO | WO2004069816 | 8/2004 |
| WO | WO2004078169 | 9/2004 |
| WO | WO2004089944 | 10/2004 |
| WO | WO2004094362 | 11/2004 |
| WO | WO2004099199 | 11/2004 |
| WO | WO2005079793 | 9/2005 |

OTHER PUBLICATIONS

Arunlakshana, O., et al., "Some quantitative use of drug antagonists", *Brit. J. Pharmacol.*, 1959, vol. 14, pp. 48-58.

Porretta, G. C., et al., "Research on antibacterial and antifungal agents", II *Farmaco. Ed. Sc.*, 1987, vol. 42, No. 9, pp. 629-639.

Modrakowski, C., et al., "Synthesis of Pyrene Containing Building Blocks for Dendrimer Synthesis", *Synthesis*, 2001, No. 14, pp. 2143-2155.

Wenkert, E., et al., "Polyene Synthesis. Ready Construction of Retinol-Carotene Fragments, (±)-6(E)-LTB$_3$ Leukotrienes, and Corticrocin", *J. Org. Chem.*, 1990, vol. 55, No. 25, pp. 6203-6214.

Bures, E., "Regioselective Preparation of 2,4-, 3,4,- and 2,3,4-Substituted Furan Rings.", *J. Org. Chem.*, 1997, vol. 62, No. 25, pp. 8741-8749.

Wang, Y., et al., "A simple synthesis of fluoroalkyl substituted dihydrofurans by rhodium(II)-catalysed 1,3-dipolar reactions", *Tetrahedron*, 2001, vol. 57, No. 16, pp. 3383-3387.

Bin, Y., "A Concise Synthesis of the Differentiating Antibiotic L-Azatyrosine", *J. Org. Chem.*, 1995, vol. 60, No. 8, pp. 2640-2641.

Doll, M. H., et al., "Irreversible Enzyme Inhibitors. Inhibitors of Guinea Pig Complement Derived by Quaternization of Substituted Pyridines with Benzyl Halides", *J. Med. Chem.*, 1976, vol. 19, No. 9, pp. 1079-1088.

Mndzhoyan, A. L., et al., *Doklady Akademii Nauk Armyanskoi SSR*, 1957, vol. 25, pp. 277-280.

Valenta, M., et al., "Experiments in the furan series. III. Preparation of some 2,3,5-trisubstituted derivatives", *Collection Czechoslov. Chem. Commun.*, 1964, vol. 29, pp. 1577-1581.
ChemBridge Product List (Jan. 17, 2002): Order No. 5929447; CAS Registry No. 383379-03-01.
ChemBridge Product List (Jan. 17, 2002): Order No. 5930664; CAS Registry No. 339253-95-01.
ChemBridge Product List (Jan. 17, 2002): Order No. 6059629; CAS Registry No. 333352-32-02.
ChemBridge Product List (Jan. 17, 2002): Order No. 5404459; CAS Registry No. 331670-05-04.
ChemBridge Product List (Jan. 17, 2002): Order No. 5404452; CAS Registry No. 331670-03-02.
ChemBridge Product List (Jan. 17, 2002): Order No. 5924300; CAS Registry No. 297137-48-05.
ChemBridge Product List (Jan. 17, 2002): Order No. 5669841; CAS Registry No. 419545-30-05.
ChemBridge Product List (Jan. 17, 2002): Order No. 6064715; CAS Registry No. 298230-06-05.
ChemBridge Product List (Jan. 17, 2002): Order No. 5678372; CAS Registry No. 419550-75-07.
Scientific Exchange Product List (Jan. 1, 2003): Order No. POD_42/0901; CAS Registry No. 339253-95-01.
Scientific Exchange Product List (Jan. 1, 2003): Order No. POD_76/0070; CAS Registry No. 333352-65-01.
Scientific Exchange Product List (Jan. 1, 2003): Order No. POD_40/0451; CAS Registry No. 331670-05-04.
Interchim Intermediates (Jul. 9, 2002): Order No. BAS 0790464; CAS Registry No. 333352-65-01.
Interchim Intermediates (Jul. 9, 2002): Order No. STOCK2S-97502; CAS Registry No. 339253-95-01.
Interchim Intermediates (Jul. 9, 2002): Order No. BAS 0790281; CAS Registry No. 333352-32-02.
Interchim Intermediates (Jul. 9, 2002): Order No. BAS 0394974; CAS Registry No. 331670-05-04.
Interchim Intermediates (Jul. 9, 2002): Order No. BAS 0394969; CAS Registry No. 331670-03-02.
Interchim Intermediates (Jul. 9, 2002): Order No. 8002-0804; CAS Registry No. 339219-13-05.
Screening Collection (Mar. 28, 2000): Order No. A0240/0010807; CAS Registry No. 333352-32-02.
Screening Collection (Mar. 28, 2000): Order No. A0973/0045487; CAS Registry No. 339253-95-01.
Screening Collection (Mar. 28, 2000): Order No. A0177/0007972; CAS Registry No. 333352-65-01.
Screening Collection (Mar. 28, 2000): Order No. A0240/0010802; CAS Registry No. 298230-06-05.
Screening Collection (Mar. 28, 2000): Order No. A0240/0010804; CAS Registry No. 339219-13-05.
TimTec Stock Library (May 19, 2003): Order No. ST4077305; CAS Registry No. 298230-06-05.
TimTec Stock Library (May 19, 2003): Order No. ST4002638; CAS Registry No. 339219-13-05.
ChemDiv, Inc. Product Library (Apr. 25, 2003): Order No. 8002-0802; CAS Registry No. 298230-06-05.
ChemDiv, Inc. Product Library (Apr. 25, 2003): Order No. 8002-0804; CAS Registry No. 339219-13-05.
Ambinter: Exploratory Library (Apr. 30, 2003): Order No. A0240/0010802; CAS Registry No. 298230-06-05.
Ambinter: Exploratory Library (Apr. 30, 2003): Order No. A0240/0010804; CAS Registry No. 339219-13-05.
Enamine Product Listing (Nov. 15, 2001): T0400-0794; CAS Registry No. 296273-50-02.
Enamine Product Listing (Nov. 15, 2001): T0400-2207; CAS Registry No. 297137-48-05.
LaboTest Stock (Jan. 2, 2002): Order No. LT00150860; CAS Registry No. 331670-05-04.
CAS No. 462078-74-6 (2003).
CAS No. 438034-05-0 (2003).
CAS No. 383379-03-1 (2003).
CAS No. 383172-85-8 (2003).
CAS No. 339253-95-1 (2003).
CAS No. 339235-50-6 (2003).
CAS No. 333352-65-1 (2003).
CAS No. 333352-32-2 (2003).
CAS No. 331670-05-4 (2003).
CAS No. 331670-03-2 (2003).
CAS No. 297137-48-5 (2003).
CAS No. 296273-50-2 (2003).
Winn et al, J. Med. Chem. 1993, 36, pp. 2676-2688.
Richard J Davis et al. $EP_4$ prostanoid receptor-mediated vasodilatation of human middle cerebral arteries. Br. J. Pharmacol. (2004) 141, 580-585.

EP$_4$ RECEPTOR ANTAGONISTS

This application is a divisional of U.S. application Ser. No. 10/766,030 (allowed), filed Jan. 29, 2004, now U.S. Pat. No. 7,196,089 which claims the benefit of GB 0302094.8 filed Jan. 29, 2003 and of Provisional Applications No. 60/443,872 filed Jan. 31, 2003 and No. 60/509,521 filed Oct. 9, 2003, the entire contents of each of which are incorporated herein by reference in this application.

This invention relates to EP$_4$ receptor antagonists, pharmaceutical compositions comprising such compounds, and the use of such compounds and compositions to treat various diseases.

BACKGROUND TO THE INVENTION

Prostanoids comprise prostaglandins (PGs) and thromboxanes (Txs) and their receptors fall into five different classes (DP, EP, FP, IP and TP) based on their sensitivity to the five naturally occurring prostanoids, PGD$_2$, PGE$_2$, PGF$_{2\alpha}$, PGI$_2$ and TxA$_2$, respectively (Coleman, R. A., Prostanoid Receptors. *IUPHAR compendium of receptor characterisation and classification*, 2$^{nd}$ edition, 338-353, ISBN 0-9533510-3-3, 2000). EP receptors (for which the endogenous ligand is PGE$_2$) have been subdivided into four types termed EP$_1$, EP$_2$, EP$_3$ and EP$_4$. These four types of EP receptors have been cloned and are distinct at both a molecular and pharmacological level (Coleman, R. A., 2000)

EP$_4$ antagonists have been shown to be useful in the treatment of pain, and in particular, in the treatment of primary headache disorders, which include migraines, and secondary headache disorders, such as drug-induced headaches (WO 00/18405 and WO 01/72302). Dilation of the cerebral vasculature and the subsequent stimulation of pain stimulating, perivascular trigeminal sensory afferent nerves is recognised to play an important role in the pathophysiology of migraine. A sterile inflammatory response, associated with activation of cycloxygenase and the generation of PGE$_2$, is also implicated in the pathophysiology of migraine. PGE$_2$ levels have been shown to be raised during migraine attacks and PGE$_2$ contributes to the pain of migraine by directly dilating cerebral arteries and by stimulating the release of vasoactive/pro-inflammatory peptides from the trigeminal nerves. These effects of PGE$_2$ are mediated in whole or in part by EP$_4$ receptors. Thus, by binding to and preventing the stimulation of EP$_4$ receptors, EP$_4$ antagonists may be used to treat the pain of migraine.

EP$_4$ antagonists may also be useful in treating a number of other conditions and diseases. For example, they may be used in:

the treatment of pain associated with rheumatoid arthritis, osteoarthritis, rheumatoid spondylitis, gouty arthritis and juvenile arthritis;

the treatment of musculoskeletal pain, lower back and neck pain, sprains and strains, neuropathic pain, sympathetically mediated pain, myositis, pain associated with cancer and fibromyalgia, pain associated with influenza or other viral infections, such as the common cold, rheumatic fever; pain associated with bowel disorders such as non-ulcer dyspepsia, irritable bowel syndrome; non-cardiac chest pain, pain associated with myocardial ischaemia, post-operative pain, headache, toothache and dysmenorrhea. Neuropathic pain syndromes include diabetic neuropathy, sciatica, non-specific lower back pain, multiple sclerosis pain, fibromyalgia, HIV-related neuropathy, post-herpetic neuralgia, trigeminal neuralgia and pain resulting from physical trauma;

the treatment of inflammatory diseases including rheumatoid and osteoarthritis, psoriasis, dermatitis, retinitis, conjunctivitis, asthma, bronchitis, chronic obstructive pulmonary disease, inflammatory bowel disease, colitis, nephritis, gingivitis and hepatitis;

the treatment of cancers including familial adenomatous polyposis, endometrial carcinoma, colorectal and cervical cancer;

the treatment of bone disorders involving altered bone formation or resorption such as osteoporosis; women's health for the treatment of myometrial and endometrial disorders;

the treatment of gastrointestinal disease including diarrhoea;

the treatment of immunological disorders such as autoimmune disease, immunological deficiency diseases, organ transplantation and increasing the latency of HIV infection;

the treatment of diseases of abnormal platelet function. (e.g. occlusive vascular diseases);

the preparation of a drug with diuretic properties to treat or prevent various oedema, hypertension, premenstrual tension, urinary calculus, oliguria, hyperphosphaturia, mesangial proliferative glomerulonephritis, chronic renal failure or the like;

the treatment of impotence or erectile dysfunction, and female sexual dysfunction;

the treatment of hair growth disorders;

the treatment of sleep disorders such as narcolepsy and insomnia;

the treatment of cardiovascular diseases and shock states associated with hypotension (e.g. septic shock);

the treatment of neurodegenerative diseases and for preventing neuronal damage following stroke, cardiac arrest, cardiopulmonary bypass, traumatic brain injury or spinal cord injury;

the treatment of tinnitus;

the treatment of dependence; and the treatment of complications of diabetes.

Although EP$_4$ antagonists are known, it is desired to find novel EP$_4$ antagonists, and in particular, EP$_4$ antagonists which are selective against other EP receptors, i.e. EP$_1$, EP$_2$ and EP$_3$.

SUMMARY OF THE INVENTION

A first aspect of the present invention provides a compound of formula (I):

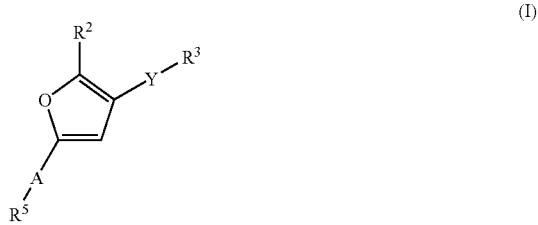

or a pharmaceutically acceptable salt thereof for use in a method of therapy, wherein:

R$^2$ is H or an optionally substituted C$_{1-4}$ alkyl group;

Y is either —(CH$_2$)$_n$—X—, where n is 1 or 2 and X is O, S, S(=O), S(=O)$_2$, or NR$^{N1}$, where R$^{N1}$ is selected from H or optionally substituted C$_{1-4}$ alkyl, or Y is —C(=O)NR$^{N2}$—, where R$^{N2}$ is selected from H, and optionally substituted C$_{1-7}$ alkyl or C$_{5-20}$ aryl;

R³ is an optionally substituted C₆ aryl group linked to a further optionally substituted C₆ aryl group, wherein if both C₆ aryl groups are benzene rings, there may be an oxygen bridge between the two rings, bound adjacent the link on both rings;

A is a single bond or a C₁₋₃ alkylene group; and

R⁵ is either:
(i) carboxy;
(ii) a group of formula (II):

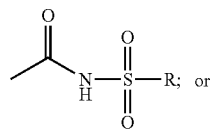

(iii) a group of formula (III):

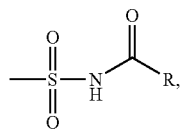

wherein R is optionally substituted C₁₋₇ alkyl, C₅₋₂₀ aryl or NR^{N3}R^{N4}, where R^{N3} and R^{N4} are independently selected from optionally substituted C₁₋₄ alkyl;
(iv) tetrazol-5-yl.

A second aspect of the present invention provides a compound of formula (I):

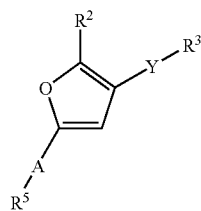

or a salt, solvate and chemically protected form thereof, wherein:

R² is H or an optionally substituted C₁₋₄ alkyl group;

Y is either —(CH₂)ₙ—X—, where n is 1 or 2 and X is O, S, S(=O), S(=O)₂ or NR^{N1}, where R^{N1} is selected from H or optionally substituted C₁₋₄ alkyl, or Y is —C(=O)NR^{N2}—, where R^{N2} is selected from H, and optionally substituted C₁₋₇ alkyl or C₅₋₂₀ aryl;

R³ is an optionally substituted C₆ aryl group linked to a further optionally substituted C₆ aryl group, wherein if both C₆ aryl groups are benzene rings, there may be an oxygen bridge between the two rings, bound adjacent the link on both rings;

A is a single bond or a C₁₋₃ alkylene group; and

R⁵ is either:
(i) carboxy;
(ii) a group of formula (II):

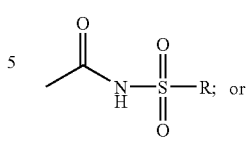

(iii) a group of formula (III):

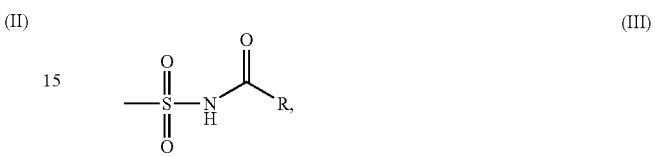

wherein R is optionally substituted C₁₋₇ alkyl, C₅₋₂₀ aryl or NR^{N3}R^{N4}, where R^{N3} and R^{N4} are independently selected from optionally substituted C₁₋₄ alkyl;
(iv) tetrazol-5-yl, except that when R² is methyl, Y is —CH₂—O— and R⁵ is carboxy or C₁₋₇ alkyl ester thereof, then R³ is not:

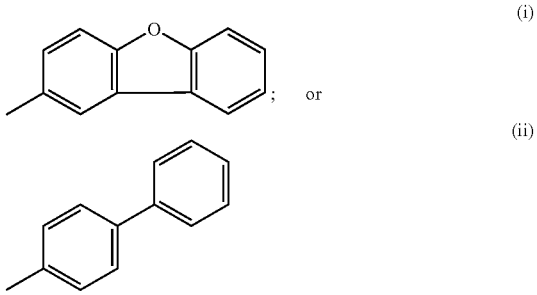

A third aspect of the present invention provides a pharmaceutical composition comprising a compound of formula (I) as defined in the first aspect or a pharmaceutically acceptable salt thereof together with a pharmaceutically acceptable carrier or diluent.

A further aspect of the present invention provides the use of a compound of formula (I) or a pharmaceutically acceptable salt thereof in the preparation of a medicament for the treatment of a condition alleviated by antagonism of an EP₄ receptor.

Another aspect of the present invention provides a method of treating a condition which can be alleviated by antagonism of an EP₄ receptor, which method comprises administering to a patient in need of treatment an effective amount of a compound of formula (I), or a pharmaceutically acceptable salt thereof.

Conditions which can be alleviated by antagonism of an EP₄ receptor are discussed above, and particularly include primary headache disorders, most particularly migraines.

The present invention also provides methods of antagonizing EP₄ receptors, in vitro or in vivo, comprising contacting a cell with an effective amount of a compound of formula (I).

In some embodiments, the compounds described above may be selective as against antagonism of the other three EP receptors, i.e. EP₁, EP₂ and EP₃. This selectivity allows for targeting of the effect of the compounds of the invention, with possible benefits in the treatment of certain conditions.

Definitions

Monodentate Groups (i.e groups with one point of covalent attachment)

Alkyl: The term "alkyl" as used herein, pertains to a monovalent moiety obtained by removing a hydrogen atom from a carbon atom of a hydrocarbon compound having from 1 to 7 carbon atoms (unless otherwise specified), which may be aliphatic or alicyclic, and which may be saturated or unsaturated. Thus, the term "alkyl" includes the sub-classes alkenyl, alkynyl, cycloalkyl, cycloalkenyl, cylcoalkynyl, etc., discussed below.

In the context of alkyl groups, the prefixes (e.g. $C_{1-4}$, $C_{1-7}$) denote the number of carbon atoms, or range of number of carbon atoms. For example, the term "$C_{1-4}$ alkyl". as used herein, pertains to an alkyl group having from 1 to 4 carbon atoms. Examples of groups of alkyl groups include $C_{1-4}$ alkyl ("lower alkyl") and $C_{1-7}$ alkyl. Note that the first prefix may vary according to other limitations; for example, for unsaturated alkyl groups, the first prefix must be at least 2; for cyclic alkyl groups, the first prefix must be at least 3; etc.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl" as used herein, pertains to an alkyl group having one or more carbon-carbon double bonds. Examples of groups of alkenyl groups include $C_{2-4}$ alkenyl and $C_{2-7}$ alkenyl. Examples of alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (1-methylvinyl, —C($CH_3$)=$CH_2$), butenyl ($C_4$), pentenyl ($C_5$), and hexenyl ($C_6$).

Alkynyl: The term "alkynyl" as used herein, pertains to an alkyl group having one or more carbon-carbon triple bonds. Examples of groups of alkynyl groups include $C_{2-4}$ alkynyl and $C_{2-7}$ alkynyl. Examples of alkynyl groups include, but are not limited to, ethynyl (ethinyl, —C≡CH) and 2-propynyl (propargyl, —$CH_2$—C≡CH).

Cycloalkyl: The term "cycloalkyl" as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated, which moiety has from 3 to 7 carbon atoms (unless otherwise specified), including from 3 to 7 ring atoms. Thus, the term "cycloalkyl" includes the sub-classes cycloalkyenyl and cycloalkynyl. Preferably, each ring has from 3 to 7 ring atoms. Examples of groups of cycloalkyl groups include $C_{3-7}$ cycloalkyl.

Examples of cycloalkyl groups include, but are not limited to, those derived from:

saturated monocyclic hydrocarbon compounds: cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$);

unsaturated monocyclic hydrocarbon compounds: cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$);

Heterocyclyl: The term "heterocyclyl" as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$ heterocyclyl" as used herein, pertains to a heterocyclyl group having 5 or 6 ring atoms. Examples of groups of heterocyclyl groups include $C_{3-20}$ heterocyclyl, $C_{5-20}$ heterocyclyl, $C_{3-15}$ heterocyclyl, $C_{5-15}$ heterocyclyl, $C_{3-12}$ heterocyclyl, $C_{5-12}$ heterocyclyl, $C_{3-10}$ heterocyclyl, $C_{5-10}$ heterocyclyl, $C_{3-7}$ heterocyclyl, $C_{5-7}$ heterocyclyl, and $C_{5-6}$ heterocyclyl.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxyrane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$) imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Aryl: The term "aryl" as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms. Examples of groups of aryl groups include $C_{3-20}$ aryl, $C_{5-20}$ aryl, $C_{5-15}$ aryl, $C_{5-12}$ aryl, $C_{5-10}$ aryl, $C_{5-7}$ aryl, $C_{5-6}$ aryl, $C_5$ aryl, and $C_6$ aryl.

The ring atoms may be all carbon atoms, as in "carboaryl groups". Examples of carboaryl groups include $C_{3-20}$ carboaryl, $C_{5-20}$ carboaryl, $C_{5-15}$ carboaryl, $C_{5-12}$ carboaryl, $C_{5-10}$ carboaryl, $C_{5-7}$ carboaryl, $C_{5-6}$ carboaryl, $C_5$ carboaryl, and $C_6$ carboaryl.

Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g., 2,3-dihydro-1H-indene) ($C_9$), indene ($C_{10}$), isoindene ($C_9$), tetralin (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of heteroaryl groups include $C_{3-20}$ heteroaryl, $C_{5-20}$ heteroaryl, $C_{5-15}$ heteroaryl, $C_{5-12}$ heteroaryl, $C_{5-10}$ heteroaryl, $C_{5-7}$ heteroaryl, $C_{5-6}$ heteroaryl, $C_5$ heteroaryl, and $C_6$ heteroaryl.

Examples of monocyclic heteroaryl groups include, but are not limited to, those derived from:

$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$), pyrazine (1,4-diazine) ($C_6$);
$N_3$: triazole ($C_5$), triazine ($C_6$); and,
$N_4$: tetrazole ($C_5$).

Examples of heteroaryl groups which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

If a heteroaryl or heterocyclyl group contains a nitrogen ring atom, this ring atom, where possible, may be in a oxidised state, as an N-oxide.

$R^3$ is defined above as an optionally substituted $C_6$ aryl group linked to a further optionally substituted $C_6$ aryl group, wherein if both $C_6$ aryl groups are benzene rings there may be an oxygen bridge between the two rings, bound adjacent the link on both rings. Thus, if both $C_6$ aryl groups are benzene rings, then $R^3$ can be optionally substituted biphenyl:

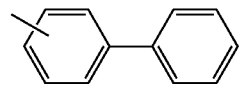

or optionally substituted dibenzofuran:

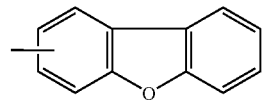

If one of the $C_6$ aryl groups is a $C_6$ heteroaryl group, then examples of $R^3$ include, but are not limited to (not showing optional substitution):

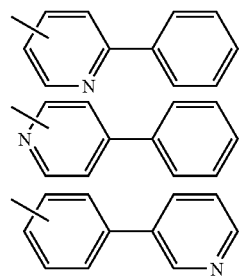 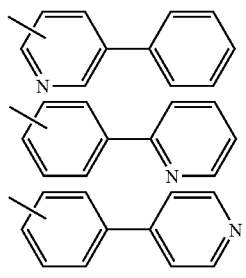

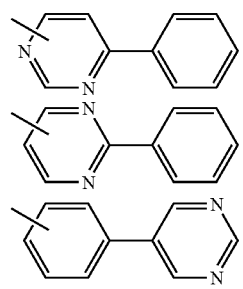 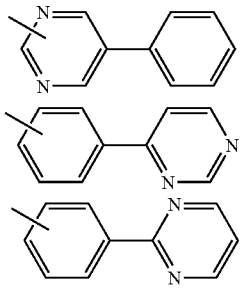

The above groups, whether alone or part of another substituent, may themselves optionally be substituted with one or more groups selected from themselves, the additional monodentate substituents listed below and alkoxylene.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

$C_{1-7}$ alkoxy: —OR, wherein R is a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Oxo (keto, -one): =O.

Thione (thioketone): =S.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of imino groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{3-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolcarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Amido (carbamoyl, carbamyl, aminocarbonyl, carboxamide): —C(=O)NR$^1$R$^1$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and R$^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

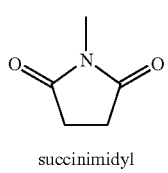

succinimidyl

-continued

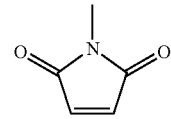

maleimidyl

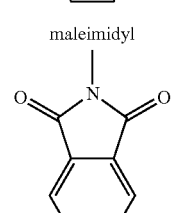

phthalimidyl

Thioamido (thiocarbamyl): —C(=S)NR$^1$R$^2$, wherein R$^1$ and R$^2$ are independently amino substituents, as defined for amino groups. Examples of thioamido groups include, but are not limited to, —C(=S)NH$_2$, —C(=S)NHCH$_3$, —C(=S)N(CH$_3$)$_2$, and —C(=S)NHCH$_2$CH$_3$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

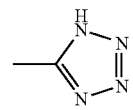

Amino: —NR$^1$R$^2$, wherein R$^1$ and R$^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$_1$), or tertiary (—NHR$^1$R$^2$), and in cationic form, may be quaternary (—$^{+NR1}$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amidine (amidino): —C(=NR)NR$_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.

Nitroso: —NO.

Cyano (nitrile, carbonitrile): —CN.

Sulfhydryl (thiol, mercapto): —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH$_3$ and —SSCH$_2$CH$_3$ Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$ C$_4$F$_9$ (nonaflyl), —S(=O)$_2$CH$_2$CF$_3$ (tresyl), —S(=O)$_2$ CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonyloxy: —OS(=O)R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)CH$_3$ and —OS(=O)CH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfonamino: —NR$^1$S(=O)R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)CH$_3$ and —N(CH$_3$)S(=O)C$_6$H$_5$.

As already mentioned, the above described groups may be substituted, and particular examples include, but are not limited to, $C_{3-20}$ aryl-$C_{1-7}$ alkyl groups, which include benzyl (phenylmethyl, PhCH$_2$—), benzhydryl (Ph$_2$CH—), trityl (triphenylmethyl, Ph$_3$C—), phenethyl (phenylethyl, Ph-CH$_2$CH$_2$—), styryl (Ph-CH=CH—) and cinnamyl (Ph-CH=CH—CH$_2$—).

Bidentate Groups (i.e. groups with two points of covalent attachment; linking groups)

Alkylene: The term "$C_{1-3}$ alkylene", as used herein, pertains to a bidentate moiety obtained by removing two hydrogen atoms from each of two different carbon atoms, of a linear hydrocarbon compound having from 1 to 3 carbon atoms, which may be saturated or unsaturated. Thus, the term "alkylene" includes the sub-classes alkenylene and alkynylene.

In this context, the prefix $C_{1-3}$ denotes the number of carbon atoms, or range of number of carbon atoms.

Examples of saturated $C_{1-3}$ alkylene groups include —CH$_2$— (methylene), —CH$_2$CH$_2$— (ethylene) and —CH$_2$CH$_2$CH$_2$— (propylene).

Examples of unsaturated $C_{1-3}$ alkylene groups (which may be termed "$C_{2-3}$ alkenylene" or "$C_{2-3}$ alkynylene", as appropriate) include —CH=CH— (vinylene), —CH=CH—CH$_2$—, —CH$_2$—CH=CH—, —C≡C—, —C≡C—CH$_2$— and —CH$_2$—C≡C—.

The $C_{1-3}$ alkylene group may be substituted by any monodentate substituent described above.

Alkoxylene: The term "alkoxylene," as used herein, pertains to a bidentate group of formula —O(CH$_2$)$_n$O—, where n is 1 or 2.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^{+HR^1}$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

Isomers, Salts, Solvates and Protected Forms

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$alkyl includes n-propyl and isopropyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

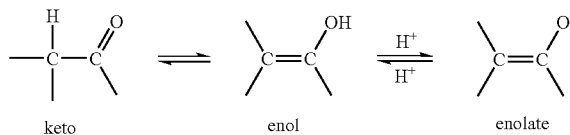

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g. pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

A wide variety of such "protecting", "blocking", or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: an acetamide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Troc), as a 2,2,2-trichloroethyloxy amide (—NH-Troc), as an allyloxy amide (—NH-Alloc), as a 2(-phenylsulfonyl)ethyloxy amide (—NH-Psec); or, in suitable cases (e.g., cyclic amines), as a nitroxide radical (>N—O).

For example, a carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "therapeutically-effective amount", as used herein, pertains to that amount of an active compound, or a material, composition or dosage form comprising an active compound, which is effective for producing some desired therapeutic effect, commensurate with a reasonable benefit/risk ratio, when administered in accordance with a desired treatment regimen. Suitable dose ranges will typically be in the range of from 0.01 to 20 mg/kg/day, preferably from 0.1 to 10 mg/kg/day.

Compositions and their Administration

Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. The active compound as defined above may be formulated as suppositories using, for example, polyalkylene glycols, acetylated triglycerides and the like, as the carrier. Liquid pharmaceutically administrable compositions can, for example, be prepared by dissolving, dispersing, etc, an active compound as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, 20th edition, pub. Lippincott, Williams & Wilkins, 2000. The composition or formulation to be administered will, in any event, contain a quantity of the active compound(s) in an amount effective to alleviate the symptoms of the subject being treated.

Dosage forms or compositions containing active ingredient in the range of 0.25 to 95% with the balance made up from non-toxic carrier may be prepared.

For oral administration, a pharmaceutically acceptable non-toxic composition is formed by the incorporation of any of the normally employed excipients, such as, for example, pharmaceutical grades of mannitol, lactose, cellulose, cellulose derivatives, sodium croscarmellose, starch, magnesium stearate, sodium saccharin, talcum, glucose, sucrose, magnesium carbonate, and the like. Such compositions take the form of solutions, suspensions, tablets, pills, capsules, powders, sustained release formulations and the like. Such compositions may contain 1%-95% active ingredient, more preferably 2-50%, most preferably 5-8%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

The percentage of active compound contained in such parental compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably, the composition will comprise 0.2-2% of the active agent in solution.

Acronyms

For convenience, many chemical moieties are represented using well known abbreviations, including but not limited to, methyl (Me), ethyl (Et), n-propyl (nPr), iso-propyl (iPr), n-butyl (nBu), sec-butyl (sBu), iso-butyl (iBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), acetonitrile (ACN), trifluoroacetic acid (TFA), dimethylformamide (DMF), tetrahydrofuran (THF), and dimethylsulfoxide (DMSO).

General Synthesis Methods

Compounds of the invention wherein R$^5$ is of formula (II):

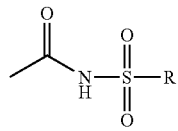
(II)

may be synthesised from the analogous compound of the invention wherein R$^5$ is carboxy, by reaction with a compound of formula 1:

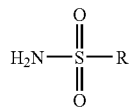
Formula 1 in basic conditions, preferably aided by a coupling agent, for example, 1-(3-dimethylaminopropyl)-3-ethylcarbodiimide hydrochloride.

Compounds of the invention wherein R$^5$ is of formula (III):

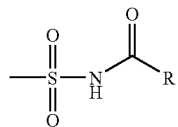
(III)

may be synthesized from a compound of formula 2:

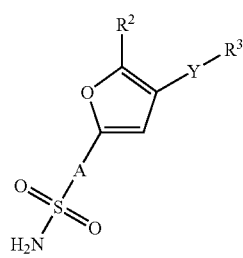
Formula 2 by reaction with a compound of formula 3:

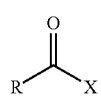
Formula 3 wherein X is either OH or halo, where if X is OH, the use of basic conditions and a coupling agent is preferred.

Compounds of formulae (I) and 2, or where the group -A-R$^5$ is present as a precursor or protected form, may be represented as compounds of formula 4:

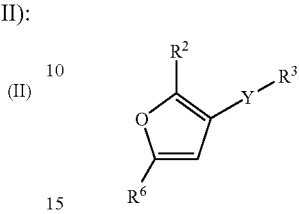
Formula 4 where R$^6$ is -A-R$^5$ or its precursor or protected form. The protecting groups used may be conventional, or the group may be resin-bound. If Y is —(CH$_2$)$_n$—O— or —(CH$_2$)$_n$—S—, then these compounds can be synthesised from compounds of formula 5:

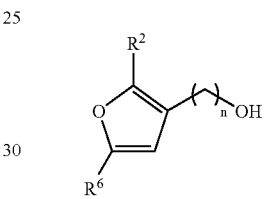
Formula 5 by one of two possible routes.

In the first route, a compound of formula 6:

 Formula 6 where X' is S or O, is coupled to a compound of formula 5 using the Mitsunobu reaction, for example by treatment with triphenyl phosphine (Ph$_3$P) and diisopropylazodicarboxylate (DIAD).

The second route is a two stage route, the first stage being the Mitsunobu coupling of a compound of formula 7a:

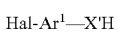 Formula 7a wherein Ar$^1$ is the first C$_6$ aryl component of R$^3$ and Hal is I or Br followed by a Suzuki coupling of a compound of formula 8a (or equivalent ester of formula 8c):

 Formula 8a

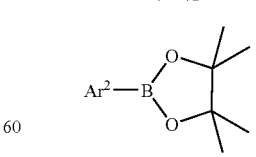 Formula 8c wherein Ar$^2$ is the second C$_6$ aryl component of R$^3$. The Suzuki coupling may be achieved using, for example, [1,1'-bis(diphenylphosphino)ferrocene]dichloropalladium (II) as the palladium catalyst.

This route may also be 'reversed' such that the Mitsunobu coupling is of a boronic acid of formula 7b (or preferably equivalent ester of formula 7c):

Formula 7b
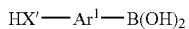

Formula 7c
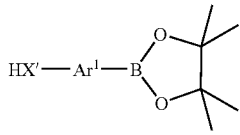

wherein Ar$^1$ is the first C$_6$ aryl component of R$^3$, followed by a Suzuki coupling of a compound of formula 8b:

Ar$^2$-Hal      Formula 8b wherein Ar$^2$ is the second C$_6$ aryl component of R$^3$ and Hal is I or Br.

If the compound of formula 7b or 7c is not readily available then a compound of formula 7d:

HX'—Ar$^1$—Br      Formula 7d may be coupled, followed by conversion of the bromo group to the required boronic acid or ester.

Compounds of formula 4 where Y is —(CH$_2$)$_n$—NH— can also be synthesized from compounds of formula 5. In one method, the alcohols of formula 5 are oxidized to the corresponding aldehyde, for example using the Dess-Martin reagent, followed by reductive coupling to an amine, which may be of formula 6':

R$^3$—NH$_2$      Formula 6' or of formula 7a', 7b' or 7c':

Formula 7a'

Formula 7b'

Formula 7c'
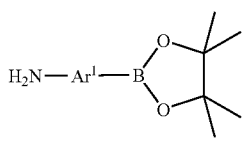

for subsequent Suzuki coupling. The reductive coupling can be carried out using sodium cyanoborohydride.

In another method, the alcohol of formula 5 is converted to the corresponding halide, using a halogenating reagent, for example conversion to chlorine using 4-methyl-benzene sulfonyl chloride, followed by coupling to an amine which may be of formula 6', or of formula 7a', 7b' or 7c' for subsequent Suzuki coupling. The amine coupling is carried out in the presence of potassium iodide, or equivalent reagents. This method can also be used to couple alcohols and thiols of formulae 6, 7a, 7b and 7d, where X' is O or S.

Compounds of formula 4:

Formula 4
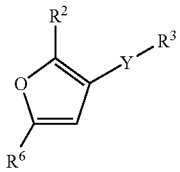

where Y is —C(=O)—NR$^{N1}$— may be synthesised from a compound of formula 9:

Formula 9

by reaction with a amine of formula 10:

Formula 10
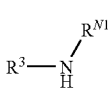

in basic conditions, preferably with the aid of a coupling agent.

Compounds of formula 9:

Formula 9
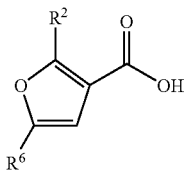

may be derived from compounds of formula 11:

Formula 11
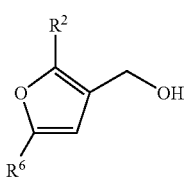

by oxidation, for example, using Jones' reagent.

Compounds of formula (I) where A is a single bond, and $R^5$ is carboxy, and compounds where the group —Y—$R^3$ is present as a precursor or protected form, may be represented as compounds of formula 12:

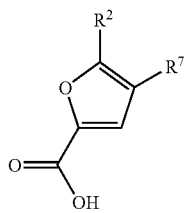

Formula 12 where $R^7$ is —Y—$R^3$ or its precursor or protected form. These compounds may be synthesised from compounds of formula 13:

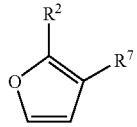

Formula 13 by treatment with n-butyllithium, followed by carbon dioxide at low temperatures.

In a similar fashion, compounds of formula 2 where A is a single bond, and $R^5$ is carboxy, and compounds where the group —Y—$R^3$ is present as a precursor or protected form, may be represented as compounds of formula 14:

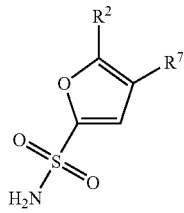

Formula 14 where $R^7$ is —Y—$R^3$ or its precursor or protected form. These compounds may be synthesised from compounds of formula 13:

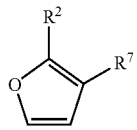

Formula 13 by treatment with a strong base and sulphur dioxide at low temperatures, followed by amination.

Compounds of formula (I) where A is a —$C_2H_4$—, and $R^5$ is carboxy, and compounds where the group —Y—$R^3$ is present as a precursor or protected form, may be represented as compounds of formula 15:

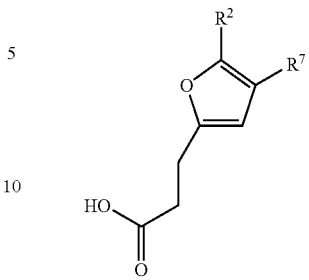

Formula 15 where $R^7$ is —Y—$R^3$ or its precursor or protected form. These compounds may be synthesised from compounds of formula 16:

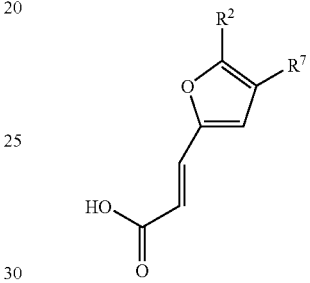

Formula 16 by hydrogenation, using a palladium catalyst.

Compounds of formula 16 may be synthesised from compounds of formula 17:

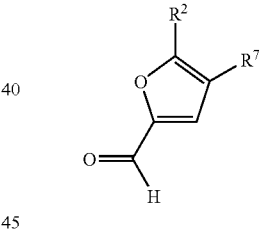

Formula 17 by the Wittig coupling of an acetic ester, using, for example, triethylphosphonoacetate as the Wittig reagent, followed by hydrolysis under alkaline conditions, e.g. lithium hydroxide in a suitable solvent, e.g. aqueous alcohol.

Compounds of formula 17 may also be used to synthesise compounds of formula 18:

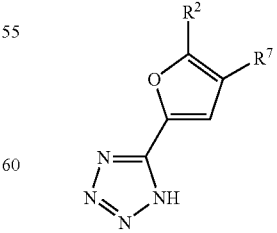

Formula 18 where $R^2$ and $R^7$ are as defined above. The reaction proceeds via a cyano intermediate which may be obtained by treating compounds of formula 17 with hydroxylamine to form the oxime derivative, which can be dehydrated to the cyano compound with, for example, 2-chloro-1,3-dimethylimidazolium chloride in the presence of a base. The cyano intermediate can be converted into compounds of formula 18 by treatment with sodium azide, in the presence of a base.

Compounds where Y is —(CH$_2$)$_n$—S(=O)— and —(CH$_2$)—S(=O)$_2$— may be obtained from the corresponding compound where Y is —(CH$_2$)$_n$—S— by oxidation with a peracid, for example 3-chloro-benzenecarboperoxoic acid.

Compounds where Y is —(CH$_2$)$_n$—NR$^{N1}$— may be obtained from the corresponding compound where Y is —(CH$_2$)$_n$—NH— by direction alkylation by R$^{N1}$I, in the presence of a weak base.

The starting materials described above are generally commercially available or synthesisable using known methods. For example, example 22A below describes a method of synthesizing 2-substituted furans.

Some of the reaction steps described above may be carried out using resins, as is shown in the examples.

Preferences

The following preferences may be combined with one another, and may be different for each aspect of the present invention.

R$^2$ is preferably selected from H or an optionally substituted C$_{1-3}$ alkyl group, more preferably H, methyl, CF$_3$ or iso-propyl, and most preferably R$^2$ is a methyl group.

Y is preferably —(CH$_2$)$_n$—X—, and n is preferably 1. X is preferably O, S or NH, with NH being the most preferred. In some embodiments the preferred option for Y is —CH$_2$—O—.

If Y is —C(=O)NR$^{N2}$, then R$^{N2}$ is preferably selected from H, and optionally substituted C$_{1-4}$ alkyl, in particular Me.

The C$_6$ aryl groups of R$^3$ are preferably independently selected from those derived from benzene and heteroaryl groups, where the heteroatom or heteroatoms are nitrogen. Most preferred are C$_6$ aryl groups derived from benzene, pyridine and 1,3-pyrimidine. It is further preferred that either both C$_6$ aryl groups are derived from benzene or that one group is derived from benzene and the other from pyridine or 1,3-pyrimidine, with pyridine being preferred, especially as the aryl group furthest from the furan core.

If both C$_6$ aryl groups are derived from benzene, it is preferred that there is not an oxygen bridge between the two rings, bound adjacent the link on both rings, i.e. that R$_3$ is optionally substituted biphenyl rather than optionally substituted dibenzofuranyl.

If one or more of the C$_6$ aryl groups is derived from pyridine, then it is preferred that the nitrogen ring atom is adjacent the link between the two rings that make up the R$^3$ group.

If one or more of the C$_6$ aryl groups is derived from 1,3-pyrimidine, then it is preferred that the link between the two rings that make up the R$^3$ group is between the two nitrogen atoms.

It is further preferred that that the single bond joining the two C$_6$ aryl groups is in the 4-position of the ring bound to Y. Thus, 4-phenyl-phenyl is preferred to 3-phenyl-phenyl; dibenzofuran-3-yl is preferred to di-benzofuran-2-yl, 4-pyridin-2-yl-phenyl is preferred to 3-pyridin-2-yl-phenyl and 6-phenyl-pyridin-3-yl is preferred to 6-phenyl-pyridin-2-yl:

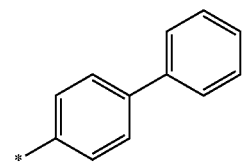

4-phenyl-phenyl

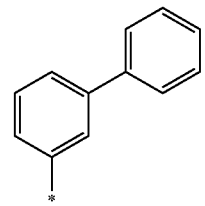

3-phenyl-phenyl

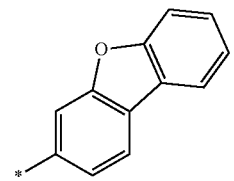

Dibenzofuran-3-yl

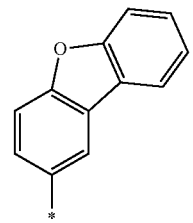

Dibenzofuran-2-yl

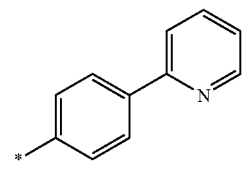

4-pyridin-2-yl-phenyl

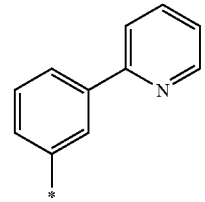

3-pyridin-2-yl-phenyl

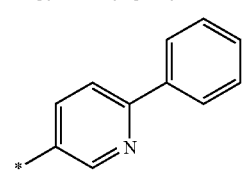

6-phenyl-pyridin-3-yl

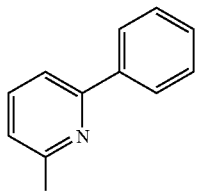

6-phenyl-pyridin-2-yl

Both $C_6$ aryl groups of $R^3$ are optionally substituted, although it is preferred that only the $C_6$ aryl group not bound to Y is substituted.

Preferred substituents on the $C_6$ aryls of $R^3$ include, but are not limited to: optionally substituted $C_{1-7}$ alkyl groups, more preferably methyl and substituted $C_{1-4}$ alkyl groups, e.g. —$CF_3$, $CH_2OH$; $C_{1-7}$ alkoxy groups, more preferably $C_{1-4}$ alkoxy groups, e.g. —OMe, —$OCF_3$, —OEt, —$OCHF_2$; $C_{1-7}$ thioether group, more preferably $C_{1-4}$ thioether group, e.g. —SMe; amino groups, optionally substituted by one or two $C_{1-4}$ alkyl groups, e.g. —$NMe_2$; halo groups, more preferably —F or —Cl; cyano; alkoxylene groups, more preferably —O—$CH_2$—O—; $C_{1-4}$ acyl groups, more preferably —C(═O)Me.

The preferred location for a substituent on the $C_6$ aryl group not bound to Y is para to the bond between the two $C_6$ aryl groups, with the meta position being less preferred. Therefore, if $R^3$ is 4-phenyl-phenyl, the substituent is preferably at the 4'-position.

In some embodiments of the present invention A is preferably a single bond, whereas in other embodiments A is preferably a $C_{1-3}$ alkylene group. In particular, when $R^5$ is carboxy, A is more preferably a $C_{1-3}$ alkylene group, with vinylene being most preferred.

$R^5$ is preferably either:
(i) a group of formula (II):

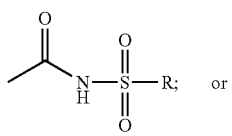

(II)

or (ii) a group of formula (III):

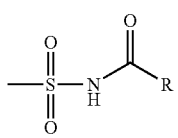

(III)

with a group of formula (II) being more preferred.

The above preference for $R^5$ is particularly applicable when $R^2$ is methyl and Y is —$CH_2$—O—.

Where $R^5$ is of formula (II) of (III), R is preferably selected from an optionally substituted $C_{5-20}$ aryl group, and an optionally substituted $C_{5-20}$ aryl-$C_{1-7}$ alkyl group, wherein the $C_{1-7}$ alkyl group is more preferably methyl. In these groups the $C_{5-20}$ aryl group is preferably a heteroaryl group, itself preferably having a single aromatic ring. Such groups may preferably be substituted with $C_{1-4}$ alkyl groups, such as methyl and hydroxy. Thus, preferred R groups include, but are not limited to: phenyl; benzyl; 3,5, dimethyl-isoxazol-4-yl; thiophen-2-yl; 5-methyl-pyridin-yl; and 4-hydroxy-phenyl.

If R in formula (II) or (III) is a $C_{1-7}$ alkyl group, it is more preferably a $C_{1-4}$ alkyl group, for example methyl or propyl.

Particularly preferred compounds of the present invention include:
4-(4'-Methoxy-biphenyl-4-yloxymethyl)-5-methyl-furan-2-carboxylic acid (4);
N-[4-(4'-Methoxy-biphenyl-4-yloxymethyl)-5-methyl-furan-2-carbonyl]-benzenesulfonamide (5);
N-[4-(4'-Methoxy-biphenyl-4-yloxymethyl)-5-methyl-furan-2-carbonyl]-C-phenyl-methanesulfonamide (6);
N-[4-(4'-Methoxy-biphenyl-4-yloxymethyl)-5-methyl-furan-2-carbonyl]-methanesulfonamide (7);
Propane-1-sulfonic acid [4-(4'-methoxy-biphenyl-4-yloxymethyl)-5-methyl-furan-2-carbonyl]-amide (8);
3,5-Dimethyl-isoxazole-4-sulfonic acid [4-(4'-methoxy-biphenyl-4-yloxymethyl)-5-methyl-furan-2-carbonyl]-amide (9);
Thiophene-2-sulfonic acid [4-(4'-methoxy-biphenyl-4-yloxymethyl)-5-methyl-furan-2-carbonyl]-amide (10);
5-Methyl-pyridyl-2-sulfonic acid [4-(4'-methoxy-biphenyl-4-yloxymethyl)-5-methyl-furan-2-carbonyl]-amide (11);
4-Aminomethyl-N-[4-(4'-methoxy-biphenyl-4-yloxymethyl)-5-methyl-furan-2-carbonyl]-benzenesulfonamide (trifluoroacetate salt) (12);
4-Hydroxy-N-[4-(4'-methoxy-biphenyl-4-yloxymethyl)-5-methyl-furan-2-carbonyl]-benzenesulfonamide (13);
4-(Biphenyl-4-yloxymethyl)-5-methyl-furan-2-carboxylic acid (18);
N-[4-(Biphenyl-4-yloxymethyl)-5-methyl-furan-2-carbonyl]-benzenesulfonamide (19);
4-(4'-Acetyl-biphenyl-4-yloxymethyl)-5-methyl-furan-2-carboxylic acid (21);
N-[4-(4'-Acetyl-biphenyl-4-yloxymethyl)-5-methyl-furan-2-carbonyl]-benzenesulfonamide (22);
4-(4'-Methoxy-biphenyl-4-ylcarbamoyl)-5-methyl-furan-2-carboxylic acid (24);
5-Benzenesulfonylaminocarbonyl-2-methyl-furan-3-carboxylic acid (4'-methoxy-biphenyl-4-yl)-amide (25);
4-(4'-Chloro-biphenyl-4-yloxymethyl)-5-methyl-furan-2-carboxylic acid (27);
4-(4-Benzo[1,3]dioxol-5-yl-phenoxymethyl)-5-methyl-furan-2-carboxylic acid (28);
[4-(Biphenyl-4-yloxymethyl)-5-methyl-furan-2-yl]-acetic acid (31);
4-(4'-Methoxy-biphenyl-4-yloxymethyl)-5-methyl-furan-2-yl]-acetic acid (32);
3-[4-(Biphenyl-4-yloxymethyl)-5-methyl-furan-2-yl]-propionic acid (37);
N-{3-[4-(Biphenyl-4-yloxymethyl)-5-methyl-furan-2-yl]-propionyl}-benzene sulfonamide (38);
3-[4-(4'-Methoxy-biphenyl-4-yloxymethyl)-5-methyl-furan-2-yl]-propionic acid (39);
N-{3-[4-(4'-Methoxy-biphenyl-4-yloxymethyl)-5-methyl-furan-2-yl]-propionyl}-benzene sulfonamide (40);
3-[4-(Biphenyl-4-yloxymethyl)-5-methyl-furan-2-yl]-acrylic acid (42);
3-[4-(4'-Methoxy-biphenyl-4-yloxymethyl)-5-methyl-furan-2-yl]-acrylic acid (43);
4-(Biphenyl-4-yloxymethyl)-5-methyl-furan-2-sulfonic acid benzylamide (46);
4-(4'-Methoxy-biphenyl-4-yloxymethyl)-5-methyl-furan-2-sulfonic acid benzylamide (49);
4-(Dibenzofuran-3-yloxymethyl)-5-methyl-furan-2-carboxylic acid (50);
4-[4-(5-Methoxy-pyridin-2-yl)-phenoxymethyl]-5-methyl-furan-2-carboxylic acid (53);

4-[6-(4-Methoxy-phenyl)-pyridin-3-yloxymethyl]-5-methyl-furan-2-carboxylic acid (56);
4-(4'-Cyano-biphenyl-4-yloxymethyl)-5-methyl-furan-2-carboxylic acid (57);
3-Morpholin-4-yl-propane-1-sulphonic acid [4-(4'-methoxy-biphenyl-4-yloxymethyl)-5-methyl-furan-2-carbonyl]-amide (59);
N-[4-(Biphenyl-4-yloxymethyl)-5-methyl-furan-2-carbonyl]-2-methyl-benzenesulphonamide (60);
4-(Biphenyl-4-yloxymethyl)-5-methyl-furan-2-sulfonic acid butyryl-amide (61);
4-(Biphenyl-4-yloxymethyl)-5-methyl -furan-2-sulfonic acid phenylacetyl-amide (62);
4-(Biphenyl-4-yloxymethyl)-5-methyl-furan-2-sulfonic acid (3,5-dimethyl-isoxazole-4-carbonyl)-amide (63);
4-(Biphenyl-4-yloxymethyl)-5-methyl-furan-2-sulfonic acid (thiophene-2-carbonyl)-amide (64);
4-(Biphenyl-4-yloxymethyl)-5-methyl-furan-2-sulfonic acid (3-methoxy-propionyl)-amide (65);
4-(Biphenyl-4-yloxymethyl)-5-methyl-furan-2-sulfonic acid (pyridin-3-yl-acetyl)-amide (66);
4-(Biphenyl-4-yloxymethyl)-5-methyl-furan-2-sulfonic acid (pyridine-4-carbonyl)-amide (67);
4-(Biphenyl-4-yloxymethyl)-5-methyl-furan-2-sulfonic acid (pyridine-3-carbonyl)-amide (68);
4-(4'-Methoxy-biphenyl-4-yloxymethyl)-5-methyl-furan-2-sulfonic acid (3,5-dimethyl-isoxazole-4-carbonyl)-amide (69);
4-[2-(Biphenyl-4-yloxy)-ethyl]-5-methyl-furan-2-carboxylic acid (72);
4-[2-(4'-Methoxy-biphenyl-4-yloxy)-ethyl]-5-methyl-furan-2-carboxylic acid (73);
4-[2-(Dibenzofuran-3-yloxy)-ethyl]-5-methyl-furan-2-carboxylic acid (74);
4-(Biphenyl-4-yloxymethyl)-furan-2-carboxylic acid (77);
4-(Dibenzofuran-2-yloxymethyl)-furan-2-carboxylic acid (78);
4-(4'-Cyano-biphenyl-4-yloxymethyl)-furan-2-carboxylic acid (79);
4-(4'-Methoxy-biphenyl-4-yloxymethyl)-furan-2-carboxylic acid (80);
4-(Dibenzofuran-3-yloxymethyl)-furan-2-carboxylic acid (81);
4-(Biphenyl-4-yloxymethyl)-5-isopropyl-furan-2-carboxylic acid (85);
5-Isopropyl-4-(4'-methoxy-biphenyl-4-yloxymethyl)-furan-2-carboxylic acid (86);
4-(Dibenzofuran-3-yloxymethyl)-5-isopropyl-furan-2-carboxylic acid (87);
4-(Biphenyl-4-yloxymethyl)-5-trifluoromethyl-furan-2-carboxylic acid (90);
4-(Biphenyl-3-yloxymethyl)-5-trifluoromethyl-furan-2-carboxylic acid (91);
4-(Dibenzofuran-2-yloxymethyl)-5-trifluoromethyl-furan-2-carboxylic acid (92);
4-(4'-Cyano-biphenyl-4-yloxymethyl)-5-trifluoromethyl-furan-2-carboxylic acid (93);
4-(4'-Methoxy-biphenyl-4-yloxymethyl)-5-trifluoromethyl-furan-2-carboxylic acid (94);
4-(Dibenzofuran-3-yloxymethyl)-5-trifluoromethyl-furan-2-carboxylic acid (95);
4-(3',4'-Dimethoxy-biphenyl-4-yloxymethyl)-5-methyl-furan-2-carboxylic acid (96);
4-(4'-Ethoxy-biphenyl-4-yloxymethyl)-5-methyl-furan-2-carboxylic acid (98);
4-(2'-Chloro-biphenyl-4-yloxymethyl)-5-methyl-furan-2-carboxylic acid (99);
4-(2',6'-Difluoro-biphenyl-4-yloxymethyl)-5-methyl-furan-2-carboxylic acid (100);
5-Methyl-4-(2'-trifluoromethyl-biphenyl-4-yloxymethyl)-furan-2-carboxylic acid (102);
4-(3'-Fluoro-biphenyl-4-yloxymethyl)-5-methyl-furan-2-carboxylic acid (104);
5-Methyl-4-(2'-methylsulfanyl-biphenyl-4-yloxymethyl)-furan-2-carboxylic acid (105);
4-(3',4'-Dimethoxy-biphenyl-3-yloxymethyl)-5-methyl-furan-2-carboxylic acid (108);
5-Methyl-4-(3'-trifluoromethyl-biphenyl-3-yloxymethyl)-furan-2-carboxylic acid (109);
4-(4'-Hydroxymethyl-biphenyl-4-yloxymethyl)-5-methyl-furan-2-carboxylic acid (110);
5-Methyl-4-(4'-methylsulfanyl-biphenyl-4-yloxymethyl)-furan-2-carboxylic acid (111);
4-(3'-Hydroxy-biphenyl-4-yloxymethyl)-5-methyl-furan-2-carboxylic acid (112);
4-(4'-Dimethylamino-biphenyl-4-yloxymethyl)-5-methyl-furan-2-carboxylic acid (113);
5-Methyl-4-(4'-trifluoromethoxy-biphenyl-4-yloxymethyl)-furan-2-carboxylic acid (114);
5-Methyl-4-(2'-trifluoromethoxy-biphenyl-4-yloxymethyl)-furan-2-carboxylic acid (115);
4-(3'-Methoxy-biphenyl-4-yloxymethyl)-5-methyl-furan-2-carboxylic acid (116);
4-(3'-Acetyl-biphenyl-4-yloxymethyl)-5-methyl-furan-2-carboxylic acid (117);
4-(4'-Fluoro-biphenyl-4-yloxymethyl)-5-methyl-furan-2-carboxylic acid (118);
N-4-(4'-Methoxy-biphen-4-yloxymethyl)-5-methyl-furan-2-carbonyl]-dimethylaminosulphonamide (122);
4-(2'-Methoxy-biphenyl-4-yloxymethyl)-5-methyl-furan-2-carboxylic acid (126);
N-[4-(2'-Methoxy-biphenyl-4-yloxymethyl)-5-methyl-furan-2-carbonyl]-benzenesulfonamide (127);
4-(4'-Difluoromethoxy-biphenyl-4-yloxymethyl)-5-methyl-furan-2-carboxylic acid (129);
N-[4-(4'-Difluoromethoxy-biphenyl-4-yloxymethyl)-5-methyl-furan-2-carbonyl]-benzenesulfonamide (130);
3,5-Dimethyl-isoxazole-4-sulfonic acid [4-(4'-difluoromethoxy-biphenyl-4-yloxymethyl)-5-methyl-furan-2-carbonyl]-amide (131);
N-{4-[4-(5-Methoxy-pyridin-2-yl)-phenoxymethyl]-5-methyl-furan-2-carbonyl}-benzenesulfonamide (132);
3,5-Dimethyl-isoxazole-4-sulfonic acid {4-[4-(5-methoxy-pyridin-2-yl)-phenoxymethyl]-5-methyl-furan-2-carbonyl}-amide (133);
N-{4-[4-(5-Methoxy-pyridin-2-yl)-phenoxymethyl]-5-methyl-furan-2-carbonyl}-2-methyl-benzenesulfonamide (134);
N-{4-[4-(5-Methoxy-1-oxy-pyridin-2-yl)-phenoxymethyl]-5-methyl-furan-2-carbonyl}-benzenesulfonamide (135);
5-Methyl-4-(4-pyrimidin-2-yl-phenoxymethyl)-furan-2-carboxylic acid (137);
N-[5-Methyl-4-(4-pyrimidin-2-yl-phenoxymethyl)-furan-2-carbonyl]-benzenesulfonamide (138);
4-(2',4'-Dimethoxy-biphenyl-4-yloxymethyl)-5-methyl-furan-2-carboxylic acid (140);
N-[4-(2',4'-Dimethoxy-biphenyl-4-yloxymethyl)-5-methyl-furan-2-carbonyl]-benzenesulfonamide (141);
3,5-Dimethyl-isoxazole-4-sulfonic acid [4-(2',4'-dimethoxy-biphenyl-4-yloxymethyl)-5-methyl-furan-2-carbonyl]-amide (142);
4-(4'-Methoxy-2'-methyl-biphenyl-4-yloxymethyl)-5-methyl-furan-2-carboxylic acid (144);
N-[4-(4'-Methoxy-2'-methyl-biphenyl-4-yloxymethyl)-5-methyl-furan-2-carbonyl]-benzenesulfonamide (145);
3,5-Dimethyl-isoxazole-4-sulfonic acid [4-(4'-methoxy-2'-methyl-biphenyl-4-yloxymethyl)-5-methyl-furan-2-carbonyl]-amide (146);

5-[4-(Biphenyl-4-yloxymethyl)-5-methyl-furan-2-yl]-1H-tetrazole (149);
4-(4'-Difluoromethoxy-biphenyl-4-ylsulfanylmethyl)-5-methyl-furan-2-carboxylic acid (153);
N-[4-(4'-Difluoromethoxy-biphenyl-4-ylsulfanylmethyl)-5-methyl-furan-2-carbonyl]-2-methyl-benzenesulfonamide (154);
N-[4-(4'-Difluoromethoxy-biphenyl-4-ylsulfanylmethyl)-5-methyl-furan-2-carbonyl]-benzenesulfonamide (155);
N-[4-(4'-Difluoromethoxy-biphenyl-4-sulfinylmethyl)-5-methyl-furan-2-carbonyl]-2-methyl-benzenesulfonamide (156);
N-[4-(4'-Difluoromethoxy-biphenyl-4-sulfonylmethyl)-5-methyl-furan-2-carbonyl]-2-methyl-benzenesulfonamide (156a);
4-(Biphenyl-4-ylaminomethyl)-5-methyl-furan-2-carboxylic acid (160);
N-[4-(Biphenyl-4-ylaminomethyl)-5-methyl-furan-2-carbonyl]-benzenesulfonamide (161);
N-[4-(Biphenyl-4-ylaminomethyl)-5-methyl-furan-2-carbonyl]-2-methyl-benzenesulfonamide (162);
N-(4-{[4-(5-Methoxy-pyridin-2-yl)-phenylamino]-methyl}-5-methyl-furan-2-carbonyl)-2-methyl-benzenesulfonamide (167);
4-[(4'-Difluoromethoxy-biphenyl-4-ylamino)-methyl]-5-methyl-furan-2-carboxylic acid (171);
N-{4-[(4'-Difluoromethoxy-biphenyl-4-ylamino)-methyl]-5-methyl-furan-2-carbonyl}-benzenesulfonamide (172);
N-{4-[(4'-Difluoromethoxy-biphenyl-4-ylamino)-methyl]-5-methyl-furan-2-carbonyl}-2-methyl-benzenesulfonamide (173);
3,5-Dimethyl-isoxazole-4-sulfonic acid {4-[(4'-difluoromethoxy-biphenyl-4-ylamino)-methyl]-5-methyl-furan-2-carbonyl}-amide (174);
4-{[(4'-Difluoromethoxy-biphenyl-4-yl)-methyl-amino]-methyl}-5-methyl-furan-2-carboxylic acid (176); and
N-(4-{[(4'-Difluoromethoxy-biphenyl-4-yl)-methyl-amino]-methyl}-5-methyl-furan-2-carbonyl)-2-methyl-benzenesulfonamide (177).

The selectivity of the compound for antagonising $EP_4$ receptors over the other EP receptors (i.e. $EP_1$, $EP_2$, $EP_3$) can be quantified by dividing the Ki for $EP_4$ (see below) by the Ki for the other EP receptors (see below). The resulting ratio is preferably 10 or more, more preferably 100 or more.

SYNTHESIS EXAMPLES

General Experimental Details

All reactions were carried out under an inert atmosphere of nitrogen.

Where products were purified by flash chromatography the stationary phase used was silica gel for chromatography, 0.035 to 0.070 mm (220 to 440 mesh) (e.g. Fluka silica gel 60). An applied pressure of nitrogen of ~10 psi was used to accelerate column elution. Thin layer chromatography (TLC) was carried out on aluminium foil plates coated with silica gel containing a fluorescent indicator (254 nm) (e.g. Fluka 60778).

Petroleum ether refers to that fraction with a boiling point of 40-60° C.

Organic solutions were dried over magnesium sulphate unless otherwise specified.

PS-TsCl refers to Polystyrene scavenger resin (loading 1.97 mmol/g)—Argonaut Technologies (P/N 800277)

Preparative HPLC System

Preparative HPLC was carried out on a C18-reverse-phase column (10×2.1 cm i.d Genesis column with 7 μm particle size), eluting with a gradient of acetonitrile (containing 0.1% trifluoroacetic acid) and water (containing 0.1% trifluoroacetic acid) at a flow rate of 5 ml/min. UV detection at 230 nm was used unless otherwise stated.

LC/MS Systems

The Liquid Chromatography Mass Spectroscopy (LC/MS) systems used are as follows.

LC/MS System A:

Mass Spectrometer—Platform LC with electrospray source operating in positive and negative Ion mode. HP1100 system running at 2.0 mL/min, 200 μL/min split to the ESI source with inline HP1100 DAD detection and SEDEX ELS detection.

Mobile Phase

A) Water 0.1% Formic Acid

B) acetonitrile 0.1% Formic Acid

| | Gradient | | |
|---|---|---|---|
| Time (min) | Flow (mL/min) | % A | % B |
| 0.00 | 2.0 | 95 | 5 |
| 0.50 | 2.0 | 95 | 5 |
| 4.50 | 2.0 | 5 | 95 |
| 5.00 | 2.0 | 5 | 95 |
| 5.50 | 2.0 | 95 | 5 |

Column—Luna 3u C18(2) 30×4.6 mm

LC/MS System B:

Mass Spectrometer—Platform II with electrospray source operating in negative ion mode. HP1100 system running at 2.0 mL/min, 200 μL/min split to the ESI source with inline HP1100 DAD detection and SEDEX ELS detection.

Mobile Phase

A) Water 0.1% Diethylamine

B) acetonitrile

| | Gradient | | |
|---|---|---|---|
| Time (min) | Flow (mL/min) | % A | % B |
| 0.00 | 2.0 | 95 | 5 |
| 0.50 | 2.0 | 95 | 5 |
| 4.00 | 2.0 | 5 | 95 |
| 4.50 | 2.0 | 5 | 95 |
| 5.00 | 2.0 | 95 | 5 |
| 20.00 | 2.0 | 95 | 5 |

Column—XTerra MS C18 3.5 μm 4.6×30 mm

LCMS System C:

Mass Spectrometer—Finnigan TSQ700 with electrospray source operating in negative ion mode. HP1050 system running at 2.0 mL/min, 200 μL/min split to the ESI source with inline HP1050 Single wavelength UV detector at 254 nm.

Mobile Phase

A) Water 0.1% Diethylamine

B) acetonitrile

| Gradient | | | |
|---|---|---|---|
| Time (min) | Flow (mL/min) | % A | % B |
| 0.00 | 2.0 | 95 | 5 |
| 1.00 | 2.0 | 95 | 5 |
| 15.00 | 2.0 | 5 | 95 |
| 17.00 | 2.0 | 5 | 95 |
| 18.00 | 2.0 | 95 | 5 |
| 20.00 | 2.0 | 95 | 5 |

Column—XTerra MS C18 3.5 μm 4.6×30 mm
LC/MS System D:
Mass Spectrometer—Finnigan TSQ700 with electrospray source operating in positive or negative ion mode. HP1050 system running at 2.0 mL/min, 200 μL/min split to the ESI source with inline HP1050 Single Wavelength UV detector at 254 nm.
Mobile Phase
A) Water 0.1% formic Acid
B) acetonitrile 0.1% formic Acid

| Gradient | | | |
|---|---|---|---|
| Time (min) | Flow (mL/min) | % A | % B |
| 0.00 | 2.0 | 95 | 5 |
| 1.00 | 2.0 | 95 | 5 |
| 15.00 | 2.0 | 5 | 95 |
| 17.00 | 2.0 | 5 | 95 |
| 18.00 | 2.0 | 95 | 5 |
| 20.00 | 2.0 | 95 | 5 |

Column—Higgins Clipius C18 5 μm 100×3.0 mm $^1$H NMR System

The $^1$H NMR spectra were recorded on a Varian Unity Inova 400, which operates at 400 MHz for 1H. It is equipped with a 5 mm inverse detection triple resonance probe for detection of $^1$H. The magnetic field is provided by a 9.4 Tesla Oxford instruments super-conducting magnet. The host computer is a Sun Microsystems SunBlade 1000 workstation. D$_6$-dimethylsulphoxide was used as solvent unless stated otherwise. Tetramethylsilane was used as internal standard. Coupling constants are reported in Hz.

Example 1

Synthesis of 4-(4'-Methoxy-biphenyl-4-yloxymethyl)-5-methyl-furan-2-carboxylic acid (4), 4-(Dibenzofuran-3-yloxymethyl)-5-methyl-furan-2-carboxylic acid (50), 4-(Dibenzofuran-2-yloxymethyl)-5-methyl-furan-2-carboxylic acid (56) and 4-(4'-Cyano-biphenyl-4-yloxymethyl)-5-methyl-furan-2-carboxylic acid (57)

(a) 3-(tert-Butyl-diphenyl-silanyloxymethyl)-2-methyl-furan (2)

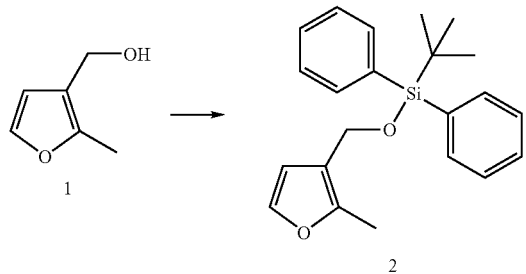

A stirred solution of (2-methyl-3-furan-3-yl)-methanol (1) (31.87 g) in N,N-dimethylformamide (250 mL) was treated simultaneously with t-butyldiphenylsilyl chloride (94 g) and imidazole (24 g) and stirring continued for 2 hours at room temperature. The reaction mixture was treated with 1.0 M hydrochloric acid (500 mL), and extracted with diethyl ether (3×500 mL). The combined organic extracts were washed successively with 1.0 M hydrochloric acid (500 mL), saturated sodium hydrogen carbonate (500 mL), then dried and concentrated in vacuo. The residue was purified by flash chromatography eluting with mixtures of diethyl ether in hexane (1:9 to 9:1 by volume) to give compound 2 as a clear oil (67.6 g).

(b) 4-(tert-Butyl-diphenyl-silanyloxymethyl)-5-methyl-furan-2-carboxylic acid (3)

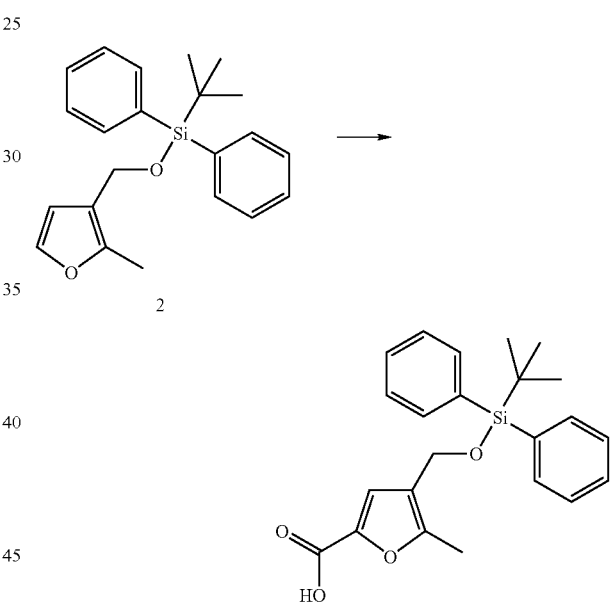

A solution of 3-(tert-Butyl-diphenyl-silanyloxymethyl)-2-methyl-furan (2) (30.0 g) in tetrahydrofuran (75 mL) was cooled to −78° C. with stirring and treated drop-wise with a solution of n-butyllithium (2.5 M in hexanes, 71 mL) over 10 mins. The cooling bath was removed for 0.5 hours and then replaced. A large excess of solid carbon dioxide was added and the mixture allowed to warm to ambient temperature. The reaction mixture was acidified, with 1.0 M hydrochloric acid to pH 2 and extracted into diethyl ether (3×500 mL). The combined extracts were washed successively with 1.0 M hydrochloric acid (500 mL), water (500 mL), dried and concentrated in vacuo. The residue was purified by flash chromatography eluting with mixtures of diethyl ether in pentane (1:5 to 5:1 by volume) to give compound 3 as a yellow oil (10.36 g). LC/MS System A: R$_t$=4.33 mins, m/z (ES$^-$)=393 (M$^-$ for C$_{23}$H$_{26}$O$_4$Si).

(c) 4-(4'-Methoxy-biphenyl-4-yloxymethyl)-5-methyl-furan-2-carboxylic acid (4)

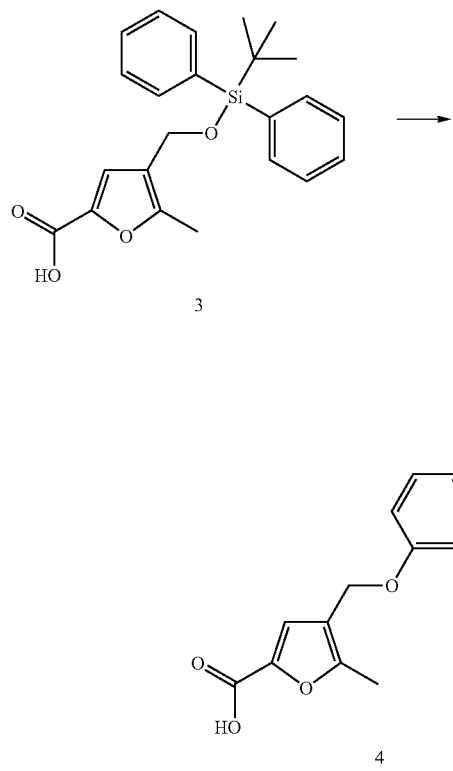

(i) 2-Chlorotrityl chloride resin (1 g of nominal loading 1.3 mmol/g) was swelled with dichloromethane (20 mL). After draining, a solution of 4-(tert-butyl-diphenyl-silanyloxymethyl)-5-methyl-furan-2-carboxylic acid (3) (0.512 g) and diisopropylethylamine (0.91 mL) in dichloromethane (10 mL) was added and the mixture was shaken at ambient temperature for 16 hours. The resin was drained, washed sequentially with dichloromethane/triethylamine/methanol (20:1:3 by volume) (3×25 mL), dichloromethane (3×25 mL), N,N-dimethylformamide (2×25 mL), dichloromethane (6×25 mL), and diethyl ether (2×25 mL) and then dried at 40° C. in vacuo.

(ii) The loaded resin from (i) (2.47 g) was swelled in tetrahydrofuran (15 mL), then treated tetrabutylammonium fluoride (12.8 mL of a 1M solution in tetrahydrofuran) and shaken at room temperature for 16 hours. The resin was drained, washed sequentially with tetrahydrofuran/water (1:1 by volume), tetrahydrofuran, N,N-dimethylformamide, dichloromethane, diethyl ether, and then dried at 40° C. in vacuo.

(iii) The loaded resin (2.83 g) from (ii) was swelled in tetrahydrofuran (15 mL), and then treated with a solution of 4-hydroxy-4'-methoxybiphenyl (2.93 g) and triphenylphosphine (3.48 g) in tetrahydrofuran (20 mL), followed by the addition of diisopropylazodicarboxylate (2.96 g). The mixture was shaken at room temperature for 16 hours. The resin was drained, washed sequentially with tetrahydrofuran/water (1:1 by volume), tetrahydrofuran, N,N-dimethylformamide, dichloromethane, and then dried at 45° C. in vacuo. The resin was treated with dichloromethane/trifluoroacetic acid (19:1 by volume) (20 mL) for 20 mins and the solution drained from the resin. This procedure was repeated. The combined solutions were concentrated in vacuo and the residue recrystallized from ethanol to afford compound 4 as a white solid (0.42 g).

LC/MS System C: $R_t$=4.00 mins, m/z (ES$^-$)=337 (M$^-$ for $C_{20}H_{18}O_5$).

(d) 4-(Dibenzofuran-3-yloxymethyl)-5-methyl-furan-2-carboxylic acid (50)

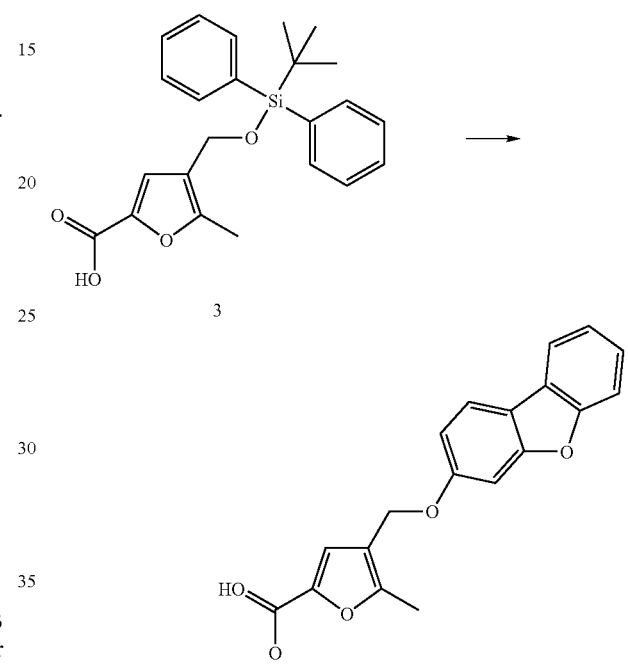

Compound (50) was prepared by adapting the procedure of Example 1(c). LC/MS System B: $R_t$=1.79 mins, m/z (ES$^-$)= 321 (M–H) for $C_{19}H_{14}O_5$.

(e) 4-(Dibenzofuran-2-yloxymethyl)-5-methyl-furan-2-carboxylic acid (56)

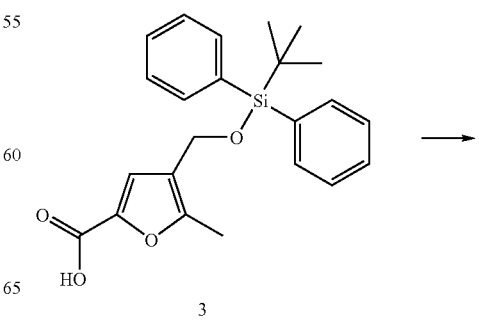

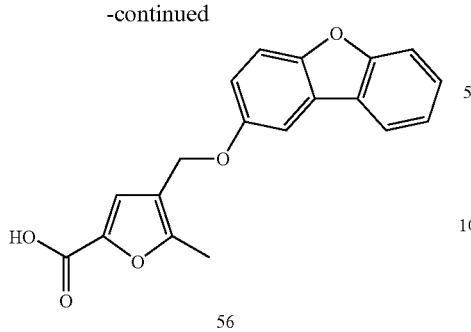

56

Compound (56) was prepared by adapting the procedure of Example 1(c). LC/MS System B: $R_t$=1.76 mins, m/z (ES$^-$)= 321 ((M–H) for $C_{19}H_{14}O_5$).

(f) 4-(4'-Cyano-biphenyl-4-yloxymethyl)-5-methyl-furan-2-carboxylic acid (57)

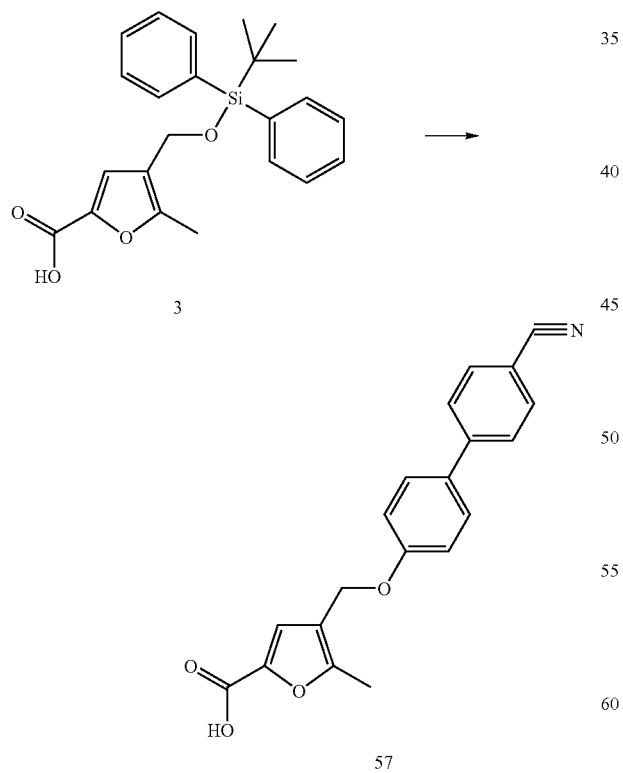

Compound (57) was prepared by adapting the procedure of Example 1(c). LC/MS System B: $R_t$=1.72 mins, m/z (ES$^-$)= 332 (M–H) for $C_{20}H_{15}NO_4$).

Example 2A

Synthesis of N-[4-(4'-Methoxy-biphenyl-4-yloxymethyl)-5-methyl-furan-2-carbonyl]-benzenesulfonamide (5)

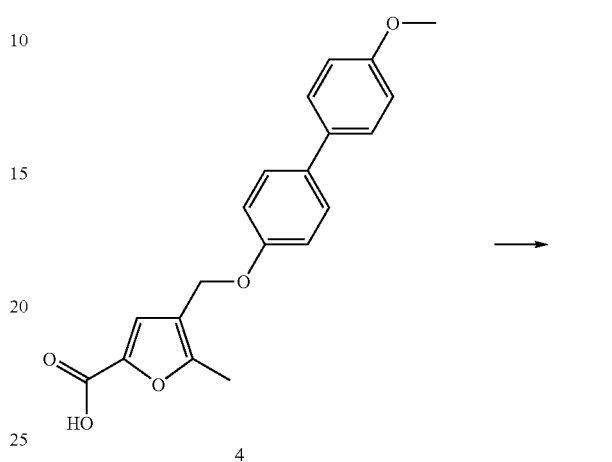

A stirred solution of 4-(4'-methoxy-biphenyl-4-yloxymethyl)-5-methyl-furan-2-carboxylic acid (4) (250 mg) in dichloromethane (50 mL) was treated with 1-(3-dimethylaminopropyl)-3-ethylcarbodiimide hydrochloride (142 mg), 4-(N,N-dimethylamino)pyridine (2 mg) and benzenesulfonamide (232 mg). After 16 hours the reaction mixture was concentrated in vacuo, the residue dissolved in ethyl acetate (200 mL) and washed successively with water (20 mL), 1.0 M hydrochloric acid (20 mL), saturated sodium hydrogen carbonate solution (20 mL), brine (20 mL), dried and concentrated in vacuo. The crude product was purified by HPLC to afford compound 5 as a white solid (30 mg). LC/MS System D: $R_t$=5.45 mins, m/z (ES$^-$)=476 (M$^-$ for $C_{26}H_{23}NO_6S$).

By adapting the procedure of Example 2A and using the appropriate sulphonamide there were prepared Examples 2B to 2G:

Example 2B

N-[4-(4'-Methoxy-biphenyl-4-yloxymethyl)-5-methyl-furan-2-carbonyl]-C-phenyl-methanesulfonamide (6)

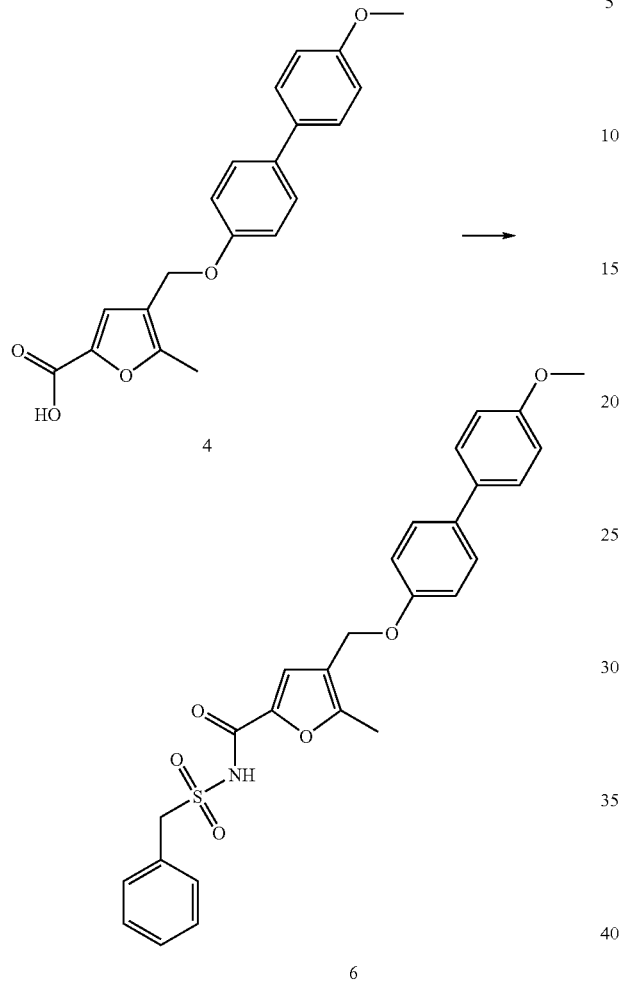

LC/MS System C: $R_t$ 5.37 mins, m/z (ES$^-$)=490 (M$^-$ for $C_{27}H_{25}NO_6S$).

Example 2C

N-[4-(4'-Methoxy-biphenyl-4-yloxymethyl)-5-methyl-furan-2-carbonyl]-methanesulfonamide (7)

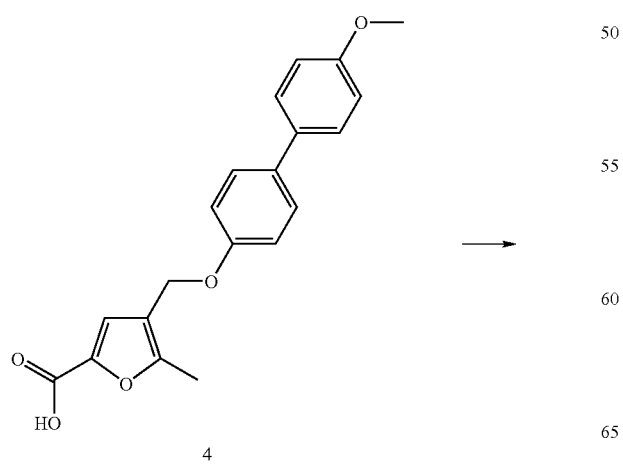

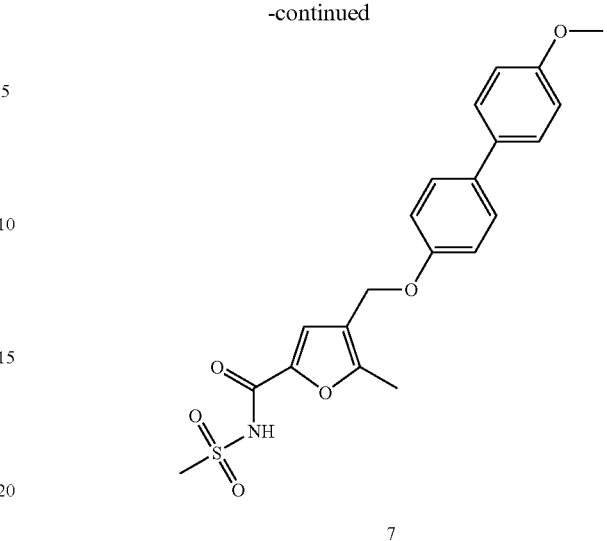

LC/MS System C: $R_t$=4.50 mins, m/z (ES$^-$)=414 (M$^-$ for $C_{21}H_{21}NO_6S$).

Example 2D

Propane-1-sulfonic acid [4-(4'-methoxy-biphenyl-4-yloxymethyl)-5-methyl-furan-2-carbonyl]-amide (8)

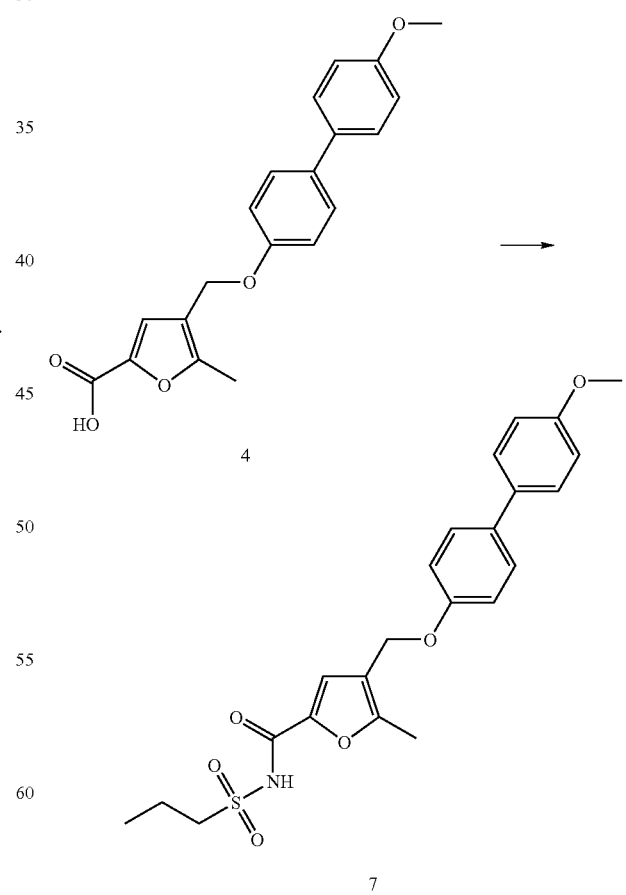

LC/MS System C: $R_t$=4.78 mins, m/z (ES$^-$)=442 (M$^-$ for $C_{23}H_{25}NO_6S$).

Example 2E 3,5-Dimethyl-isoxazole-4-sulfonic acid [4-(4'-methoxy-biphenyl-4-yloxymethyl)-5-methyl-furan-2-carbonyl]-amide (9)

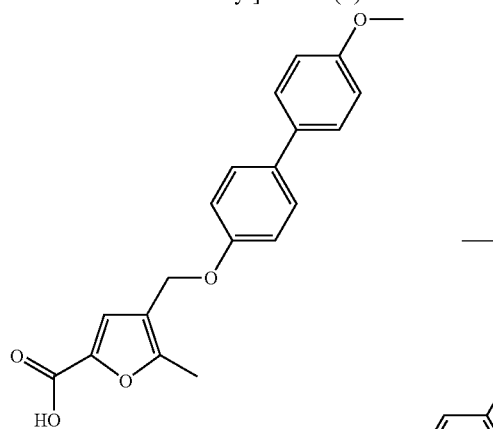

4

→

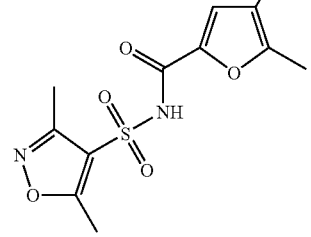

9

LC/MS System C: $R_t$=4.91 mins, m/z (ES$^-$)=495 (M$^-$ for $C_{25}H_{24}N_2O_7S$).

Example 2F

Synthesis of Thiophene-2-sulfonic acid [4-(4'-methoxy-biphenyl-4-yloxymethyl)-5-methyl-furan-2-carbonyl]-amide (10)

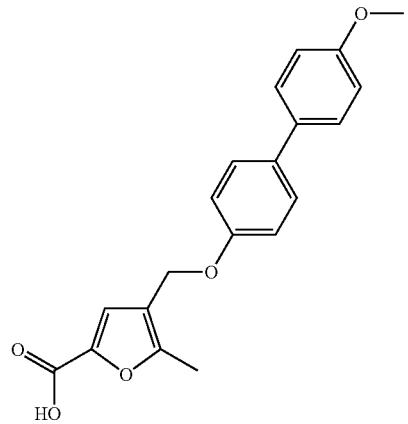

4

→

-continued

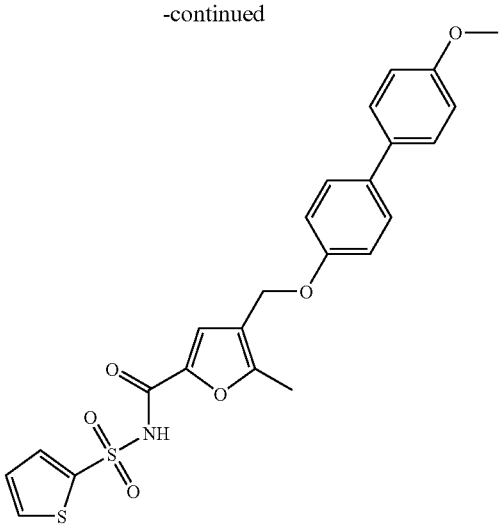

10

LC/MS System C: $R_t$=4.94 mins, m/z (ES$^-$)=482 (M$^-$ for $C_{24}H_{21}NO_6S_2$).

Example 2G

5-Methyl-pyridyl-2-sulfonic acid [4-(4'-methoxy-biphenyl-4-yloxymethyl)-5-methyl-furan-2-carbonyl]-amide (11)

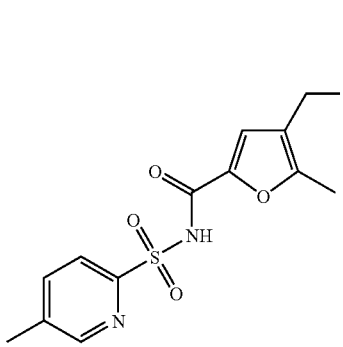

4

→

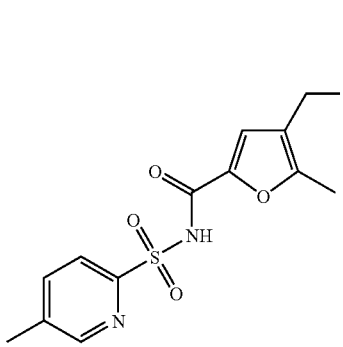

11

LC/MS System D: $R_t$=10.09 mins, m/z (ES$^+$)=493 (MH$^+$ for $C_{26}H_{24}NO_6S$).

Example 2H

Synthesis of 4-Aminomethyl-N-[4-(4'-methoxy-biphenyl-4-yloxymethyl)-5-methyl-furan-2-carbonyl]-benzenesulfonamide trifluoroacetate (12)

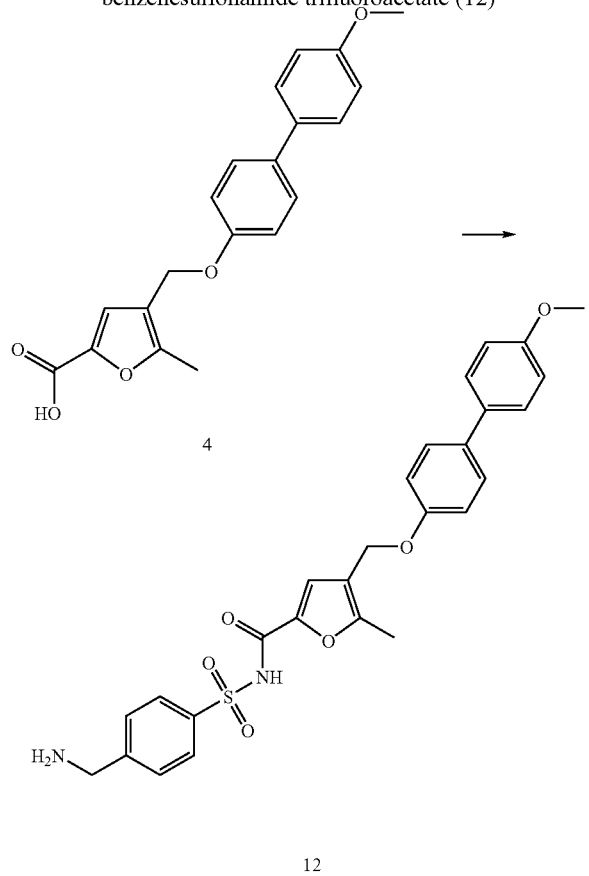

4-(4'-Methoxy-biphenyl-4-yloxymethyl)-5-methyl-furan-2-carboxylic acid (4) (50 mg) was reacted with (4-sulphamoyl-benzyl)-carbamic acid tert-butyl ester (85 mg) in an analogous manner to that described in Example 2A. The intermediate tert-butyl carbamate was hydrolysed with 1% trifluoroacetic acid/dichloromethane over 24 hours, then concentrated in vacuo to give compound 12 as a white solid (10 mg). LC/MS System C: $R_t$=4.67 mins, m/z (ES$^-$)=493 (M$^-$ 1 for $C_{27}H_{26}N_2O_6S$).

Example 2I

Synthesis of 4-Hydroxy-N-[4-(4'-methoxy-biphenyl-4-yloxymethyl)-5-methyl-furan-2-carbonyl]-benzenesulfonamide (13)

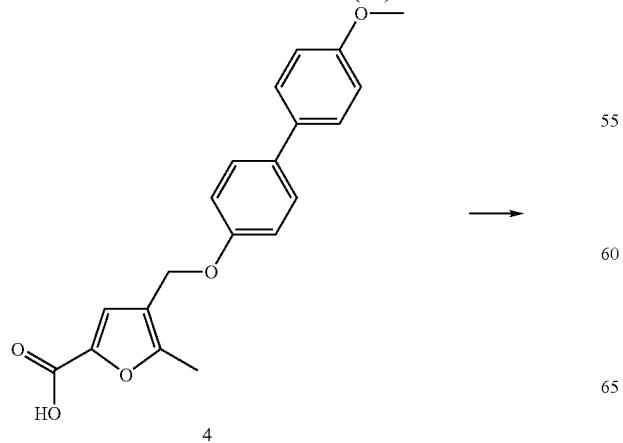

-continued

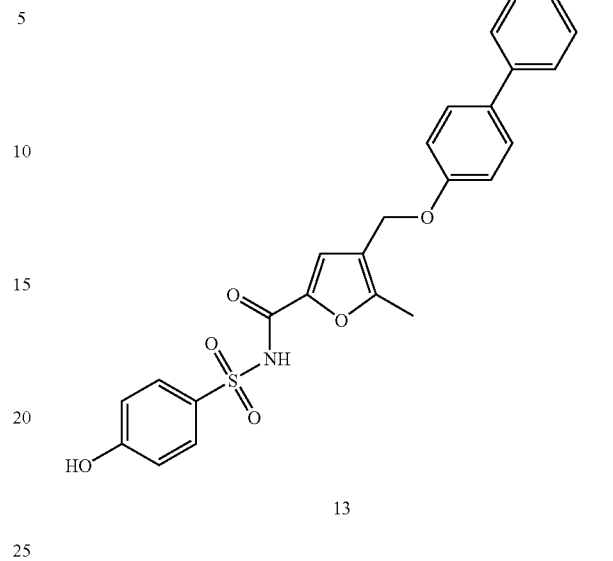

4-(4'-Methoxy-biphenyl-4-yloxymethyl)-5-methyl-furan-2-carboxylic acid (4) (50 mg) was reacted with acetic acid 4-sulphamoyl-phenyl ester (64 mg) in an analogous manner to that described in Example 2A. The acetic ester intermediate was hydrolysed with sodium methoxide (80 mg) in a mixture of methanol (10 mL) and water (1 mL) for 1 hour. The solution was concentrated in vacuo then partitioned between dichloromethane (10 mL) and water (10 mL). The organic layer was washed with brine (10 mL), dried, filtered and concentrated in vacuo. The crude product was purified by preparative HPLC (starting at 30% acetonitrile and increasing at a rate of 1% per minute up to 98% acetonitrile) to give compound 13 as a white solid (15 mg). LC/MS System C: $R_t$=3.50 mins, m/z (ES$^-$)=492 (M$^-$ for $C_{26}H_{23}N_2O_7S$).

Example 3

Synthesis of 4-(Biphenyl-4-yloxymethyl)-5-methyl-furan-2-carboxylic acid (18)

(a) Triisopropyl-(2-methyl-furan-3-ylmethoxy)-silane (14)

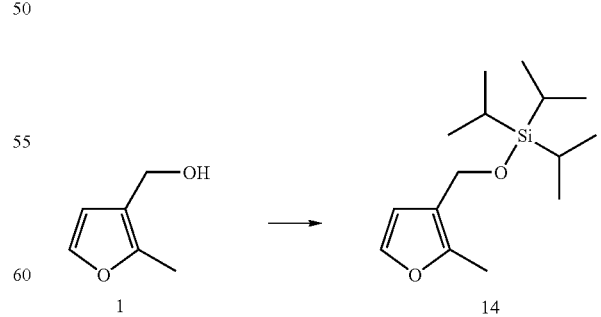

Triisopropyl-(2-methyl-furan-3-ylmethoxy)-silane was prepared from (2-methyl-furan-3-yl)-methanol (1)(24.22 g) in an analogous manner to that described in Example 1 to give compound 14 as a clear oil (54.0 g).

(b) 5-Methyl-4-triisopropylsilanyloxymethyl-furan-2-carboxylic acid methyl ester (15)

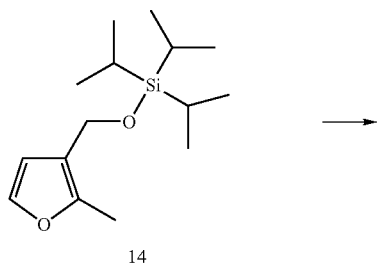

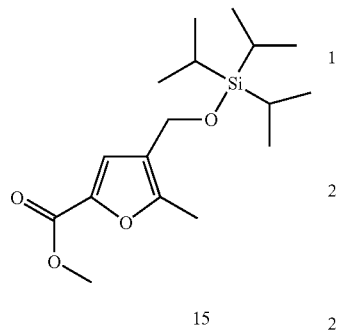

A solution of triisopropyl-(2-methyl-furan-3-ylmethoxy)-silane (14) (10.0 g) in tetrahydrofuran (300 mL) was cooled to −78° C. with stirring was treated drop-wise with sec-butyl-lithium (3.0 M in cyclohexane, 37 mL). After 1 hour the reaction mixture was treated drop-wise with a solution of methyl chloroformate (5.2 g) in tetrahydrofuran (30 mL) over 10 mins and stirring was continued at −78° C. for 1 hour. The reaction mixture was then treated with saturated ammonium chloride solution (300 mL) and allowed to warm to ambient temperature. The two layers were separated and the organic phase washed with brine (300 mL), dried and concentrated in vacuo. The residue was purified by flash chromatography eluting with ethyl acetate/pentane (1:9 by volume) to give compound 15 as a clear oil.

(c) 4-Hydroxymethyl-5-methyl-furan-2-carboxylic acid methyl ester (16)

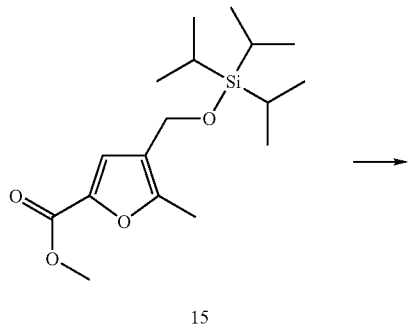

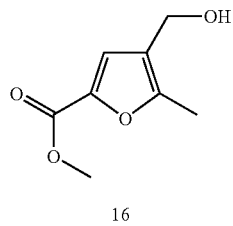

A stirred solution of 5-methyl-4-triisopropylsilanyloxymethyl-furan-2-carboxylic acid methyl ester (15) (5.2 g) in tetrahydrofuran (200 mL) was treated with tetrabutylammonium fluoride (1.0 M solution in tetrahydrofuran, 3.2 mL) and stirring continued for 16 hours. The reaction mixture was concentrated in vacuo and the residue taken up in ethyl acetate (350 mL) and washed with water (150 mL). The aqueous phase was re-extracted with ethyl acetate (2×100 mL). The combined extracts were dried, concentrated in vacuo and the residue was purified by flash chromatography eluting with ethyl acetate/pentane (1:1 by volume) to give compound 16 as a yellow oil.

(d) 4-(Biphenyl-4-yloxymethyl)-5-methyl-furan-2-carboxylic acid methyl ester (17)

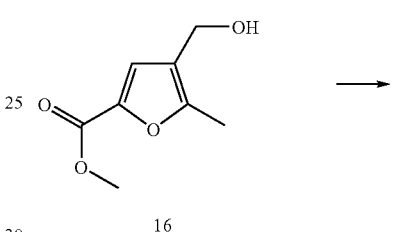

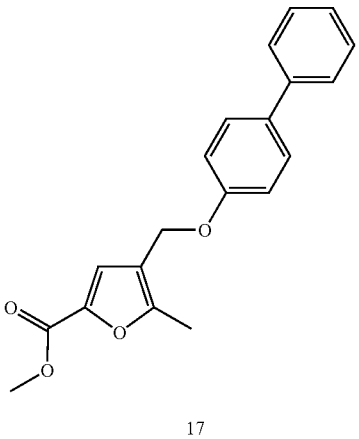

A solution of 4-hydroxymethyl-5-methyl-furan-2-carboxylic acid methyl ester (16) (1 g) in anhydrous tetrahydrofuran (20 mL) was cooled to 0° C. under a nitrogen atmosphere. 4-Hydroxybiphenyl (3 g) and triphenylphosphine (4.61 g) were added and the mixture was treated with di-isopropylazodicarboxylate (3.46 mL) dropwise. The mixture was stirred at 0° C. for 10 min then cooling was removed and the mixture stirred for a further 3 hours. The solvent was removed in vacuo and the residue was partitioned between ethyl acetate (50 mL) and water (100 mL). The organic phase was separated, dried and evaporated. The residue was purified by flash chromatography, eluting with pentane/ethyl acetate 9:1 by volume to give a mixture of the title compound and 4-hydroxybiphenyl (1.8 g). This material was purified further by flash chromatography eluting with dichloromethane/methanol 99:1 by volume to give compound 17 as a white solid (200 mg). LCMS System A: $R_t$=4.2 mins.

(e) 4-(Biphenyl-4-yloxymethyl)-5-methyl-furan-2-carboxylic acid (18)

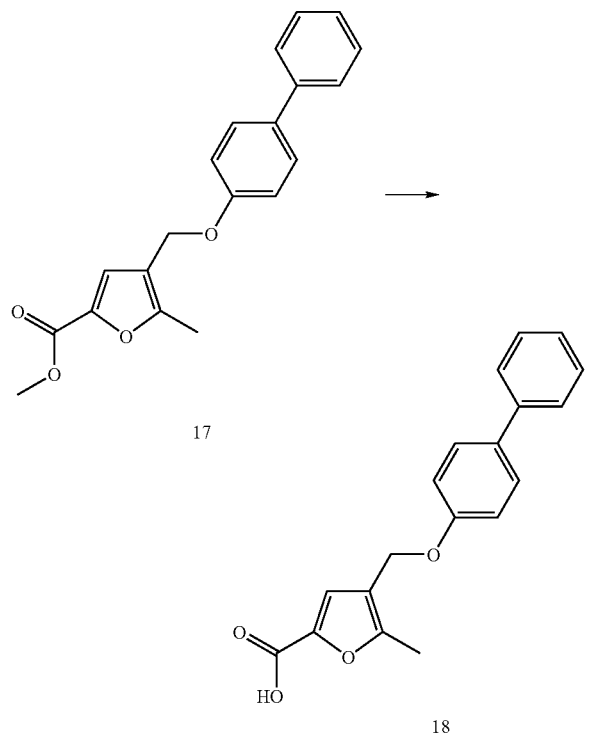

1M Aqueous lithium hydroxide (18 mL) was added to solution of 4-(biphenyl-4-yloxymethyl)-5-methyl-furan-2-carboxylic acid methyl ester (17) (1 g) in tetrahydrofuran/methanol (2:1 by volume, 100 mL) and the mixture stirred at room temperature for 5 h. The solvent was removed in vacuo, the residue dissolved in water (20 mL) and the solution acidified to pH6 with aqueous dilute hydrochloric acid. The mixture was evaporated to dryness and the residue was purified by HPLC to afford compound 18 as a white solid (210 mg). LC/MS System B: $R_t$=4.80 mins, m/z=307 ((M−1) for $C_{19}H_{16}O_4$).

Example 4

Synthesis of N-[4-(Biphenyl-4-yloxymethyl)-5-methyl-furan-2-carbonyl]-benzenesulfonamide (19)

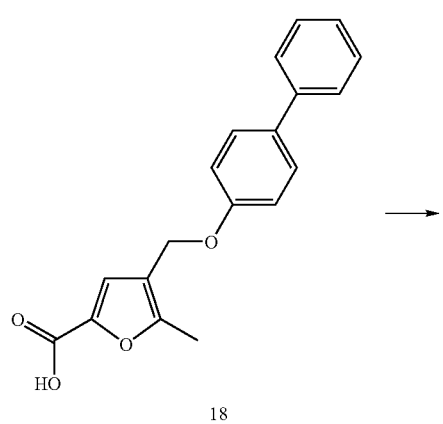

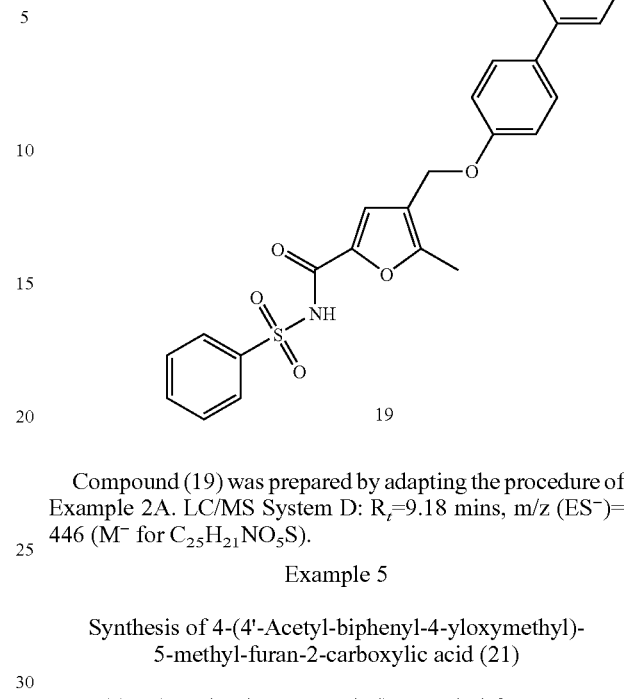

Compound (19) was prepared by adapting the procedure of Example 2A. LC/MS System D: $R_t$=9.18 mins, m/z (ES⁻)= 446 (M⁻ for $C_{25}H_{21}NO_5S$).

Example 5

Synthesis of 4-(4'-Acetyl-biphenyl-4-yloxymethyl)-5-methyl-furan-2-carboxylic acid (21)

(a) 4-(4-Iodo-phenoxymethyl)-5-methyl-furan-2-carboxylic acid methyl ester (20)

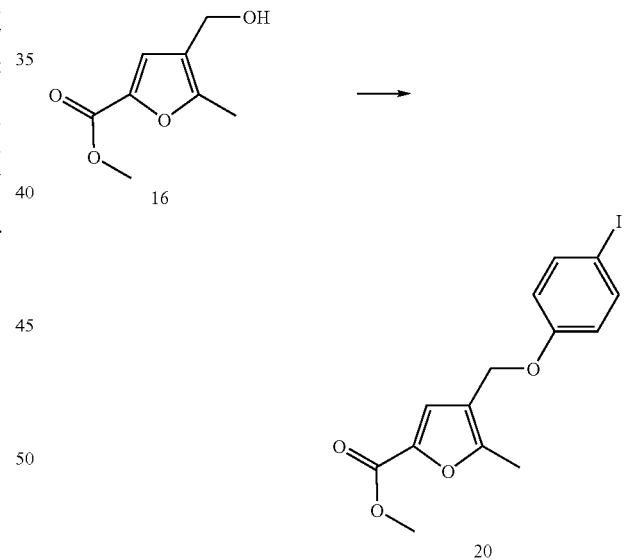

A solution of 4-hydroxymethyl-5-methyl-furan-2-carboxylic acid methyl ester (16) (1.14 g) in tetrahydrofuran (15 mL) was cooled to 0° C. with stirring and treated with 4-iodophenyl (4.6 g), triphenylphosphine (5.5 g) and diisopropylazodicarboxylate (4.2 g). After 10 minutes the cooling bath was removed. After 3 hours the reaction mixture was concentrated in vacuo and taken up in ethyl acetate (100 mL) and washed successively with water (100 mL), 1.0 M aqueous sodium hydroxide solution (100 mL), dried and concentrated in vacuo. The residue was purified by flash chromatography eluting with ethyl acetate/hexane (1:4 by volume) to give compound 20 as a white solid (1.58 g).

(b) 4-(4'-Acetyl-biphenyl-4-yloxymethyl)-5-methyl-furan-2-carboxylic acid (21)

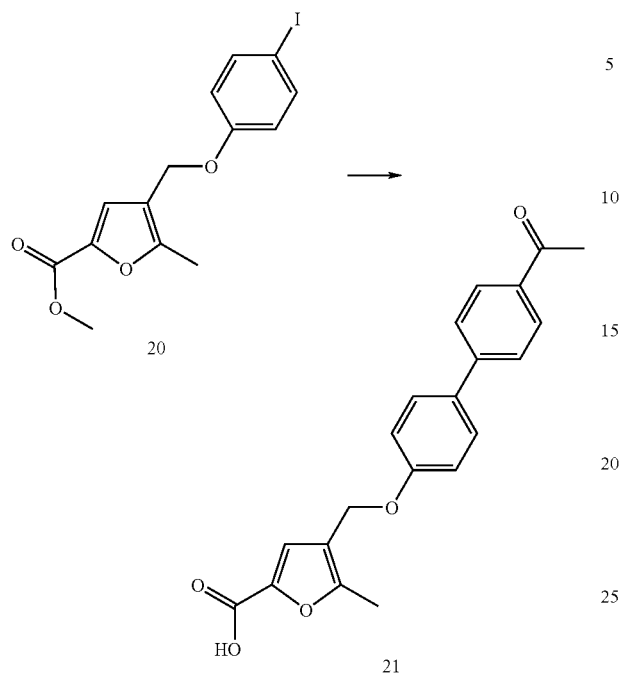

A stirred mixture of 4-(4-iodo-phenoxymethyl)-5-methyl-furan-2-carboxylic acid methyl ester (20) (0.26 g), 4-acetylphenylboronic acid (0.15 g), N,N-dimethylformamide (30 mL), potassium acetate (0.26 g) and [1,1'-bis(diphenylphosphino) ferrocene]dichloropalladium(II), complex with dichloromethane (1:1) (40 mg) was heated at 90° C. overnight. The reaction mixture was concentrated in vacuo, dissolved in ethyl acetate (30 mL) and washed successively with water (30 mL), brine (30 mL), dried and concentrated in vacuo. The residue was dissolved in a mixture of tetrahydrofuran/methanol (2:1 by volume) (30 mL) and 1.0 M aqueous lithium hydroxide solution (6.78 mL) and stirred for 16 hours. The reaction mixture was acidified to pH 2 using 0.1M hydrochloric acid and extracted with ethyl acetate (3×25 mL). The extract was dried, concentrated in vacuo and the residue purified by HPLC to give compound 21 as a white solid (50 mg). LC/MS System C: $R_t$=4.18 mins, m/z (ES$^-$)=349 (M$^-$ for $C_{21}H_{18}O_5$).

Example 6

Synthesis of N-[4-(4'-Acetyl-biphenyl-4-yloxymethyl)-5-methyl-furan-2-carbonyl]-benzenesulfonamide (22)

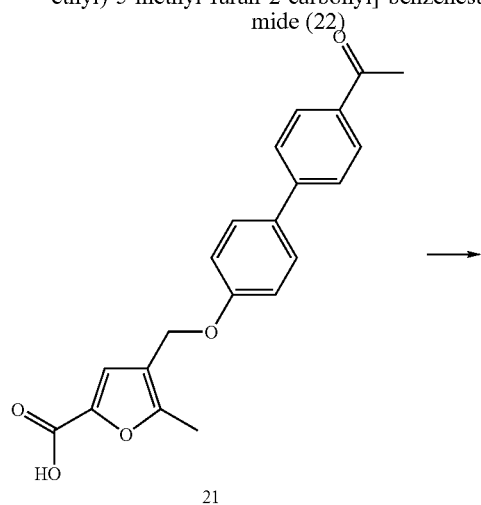

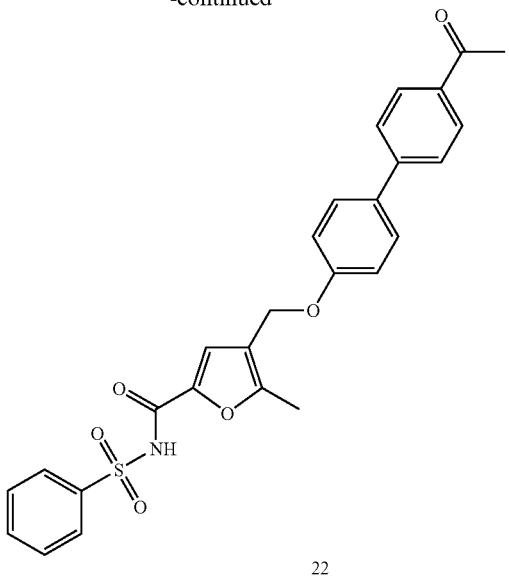

Compound (22) was prepared by adapting the procedure of Example 2A. LC/MS System D: $R_t$=9.87 mins, m/z (ES$^+$)= 490 (MH$^+$ for $C_{27}H_{23}NO_6S$).

Example 7

Synthesis of 4-(4'-Methoxy-biphenyl-4-ylcarbamoyl)-5-methyl-furan-2-carboxylic acid (24)

(a) 5-methyl-furan-2,4-dicarboxylic acid-2-methyl ester (23)

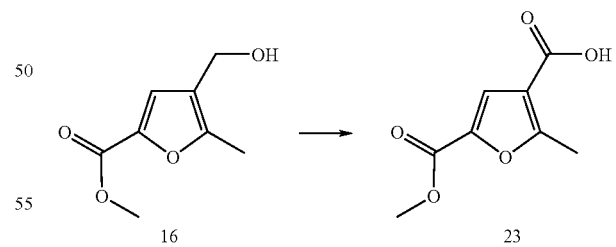

Jones' reagent (Prepared according to Fieser and Fieser, Reagents for Organic Synthesis, Volume 1, page 142, 1967) was added drop-wise to a stirred solution of 4-hydroxymethyl-5-methyl-furan-2-carboxylic acid methyl ester (16) (100 mg) in acetone (10 mL) until the orange colouration just remained. Stirring was continued for a further 5 hours then the reaction mixture was diluted with diethyl ether (20 mL) and filtered. The filtrate was dried and concentrated in vacuo to afford compound 23 as a buff coloured solid.

(b) 4-(4'-Methoxy-biphenyl-4-ylcarbamoyl)-5-methyl-furan-2-carboxylic acid (24)

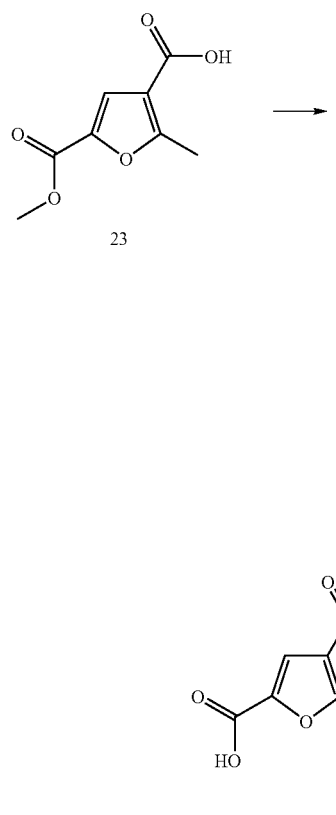

Example 8

Synthesis of 5-Benzenesulfonylaminocarbonyl-2-methyl-furan-3-carboxylic acid (4'-methoxy-biphenyl-4-yl)-amide (25)

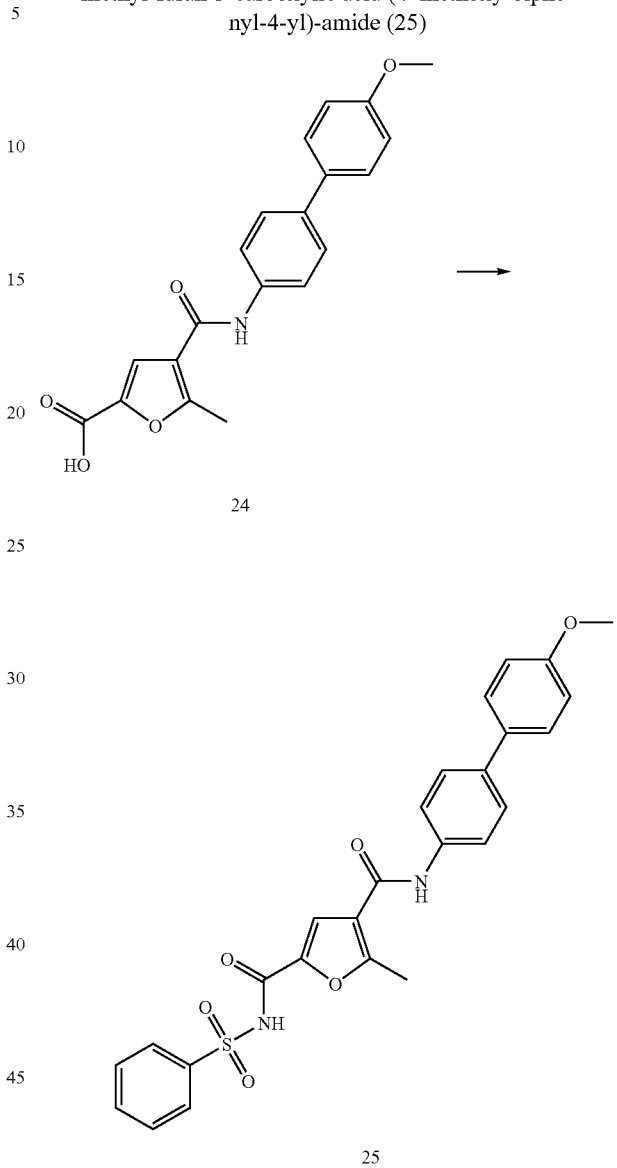

To a solution of 5-methyl-furan-2,4-dicarboxylic acid-2-methyl ester (23) (100 mg) in N,N-dimethylformamide (3.0 mL) was added O—(7-azabenzotriazol-1-yl)-N,N,N',N'-tetramethyluronium hexafluorophosphate (228 mg), diisopropylethylamine (0.56 mL) and 4'-methoxy-biphenyl-4-ylamine (120 mg). The resulting solution was stirred at room temperature for 2 hours. The reaction mixture was diluted with ethyl acetate (20 mL) and washed successively with water (2×20 mL), 0.1M hydrochloric acid (20 mL), water (20 mL), saturated sodium hydrogen carbonate (10 mL) and brine (10 mL). This solution was dried and concentrated in vacuo. The residue (170 mg) was dissolved in dichloromethane (5 mL), treated with triethylamine (0.3 mL) and a scavenger resin PS-TsCl (0.6 g) and the mixture shaken for 3 hours at room temperature. The reaction mixture was filtered and concentrated in-vacuo. The residue was dissolved in methanol/tetrahydrofuran (1:3 by volume) (20 mL), treated with 1.0 M aqueous lithium hydroxide solution (2.0 mL) and allowed to stir at room temperature for 4 hours. The pH of the reaction mixture was adjusted to between pH 4 and pH 5 by careful addition of 1.0 M hydrochloric acid (1.0 mL) and partly concentrated in vacuo. The residue was then partitioned between ethyl acetate (2×25 mL) and water (25 mL) and the combined organic extracts were washed with brine (35 mL), dried ($Na_2SO_4$), and concentrated in vacuo afforded compound 24 as beige solid (58 mg). LC/MS System D: $R_t$=7.23 mins, m/z ($ES^+$)=351 ($MH^+$ for $C_{20}H_{17}NO_5$).

Compound 25 was synthesised from 4-(4'-Methoxy-biphenyl-4-ylcarbamoyl)-5-methyl-furan-2-carboxylic acid (24) (35 mg) in an analogous manner to that described in Example 2A to give the title compound as a white solid (7 mg). LC/MS System A: $R_t$=3.86 mins, m/z ($ES^-$)=489 (M−1 for $C_{26}H_{22}N_2O_6S$).

Example 9

Synthesis of 4-(4'-Chloro-biphenyl-4-yloxymethyl)-5-methyl-furan-2-carboxylic acid (27) and 4-(4-Benzo[1,3]dioxol-5-yl-phenoxymethyl)-5-methyl-furan-2-carboxylic acid (28)

(a) 4-(4-Iodo-phenoxymethyl)-5-methyl-furan-2-carboxylic acid (26)

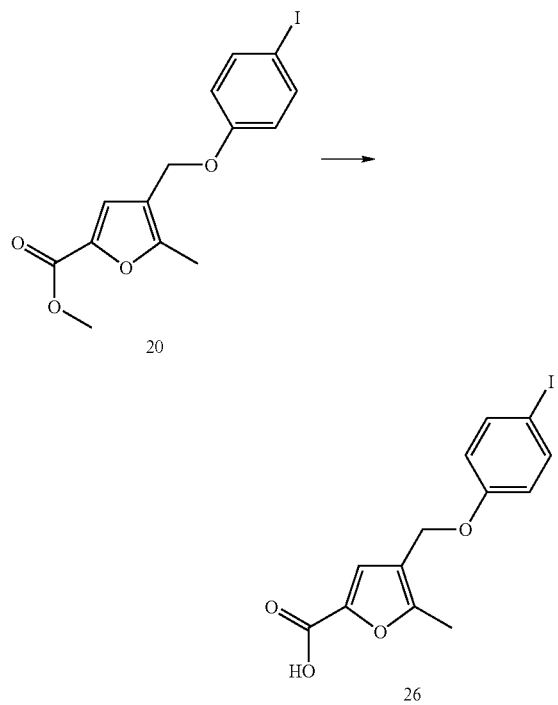

A stirred solution of 4-(4-iodo-phenoxymethyl)-5-methyl-furan-2-carboxylic acid methyl ester (20) (2.7 g) in tetrahydrofuran (25 mL) was treated with a solution of lithium hydroxide (1.5 g) in water (2 mL). After 3 hours the reaction mixture was diluted with water and acidified to pH 2 with 1.0 M hydrochloric acid. The white precipitate was filtered off and dried in vacuo. The solid was triturated with ethyl acetate at 0° C. then collected by filtration to give compound 26 as a white solid (1.83 g). LC/MS system A: $R_t$=1.74 min.

(b) 4-(4'-Chloro-biphenyl-4-yloxymethyl)-5-methyl-furan-2-carboxylic acid (27)

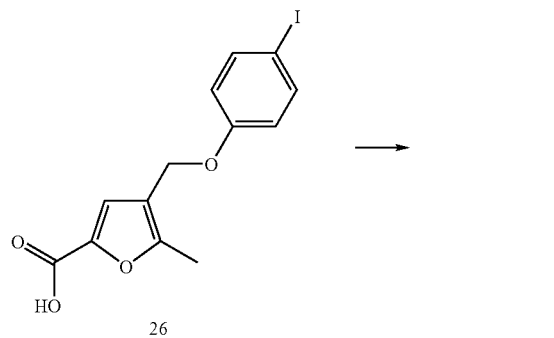

-continued

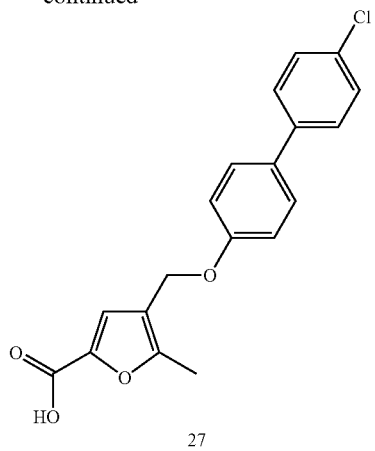

(i) 2-Chlorotrityl chloride resin (2.55 g of nominal loading 1.3 mmol/g) was swelled with dichloromethane (20 mL). After draining, a solution of 4-(4-iodo-phenoxymethyl)-5-methyl-furan-2-carboxylic acid (26) (1.18 g) and diisopropylethylamine (2.3 mL) in dichloromethane (30 mL) was added and the mixture was shaken at room temperature for 72 hours. The resin was drained, washed sequentially with dichloromethane/triethylamine/methanol (20:1:3 by volume) (3×30 mL), dichloromethane (6×30 mL), N,N-dimethylformamide (2×25 mL), dichloromethane (6×25 mL), and diethyl ether (2×25 mL) and dried at 40° C. in vacuo.

(ii) A stirred mixture of the resin from (i) (0.38 g), 4-chlorophenylboronic acid (0.30 g), [1,1'-bis-(diphenylphosphino)-ferrocene]-dichloropalladium(II) complex with dichloromethane (1:1) (30 mg), potassium acetate (0.20 g) in N,N-dimethylformamide (15 mL) was heated at 40° C. for 48 hours. The resin was drained, then washed sequentially with tetrahydrofuran/water (1:1 by volume), tetrahydrofuran, N,N-dimethylformamide, dichloromethane, diethyl ether and then dried at 45° C. in vacuo. The resin was treated with dichloromethane/trifluoroacetic acid (19:1 by volume) (20 mL) for 20 mins and the solution drained from the resin. This procedure was repeated. The combined solutions were concentrated in vacuo and the residue purified by HPLC to afford compound 27 as a white solid (43 mg). LC/MS System D: $R_t$=8.83 mins, m/z (ES$^-$)=341 (M$^-$ for C$_{19}$H$_{15}$ClO$_4$).

(c) 4-(4-Benzo[1,3]dioxol-5-yl-phenoxymethyl)-5-methyl-furan-2-carboxylic acid (28)

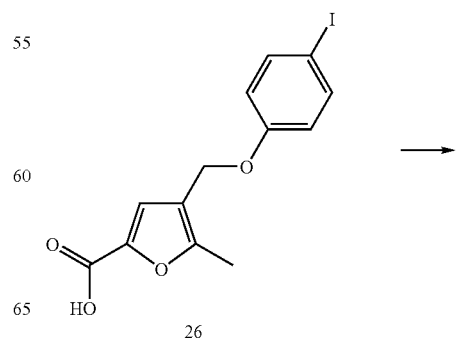

-continued

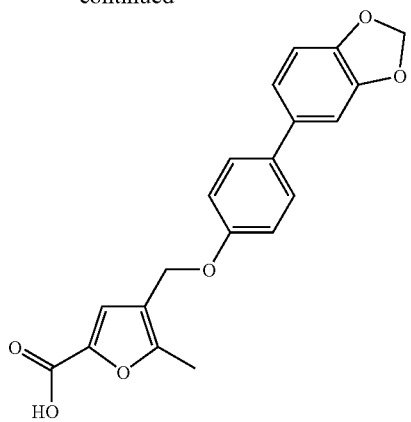

Compound 28 was synthesised from the resin from (i) in step (b) above and 3,4-methylenedioxyphenylboronic acid in an analogous manner to that described in step (ii) above. LC/MS System C: $R_t$=4.60 mins, m/z (ES⁻)=351 (M⁻ for $C_{20}H_{16}O_6$).

Example 10

Synthesis of [4-(Biphenyl-4-yloxymethyl)-5-methyl-furan-2-yl]-acetic acid (31) and 4-(4'-Methoxy-biphenyl-4-yloxymethyl)-5-methyl-furan-2-yl]-acetic acid (32)

(a) (5-Methyl-4-triisopropylsilanyloxymethyl-furan-2-yl)-acetic acid ethyl ester (29)

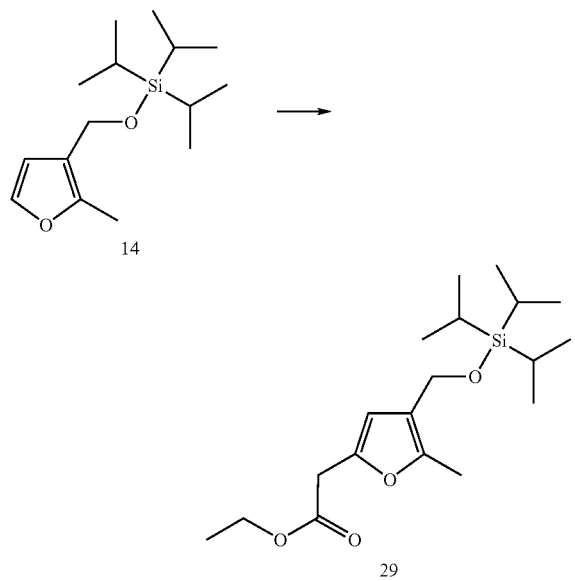

A solution of triisopropyl-(2-methyl-furan-3-ylmethoxy)-silane (14) (5.0 g) in tetrahydrofuran (15 mL) was cooled to −78° C. with stirring. This solution was treated drop-wise with n-butyl lithium (2.5 M in hexanes, 8.94 mL). The resulting solution was warmed to 0° C. and allowed to stand for 30 minutes after which a solution of dried zinc chloride (3.04 g) in tetrahydrofuran (10 mL) was added and the resulting solution allowed to stand for a further 1 hour at room temperature. Concurrently, a second reaction vessel was charged with tetrahydrofuran (10 mL), nickel(II) acetylacetonate (120 mg), and triphenylphosphine (122 mg) and cooled (−5° C.). Ethyl bromoacetate (1.03 mL) was added to this mixture, followed by the addition of the previously prepared solution of the furyl-zinc chloride. The resulting reaction mixture was allowed to warm to room temperature then stirred for a further 16 hours at room temperature. The reaction was quenched by the addition of saturated ammonium chloride solution (100 mL) and extracted with ethyl acetate (3×150 mL). The combined organic extracts were successively washed with water (200 mL) and brine (250 mL), dried, filtered and concentrated in vacuo. The residue was purified by flash chromatography using a gradient elution (diethyl ether/petroleum ether (40-60°) 1:49 to 1:25 by volume) to give compound 29 as a clear oil (1.44 g). LC/MS System A: $R_t$=5.16 min.

(b) (4-Hydroxymethyl-5-methyl-furan-2-yl)-acetic acid ethyl ester (30)

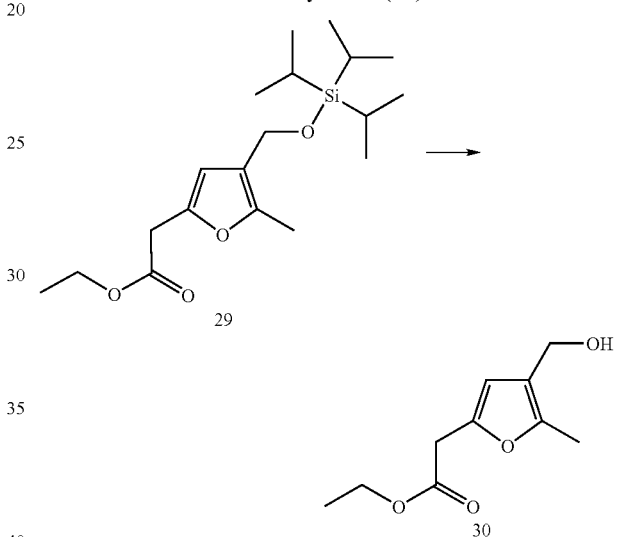

A solution of (5-methyl-4-triisopropylsilanyloxymethyl-furan-2-yl)-acetic acid ethyl ester (29) (0.5 g) in tetrahydrofuran (3.0 mL) was cooled to 0° C. with stirring and treated with tetrabutylammonium fluoride (1.0 M solution in tetrahydrofuran, 2.82 mL) under argon. After 30 minutes, the resulting solution was concentrated in-vacuo and partitioned between water (30 mL) and ethyl acetate (4×25 mL). The combined organic extracts were washed with brine (50 mL), dried ($Na_2SO_4$), filtered and concentrated in vacuo. The residue was purified by flash chromatography eluting with diethyl ether/petroleum ether (1:1 by volume) to give compound 30 as a clear oil (188 mg). LC/MS System A: $R_t$=2.34 mins.

(c) [4-(Biphenyl-4-yloxymethyl)-5-methyl-furan-2-yl]-acetic acid (31)

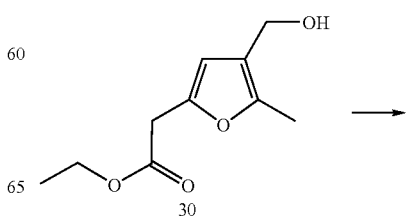

-continued

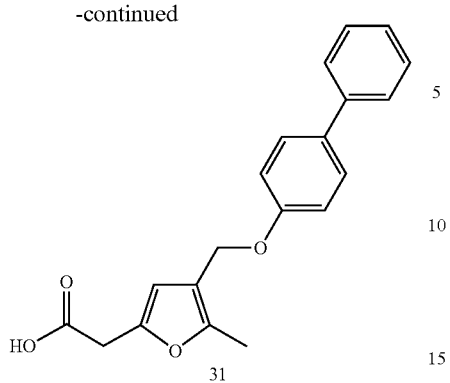

Compound (31) was prepared from compound (30) in an analagous manner to the methods described in Examples 3(d) and 3(e). LC/MS System C: $R_t$=4.97 mins, m/z (ES⁻)=321 (M⁻ for $C_{20}H_{18}O_4$).

(d) [4-(4'-Methoxy-biphenyl-4-yloxymethyl)-5-methyl-furan-2-yl]-acetic acid (32)

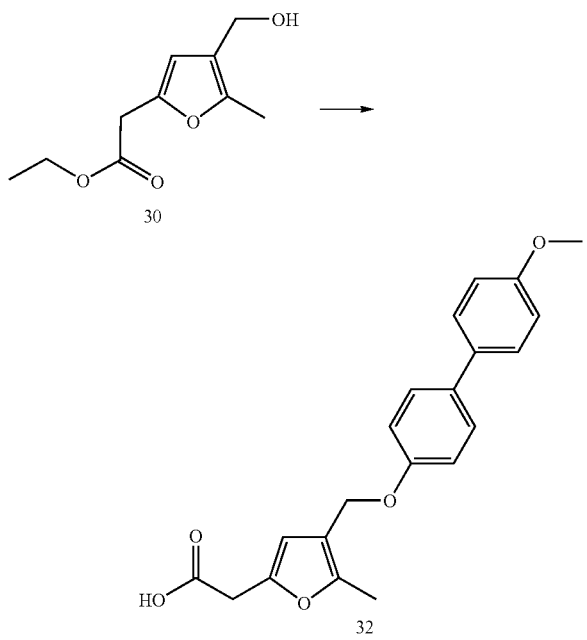

Compound (32) was prepared from compound (30) in an analagous manner to the methods described in Examples 3(d) and 3(e). LC/MS System C: $R_t$=4.94 mins, m/z (ES⁻)=351 (M⁻ for $C_{21}H_{20}O_5$).

Example 11

Synthesis of 3-(Biphenyl-4-yloxymethyl)-5-methyl-furan-2-yl]-propionic acid (37) and N-{3-[4-(Biphenyl-4-yloxymethyl)-5-methyl-furan-2-yl]-propionyl}-benzene sulfonamide (38)

(a) 5-Methyl-4-triisopropylsilanyloxymethyl-furan-2-carbaldehyde (33)

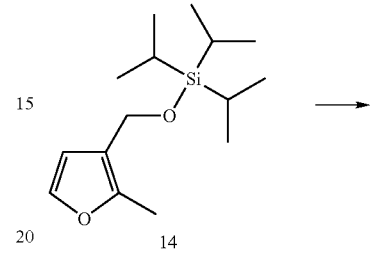

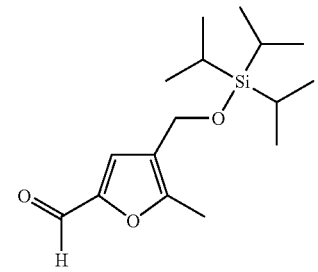

A solution of triisopropyl-(2-methyl-furan-3-ylmethoxy)-silane (14) (10 g) in tetrahydrofuran (250 mL) was cooled to −78° C. with stirring, and then sec-butyllithium (1.3 M in cyclohexane; 37.25 mL) was added drop-wise over 10 mins. After stirring for 45 mins at −78° C., the cooling bath was removed for a period of 15 mins then re-introduced. A solution of N,N-dimethylformamide (14.4 mL) in tetrahydrofuran (25 mL) was added drop-wise and the resulting reaction mixture was stirred at −78° C. for a further 2 hours. The reaction mixture was allowed to warm to room temperature and then poured into saturated ammonium chloride solution (150 mL). This mixture was extracted with diethyl ether (2×350 mL), and the combined organic extracts were washed with water (500 mL) and brine (500 mL), dried, and concentrated in vacuo to give compound 33 as an amber coloured oil. LC/MS System A: $R_t$=4.86 mins.

(b) 3-(5-Methyl-4-triisopropylsilanyloxymethyl-furan-2-yl)-acrylic acid ethyl ester (34)

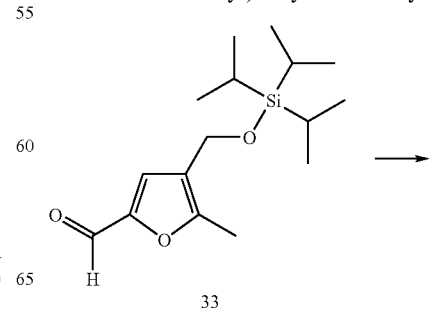

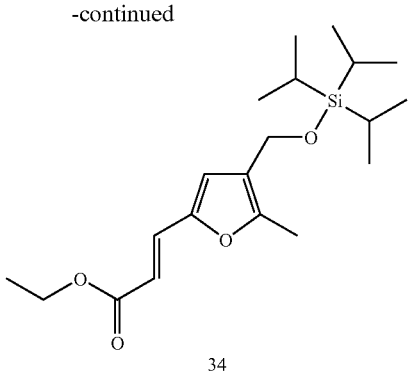

A stirred solution of 5-methyl-4-triisopropylsilanyloxymethyl-furan-2-carbaldehyde (33) (10.6 g) in tetrahydrofuran (25 mL) was treated with triethylphosphonoacatete (7.81 mL) and lithium hydroxide (1.65 g). The resulting mixture was stirred for 16 hours then concentrated in vacuo and the residue partitioned between water (100 mL) and diethyl ether (3×100 mL). The combined organic extracts were further washed with water (200 mL) and brine (200 mL), then dried ($Na_2SO_4$) and concentrated in vacuo. The residue was purified by flash chromatography eluting with diethyl ether/petroleum ether (1:40 by volume) to give compound 34 as a clear yellow oil (10.56 g). LC/MS System A: $R_t$=4.59 mins.

(c) 3-(5-Methyl-4-triisopropylsilanyloxymethyl-furan-2-yl)-propionic acid ethyl ester (35)

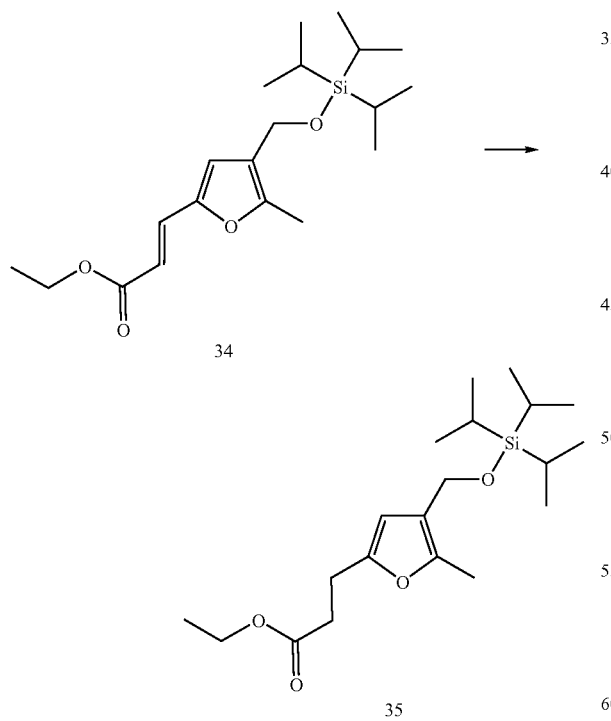

A solution of 3-(5-methyl-4-triisopropylsilanyloxymethyl-furan-2-yl)-acrylic acid ethyl ester (34) (1.0 g) in ethyl acetate (70 mL) was treated with 5% w/w palladium on carbon (350 mg) and hydrogenated at 1 atmosphere for exactly 1¼ hours at room temperature. The reaction mixture was filtered through filter-aid and then concentrated in vacuo to afford compound 35 as a clear oil (1.05 g). LC/MS System A: $R_t$=5.52 mins.

(d) 3-(4-Hydroxymethyl-5-methyl-furan-2-yl)-propionic acid ethyl ester (36)

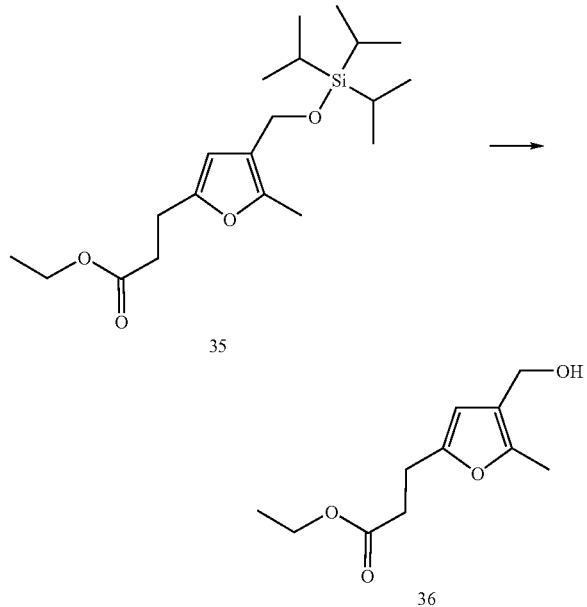

Compound (36) was prepared in the form of a clear oil from compound (35) by adapting the procedure described in Example 3(c). LC/MS System A: $R_t$=2.68 mins.

(e) 3-[4-(Biphenyl-4-yloxymethyl)-5-methyl-furan-2-yl]-propionic acid (37)

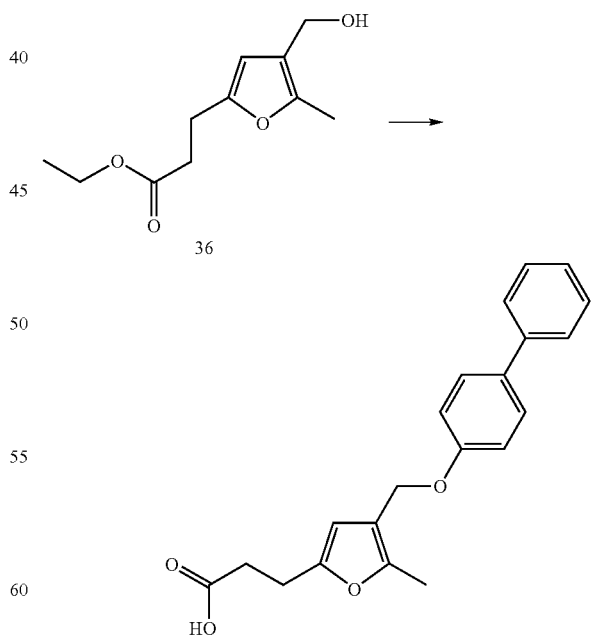

To a stirred, cooled 0° C. solution, in tetrahydrofuran (2.5 mL), a solution of 3-(4-hydroxymethyl-5-methyl-furan-2-yl)-propionic acid ethyl ester (36) (400 mg) in tetrahydrofuran (2.5 mL) was cooled to 0° C. and treated successively with triphenylphosphine (542 mg), biphenyl-4-ol (353 mg) and diisopropylazodicarboxylate (0.41 mL). After stirring for 10 mins at 0° C. the reaction mixture was allowed to warm to room temperature and then stirred for a further 16 hours. The reaction mixture was concentrated in-vacuo then re-dissolved in dichloromethane (15 mL) and treated with triethylamine (1.50 mL) and a scavenger resin PS-TsCl (2.5 g) and the mixture was shaken for 6 hours at room temperature. The reaction mixture was purified by flash chromatography, eluting with a mixture of diethyl ether in petroleum ether (40-60° C.) (7:93 by volume). The purified product (320 mg) was dissolved in methanol/tetrahydrofuran (2:1 by volume) (18 mL), treated with 1.0 M aqueous lithium hydroxide solution (9 mL) and allowed to stir at room temperature for 6 hours. The pH of the reaction mixture was adjusted to between pH4 and pH5 by the addition of 1.0 M hydrochloric acid (~5.0 mL), then treated with saturated ammonium chloride (100 mL) and extracted with ethyl acetate (2×100 mL). The combined organic extracts were further washed with brine (35 mL), then dried (sodium sulphate) and concentrated in vacuo. A sample of the crude product (50 mg) was purified by HPLC to give compound 37 as white solid (25 mg). LC/MS System C: $R_t$=5.33 mins, m/z (ES⁻)=335 (M⁻ for $C_{21}H_{20}O_4$).

(f) N-{3-[4-(Biphenyl-4-yloxymethyl)-5-methyl-furan-2-yl]-propionyl}-benzene sulfonamide (38)

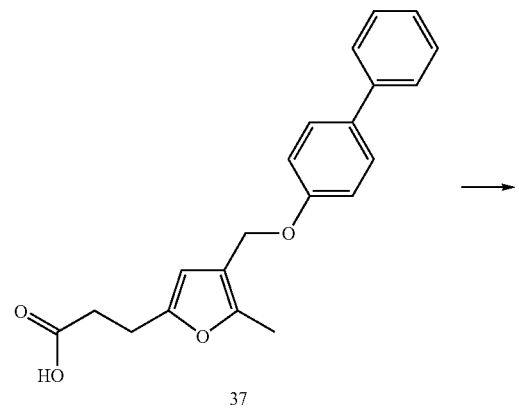

37

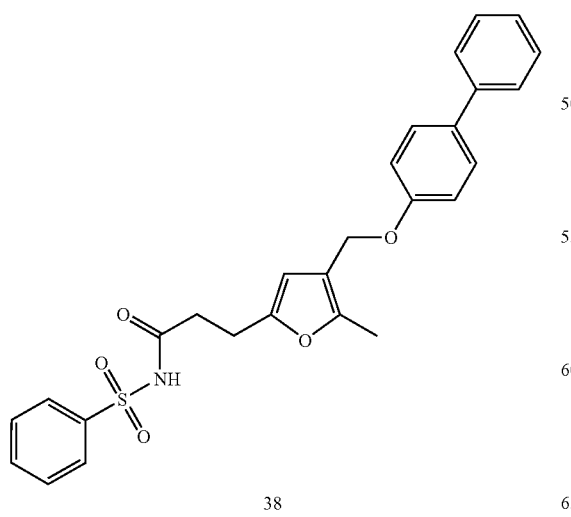

38

Compound (38) was prepared from compound (37) by the procedure of Example 2A. LC/MS System C: $R_t$=5.82 mins, m/z (ES⁻)=475 (M⁻ for $C_{27}H_{25}O_5S$).

Example 12

Synthesis of 3-[4-(4'-Methoxy-biphenyl-4-yloxymethyl)-5-methyl-furan-2-yl]-propionic acid (39) and N-{3-[4-(4'-Methoxy-biphenyl-4-yloxymethyl)-5-methyl-furan-2-yl]-propionyl}-benzene sulfonamide (40)

(a) 3-[4-(4'-Methoxy-biphenyl-4-yloxymethyl)-5-methyl-furan-2-yl]-propionic acid (39)

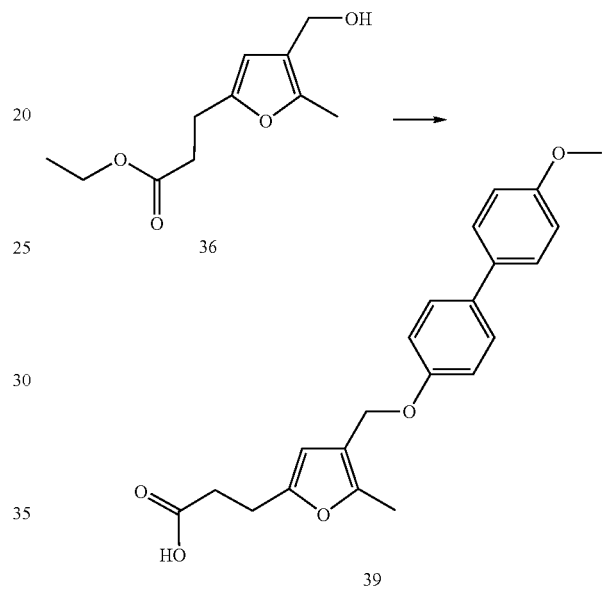

Compound (39) was prepared from compound (36) in an analogous manner to that described in Example 11(e). LC/MS System C: $R_t$=5.31 mins, m/z (ES⁻)=365 (M⁻ for $C_{22}H_{22}O_5$).

(b) N-{3-[4-(4'-Methoxy-biphenyl-4-yloxymethyl)-5-methyl-furan-2-yl]-propionyl}-benzene sulfonamide (40)

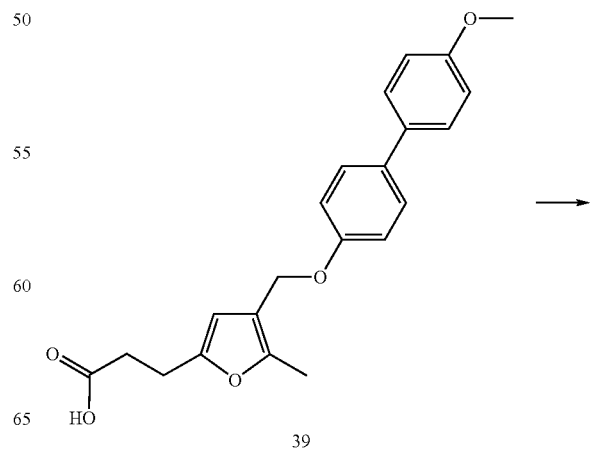

39

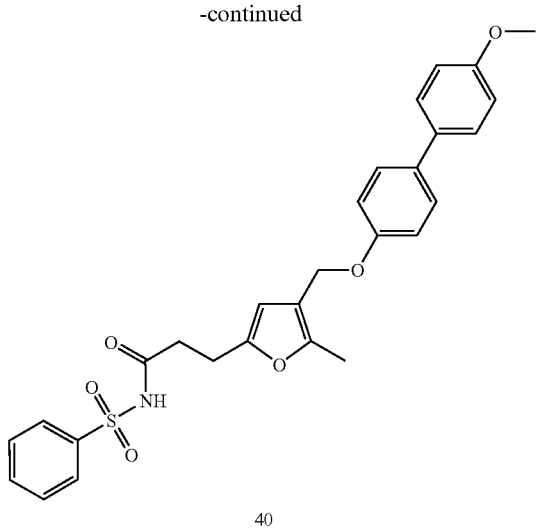

40

Compound (40) was prepared from compound (39) by the procedure of Example 2A. LC/MS System C: $R_t$=5.78 mins, m/z (ES$^-$)=504 (M$^-$ for $C_{28}H_{27}NO_6S$).

Example 13

Synthesis of 3-[4-(Biphenyl-4-yloxymethyl)-5-methyl-furan-2-yl]-acrylic acid (42) and 3-[4-(4'-Methoxy-biphenyl-4-yloxymethyl)-5-methyl-furan-2-yl]-acrylic acid (43)

(a) 3-(4-Hydroxymethyl-5-methyl-furan-2-yl)-acrylic acid ethyl ester (41)

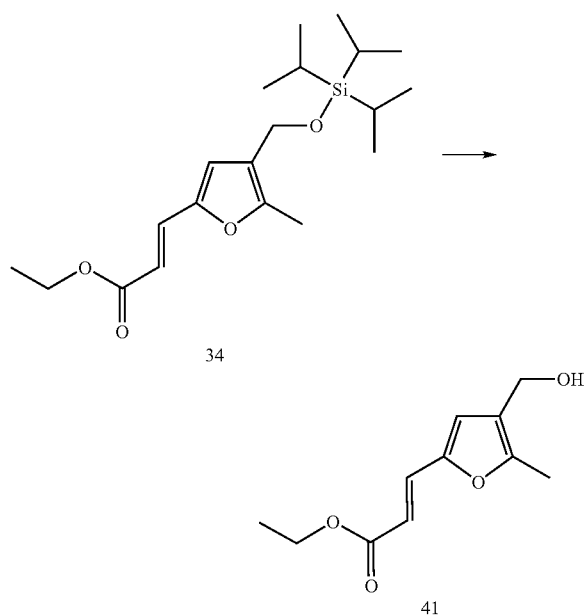

Compound (41) was prepared in the form of a yellow oil from compound (34) by adapting the procedure described in Example 3(c). LC/MS System A: $R_t$=2.82 mins.

(b) 3-[4-(Biphenyl-4-yloxymethyl)-5-methyl-furan-2-yl]-acrylic acid (42)

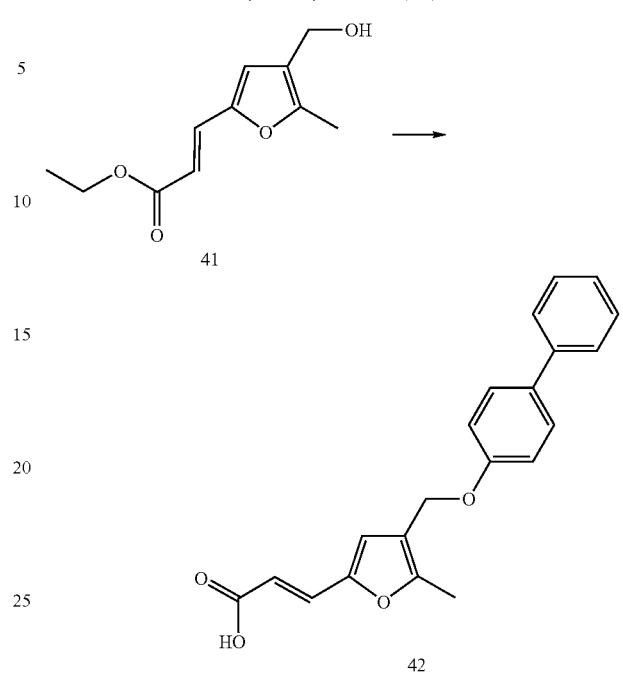

Compound (42) was prepared from compound (41) by adapting the procedure of Example 11(e). LC/MS System C: $R_t$=4.91 mins, m/z (ES$^-$)=333 (M$^-$ for $C_{21}H_{18}O_4$).

(c) 3-[4-(4'-Methoxy-biphenyl-4-yloxymethyl)-5-methyl-furan-2-yl]-acrylic acid (43)

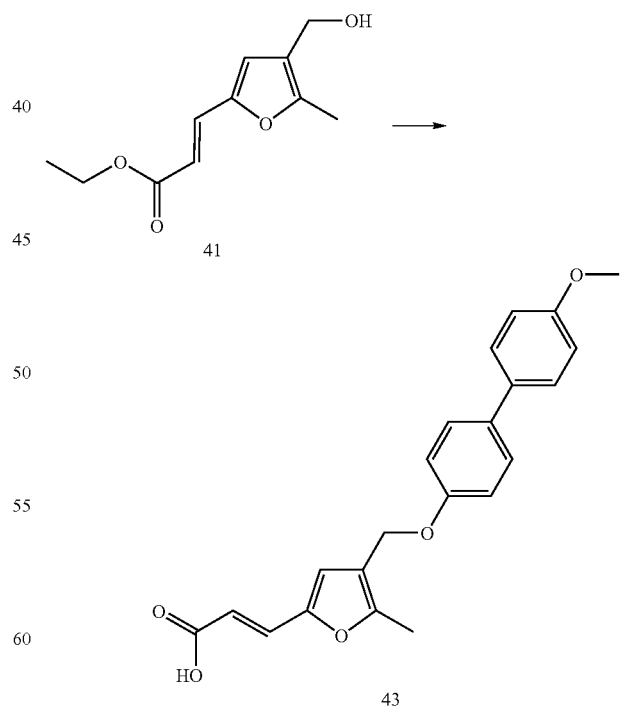

Compound (43) was prepared from compound (41) by adapting the procedure of Example 11(e). LC/MS System C: $R_t$=4.85 mins, m/z (ES$^-$)=363 (M$^-$ for $C_{22}H_{20}O_5$).

Example 14A

Synthesis of 4-(Biphenyl-4-yloxymethyl)-5-methyl-furan-2-sulfonic acid benzoylamide (46)

(a) 3-(Biphenyl-4-yloxymethyl)-2-methyl-furan (44)

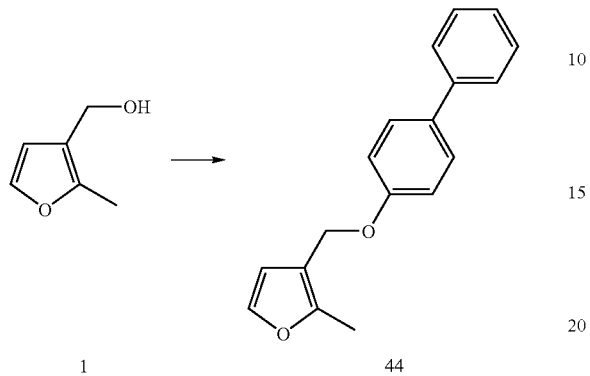

A solution of (2-methyl-furan-3-yl)-methanol (1)(5.0 g) in diethyl ether (75 mL) was cooled to 0° C. with stirring and treated with triphenylphosphine (12.85 g) and biphenyl-4-ol (7.59 g). The resulting solution was then treated drop-wise with diisopropylazodicarboxylate (9.75 mL). After stirring for 10 minutes at 0° C. the reaction mixture was allowed to warm to room temperature and then stirred for a further 3 hours. The reaction mixture was then filtered and concentrated in vacuo. The residue was purified by flash chromatography, eluting with diethyl ether/petroleum ether (1:19 by volume), to give compound 44 as a white solid (7.0 g). LC/MS System A: $R_f$=4.38 mins.

(b) 4-(Biphenyl-4-yloxymethyl)-5-methyl-furan-2-sulfonic acid amide (45)

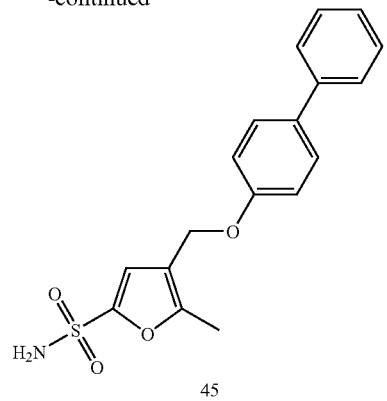

A solution of 3-(biphenyl-4-yloxymethyl)-2-methyl-furan (44) (5 g) in tetrahydrofuran (30 mL) was cooled to −78° C. with stirring and was treated with butyllithium (2.5 M in hexanes; 9.84 mL) drop-wise over 10 minutes. After stirring for 45 mins at −78° C., cooling was removed for a period of 15 minutes then re-introduced. A stream of sulphur dioxide gas was then passed over the surface of the reaction mixture until the pH of the reaction was between pH6 and pH7. Stirring was continued for a further 1.5 hours at −78° C. and then pentane was added (50 mL). The resulting precipitate was collected by filtration and then re-suspended in water (75 mL). This suspension was cooled to 0° C. and treated with sodium acetate (3.88 g) and hydroxylamine-O-sulfonic acid (2.67 g) and stirred at room temperature for 16 hours. The reaction mixture was diluted with water (300 mL) and extracted into ethyl acetate (3×250 mL). The combined organic extracts were washed successively with saturated sodium hydrogen carbonate (300 mL) and brine (300 mL), dried, and concentrated in vacuo. This material was purified by flash chromatography, eluting with diethyl ether/petroleum ether (2:3 by volume) to give a beige coloured solid (998 mg). A sample of this material (100 mg) was further purified by HPLC to give compound 45 as white solid (55 mg). LC/MS System A: $R_f$=3.70 mins.

(c) 4-(Biphenyl-4-yloxymethyl)-5-methyl-furan-2-sulfonic acid benzoylamide (46)

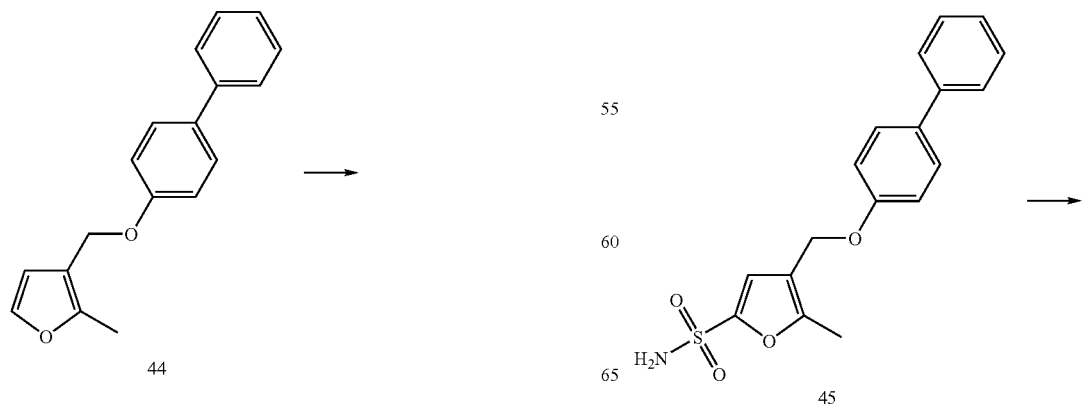

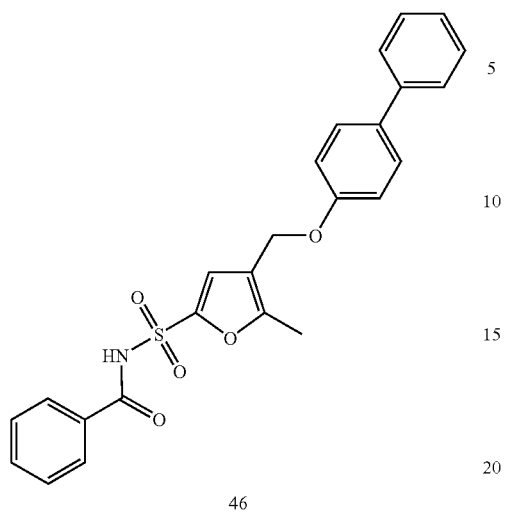

46

To a stirred solution of benzoic acid (61 mg) in a mixture of tetrahydrofuran (10 mL) and N,N-dimethylformamide (5 mL) was added 4-(N,N-dimethylamino)pyridine (3.0 mg), 1-(3-dimethylaminopropyl)-3-ethylcarbodiimide hydrochloride (118 mg) and 4-(biphenyl-4-yloxymethyl)-5-methyl-furan-2-sulfonic acid amide (45) (206 mg). After 16 hours at room temperature the reaction mixture was concentrated in-vacuo, then partitioned between 0.1M hydrochloric acid (30 mL) and ethyl acetate (3×30 mL). The combined organic extracts were washed with brine (25 mL), dried (MgSO$_4$) and concentrated in vacuo. The crude product was purified by HPLC to give compound 46 as light beige solid (17 mg). LC/MS System C: R$_t$=5.69 mins, m/z (ES$^-$)=446 (M$^-$ for C$_{25}$H$_{21}$NO$_5$S).

Example 14B

Synthesis of 4-(Biphenyl-4-yloxymethyl)-5-methyl-furan-2-sulphonic acid butyryl-amide (61)

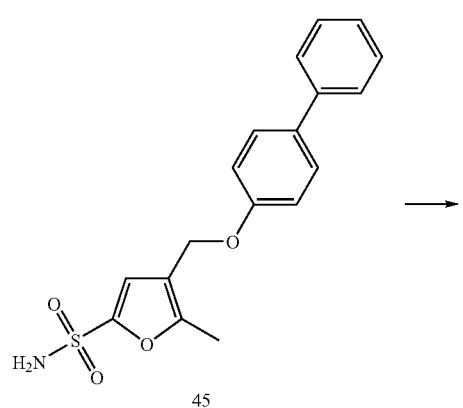

45

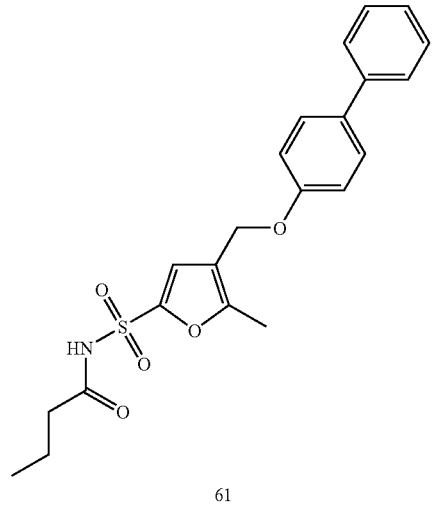

61

To a stirred solution of 4-(biphenyl-4-yloxymethyl)-5-methyl-furan-2-sulphonic acid amide (45) (50 mg, 0.146 mmoles) in dichloromethane (5.0 ml) was added triethylamine (26 μl, 0.189 mmoles), dimethyl-pyridin-4-yl-amine (1 mg) and butyryl chloride (19 μl, 0.184 mmoles). After stirring for 16 hours at room temperature the reaction mixture was concentrated in-vacuo, and the residue was purified by HPLC to give compound 61 as an off-white solid (48 mg). LC/MS System C: R$_t$=3.82 mins, m/z (ES$^-$)=412 ((M–H) for C$_{22}$H$_{23}$NO$_5$S).

By adapting the procedure of Example 14B there were prepared Examples 14C to 14E:

Example 14C 4-(Biphenyl-4-yloxymethyl)-5-methyl-furan-2-sulphonic acid phenylacetyl-amide (62)

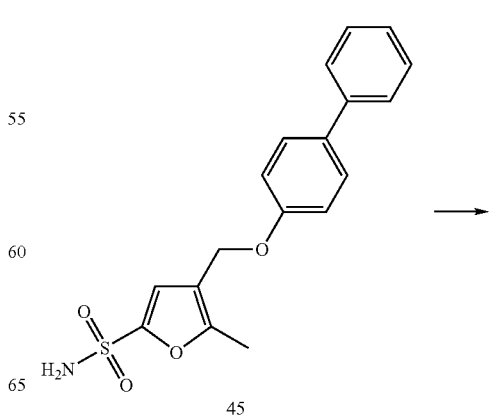

45

-continued

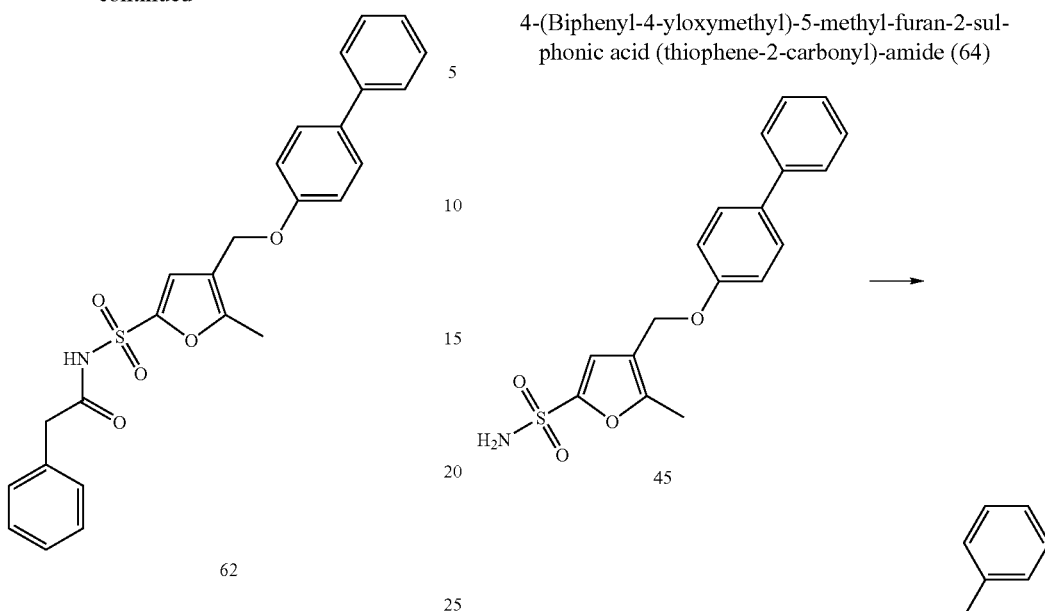

LC/MS System C: $R_t$=4.20 mins, m/z (ES$^-$)=460 ((M−H) for $C_{26}H_{23}NO_5S$).

Example 14D 4-(Biphenyl-4-yloxymethyl)-5-methyl-furan-2-sulphonic acid (3,5-dimethyl-isoxazole-4-carbonyl)-amide (63)

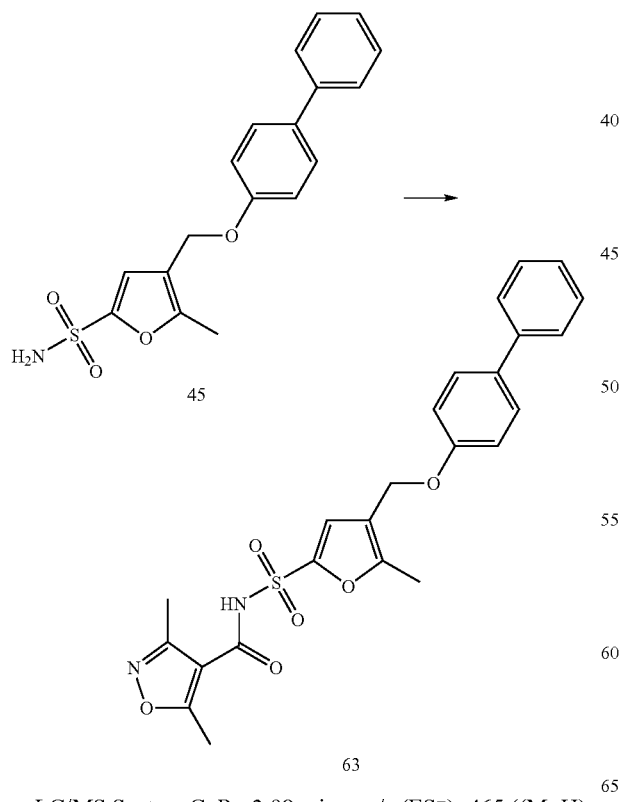

LC/MS System C: $R_t$=3.98 mins, m/z (ES$^-$)=465 ((M−H) for $C_{24}H_{22}N_2O_6S$).

Example 14E 4-(Biphenyl-4-yloxymethyl)-5-methyl-furan-2-sulphonic acid (thiophene-2-carbonyl)-amide (64)

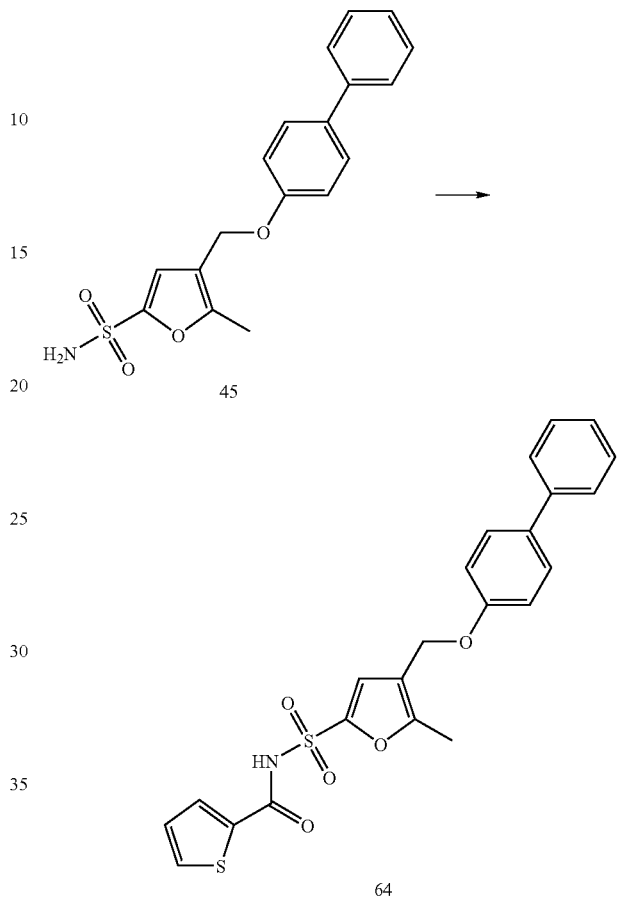

LC/MS System C: $R_t$=4.06 mins, m/z (ES$^-$)=452 ((M−H) for $C_{23}H_2NO_5S_2$).

Example 14F

Synthesis of 4-(Biphenyl-4-yloxymethyl)-5-methyl-furan-2-sulphonic acid (3-methoxy-propionyl)-amide (65)

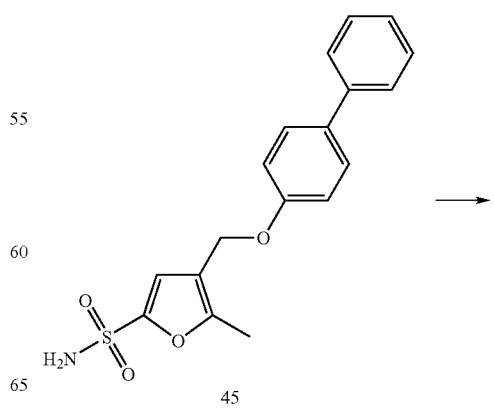

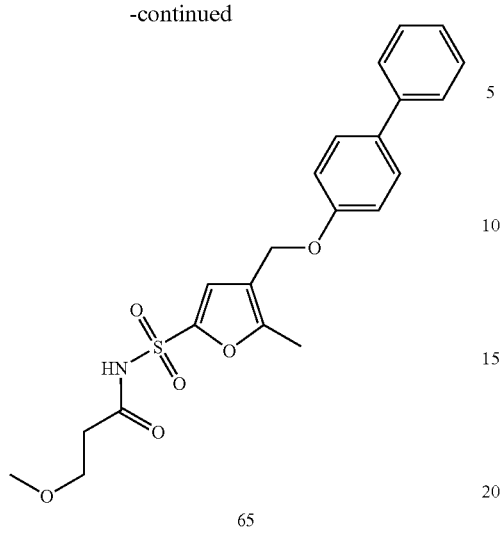

65

To a stirred solution of 4-(biphenyl-4-yloxymethyl)-5-methyl-furan-2-sulphonic acid amide (45) (50 mg, 0.146 mmoles) in N,N-dimethylformamide (4.0 ml) was added diisopropylethylamine (85 µl, 0.480 mmoles) then a solution of 3-methoxypropionic acid (14 µl, 0.146 mmoles) in N,N-dimethylformamide (11.0 ml). O-(7-Azabenzotriazol-1-yl)-N,N,N',N'-tetramethyluronium hexafluorophosphate (61 mg, 0.160 mmoles) in N,N-dimethylformamide (1.0 ml) was added and the solution stirred at room temperature for 16 hours. The reaction mixture was concentrated in-vacuo, and the residue was purified by HPLC to give compound 65 as a white solid (42 mg). LC/MS System A: $R_t$=3.80 mins, m/z (ES$^-$)=428 ((M−H) for $C_{22}H_{23}NO_6S$).

By adapting the procedure of Example 14F there were prepared Examples 14G to 14I:

Example 14G 4-(Biphenyl-4-yloxymethyl)-5-methyl-furan-2-sulphonic acid (pyridin-3-yl-acetyl)-amide (66)

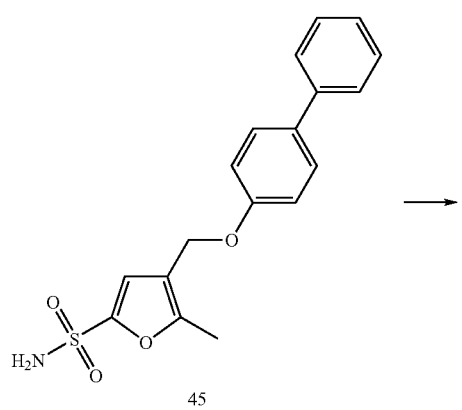

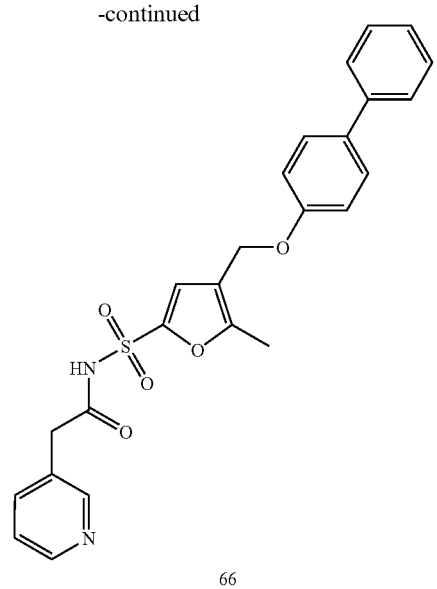

66

LC/MS System D: $R_t$=5.64 mins, m/z (ES$^+$)=463 ((M+H) for $C_{25}H_{22}N_2O_5S$).

Example 14H 4-(Biphenyl-4-yloxymethyl)-5-methyl-furan-2-sulphonic acid (pyridine-4-carbonyl)-amide (67)

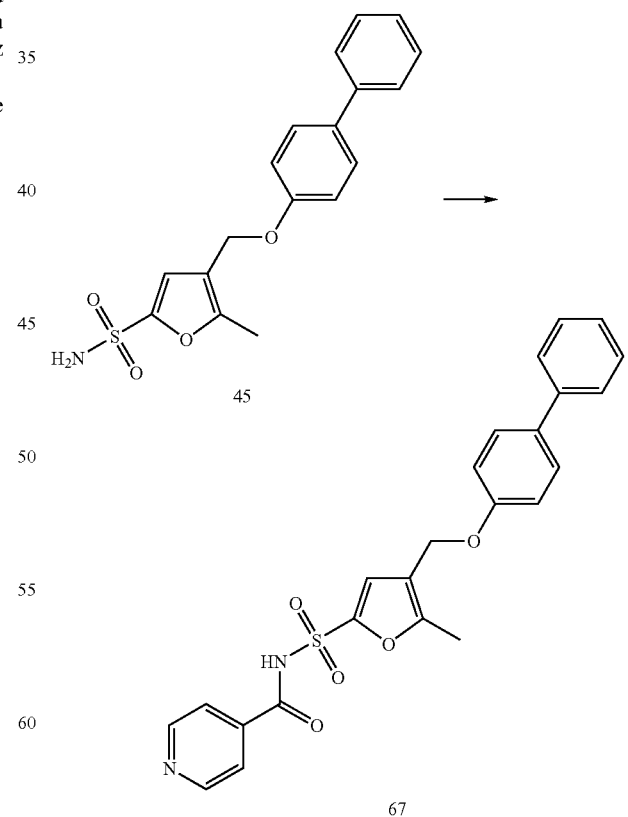

67

LC/MS System D: $R_t$=5.85 mins, m/z (ES$^+$)=449 ((M+H) for $C_{24}H_{20}N_2O_5S$).

Example 14I 4-(Biphenyl-4-yloxymethyl)-5-methyl-furan-2-sulphonic acid (pyridine-3-carbonyl)-amide (68)

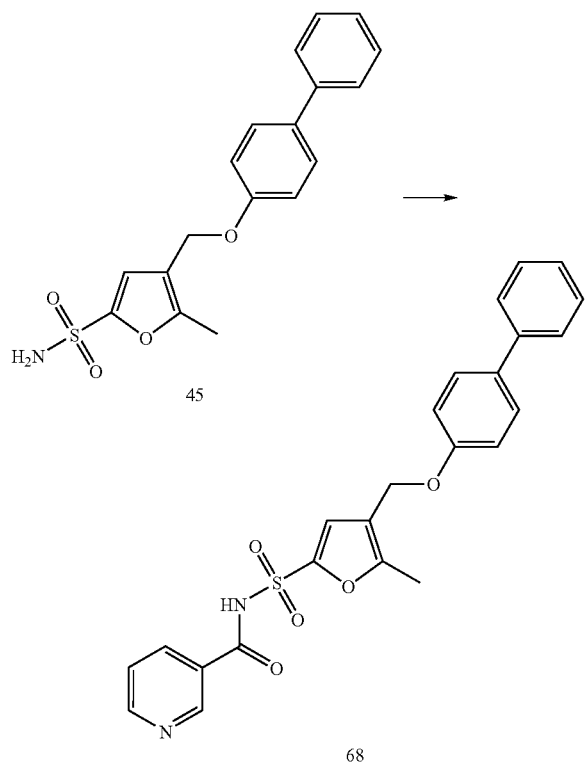

LC/MS System D: $R_t$=5.92 mins, m/z (ES$^+$)=449 ((M+H) for $C_{24}H_{20}N_2O_5S$).

Example 15

Synthesis of 4-(4'-Methoxy-biphenyl-4-yloxymethyl)-5-methyl-furan-2-sulfonic acid benzoylamide (49) and 4-(4'-Methoxy-biphenyl-4-yloxymethyl)-5-methyl-furan-2-sulfonic acid (3,5-dimethyl-isoxazole-4-carbonyl)-amide (69)

(a) 3-(4'-Methoxy-biphenyl-4-yloxymethyl)-2-methyl-furan (47)

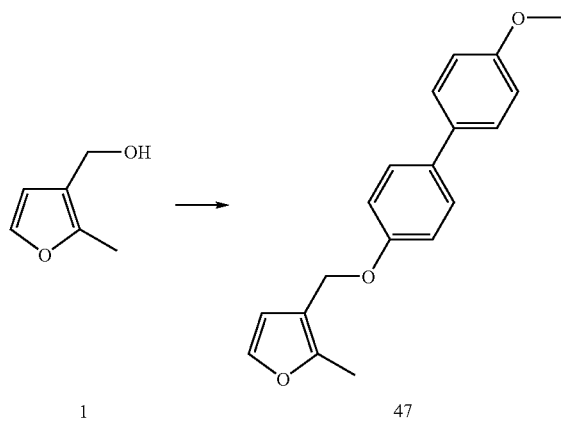

Compound 47 was prepared by adapting the procedure of Example 14A(a). LC/MS System A: $R_t$=4.58 mins.

(b) 4-(4'-Methoxy-biphenyl-4-yloxymethyl)-5-methyl-furan-2-sulfonic acid amide (48)

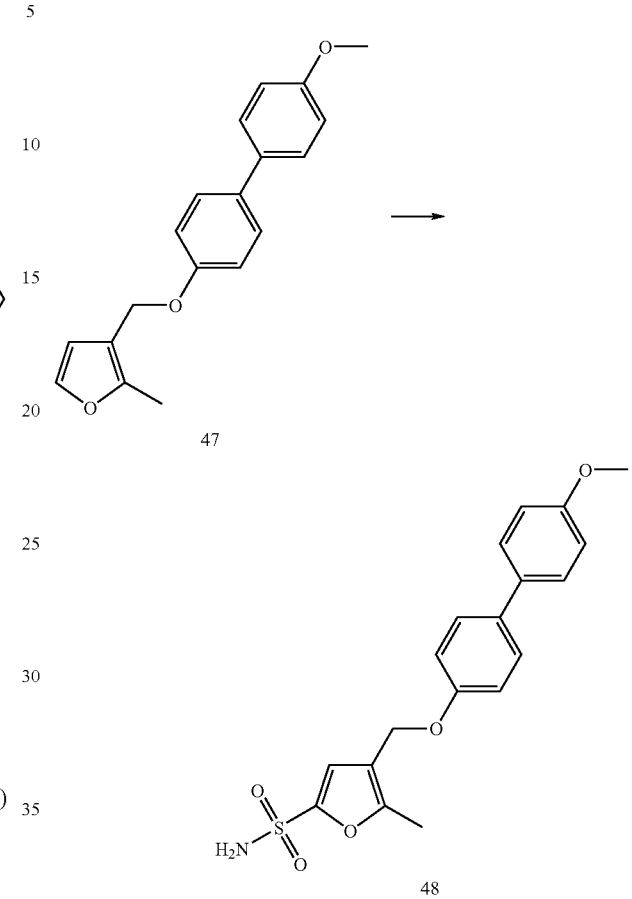

Compound (48) was prepared from compound (47) by the procedure of Example 14A(b). LC/MS System A: $R_t$=3.63 mins.

(c) 4-(4'-Methoxy-biphenyl-4-yloxymethyl)-5-methyl-furan-2-sulfonic acid benzoylamide (49)

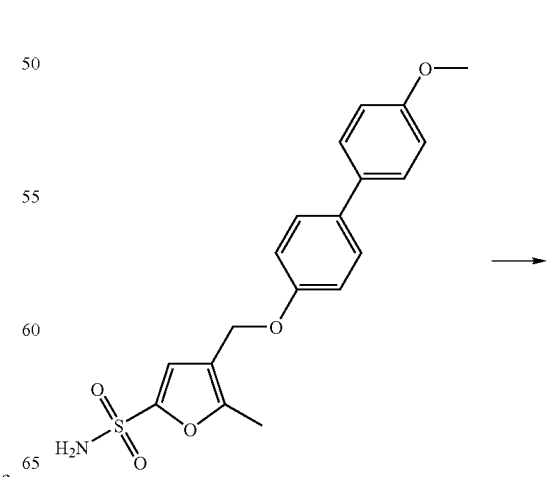

73

-continued

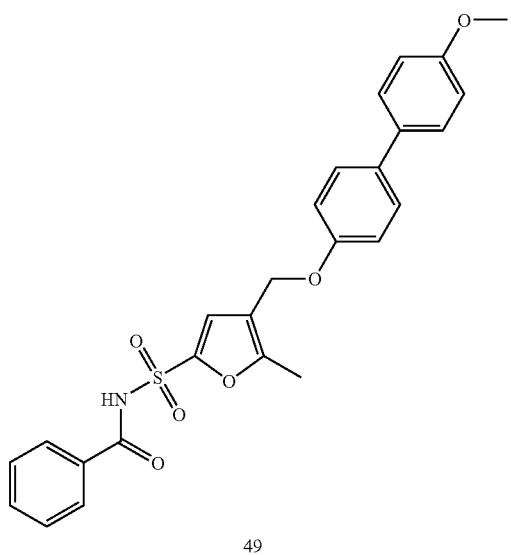

49

Compound (49) was prepared from compound (48) by the procedure of Example 14B. LC/MS System C: $R_t$=5.37 mins, m/z (ES⁻) 476 (M⁻ for $C_{26}H_{23}NO_6S$).

(d) 4-(4'-Methoxy-biphenyl-4-yloxymethyl)-5-methyl-furan-2-sulphonic acid (3,5-dimethyl-isoxazole-4-carbonyl)-amide (69)

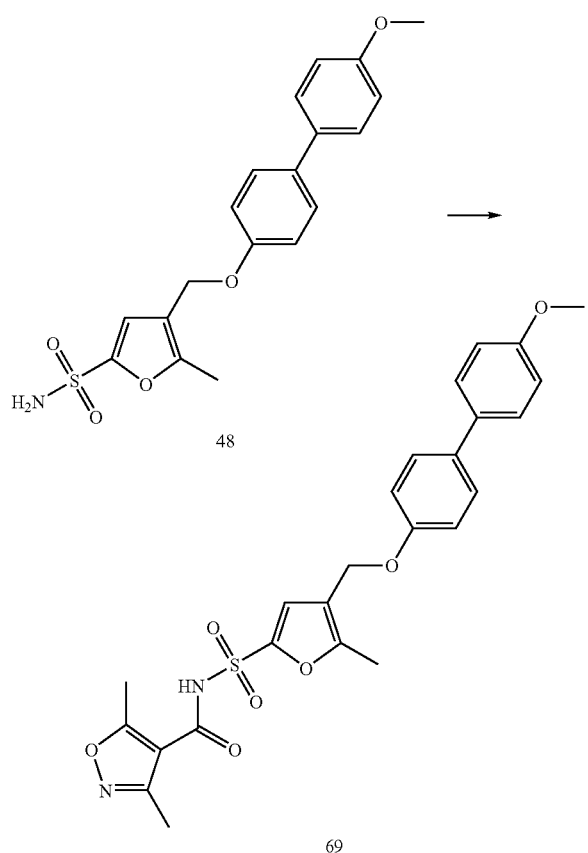

Compound (69) was prepared from compound (48) by adapting the procedure of example 14B. LC/MS System C: $R_t$=4.45 mins, m/z (ES⁻)=495 ((M–H) for $C_{25}H_{24}N_2O_7S$).

74

Example 16

Synthesis of 4-[4-(5-Methoxy-pyridin-2-yl)-phenoxymethyl]-5-methyl-furan-2-carboxylic acid (53)

(a) 5-Methyl-4-[4-(4,4,5,5-tetramethyl-[1,3,2]dioxaborolan-2-yl)-phenoxymethyl]-furan-2-carboxylic acid methyl ester (51)

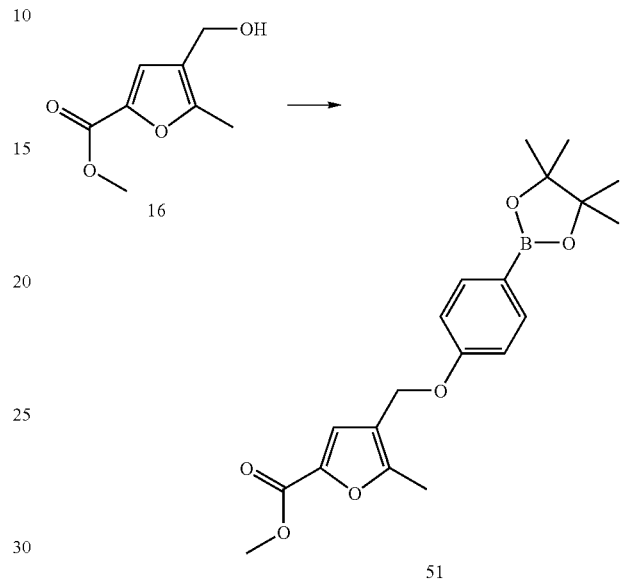

A mixture of 4-hydroxymethyl-5-methyl-furan-2-carboxylic acid methyl ester (16) (0.5 g), 4-(4,4,5,5-tetramethyl-[1,3,2]dioxaborolan-2-yl)-phenol (1.9 g) and triphenylphosphine (2.3 g) in dry tetrahydrofuran (20 mL) under a nitrogen atmosphere was cooled to 0° C. Di-isopropylazodicarboxylate (1.8 mL) was added drop-wise and the mixture was stirred at room temperature for 72 hours. After concentrating in vacuo, the residue was partitioned between ethyl acetate and water. The organic phase was washed with brine, dried (MgSO₄) and concentrated in vacuo. The residue was extracted with pentane and the pentane phase was decanted and concentrated to give compound 51 as an oil. This was used without further purification.

(b) 4-[4-(5-Methoxy-pyridin-2-yl)-phenoxymethyl]-5-methyl-furan-2-carboxylic acid methyl ester (52)

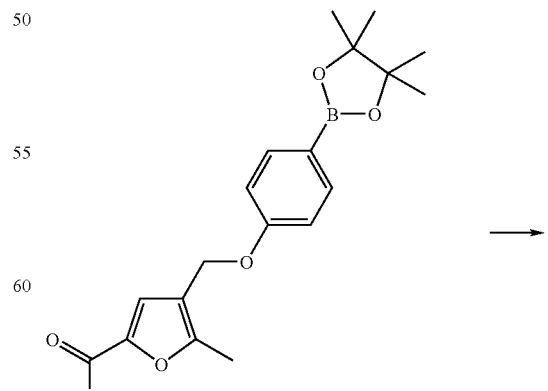

51

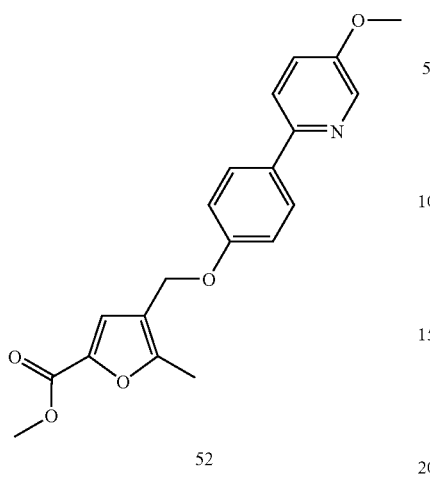

52

A mixture of 5-methyl-4-[4-(4,4,5,5-tetramethyl-[1,3,2] dioxaborolan-2-yl)-phenoxymethyl]-furan-2-carboxylic acid methyl ester (51) (126 mg), 2M aqueous cesium carbonate (0.6 mL) and 2-iodo-5-methoxypyridine (95 mg) in 1,4-dioxan (10 mL) under an argon atmosphere was sonicated to expel traces of oxygen. [1,1'-Bis-(diphenylphosphino) ferrocene]dichloropalladium (II) (8 mg) was added and the mixture heated at 95° C. for 18 hours. After cooling, the mixture was acidified to pH6 with 1M aqueous hydrochloric acid and partitioned between ethyl acetate and water. The organic phase was dried (MgSO$_4$) and evaporated to give compound 52 as an oil (70 mg), which was used directly in the next step. LC/MS System A: $R_t$=3.23 mins, m/z=354 ((M+H) for $C_{20}H_{19}NO_5$).

(c) 4-[4-(5-Methoxy-pyridin-2-yl)-phenoxymethyl]-5-methyl-furan-2-carboxylic acid (53)

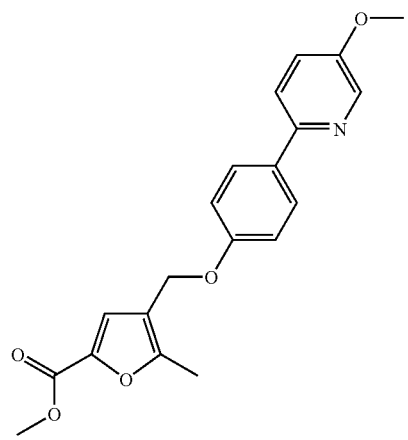

52

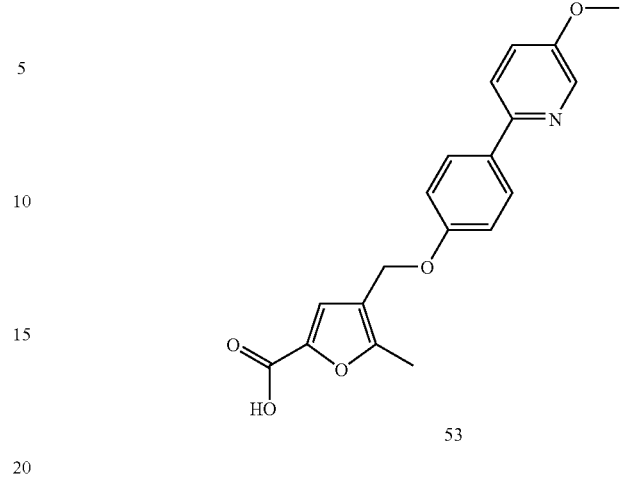

53

Method 1

A solution of 4-[4-(5-methoxy-pyridin-2-yl)-phenoxymethyl]-5-methyl-furan-2-carboxylic acid methyl ester (52) (118 mg, 0.33 mmoles) in dry tetrahydrofuran (10 ml) was treated with potassium trimethylsilanoate (260 mg, 2.0 mmoles) and the mixture stirred under an argon atmosphere for 2 hours. After evaporation of the solvent the residue was purified by HPLC (gradient: 18% acetonitrile/82% water containing 0.1% trifluoroacetic acid to 98% acetonitrile/2% water at a rate of 1%/min) to afford compound 53 (60 mg) as a white solid.

Method 2

A mixture of 4-[4-(5-methoxy-pyridin-2-yl)-phenoxymethyl]-5-methyl-furan-2-carboxylic acid methyl ester (52) (70 mg) and 1M aqueous lithium hydroxide (1 mL) in tetrahydrofuran/methanol (2:1 by volume) (12 mL) was stirred at room temperature for 16 hours. The reaction mixture was acidified to between pH6 and pH7, and partitioned between ethyl acetate and water. The organic phase was separated, washed with brine and dried (MgSO$_4$). After removal of the solvent, the residue was purified by HPLC. Compound 53 was obtained as a solid (2.5 mg). LC/MS System A: $R_t$=2.90 mins, m/z (ES$^+$)=340 ((M+H) for $C_{19}H_{17}NO_5$).

Example 17

Synthesis of 4-[6-(4-Methoxy-phenyl)-pyridin-3-yloxymethyl]-5-methyl-furan-2-carboxylic acid (56)

(a) 4-(6-iodo-pyridin-3-yloxymethyl)-5-methyl-furan-2-carboxylic acid methyl ester (54)

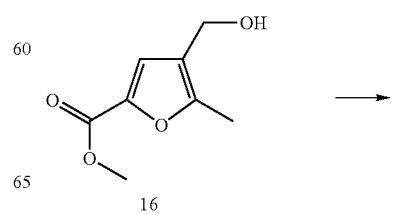

16

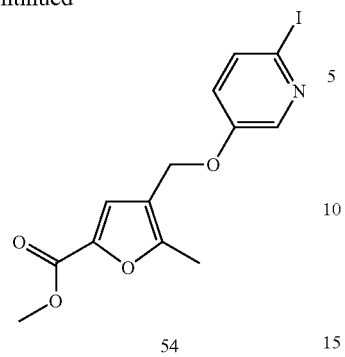

54

Compound (54) was prepared from compound (16) and 2-iodo-5-hydroxy-pyridine in a manner analagous to that described in Example 5(a). LC/MS System A: $R_t$=3.52 mins, m/z=374 (M+H) for $C_{13}H_{12}INO_4$)

(b) 4-[6-(4-Methoxy-phenyl)-pyridin-3-yloxymethyl]-5-methyl-furan-2-carboxylic acid methyl ester (55)

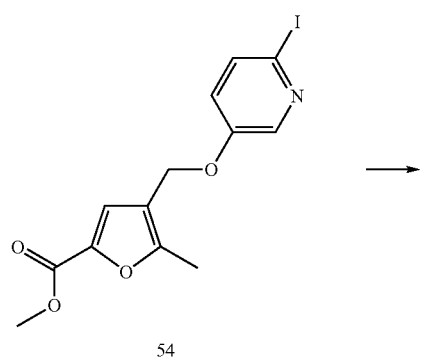

54

→

55

Compound (55) was prepared from compound (54) by adapting the procedure of Example 5(b). LC/MS System A: $R_t$=3.37 mins, m/z=354 ((M+H) for $C_{20}H_{19}NO_5$).

(c) 4-[6-(4-Methoxy-phenyl)-pyridin-3-yloxymethyl]-5-methyl-furan-2-carboxylic acid (56)

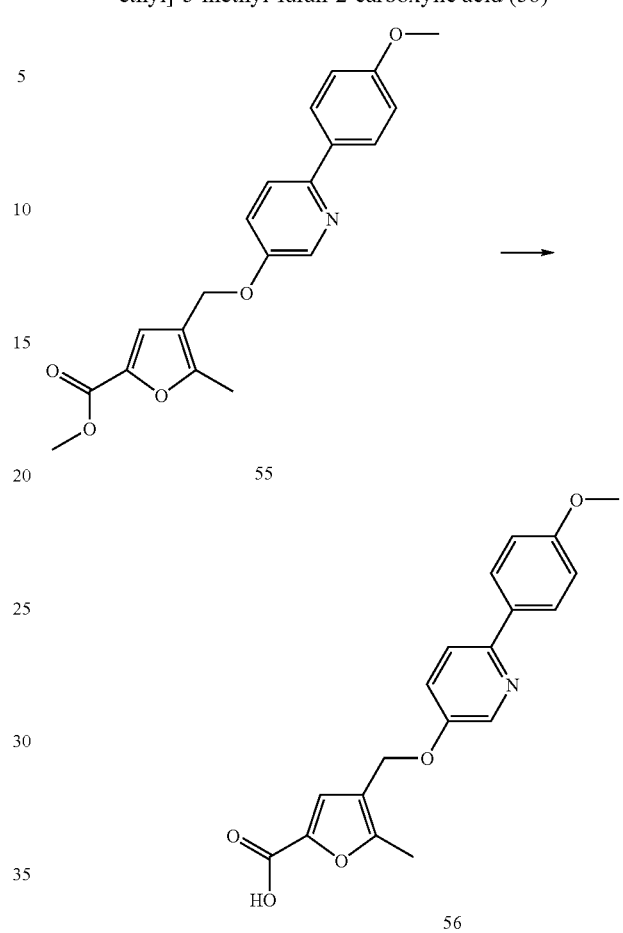

55

→

56

Compound (56) was prepared from compound (55) by adapting the procedure of Example 16(c). LC/MS System A: $R_t$=2.79 mins, m/z (ES⁺)=340 ((M+H) for $C_{19}H_{17}NO_5$)

Example 18

Synthesis of 3-Morpholin-4-yl-propane-1-sulphonic acid [4-(4'-methoxy-biphenyl-4-yloxymethyl)-5-methyl-furan-2-carbonyl]-amide (59)

(a) 3-Morpholin-4-yl-propane-1-sulfonic acid amide (58)

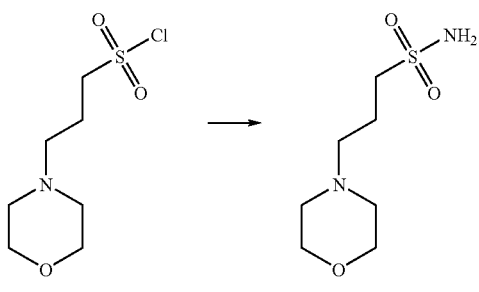

58

Dichloromethane (40 ml) was saturated with ammonia gas with cooling (dry ice/acetone), and then 3-morpholin-4-yl-propane-1-sulphonyl chloride (279 mg, 1.23 mmoles) was added. The mixture was stirred at room temperature for 24 hours. The mixture was filtered, the filtrate evaporated and the residue was dried at 40° C. in vacuo to afford compound 58 (210 mg) as a gum. LC/MS System A; $R_t$=0.28 mins, m/z (ES$^+$)=209 (M+H for $C_7H_{16}N_2O_3S$).

(b) 3-Morpholin-4-yl-propane-1-sulphonic acid [4-(4'-methoxy-biphenyl-4-yloxymethyl)-5-methyl-furan-2-carbonyl]-amide (59)

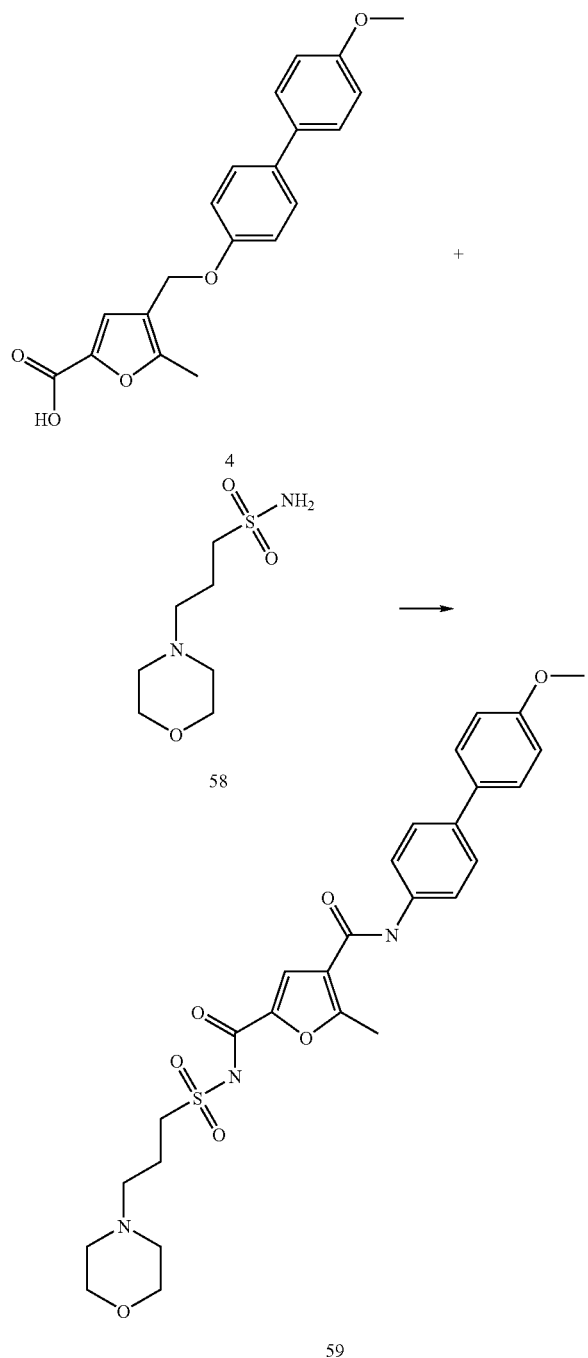

Compound (59) was prepared from compounds (4) and (58) by adapting the procedure of Example 2A. LC/MS System D; $R_t$=4.97 mins, m/z (ES$^+$)=529 (M+H for $C_{27}H_{32}N_2O_7S$).

Example 19

Synthesis of N-[4-(Biphenyl-4-yloxymethyl)-5-methyl-furan-2-carbonyl]-2-methyl-benzenesulphonamide (60)

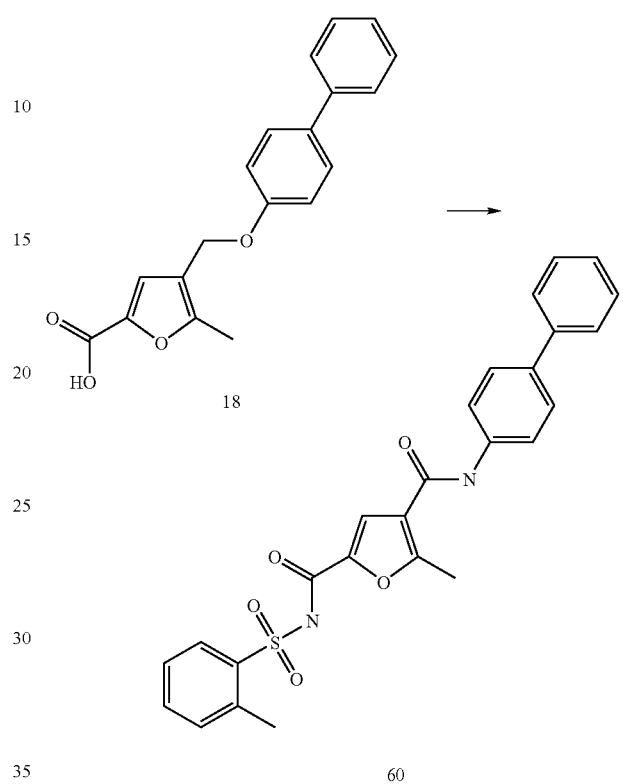

A stirred solution of 4-(biphenyl-4-yloxymethyl)-5-methyl-furan-2-carboxylic acid (18) (50 mg, 0.162 mmoles), 2-methyl-benzenesulphonamide (42 mg, 0.243 mmoles) and 4-(N,N-dimethylamino)-pyridine (2.5 mg) in a mixture of tetrahydrofuran (8 ml) and acetonitrile (2 ml) was treated with 1-(3-dimethylaminopropyl)-3-ethylcarbodiimide hydrochloride (38 mg, 0.194 mmoles). The mixture was stirred at room temperature for 16 hours under an argon atmosphere. The reaction mixture was concentrated in vacuo and the residue was purified by HPLC to afford compound 60 (20 mg) as a white solid. LC/MS System D; $R_t$=11.09 mins, m/z (ES$^+$)= 462 (M+H for $C_{26}H_{23}NO_5S$).

Example 20A

Synthesis of 4-[2-(Biphenyl-4-yloxy)-ethyl]-5-methyl-furan-2-carboxylic acid (72)

(a) tert-Butyl-[2-(2-methyl-furan-3-yl)-ethoxy]-diphenyl-silane (70)

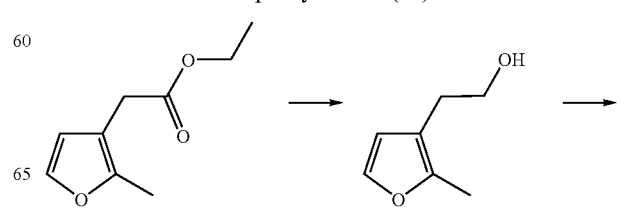

-continued

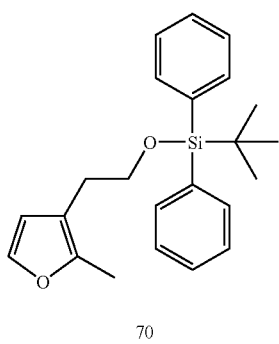

70

(i) A solution of (2-methyl-furan-3-yl)-acetic acid ethyl ester (11.8 g, 70.2 mmoles) in tetrahydrofuran (50 ml) was added to a stirred suspension of lithium aluminium hydride (2.66 g, 70.2 mmoles) under a nitrogen atmosphere and with cooling to 0° C. When the addition was complete the mixture was stirred at room temperature for 3 hours, then quenched by the addition of excess acetone. After acidifying with 10% aqueous hydrochloric acid the mixture was extracted three times with diethyl ether. The combined extracts were dried and evaporated to afford crude 2-(2-methyl-furan-3-yl)-ethanol as a yellow oil.

(ii) Compound (70) was prepared in the form of a pale yellow oil from crude 2-(2-methyl-furan-3-yl)-ethanol (from (i)) by adapting the procedure of Example 1(a).

(b) 4-[2-(tert-Butyl-diphenyl-silanyloxy)-ethyl]-5-methyl-furan-2-carboxylic acid (71)

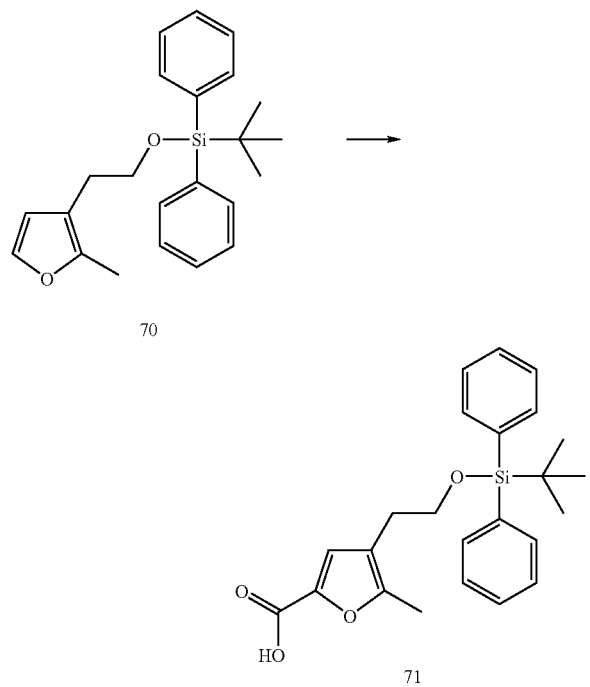

Compound (71) was prepared in the form of a pale yellow oil from compound (70) by adapting the procedure of Example 1(b).

(c) 4-[2-(Biphenyl-4-yloxy)-ethyl]-5-methyl-furan-2-carboxylic acid (72)

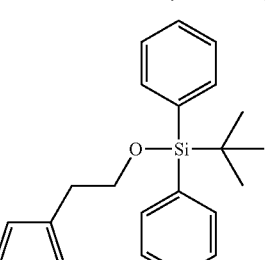

71

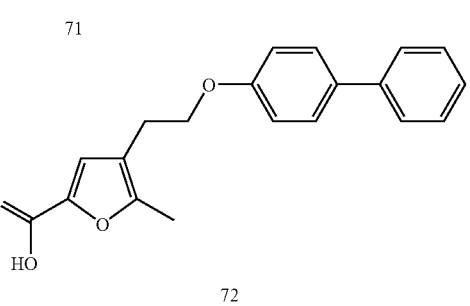

72

Compound (72) was prepared from compound (71) in an analogous manner to the methods described in Example 1(c).

LC/MS System B: $R_t$=1.86 mins, m/z (ES$^-$)=321 ((M–H) for $C_{20}H_{18}O_4$)

Example 20B

Synthesis of 4-[2-(4'-Methoxy-biphenyl-4-yloxy)-ethyl]-5-methyl-furan-2-carboxylic acid (73)

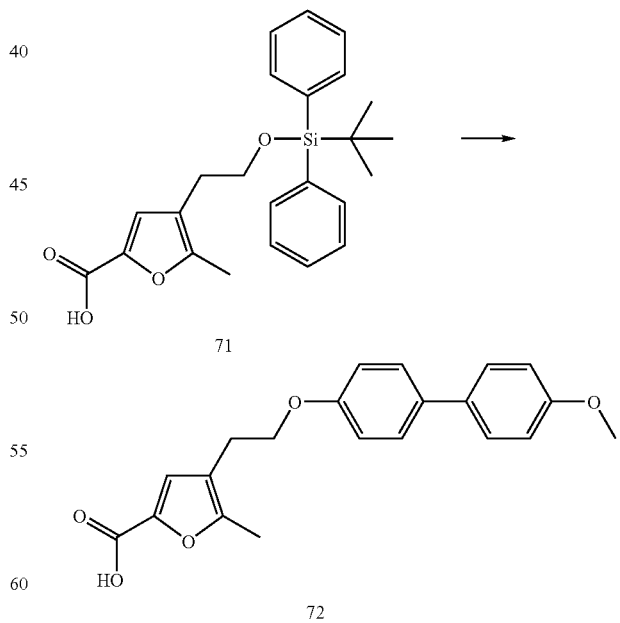

Compound (73) was prepared from compound (71) in an analogous manner to the methods described in Example 1(c).

LC/MS System B: $R_t$=1.86 mins, m/z (ES$^-$)=351 ((M–H) for $C_{21}H_{20}O_5$).

Example 20C

Synthesis of 4-[2-(Dibenzofuran-3-yloxy)-ethyl]-5-methyl-furan-2-carboxylic acid (74)

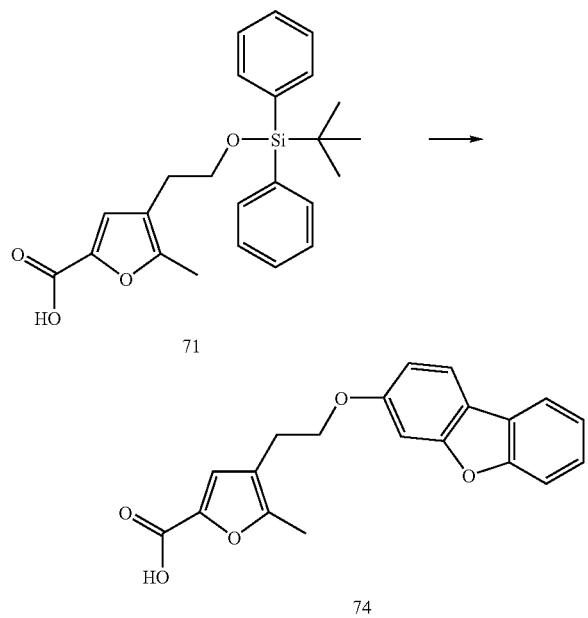

Compound (74) was prepared from compound (71) in an analogous manner to the methods described in Example 1(c).

LC/MS System B: $R_t$=1.86 mins, m/z (ES⁻)=335 ((M–H) for $C_{20}H_{16}O_5$).

Example 21A

Synthesis of 4-(Biphenyl-4-yloxymethyl)-furan-2-carboxylic acid (77)

(a) 4-Hydroxymethyl-furan-2-carboxylic acid (75)

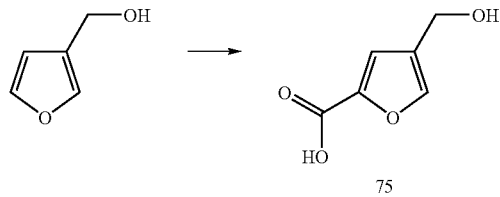

A solution of furan-3-yl-methanol (1.6 g, 16.5 mmoles) in dry tetrahydrofuran (25 ml) under an argon atmosphere was cooled to –78° C. and treated dropwise with n-butyl-lithium (9.2 mL, 23 mmoles of a 2.5M solution in hexanes). After 1 hour, sec-butyl-lithium (14.0 ml, 18.2 mmoles of a 1.3M solution in hexanes) was added. After stirring for a further 4 hours at –78° C., the mixture was quenched by the addition of a large excess of solid carbon dioxide. The mixture was allowed to warm to room temperature and was added to a mixture of ethyl acetate and 1M aqueous hydrochloric acid (60 ml). The organic phase was separated, washed with brine, dried, and evaporated. The residue was dissolved in dichloromethane and on standing a cream solid precipitated. The precipitate was collected and dried to afford compound 75 as cream solid (0.4 g).

(b) 4-(tert-Butyl-dimethyl-silanyloxymethyl)-furan-2-carboxylic acid (76)

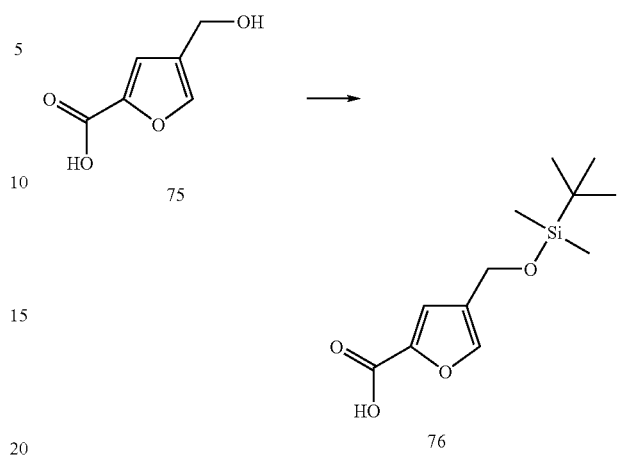

A mixture of 4-hydroxymethyl-furan-2-carboxylic acid (75) (1.4 g, 9.85 mmoles), tert-butyl-chloro-dimethyl-silane (3.2 g, 21 mmoles) and imidazole (2.14 g, 31.5 mmoles) in dry DMF (35 ml) was stirred at room temperature for 24 hours. Excess methanol (~3 ml) was added and the mixture stirred for a further 3 hours. After partitioning between ethyl acetate and water, the aqueous phase was acidified to pH=1 with 2M aqueous hydrochloric acid and re-extracted with ethyl acetate. The combined ethyl acetate phases were washed with water, dried (MgSO₄), and the solvent evaporated to give compound 76 as a white solid (2.4 g).

(c) 4-(Biphenyl-4-yloxymethyl)-furan-2-carboxylic acid (77)

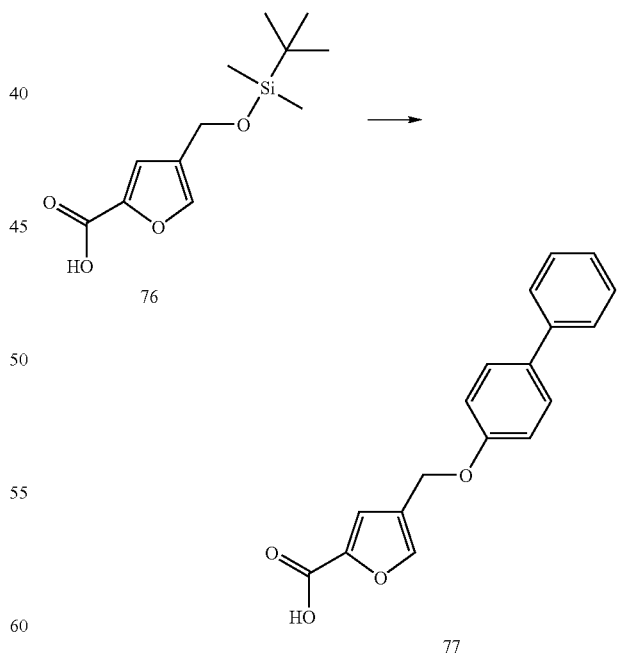

Compound (77) was prepared from compound (76) in an analogous manner to the methods described in Example 1(c). LC/MS System B; $R_t$=1.72 mins, m/z (ES⁻)=293 (M–H for $C_{18}H_{14}O_4$).

85

Example 21B

Synthesis of 4-(Dibenzofuran-2-yloxymethyl)-furan-2-carboxylic acid (78)

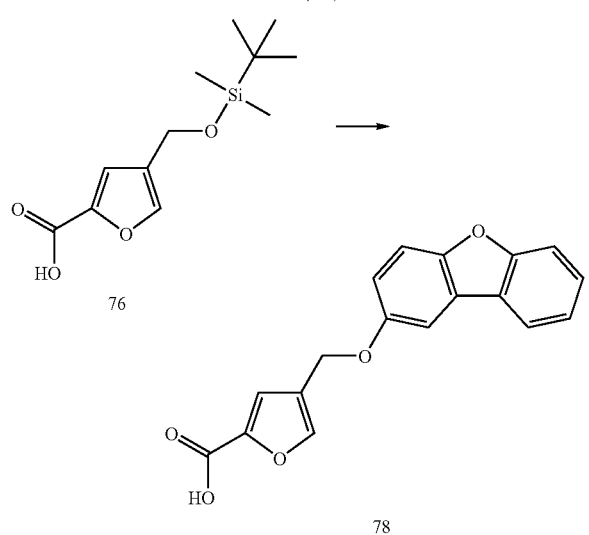

Compound (78) was prepared from compound (76) in an analogous manner to the methods described in Example 1(c). LC/MS System B; $R_t$=1.72 mins, m/z (ES$^-$)=307 (M–H for $C_{18}H_{12}O_5$).

Example 21C

Synthesis of 4-(4'-Cyano-biphenyl-4-yloxymethyl)-furan-2-carboxylic acid (79)

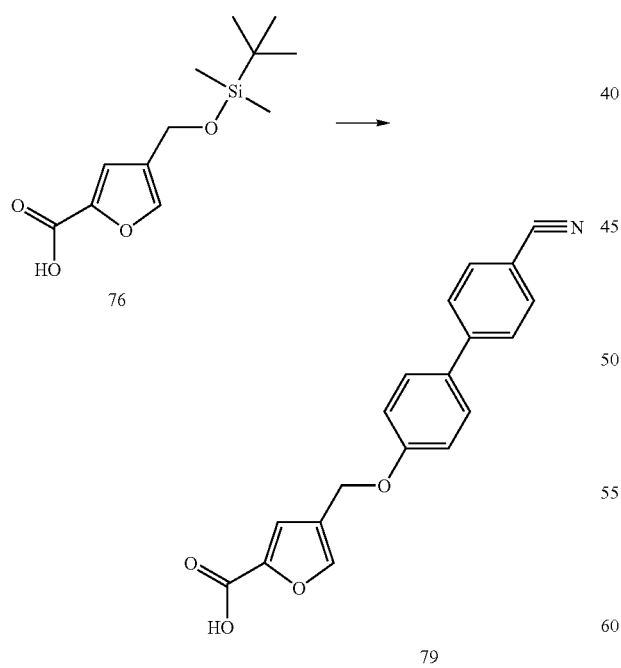

Compound (79) was prepared from compound (76) in an analogous manner to the methods described in Example 1(c). LC/MS System B; $R_t$=1.65 mins, m/z (ES$^-$)=318 (M–H for $C_{19}H_{13}NO_4$).

86

Example 21D

Synthesis of 4-(4'-Methoxy-biphenyl-4-yloxymethyl)-furan-2-carboxylic acid (80)

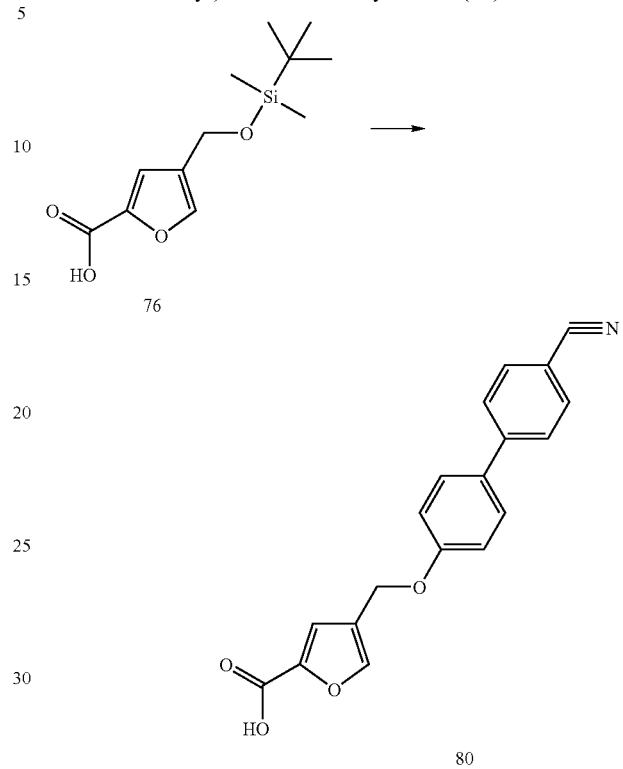

Compound (80) was prepared from compound (76) in an analogous manner to the methods described in Example 1(c). LC/MS System B; $R_t$=1.72 mins, m/z (ES$^-$)=323 (M–H for $C_{19}H_{16}O_5$).

Example 21E

Synthesis of 4-(Dibenzofuran-3-yloxymethyl)-furan-2-carboxylic acid (81)

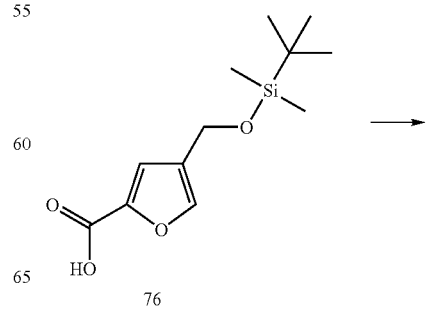

-continued

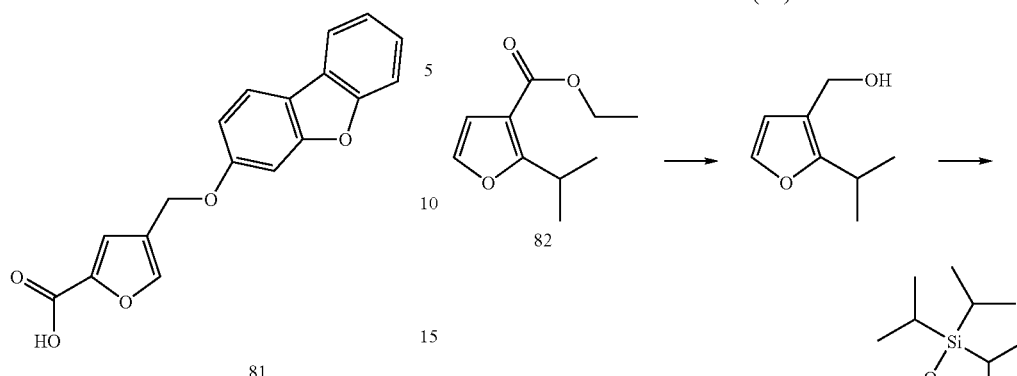

81

Compound (81) was prepared from compound (76) in an analogous manner to the methods described in Example 1(c). LC/MS System B; $R_t$=1.75 mins, m/z (ES⁻)=307 (M–H for $C_{18}H_{12}O_5$).

Example 22A

Synthesis of 4-(Biphenyl-4-yloxymethyl)-5-isopropyl-furan-2-carboxylic acid (85)

(a) 2-Isopropyl-furan-3-carboxylic acid ethyl ester (82)

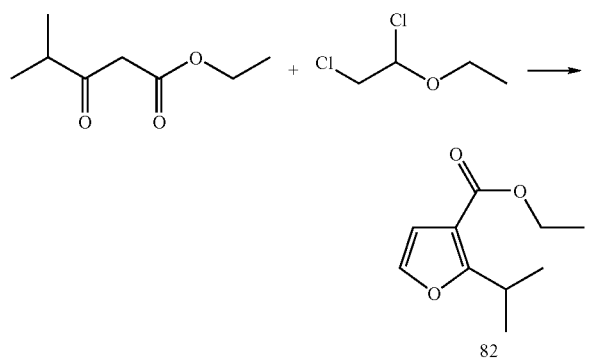

82

An ice-chilled solution of sodium hydroxide (1.9 g) in water (25 ml) was added, during 40 minutes, to a stirred solution of 4-methyl-3-oxo-pentanoic acid ethyl ester (3 g, 18.96 mmoles) and 1,2-dichloro-1-ethoxy-ethane (3.3 g, 35.19 mmole) in diethyl ether (15 ml) with ice bath cooling. When the addition was complete the mixture was stirred rapidly for 1 hour, then the ethereal layer was separated, washed with water and dried. Evaporation of the solvent gave a yellow oil, which was purified by flash chromatography using a gradient elution from neat pentane to pentane/diethyl ether 9:1 v/v as eluent, to afford compound 82 as an oil (2.4 g).

(b) Tri-isopropyl-(2-isopropyl-furan-3-ylmethoxy)-silane (83)

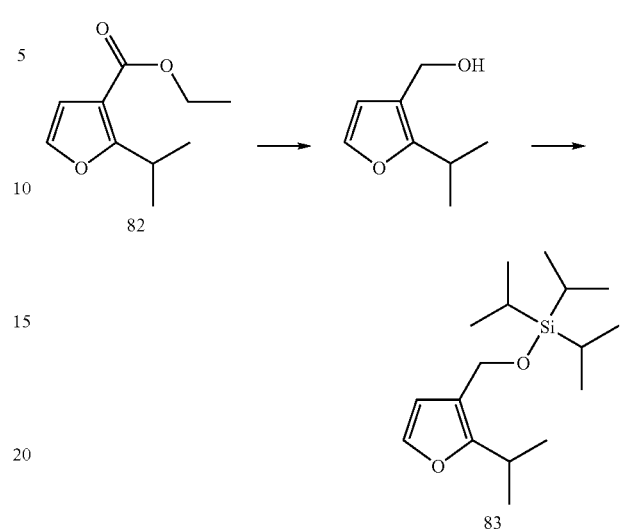

(i) A solution of 2-isopropyl-furan-3-carboxylic acid ethyl ester (82) (4.0 g, 21.95 mmoles) in tetrahydrofuran (70 ml) was treated portionwise during 0.5 h with lithium aluminium hydride (0.7 g, 18.4 mmoles) under a nitrogen atmosphere. When the addition was complete the mixture was stirred at room temperature for 18 hours, then quenched by the addition of excess acetone (1 ml) and then water (1 ml). After diluting with ethyl acetate (150 ml) the grey precipitate was removed by filtration. The filtrate was evaporated and the residue dissolved in diethyl ether and dried. Evaporation of the solvent afforded (2-isopropyl-furan-3-yl)-methanol. This material was used immediately in the next step.

(ii) A solution of the (2-isopropyl-furan-3-yl)-methanol from (i) in dry dichloromethane (120 ml) was treated with chloro-tri-isopropyl-silane (5.2 g, 27.0 mmoles) and imidazole (3.0 g, 44.0 mmoles) and the mixture was stirred overnight at room temperature. The reaction mixture was washed sequentially with 2M aqueous hydrochloric acid, water, saturated aqueous sodium bicarbonate, water and brine. After drying, evaporation of the solvents afforded a colourless oil, which heated at 125° C. under reduced pressure (10 millibars). The residue was compound 83 obtained as a pale yellow oil.

(c) 5-Isopropyl-4-triisopropylsilanyloxymethyl-furan-2-carboxylic acid (84)

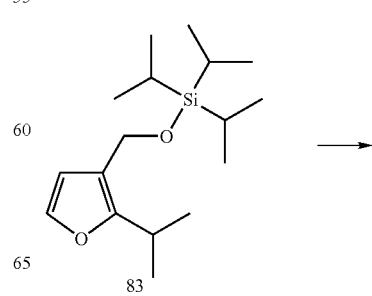

83

-continued

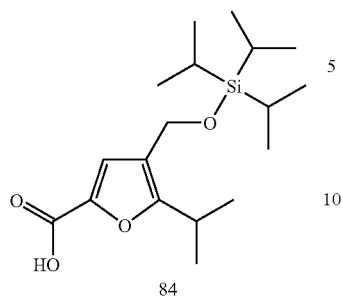
84

Compound (84) was prepared in the form of a cream solid from compound (83) by adapting the procedure of Example 1(b).

(d) 4-(Biphenyl-4-yloxymethyl)-5-isopropyl-furan-2-carboxylic acid (85)

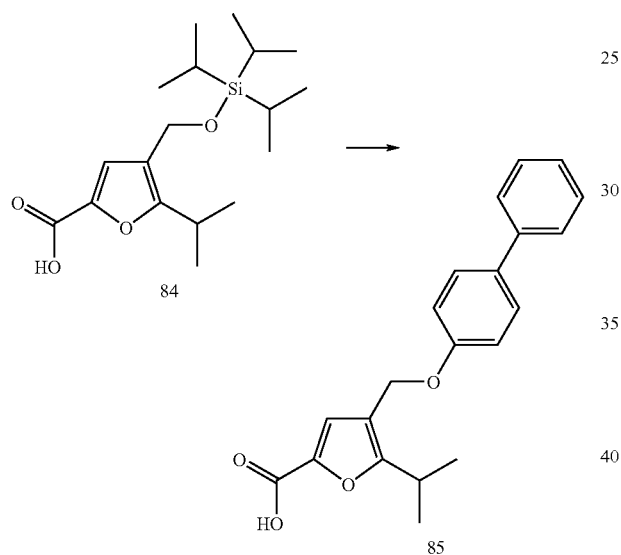

Compound (85) was prepared from compound (84) in an analogous manner to the methods described in Example 1(c).
LC/MS System B; $R_t$=1.93 mins, m/z (ES$^-$)=335 (M–H for $C_{21}H_{20}O_4$).

Example 22B

Synthesis of 5-Isopropyl-4-(4'-methoxy-biphenyl-4-yloxymethyl)-furan-2-carboxylic acid (86)

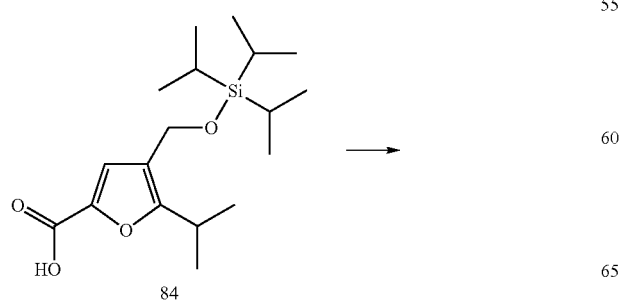
84

-continued

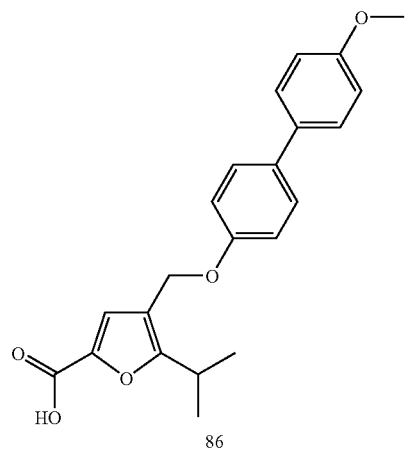
86

Compound (86) was prepared from compound (84) in an analogous manner to the methods described in Example 1(c). LC/MS System B; $R_t$=1.93 mins, m/z (ES$^-$)=365 (M–H for $C_{22}H_{22}O_5$).

Example 22C

Synthesis of 4-(Dibenzofuran-3-yloxymethyl)-5-isopropyl-furan-2-carboxylic acid (87)

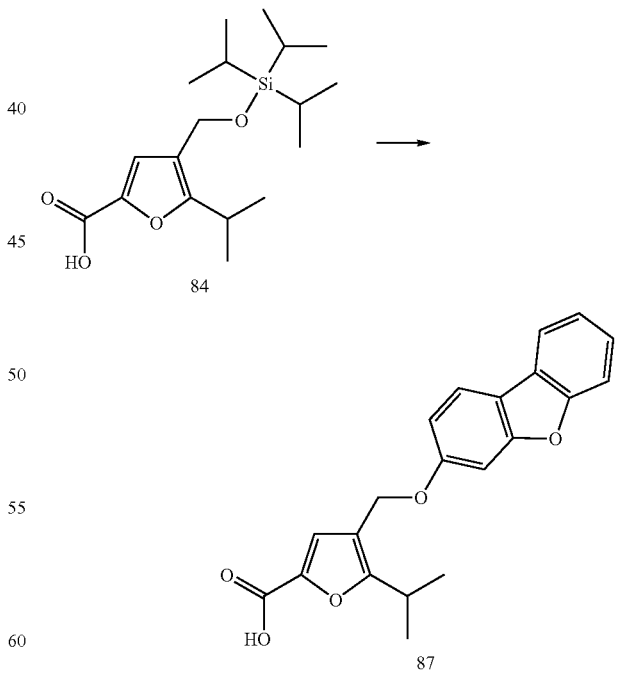

Compound (87) was prepared from compound (84) in an analogous manner to the methods described in Example 1(c). LC/MS System B; $R_t$=1.93 mins, m/z (ES$^-$)=349 (M–H for $C_{21}H_{18}O_5$).

Example 23A

Synthesis of 4-(Biphenyl-4-yloxymethyl)-5-trifluoromethyl-furan-2-carboxylic acid (90)

(a) Tri-isopropyl-(2-trifluoromethyl-furan-3-yl-methoxy)-silane (88)

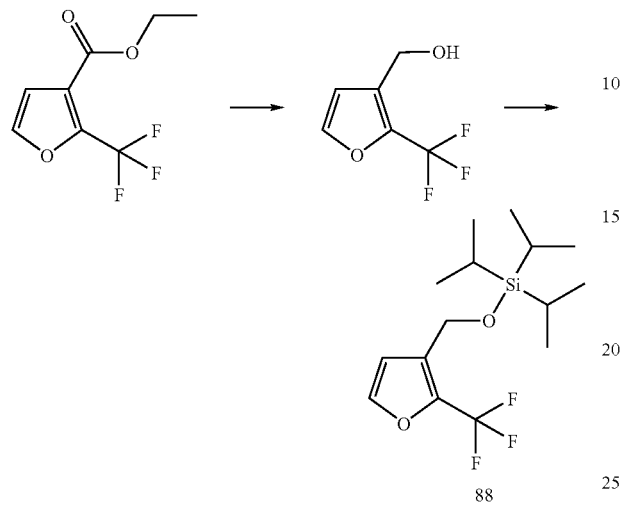

88

(i) A solution of 2-trifluoromethyl-furan-3-carboxylic acid ethyl ester (2.2 g, 10.5 mmoles) in tetrahydrofuran (150 ml) was treated portionwise during 0.5 h with lithium aluminium hydride (0.55 g, 14.5 mmoles) under a nitrogen atmosphere. When the addition was complete the mixture was stirred at room temperature for 18 h, then quenched by the addition of excess acetone (1 ml) and then water (1 ml). After diluting with ethyl acetate (200 ml) the grey precipitate was removed by filtration. The filtrate was dried and evaporation of the solvent afforded (2-trifluoromethyl-furan-3-yl)-methanol as a colourless oil. This material was used immediately in the next step.

(ii) A solution of the (2-trifluoromethyl-furan-3-yl)-methanol from (i) in dry dichloromethane (180 ml) was treated with chloro-tri-isopropyl-silane (2.6 g, 13.4 mmoles) and imidazole (1.45 g, 21.3 mmoles) and the mixture was stirred overnight at room temperature. Further aliquots of chloro-tri-isopropyl-silane (0.9 g, 4.64 mmoles) and imidazole (0.5 g, 7.34 mmoles) were added and the mixture was stirred for 3 h. The reaction mixture was diluted with water, the organic phase separated and washed sequentially with 0.1M aqueous hydrochloric acid, water, saturated aqueous sodium bicarbonate, water and brine. After drying, evaporation of the solvents afforded a colourless oil. The oil was distilled under reduced pressure (0.05 torr) in a Kugelruhr apparatus collecting the fraction boiling at an oven temperature of 125±20° C. to afford compound 88 as a colourless oil.

(b) 5-Trifluoromethyl-4-triisopropylsilanyloxymethyl-furan-2-carboxylic acid (89)

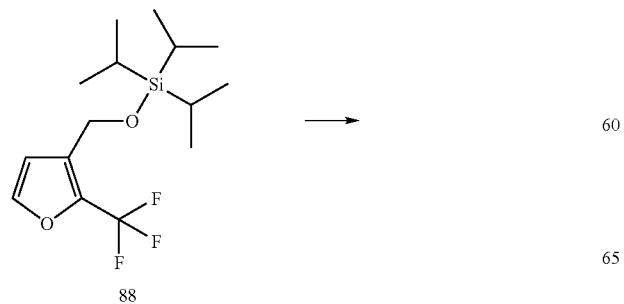

88

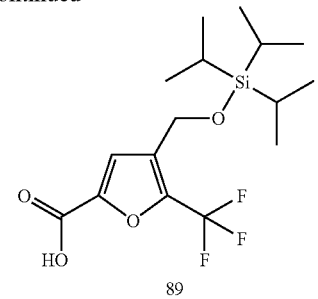

89

A stirred solution of tri-isopropyl-(2-trifluoromethyl-furan-3-ylmethoxy)-silane (88) (2.0 g, 6.24 mmoles) in tetrahydrofuran (70 ml) under argon was cooled to −78° C. and treated with sec-butyl-lithium (2.2 ml, 2.86 mmoles of a 1.3M solution in cyclohexane). After 1 h at −78° C., excess solid carbon dioxide, which had been pre-washed with tetrahydrofuran, was added and the mixture was allowed to warm to room temperature. The mixture was acidified to pH=4 with dilute aqueous hydrochloric acid and extracted several times with ethyl acetate. The combined extracts were dried ($MgSO_4$) and solvent removed to afford compound (89) as an off-white solid (1.2 g).

(c) 4-(Biphenyl-4-yloxymethyl)-5-trifluoromethyl-furan-2-carboxylic acid (90)

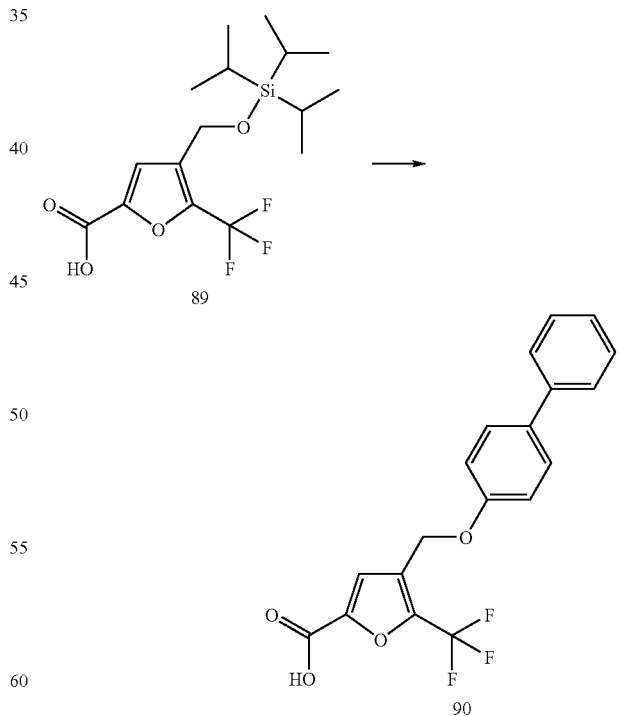

Compound (90) was prepared from compound (89) in an analogous manner to the methods described in Example 1(c). The product was purified by HPLC. LC/MS System B; $R_t$=1.97 mins, m/z (ES$^-$)=361 (M−H for $C_{19}H_{13}F_3O_4$).

Example 23B

Synthesis of 4-(Biphenyl-3-yloxymethyl)-5-trifluoromethyl-furan-2-carboxylic acid (91)

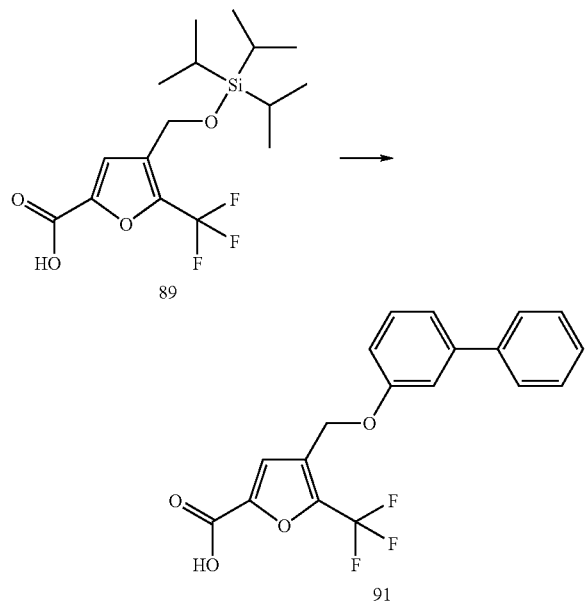

Compound (91) was prepared from compound (89) in an analogous manner to the methods described in Example 1(c). The product was purified by HPLC. LC/MS System B; $R_t$=1.97 mins, m/z (ES⁻)=361 (M–H for $C_{19}H_{13}F_3O_4$).

Example 23C

Synthesis of 4-(Dibenzofuran-2-yloxymethyl)-5-trifluoromethyl-furan-2-carboxylic acid (92)

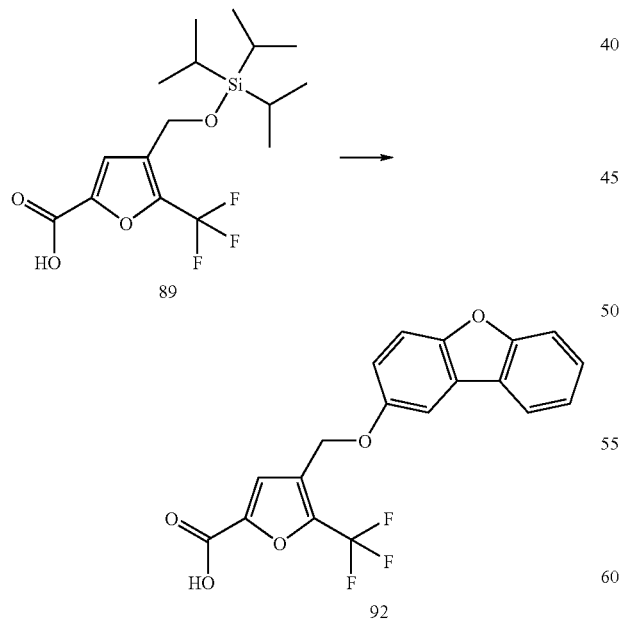

Compound (92) was prepared from compound (89) in an analogous manner to the methods described in Example 1(c). The product was purified by HPLC. LC/MS System B; $R_t$=1.97 mins, m/z (ES⁻)=375 (M–H for $C_{19}H_{11}F_3O_5$).

Example 23D 4-(4'-Cyano-biphenyl-4-yloxymethyl)-5-trifluoromethyl-furan-2-carboxylic acid (93)

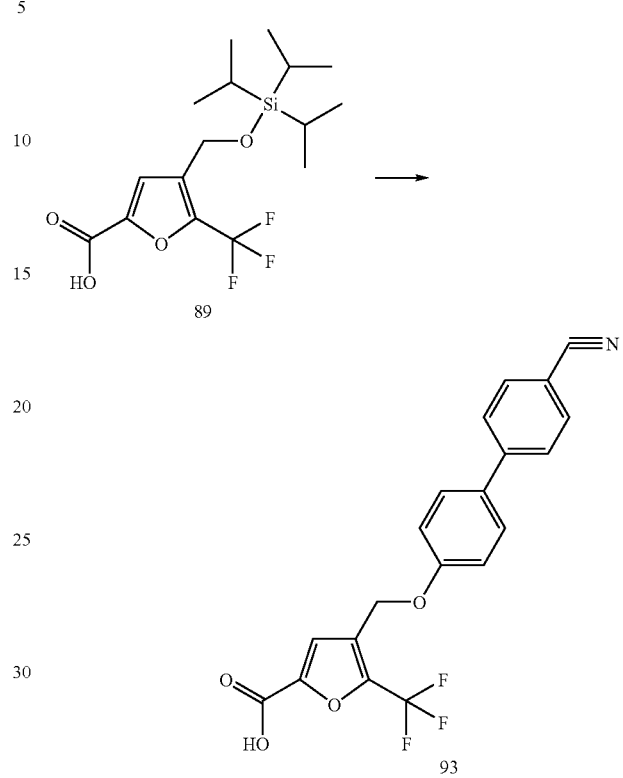

Compound (93) was prepared from compound (89) in an analogous manner to the methods described in Example 1(c).

The product was purified by HPLC. LC/MS System B; $R_t$=1.89 mins, m/z (ES⁻)=386 (M–H for $C_{20}H_{12}F_3NO_4$).

Example 23E

Synthesis of 4-(4'-Methoxy-biphenyl-4-yloxymethyl)-5-trifluoromethyl-furan-2-carboxylic acid (94)

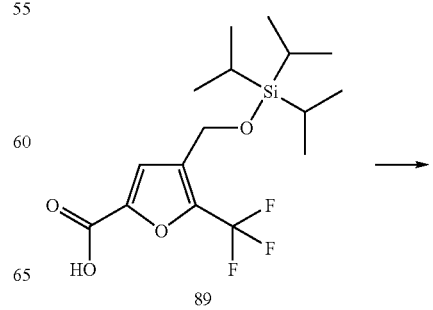

Example 23F

4-(Dibenzofuran-3-yloxymethyl)-5-trifluoromethyl-furan-2-carboxylic acid (95)

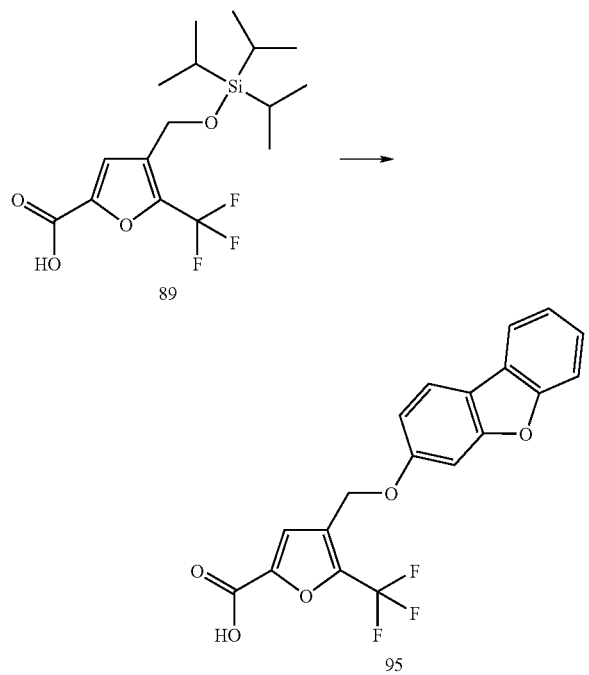

Compound (94) was prepared from compound (89) in an analogous manner to the methods described in Example 1(c). The product was purified by HPLC. LC/MS System B; $R_t$=1.97 mins, m/z (ES$^-$)=391 (M−H for $C_{20}H_{15}F_3O_5$).

Compound (95) was prepared from compound (89) in an analogous manner to the methods described in Example 1(c). The product was purified by HPLC. LC/MS System B; $R_t$=1.97 mins, m/z (ES$^-$)=375 (M−H for $C_{19}H_{11}F_3O_5$).

Example 24A

Synthesis of 4-(3',4'-Dimethoxy-biphenyl-4-yloxymethyl)-5-methyl-furan-2-carboxylic acid (96)

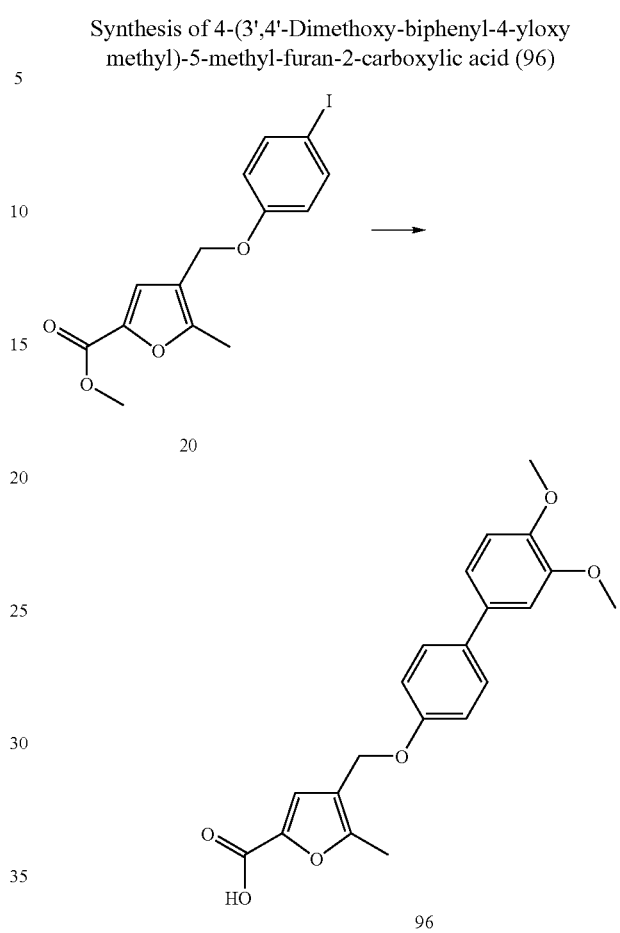

A stirred mixture of 4-(4-iodo-phenoxymethyl)-5-methyl-furan-2-carboxylic acid methyl ester (20) (0.025 g, 0.067 mmoles), (3,4-dimethoxyphenyl)-boronic acid (0.017 g, 0.093 mmoles), N,N-dimethylformamide (3 mL), potassium acetate (0.026 g) and [1,1'-bis(diphenylphosphino)ferrocene]dichloropalladium(II), complex with dichloromethane (1:1) (4 mg) was stirred at room temperature under an argon atmosphere for 24 h. The reaction mixture was diluted with water and extracted with ethyl acetate. The extracts were washed with water, dried and concentrated in vacuo. The residue was dissolved in a mixture of tetrahydrofuran/methanol (2:1 by volume) (2.5 mL) and 1.0 M aqueous lithium hydroxide solution (0.5 mL), and stirred for 16 hours. The reaction mixture was acidified to pH=6 using 1M hydrochloric acid and extracted with ethyl acetate (3×25 mL). The extracts were dried, concentrated in vacuo and the residue purified by HPLC (gradient: 30% acetonitrile/70% water containing 0.1% trifluoroacetic acid to 70% acetonitrile/30% water at a rate of 1%/min) to give compound 96 as a solid (15 mg). LC/MS System B; $R_t$=1.65 mins, m/z (ES$^-$)=367 (M−H for $C_{21}H_{20}O_6$).

Example 24B

Alternate synthesis of 4-(4-Benzo[1,3]dioxol-5-yl-phenoxymethyl)-5-methyl-furan-2-carboxylic acid (28)

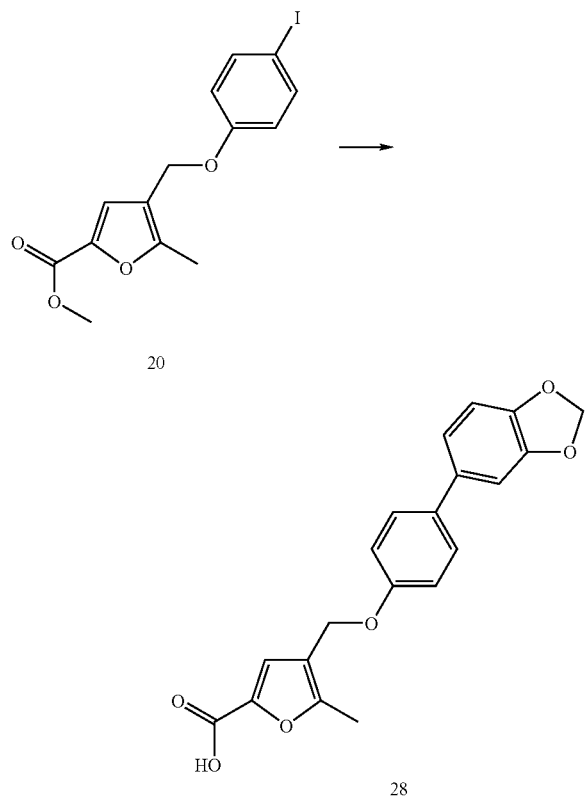

Compound (28) was prepared from compound (20) and (3,4-methylenedioxyphenyl)-boronic acid by adapting the procedure of Example 24A. LC/MS System B; $R_t$=1.76 mins, m/z (ES⁻)=351 (M−H for $C_{20}H_{16}O_6$)

Example 24C 4-(4'-Ethoxy-biphenyl-4-yloxymethyl)-5-methyl-furan-2-carboxylic acid (98)

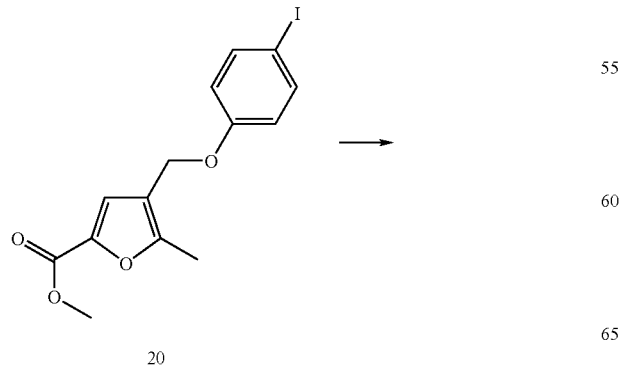

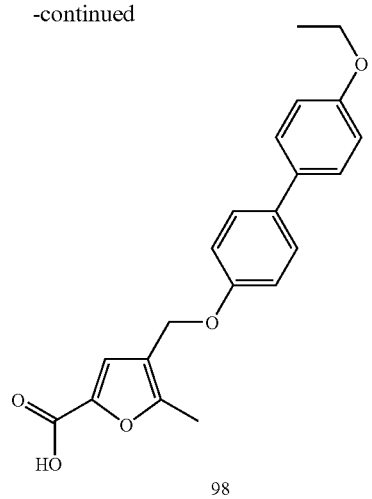

Compound (98) was prepared from compound (20) and (4-ethoxyphenyl)-boronic acid by an adapting the procedure of Example 24A. LC/MS System B; $R_t$=1.86 mins, m/z (ES⁻)=351 (M−H for $C_{21}H_{20}O_5$).

Example 25A

Synthesis of 4-(2'-Chloro-biphenyl-4-yloxymethyl)-5-methyl-furan-2-carboxylic acid (99)

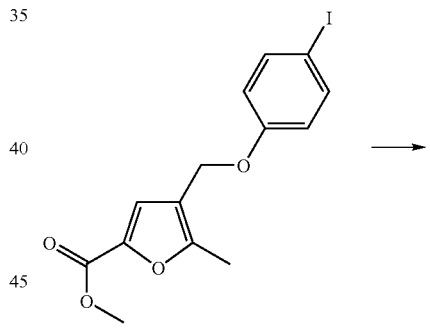

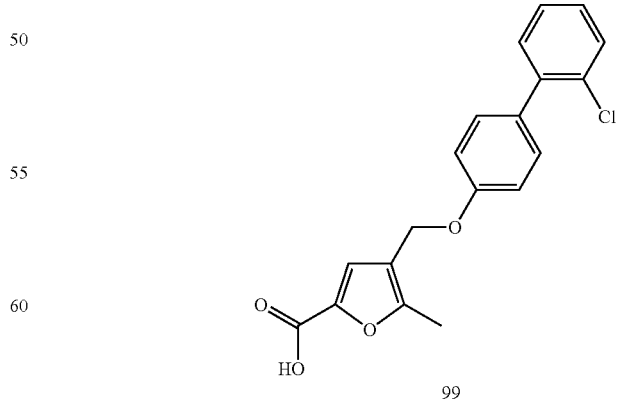

Compound (99) was prepared from compound (20) and (2-chlorophenyl)-boronic acid by adapting the procedure of Example 5(b). LC/MS System B; $R_t$=1.86 mins, m/z (ES⁻)= 341 and 343 (M−H for $C_{19}H_{15}ClO_4$).

Example 25B

Synthesis of 4-(2',6'-Difluoro-biphenyl-4-yloxymethyl)-5-methyl-furan-2-carboxylic acid (100)

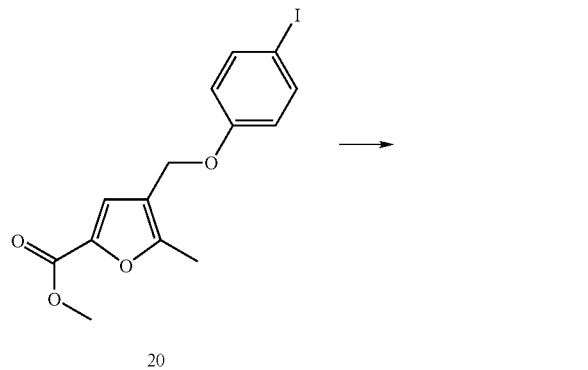

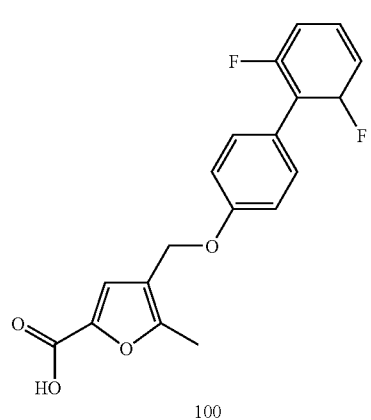

Compound (100) was prepared from compound (20) and (2,6-difluorophenyl)-boronic acid by adapting the procedure of Example 5(b). LC/MS System B; $R_t$=1.83 mins, m/z (ES⁻)= 343 (M−H for $C_{19}H_{14}F_2O_4$).

Example 25C

Synthesis of 5-Methyl-4-(2'-trifluoromethyl-biphenyl-4-yloxymethyl)-furan-2-carboxylic acid (102)

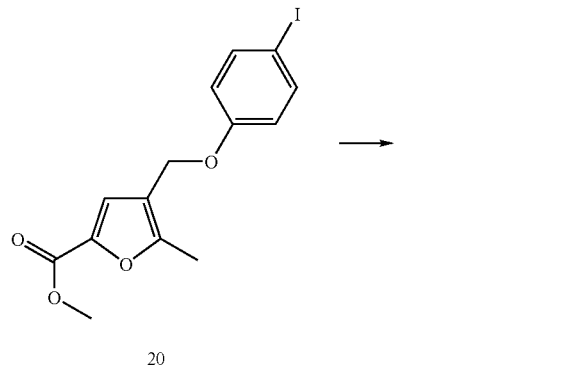

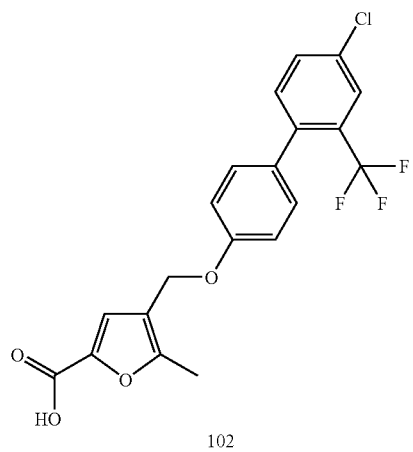

Compound (102) was prepared from compound (20) and (2-trifluoromethyl-phenyl)-boronic acid by adapting the procedure of Example 5(b). LC/MS System B; $R_t$=1.93 mins, m/z (ES⁻)=375 (M−H for $C_{20}H_{15}F_3O_4$).

Example 25D

Alternate synthesis of 4-(4'-Chloro-biphenyl-4-yloxymethyl)-5-methyl-furan-2-carboxylic acid (27)

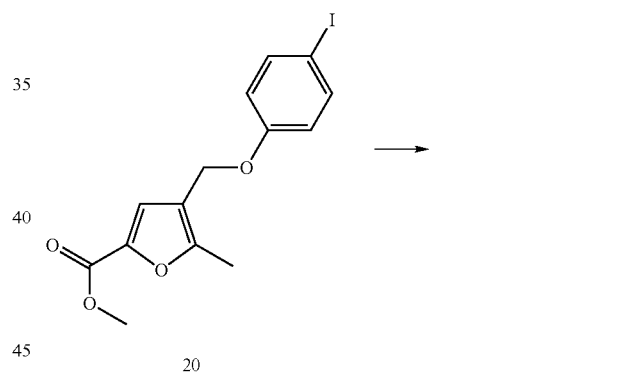

Compound (77) was prepared from compound (20) and (4-chloro-phenyl)-boronic acid by adapting the procedure of Example 5(b). LC/MS System B; $R_t$=1.93 mins, m/z (ES⁻)= 341 and 343 (M–H for $C_{19}H_{15}ClO_4$).

Example 25E

Synthesis of 4-(3'-Fluoro-biphenyl-4-yloxymethyl)-5-methyl-furan-2-carboxylic acid (104)

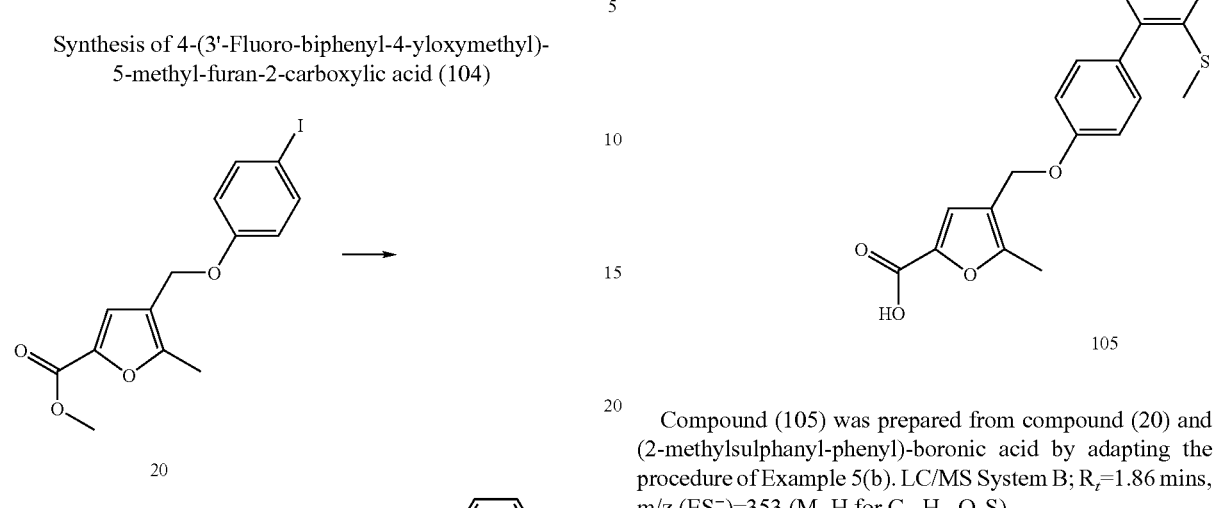

Compound (104) was prepared from compound (20) and (3-fluoro-phenyl)-boronic acid by adapting the procedure of Example 5(b). LC/MS System B; $R_t$=1.83 mins, m/z (ES)= 325 (M–H for $C_{19}H_{15}FO_4$).

Example 25F

5-Methyl-4-(2'-methylsulphanyl-biphenyl-4-yloxymethyl)-furan-2-carboxylic acid (105)

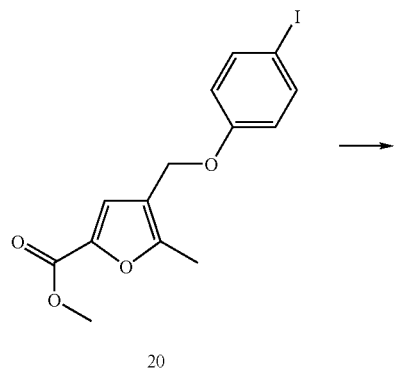

-continued

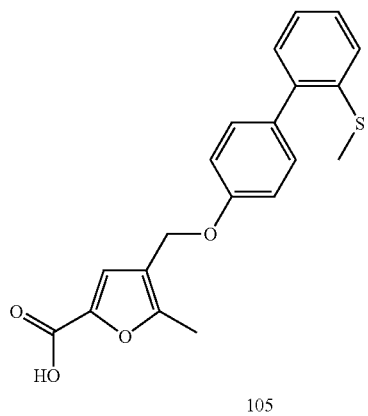

Compound (105) was prepared from compound (20) and (2-methylsulphanyl-phenyl)-boronic acid by adapting the procedure of Example 5(b). LC/MS System B; $R_t$=1.86 mins, m/z (ES⁻)=353 (M–H for $C_{20}H_{18}O_4S$).

Example 26A

Synthesis of 4-(3',4'-Dimethoxy-biphenyl-3-yloxymethyl)-5-methyl-furan-2-carboxylic acid (108)

(a) 4-(3-Iodo-phenoxymethyl)-5-methyl-furan-2-carboxylic acid methyl ester (106)

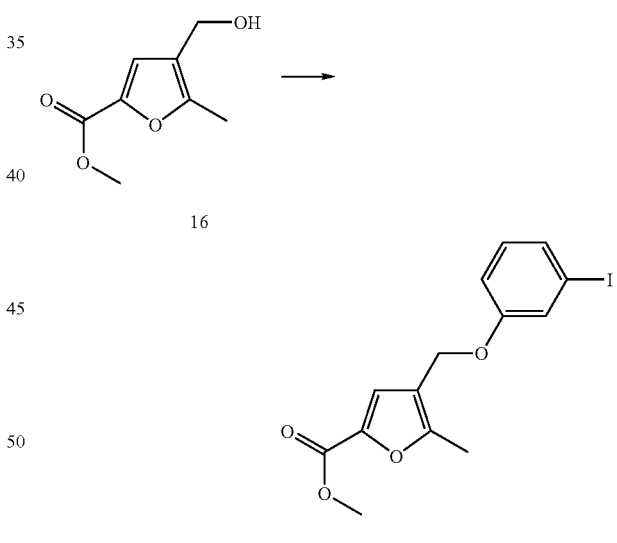

A mixture of 4-hydroxymethyl-5-methyl-furan-2-carboxylic acid methyl ester (16) (1.85 g, 10.9 mmoles), 3-iodophenyl (3.6 g, 16.35 mmoles), triphenylphosphine (4.3 g, 16.35 mmoles) in tetrahydrofuran (15 mL) was cooled to 0° C. Diisopropylazodicarboxylate (3.3 g, 16.35 mmoles) was added and the mixture was allowed to warm to room temperature, then stirred for 72 h. The tetrahydrofuran was evaporated and the residue purified by flash chromatography using hexane/ethyl acetate 7:3 v/v as eluent to give compound 106 (2.8 g). This was used directly in step (b).

(b) 4-(3-Iodo-phenoxymethyl)-5-methyl-furan-2-carboxylic acid (107)

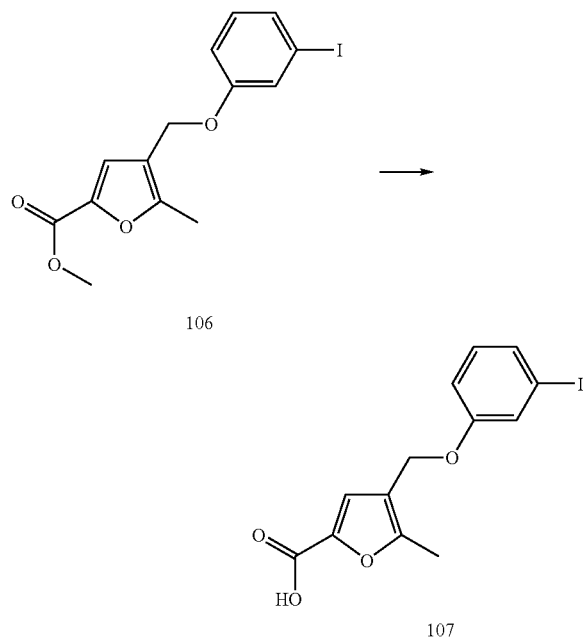

A mixture of 4-(3-iodo-phenoxymethyl)-5-methyl-furan-2-carboxylic acid methyl ester (106) (2.7 g, 7.25 mmoles) and lithium hydroxide (1.5 g, 36.25 mmoles) in tetrahydrofuran (25 ml) containing water (2 ml) was stirred at room temperature for 3 h. The tetrahydrofuran was evaporated, the residue was diluted with water and the mixture acidified to pH=1 with 1M aqueous hydrochloric acid. The precipitate was collected washed with water and dried at 70° C. in vacuo to give compound 107 (1.76 g) as a white solid. LC/MS System B; $R_t$=3.51 mins, m/z (ES−)=357 (M−H for $C_{13}H_{11}IO_4$).

(c) 4-(3',4'-Dimethoxy-biphenyl-3-yloxymethyl)-5-methyl-furan-2-carboxylic acid (108)

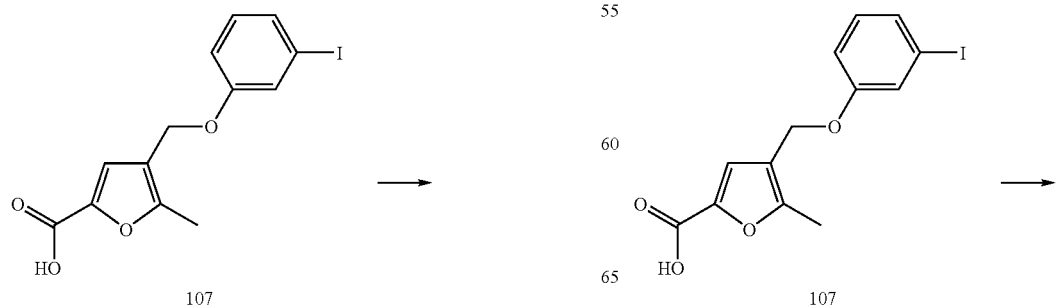

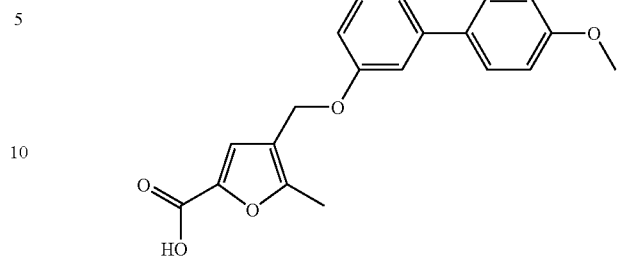

(i) 2-Chlorotrityl chloride resin (2.5 g of nominal loading 1.3 mmol/g) was swelled with dichloromethane (120 mL). After draining, a solution of 4-(3-iodo-phenoxymethyl)-5-methyl-furan-2-carboxylic acid (107) (1.16 g, 3.24 mmoles) and diisopropylethylamine (2.25 mL, 12.96 mmoles) in dichloromethane (20 mL) was added and the mixture was shaken at ambient temperature for 72 hours. The resin was drained, washed sequentially with dichloromethane/triethylamine/methanol (20:1:3 by volume) (3×30 mL), dichloromethane (4×30 mL), N,N-dimethylformamide (4×30 mL), dichloromethane (6×30 mL), and diethyl ether (3×30 mL) and then dried at 40° C. in vacuo.

(ii) The loaded resin (110 mg) from (i) was treated with a mixture of (3,4-dimethoxyphenyl)-boronic acid (119.7 mg, 0.65 mmoles), [1,1'-bis(diphenylphosphino) ferrocene] dichloropalladium(II) complex with dichloromethane (1:1) (10.6 mg) and potassium acetate (0.064 g, 0.65 mmoles) in N,N-dimethylformamide (5 mL) and the mixture was agitated at 100° C. for 24 hours. The resin was drained, washed sequentially with tetrahydrofuran/water (1:1 v/v) (2×5 mL), tetrahydrofuran (2×5 mL), N,N-dimethylformamide (3×5 mL), dichloromethane (6×5 mL) and diethyl ether (2×5 ml), then dried at 45° C. in vacuo.

The resin was treated with dichloromethane/trifluoroacetic acid (19:1 by volume) (3 mL) for 30 mins and the solution drained from the resin. This procedure was repeated. The combined solutions were concentrated in vacuo and the residue purified by hplc (gradient: 30% acetonitrile/70% water containing 0.1% trifluoroacetic acid to 90% acetonitrile/10% water at a rate of 1%/min) to afford compound 108 (24.9 mg) as a solid. LC/MS System B; $R_t$=1.69 mins, m/z (ES−)=367 (M−H for $C_{21}H_{20}O_6$).

Example 26B

Synthesis of 5-Methyl-4-(3'-trifluoromethyl-biphenyl-3-yloxymethyl)-furan-2-carboxylic acid (109)

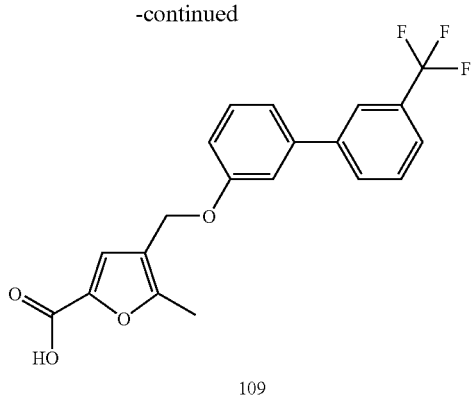

109

Compound (109) was prepared from compound (107) and (3-trifluoromethyl-phenyl)-boronic acid by adapting the procedure of Example 26A(c). LC/MS System B; $R_t$=1.97 mins, m/z (ES⁻)=375 (M–H for $C_{20}H_{15}F_3O_4$).

Example 27A

Synthesis of 4-(4'-Hydroxymethyl-biphenyl-4-yloxymethyl)-5-methyl-furan-2-carboxylic acid (110)

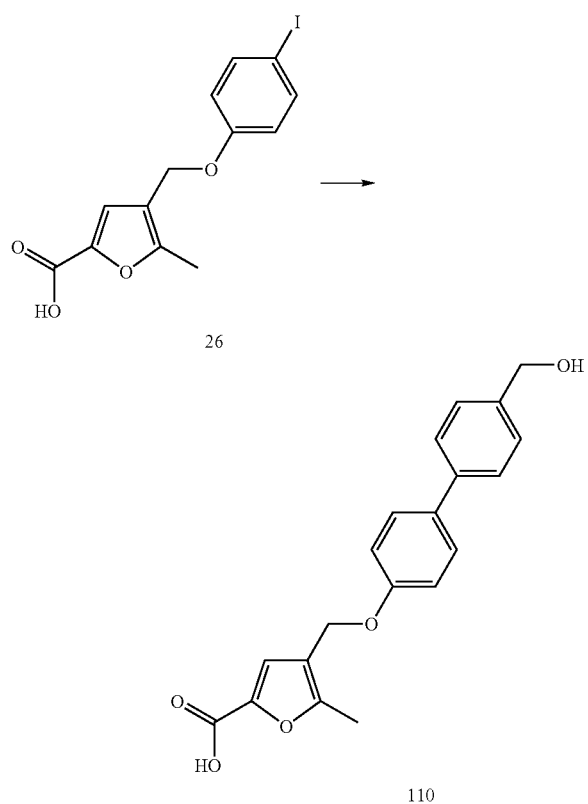

(i) 2-Chlorotrityl chloride resin (3.9 g of nominal loading 1.3 mmol/g) was swelled with dichloromethane (40 mL). After draining, a solution of 4-(4-iodo-phenoxymethyl)-5-methyl-furan-2-carboxylic acid (26) (1.78 g, 3.3 mmoles) and diisopropylethylamine (2.3 mL) in dichloromethane (30 mL) was added and the mixture was shaken at room temperature for 72 hours. The resin was drained, washed sequentially with dichloromethane/triethylamine/methanol (20:1:3 by volume) (3×30 mL), dichloromethane (6×30 mL), N,N-dimethylformamide (2×25 mL), dichloromethane (6×25 mL), and diethyl ether (2×25 mL) and dried at 40° C. in vacuo.

(ii) The loaded resin (110 mg) from (i) was treated with a mixture of (4-hydroxymethyl-phenyl)-boronic acid (98.3 mg, 0.65 mmoles), [1,1'-bis(diphenylphosphino) ferrocene] dichloropalladium(II) complex with dichloromethane (1:1) (10.6 mg) and cesium carbonate (0.212 g, 0.65 mmoles) in N,N-dimethylformamide (5 mL) and the mixture was agitated at 40° C. under a nitrogen atmosphere for 72 hours. The resin was drained, washed sequentially with tetrahydrofuran/water (1:1 v/v) (2×5 mL), tetrahydrofuran (2×5 mL), N,N-dimethylformamide (3×5 mL), dichloromethane (6×5 mL) and diethyl ether (2×5 ml), then dried at 45° C. in vacuo.

The resin was treated with dichloromethane/trifluoroacetic acid (19:1 by volume) (3 mL) for 30 mins and the solution drained from the resin. This procedure was repeated. The combined solutions were concentrated in vacuo and the residue purified by hplc (gradient: 30% acetonitrile/70% water containing 0.1% trifluoroacetic acid to 90% acetonitrile/10% water at a rate of 1%/min) to compound 110 (18.3 mg) as a solid. LC/MS System B; $R_t$=1.48 mins, m/z (ES⁻=337 (M–H for $C_{20}H_{18}O_5$).

Example 27B

Synthesis of 5-Methyl-4-(4'-methylsulphanyl-biphenyl-4-yloxymethyl)-furan-2-carboxylic acid (111)

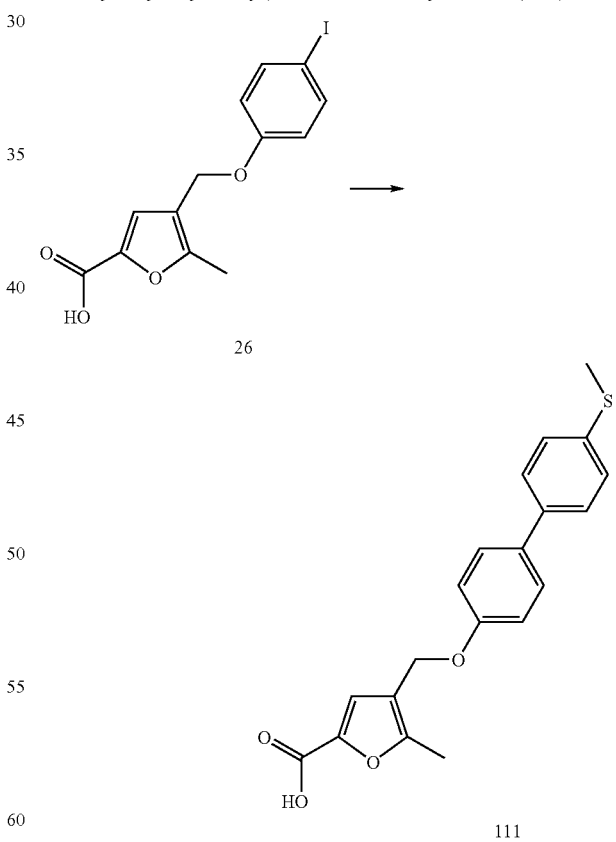

The loaded resin (110 mg) (from example 27A, (i)) was treated with a mixture of (4-methylsulphanyl-phenyl)-boronic acid (109 mg, 0.65 mmoles), [1,1'-bis(diphenylphosphino) ferrocene]dichloropalladium(II) complex with dichloromethane (1:1) (10.6 mg) and potassium acetate (0.064 g, 0.65 mmoles) in N,N-dimethylformamide (5 mL) and the mixture was agitated at 40° C. for 60 hours. The resin was drained, washed sequentially with tetrahydrofuran/water (1:1 v/v) (2×5 mL), tetrahydrofuran (2×5 mL), N,N-dimethylformamide (3×5 mL), dichloromethane (6×5 mL) and diethyl ether (2×5 ml), then dried at 45° C. in vacuo.

The resin was treated with dichloromethane/trifluoroacetic acid (19:1 by volume) (3 mL) for 30 mins and the solution drained from the resin. This procedure was repeated. The combined solutions were concentrated in vacuo and the residue purified by hplc (gradient: 30% acetonitrile/70% water containing 0.1% trifluoroacetic acid to 90% acetonitrile/10% water at a rate of 1%/min) to afford compound 111 (5.0 mg) as a solid. LC/MS System B; $R_t$=1.90 mins, m/z (ES$^-$)=353 (M–H for $C_{20}H_{18}O_4S$).

Example 27C

Synthesis of 4-(3'-Hydroxy-biphenyl-4-yloxymethyl)-5-methyl-furan-2-carboxylic acid (112)

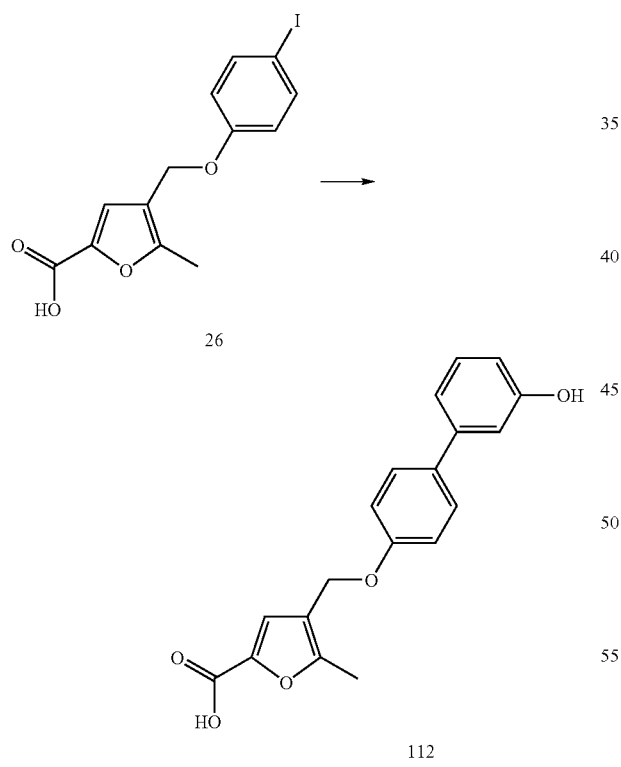

Compound (112) was prepared from compound (26) and (3-hydroxy-phenyl)-boronic acid by adapting the procedure of Example 27A. LC/MS System B; $R_t$=1.23 mins, m/z (ES$^-$)=323 (M–H for $C_{19}H_{16}O_5$).

Example 27D 4-(4'-Dimethylamino-biphenyl-4-yloxymethyl)-5-methyl-furan-2-carboxylic acid (113)

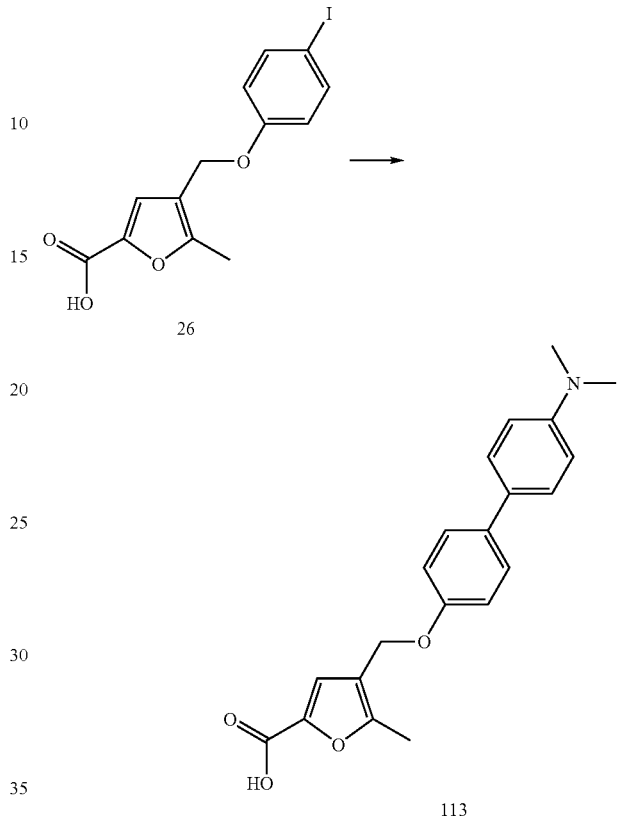

Compound (113) was prepared from compound (26) and (4-dimethylamino-phenyl)-boronic acid by adapting the procedure of Example 27B. LC/MS System B; $R_t$=1.83 mins, m/z (ES$^-$)=350 (M–H for $C_{21}H_{21}NO_4$).

Example 27E

Synthesis of 5-Methyl-4-(4'-trifluoromethoxy-biphenyl-4-yloxymethyl)-furan-2-carboxylic acid (114)

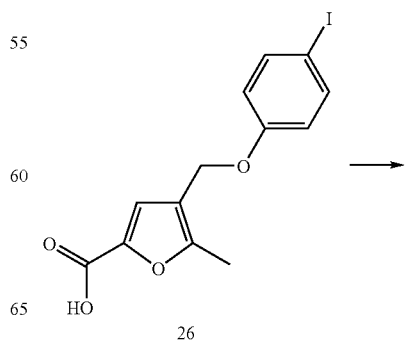

-continued

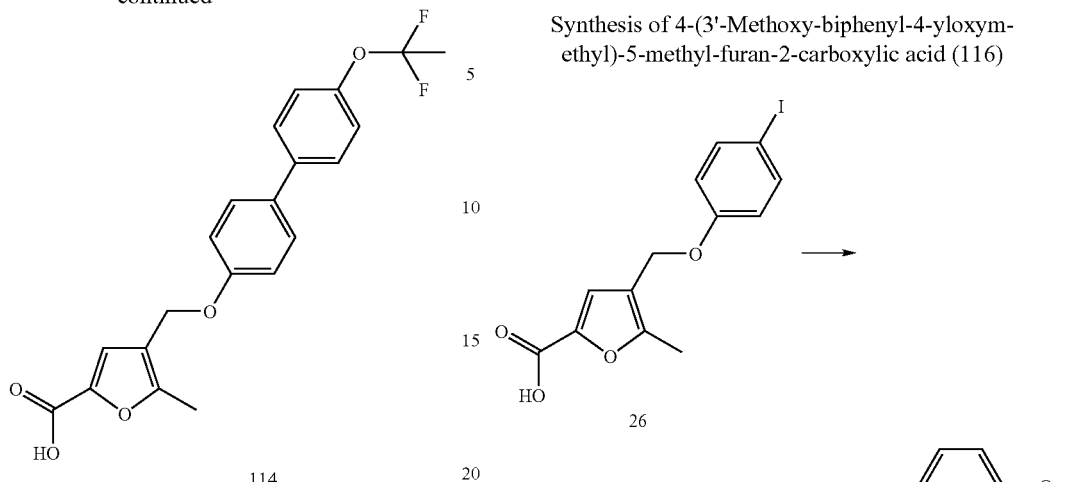

114

Compound (114) was prepared from compound (26) and (4-trifluoromethoxy-phenyl)-boronic acid by adapting the procedure of Example 27B. LC/MS System C; $R_t$=11.01 mins, m/z (ES$^-$)=391 (M–H for $C_{20}H_{15}F_3O_5$).

Example 27F

5-Methyl-4-(2'-trifluoromethoxy-biphenyl-4-yloxymethyl)-furan-2-carboxylic acid (115)

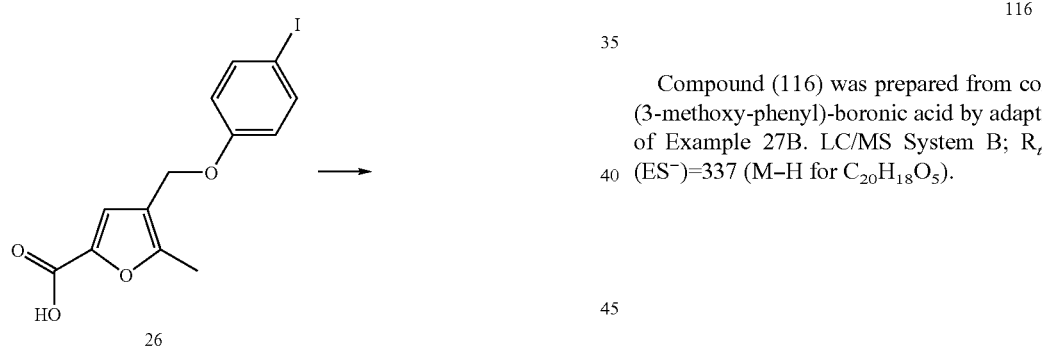

115

Compound (115) was prepared from compound (26) and (2-trifluoromethoxy-phenyl)-boronic acid by adapting the procedure of Example 27B. LC/MS System B; $R_t$=1.97 mins, m/z (ES$^-$)=391 (M–H for $C_{20}H_{15}F_3O_5$).

Example 27G

Synthesis of 4-(3'-Methoxy-biphenyl-4-yloxymethyl)-5-methyl-furan-2-carboxylic acid (116)

26

116

Compound (116) was prepared from compound (26) and (3-methoxy-phenyl)-boronic acid by adapting the procedure of Example 27B. LC/MS System B; $R_t$=1.79 mins, m/z (ES$^-$)=337 (M–H for $C_{20}H_{18}O_5$).

Example 27H

Synthesis of 4-(3'-Acetyl-biphenyl-4-yloxymethyl)-5-methyl-furan-2-carboxylic acid (117)

26

-continued

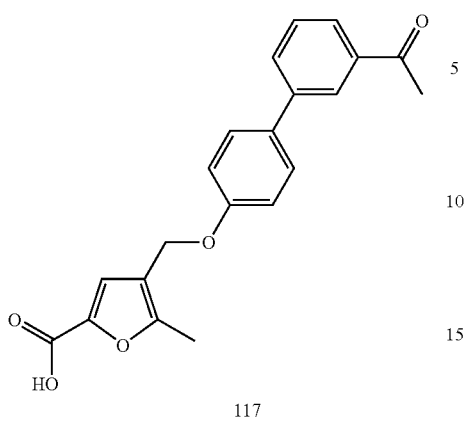

117

Compound (117) was prepared from compound (26) and (3-acetyl-phenyl)-boronic acid by adapting the procedure of Example 27B. LC/MS System B; $R_t$=1.69 mins, m/z (ES⁻)= 349 (M−H for $C_{21}H_{18}O_5$)

Example 27I

Synthesis of 4-(4'-Fluoro-biphenyl-4-yloxymethyl)-5-methyl-furan-2-carboxylic acid (118)

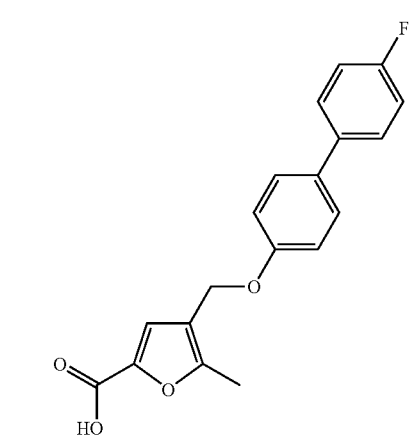

Compound (118) was prepared from compound (26) and (4-fluoro-phenyl)-boronic acid by adapting the procedure of Example 27B. LC/MS System B; $R_t$=1.79 mins, m/z (ES⁻)= 325 (M−H for $C_{19}H_{15}FO_4$).

Example 28

Synthesis of N-[4-(4'-Methoxy-biphenyl-4-yloxymethyl)-5-methyl-furan-2-carbonyl]-dimethylaminosulphonamide (122)

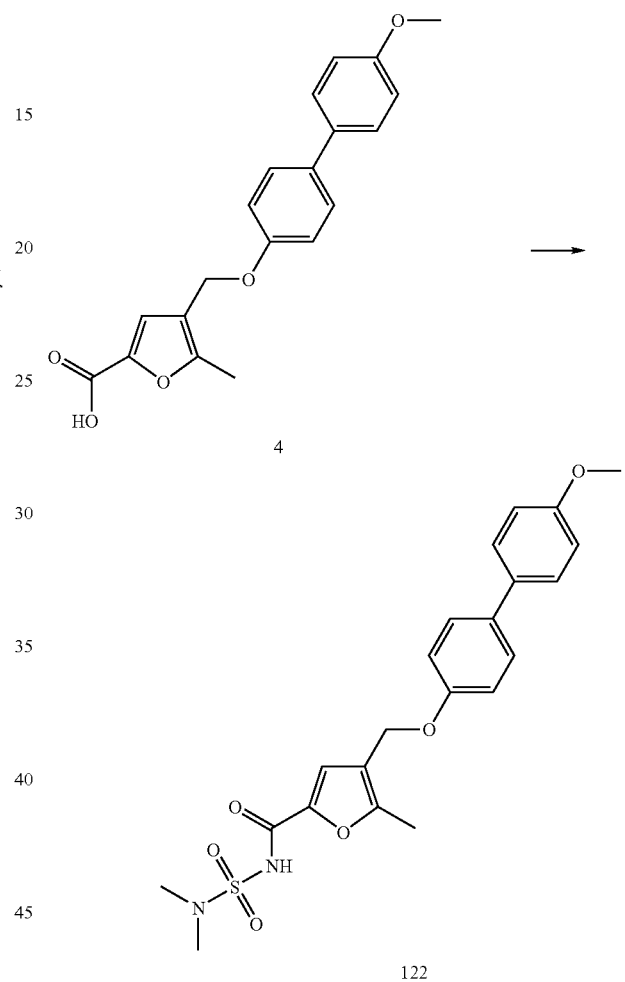

N,N-Dimethylsulphamide (73 mg, 0.59 mmoles), 1-[3-(dimethylamino)propyl]-3-ethylcarbodiimide hydrochloride (31 mg, 0.162 mmoles) and dimethyl-pyridin-4-yl-amine (1 mg) were added to a stirred solution of 4-(4'-methoxy-biphenyl-4-yloxymethyl)-5-methyl-furan-2-carboxylic acid (4)(50 mg, 0.148 mmoles) in dichloromethane (20 ml). The mixture was stirred under an argon atmosphere for 18 hours. After evaporation of the solvent, the residue was partitioned between dichloromethane and water. The aqueous phase was separated and extracted with dichloromethane. The combined extracts were washed with 1M aqueous hydrochloric acid, saturated aqueous sodium bicarbonate, brine and dried (MgSO₄). Evaporation of the solvent afforded the crude product, which was purified by HPLC (gradient: 30% acetonitrile/ 70% water containing 0.1% trifluoroacetic acid to 98% acetonitrile/2% water at a rate of 1%/min) to afford compound 122 (23.5 mg) as a white solid. LC/MS System C: $R_t$=3.67 mins, m/z (ES⁻)=443 ((M−H) for $C_{22}H_{24}N_2O_6S$).

Example 29

Alternative synthesis of 4-(4'-Fluoro-biphenyl-4-yloxymethyl)-5-methyl-furan-2-carboxylic acid (118)

(a) 3-(4-Iodo-phenoxymethyl)-2-methyl-furan (123)

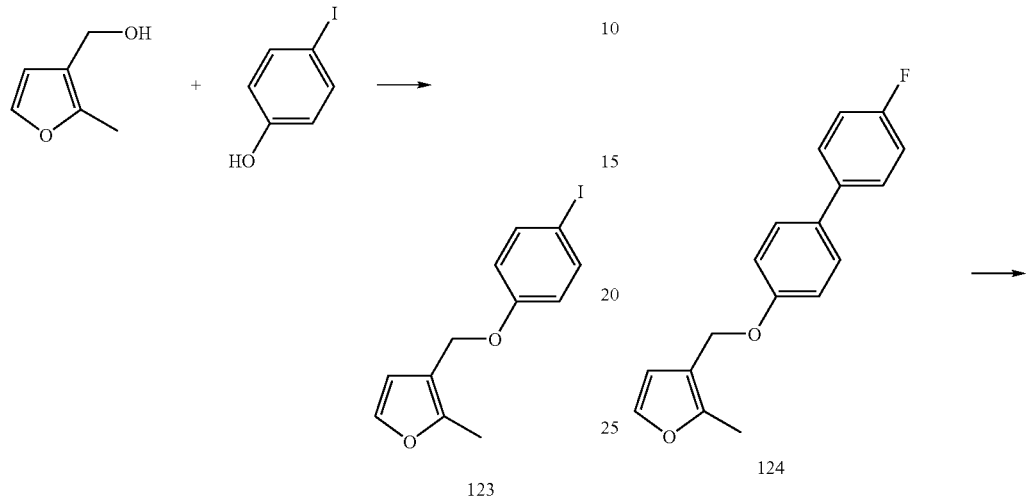

3-(4-Iodo-phenoxymethyl)-2-methyl-furan was prepared from (2-methyl-furan-3-yl)-methanol and 4-iodo-phenol in an analogous manner to that described in Example 14(a).

(b) 3-(4'-Fluoro-biphenyl-4-yloxymethyl)-2-methyl-furan (124)

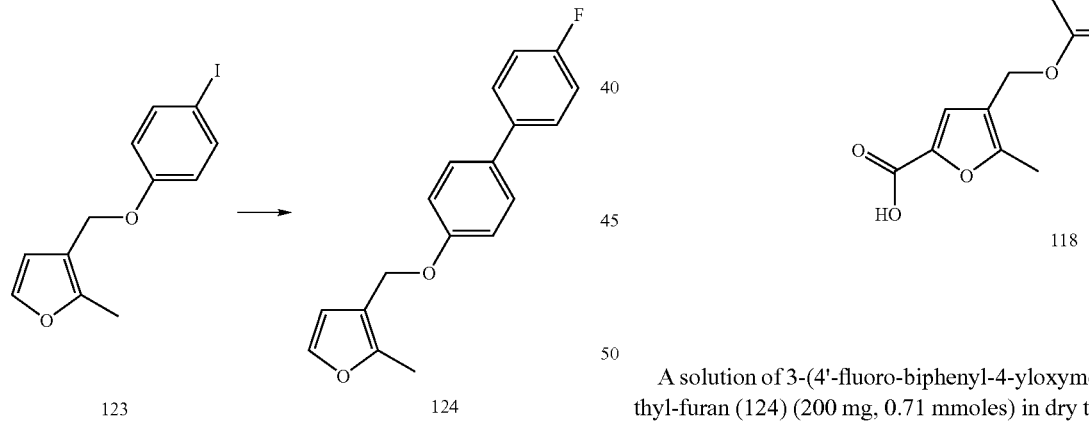

A mixture of (4-fluoro-phenyl)-boronic acid (300 mg, 2.1 mmoles), 3-(4-iodophenoxymethyl)-2-methyl-furan (123). (500 mg, 1.6 mmoles) and potassium acetate (0.6 g) in N,N-dimethylformamide (70 mL) was degassed, treated with [1,1'-bis(diphenylphosphino) ferrocene]dichloropalladium (II) complex with dichloromethane (1:1) (90 mg) and the mixture was agitated at 95° C. for 12 hours under an argon atmosphere. The mixture was concentrated in vacuo, partitioned between water (100 ml) and diethyl ether (200 ml). The aqueous phase was re-extracted with diethyl ether, and the combined ethereal phases were dried and evaporated. The residue was purified by flash chromatography, using diethyl ether as eluent, to afford compound 124 (200 mg) as a solid. This material was used directly.

(c) 4-(4'-Fluoro-biphenyl-4-yloxymethyl)-5-methyl-furan-2-carboxylic acid (118)

A solution of 3-(4'-fluoro-biphenyl-4-yloxymethyl)-2-methyl-furan (124) (200 mg, 0.71 mmoles) in dry tetrahydrofuran (15 ml) was cooled to −70° C. and stirred under an argon atmosphere. The mixture was treated dropwise with sec-butyl lithium (0.6 ml, of a 1.3M solution in cyclohexane) and stirred for 1 hour at −70° C. The reaction was quenched by the addition of excess solid carbon dioxide and allowed to warm to room temperature. The mixture was diluted with water, washed with diethyl ether and the aqueous phase acidified to pH=6 with dilute aqueous hydrochloric acid. The mixture was extracted with ethyl acetate, the extracts dried (MgSO$_4$), and solvent removed in vacuo to give a yellow oil. The oil was purified by hplc to afford compound 118 (15 mg) as a solid. LC/MS System A; $R_t$=3.71 mins, m/z (ES$^−$)=325 (M−H for $C_{19}H_{15}FO_4$).

Example 30

Synthesis of 4-(2'-Methoxy-biphenyl-4-yloxymethyl)-5-methyl-furan-2-carboxylic acid (126) and N-[4-(2'-Methoxy-biphenyl-4-yloxymethyl)-5-methyl-furan-2-carbonyl]-benzenesulfonamide (127)

(a) 4-(2'-Methoxy-biphenyl-4-yloxymethyl)-5-methyl-furan-2-carboxylic acid methyl ester (125)

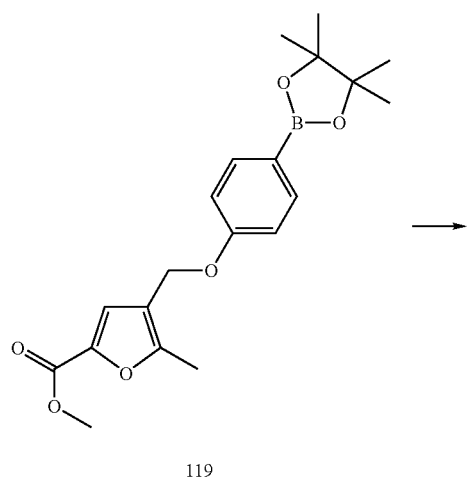

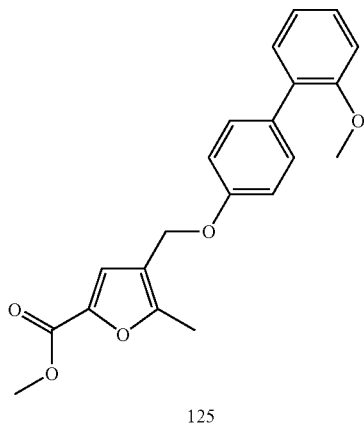

A degassed mixture of 5-methyl-4-[4-(4,4,5,5-tetramethyl-[1,3,2]dioxaborolan-2-yl)-phenoxymethyl]-furan-2-carboxylic acid methyl ester (119) (200 mg, 0.54 mmoles), 1-bromo-2-methoxy-benzene (80 µl, 0.65 mmoles), 2M aqueous cesium carbonate (11.0 ml) and), [1,1'-bis(diphenylphosphino) ferrocene]dichloropalladium(II) complex with dichloromethane (1:1) (44 mg) in 1,4-dioxan (30 ml), under an argon atmosphere was heated at 95° C. for 18 hours. After cooling, the mixture was concentrated, the residue dissolved in ethyl acetate and washed with brine and dried. After evaporation of the solvent, the residue was purified by flash chromatography using cyclohexane/ethyl acetate 9:1 v/v as eluent to afford compound 125 (40 mg) as an oil. LC/MS System A; $R_t$=4.14 mins, m/z (ES$^+$)=353 weak (M+H for $C_{21}H_{20}O_5$).

(b) 4-(2'-Methoxy-biphenyl-4-yloxymethyl)-5-methyl-furan-2-carboxylic acid (126)

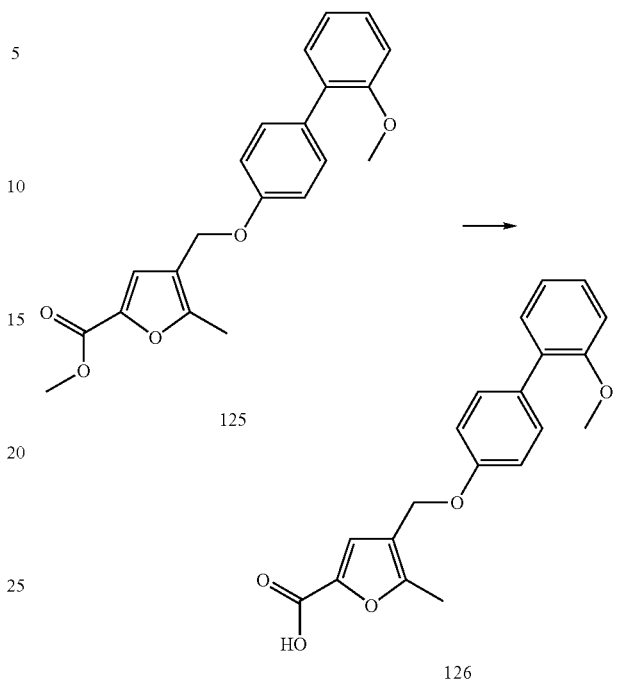

A solution of 4-(2'-methoxy-biphenyl-4-yloxymethyl)-5-methyl-furan-2-carboxylic acid methyl ester (125) (40 mg, 0.11 mmoles) in dry tetrahydrofuran (25 ml) was treated with potassium trimethylsilanoate (73 mg, 0.56 mmoles) and the mixture stirred under an argon atmosphere for 16 h. After evaporation of the solvent the residue was acidified to pH=2 with 0.1M aqueous hydrochloric acid and the mixture extracted with ethyl acetate. The dried extracts were evaporated and the residue pumped under high vacuum at 40° C. to afford compound 126 (29 mg) as an off-white solid. LC/MS System D; $R_t$=8.30 mins, m/z (ES$^+$) 339 (M+H for $C_{20}H_{18}O_5$).

(c) N-[4-(2'-Methoxy-biphenyl-4-yloxymethyl)-5-methyl-furan-2-carbonyl]-benzenesulphonamide (127)

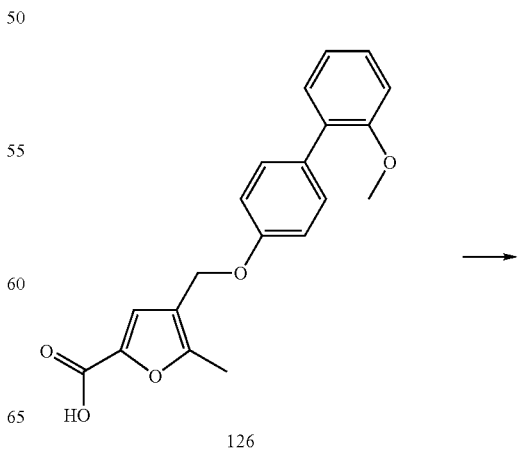

-continued

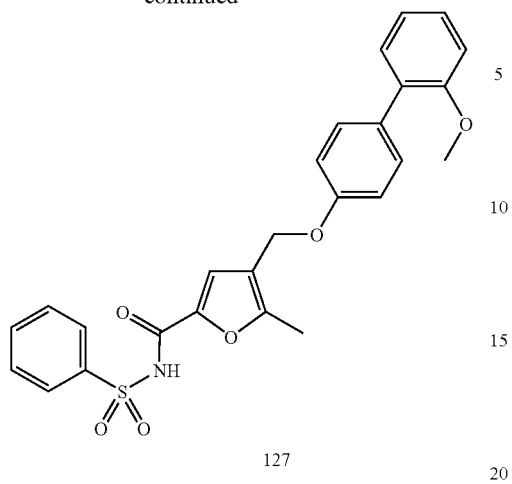

127

Compound (127) was prepared from compound (126) by adapting the procedure of Example 2A. LC/MS System D; $R_t$=9.17 mins, m/z (ES$^+$)=478 (M+H for $C_{26}H_{23}NO_6S$).

Example 31

Synthesis of 4-(4'-Difluoromethoxy-biphenyl-4-yloxymethyl)-5-methyl-furan-2-carboxylic acid (129), N-[4-(4'-Difluoromethoxy-biphenyl-4-yloxymethyl)-5-methyl-furan-2-carbonyl]-benzenesulfonamide (130) and 3,5-Dimethyl-isoxazole-4-sulfonic acid [4-(4'-difluoromethoxy-biphenyl-4-yloxymethyl)-5-methyl-furan-2-carbonyl]-amide (131)

(a) 4-(4'-difluoromethoxy-biphenyl-4-yloxymethyl)-5-methyl-furan-2-carboxylic acid methyl ester (128)

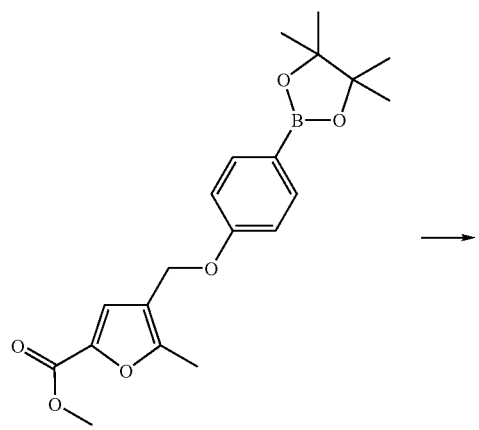

119

-continued

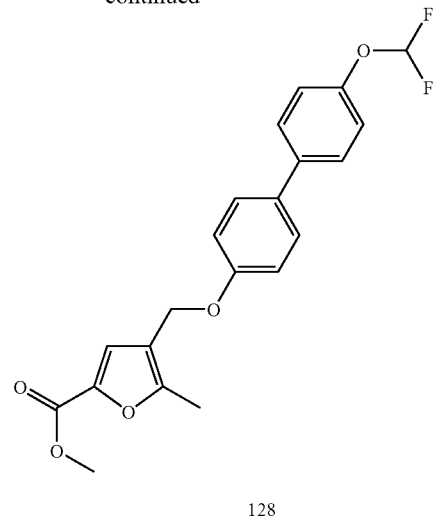

128

A degassed mixture of 5-methyl-4-[4-(4,4,5,5-tetramethyl-[1,3,2]dioxaborolan-2-yl)-phenoxymethyl]-furan-2-carboxylic acid methyl ester (119) (200 mg, 0.54 mmoles), 4-difluoromethoxy-1-iodo-benzene (175 mg, 0.65 mmoles), 2M aqueous cesium carbonate (0.81 ml) and), [1,1'-bis(diphenylphosphino) ferrocene]dichloropalladium(II) complex with dichloromethane (1:1) (20 mg) in 1,4-dioxan (10 ml), under an argon atmosphere was heated at 80° C. for 20 h. Further quantities of 4-difluoromethoxy-1-iodo-benzene (87.5 mg, 0.0.27 mmoles) and [1,1'-bis(diphenylphosphino)ferrocene]dichloropalladium(II) complex with dichloromethane (1:1) (10 mg) were added and heating at 80° C. was continued for 4 hours. After cooling, the mixture was concentrated. The residue was dissolved in dichloromethane and washed with water and brine, and dried. The solvent was evaporated and the residue was purified by flash chromatography using petrol (40-60°)/diethyl ether 9:1 v/v as eluent to afford compound 128 (120 mg) as a wax. LC/MS System A; $R_t$=4.14 mins.

(b) 4-(4'-Di fluoromethoxy-biphenyl-4-yloxymethyl)-5-methyl-furan-2-carboxylic acid (129)

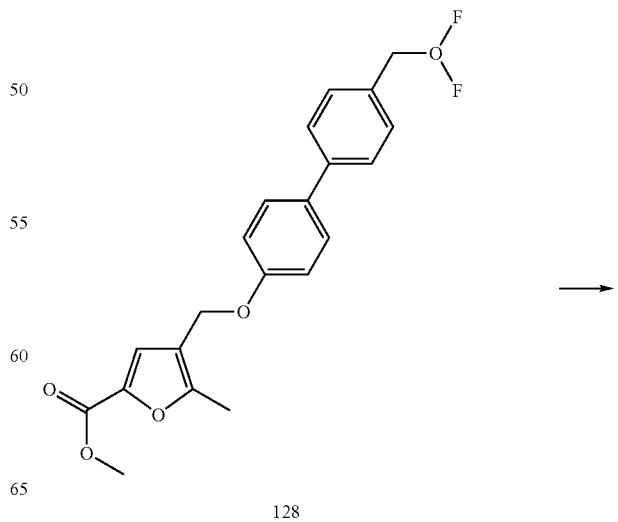

128

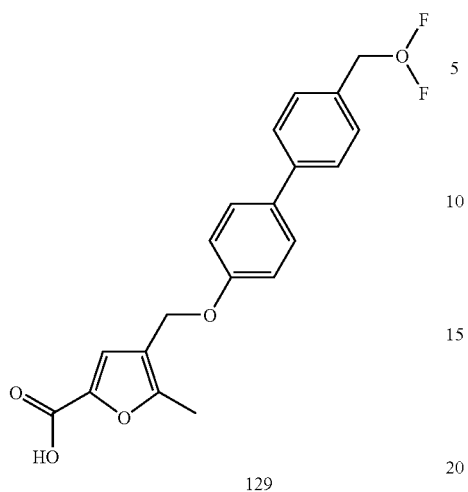

129

Compound (129) was prepared from compound (128) by adapting the procedure of Example 30(b). LC/MS System C; $R_t$=8.53 mins, m/z (ES$^-$)=373 (M–H for $C_{20}H_{16}F_2O_5$).

(c) N-[4-(4'-Difluoromethoxy-biphenyl-4-yloxymethyl)-5-methyl-furan-2-carbonyl]-benzenesulphonamide (130)

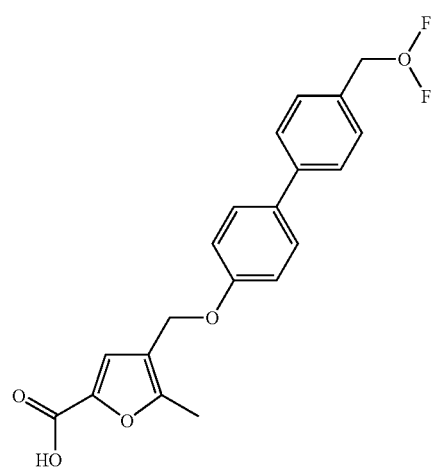

129

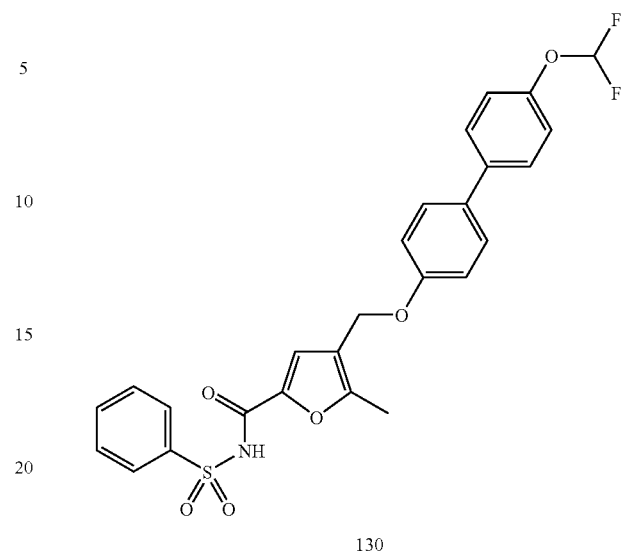

130

Compound (130) was prepared from compound (129) by adapting the procedure of Example 2A. LC/MS System C; $R_t$=9.50 mins, m/z (ES$^-$)=512 (M–H for $C_{26}H_{21}F_2NO_6S$).

(d) 3,5-Dimethyl-isoxazole-4-sulphonic acid [4-(4'-difluoromethoxy-biphenyl-4-yloxymethyl)-5-methyl-furan-2-carbonyl]-amide (131)

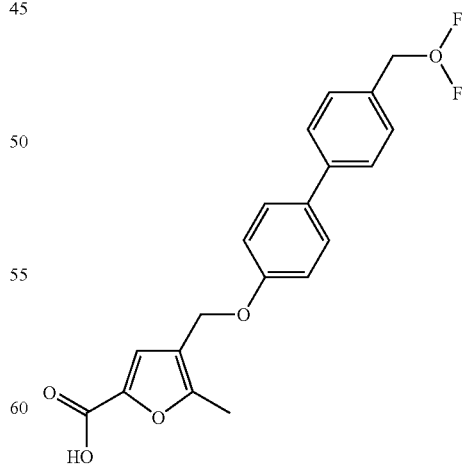

129

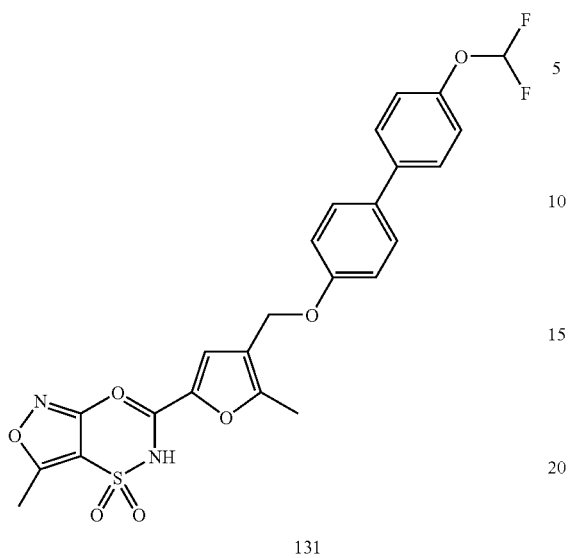

131

Compound (131) was prepared from compound (129) by adapting the procedure of Example 2A. LC/MS System C; $R_t$=9.47 mins, m/z (ES⁻)=531 (M−H for $C_{25}H_{22}F_2N_2O_7S$).

Example 32

Synthesis of N-{4-[4-(5-Methoxy-pyridin-2-yl)-phenoxymethyl]-5-methyl-furan-2-carbonyl}-benzenesulfonamide (132), 3,5-Dimethyl-isoxazole-4-sulfonic acid {4-[4-(5-methoxy-pyridin-2-yl)-phenoxymethyl]-5-methyl-furan-2-carbonyl}-amide (133), N-{4-[4-(5-Methoxy-pyridin-2-yl)-phenoxymethyl]-5-methyl-furan-2-carbonyl}-2-methyl-benzenesulfonamide (134) and N-{4-[4-(5-Methoxy-1-oxy-pyridin-2-yl)-phenoxymethyl]-5-methyl-furan-2-carbonyl}-benzenesulfonamide (135).

(a) N-{4-[4-(5-Methoxy-pyridin-2-yl)-phenoxymethyl]-5-methyl-furan-2-carbonyl}-benzenesulphonamide (132)

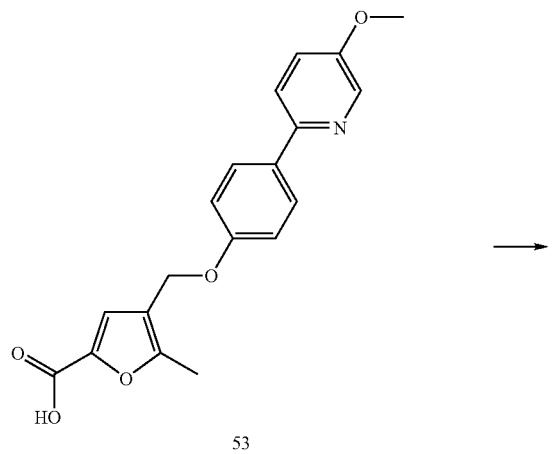

53

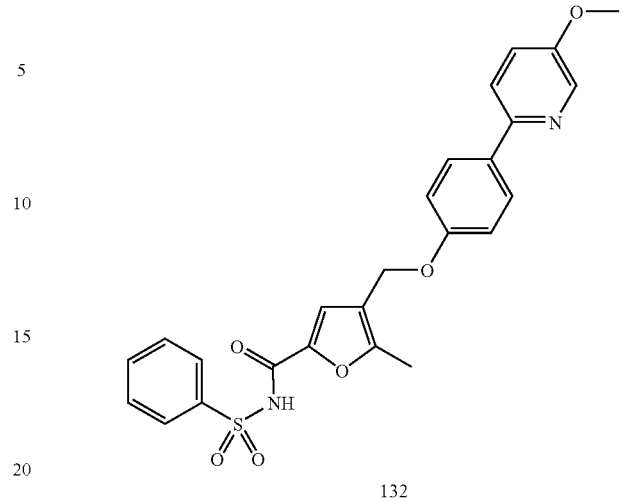

132

Compound (132) was prepared from compound (53) by adapting the procedure of Example 2A. LC/MS System D; $R_t$=7.10 mins, m/z (ES⁺)=479 (M+H for $C_{25}H_{22}N_2O_6S$).

(b) 3,5-Dimethyl-isoxazole-4-sulphonic acid {4-[4-(5-methoxy-pyridin-2-yl)-phenoxymethyl]-5-methyl-furan-2-carbonyl}-amide (133)

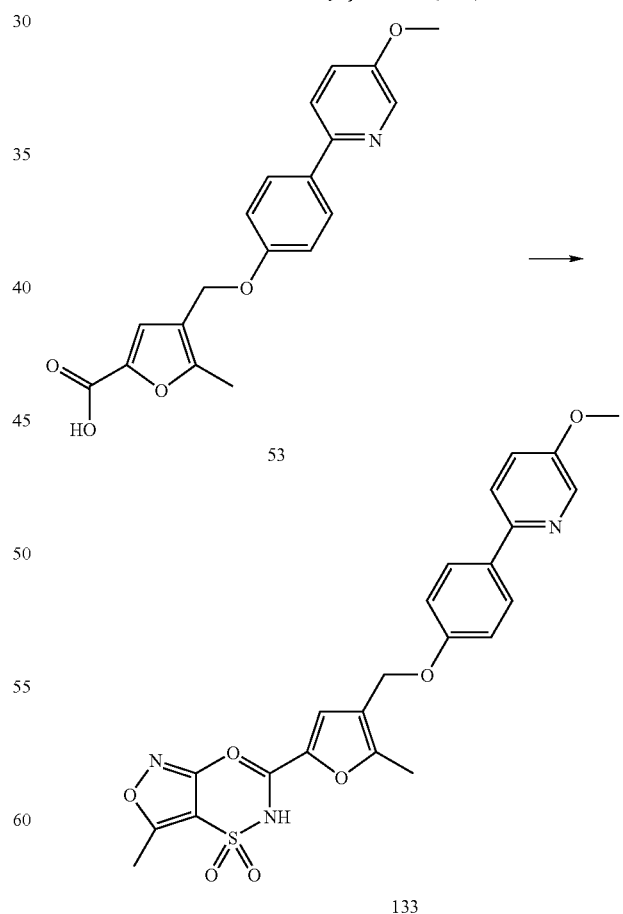

Compound (133) was prepared from compound (53) by adapting the procedure of Example 2A. LC/MS System D; $R_t$=7.83 mins, m/z (ES⁺)=498 (M+H for $C_{24}H_{23}N_3O_7S$).

(c) N-{4-[4-(5-Methoxy-pyridin-2-yl)-phenoxymethyl]-5-methyl-furan-2-carbonyl}-2-methyl-benzenesulphonamide (134)

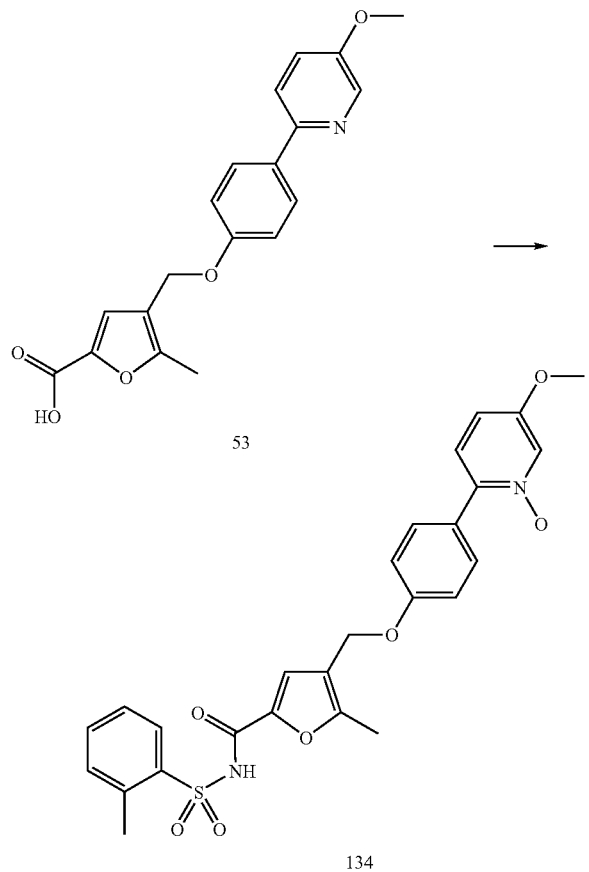

Compound (134) was prepared from compound (53) by adapting the procedure of Example 2A. LC/MS System D; $R_t$=8.43 mins, m/z (ES$^+$)=493 (M+H for $C_{26}H_{24}N_2O_6S$).

(d) N-{4-[4-(5-Methoxy-1-oxy-pyridin-2-yl)-phenoxymethyl]-5-methyl-furan-2-carbonyl}-benzenesulphonamide (135)

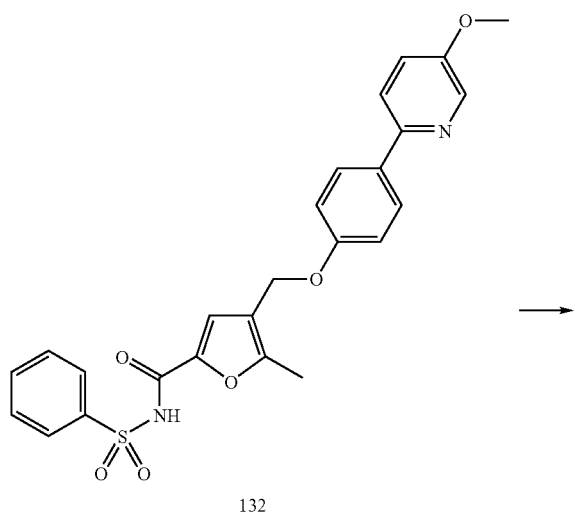

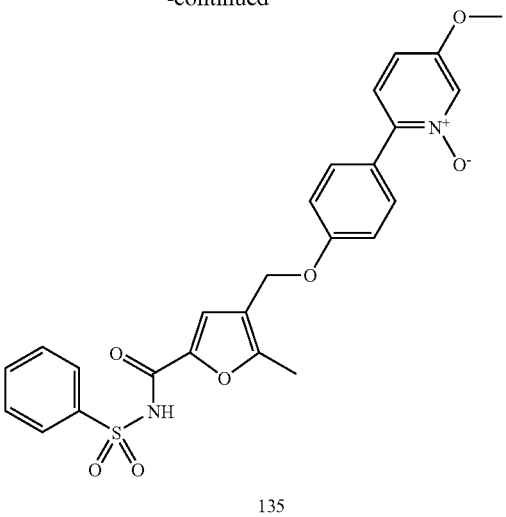

A solution of N-{4-[4-(5-methoxy-pyridin-2-yl)-phenoxymethyl]-5-methyl-furan-2-carbonyl}-benzenesulphonamide (132) (25 mg, 0.042 mmoles) in a mixture of methanol (0.5 ml) and chloroform (1 ml) was treated dropwise with a solution of 3-chloro-benzenecarboperoxoic acid (10.6 mg of 72% wt. % peracid) in chloroform (1.5 ml). After stirring for 21 hours at room temperature, a further quantity of 3-chloro-benzenecarboperoxoic acid (8.0 mg of 72% wt. % peracid) in chloroform (1 ml) was added and the mixture stirred for 6 hours. Another aliquot of 3-chloro-benzenecarboperoxoic acid (8.0 mg of 72% wt. % peracid) in chloroform (1 ml) was added and stirring continued for 21 hours. The mixture was evaporated and the residue was purified by HPLC (gradient: 25% acetonitrile/75,% water containing 0.1% trifluoroacetic acid to 98% acetonitrile/2% water at a rate of 1%/min) to afford compound 135 (6 mg) as a solid. LC/MS System A; $R_t$=3.03 mins, m/z (ES$^+$)=495 (M+H for $C_{25}H_{22}N_2O_7S$).

Example 33

Synthesis of 5-Methyl-4-(4-pyrimidin-2-yl-phenoxymethyl)-furan-2-carboxylic acid (137) and N-[5-Methyl-4-(4-pyrimidin-2-yl-phenoxymethyl)-furan-2-carbonyl]-benzenesulfonamide (138)

(a) 5-Methyl-4-(4-pyrimidin-2-yl-phenoxymethyl)-furan-2-carboxylic acid methyl ester (136)

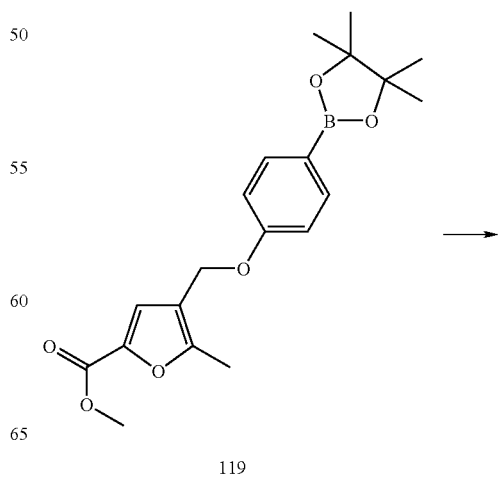

-continued

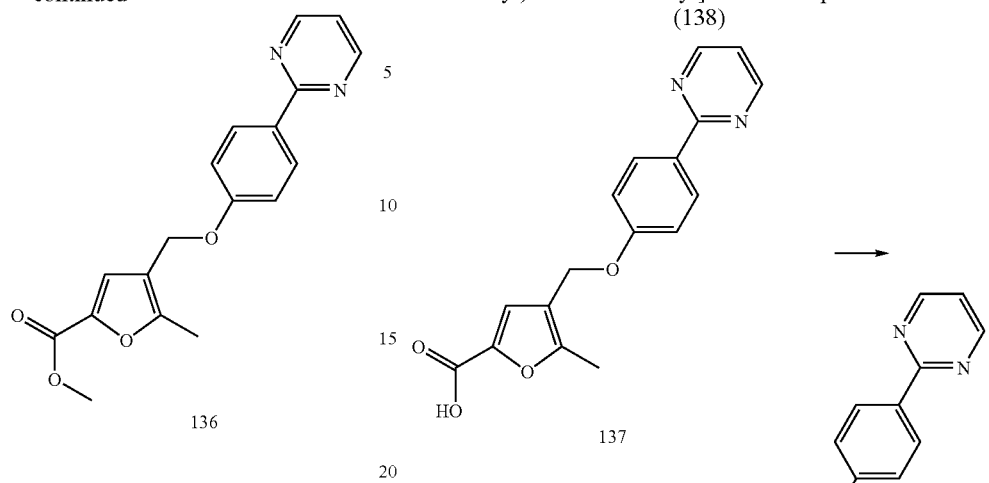

136

Compound (136) was prepared from compound (119) and 2-bromo-pyrimidine by adapting the procedure of Example 30(a). LC/MS System A; $R_t$=3.43 mins, m/z (ES$^+$)=325 (M+H for $C_{18}H_{16}N_2O_4$).

(b) 5-Methyl-4-(4-pyrimidin-2-yl-phenoxymethyl)-furan-2-carboxylic acid (137)

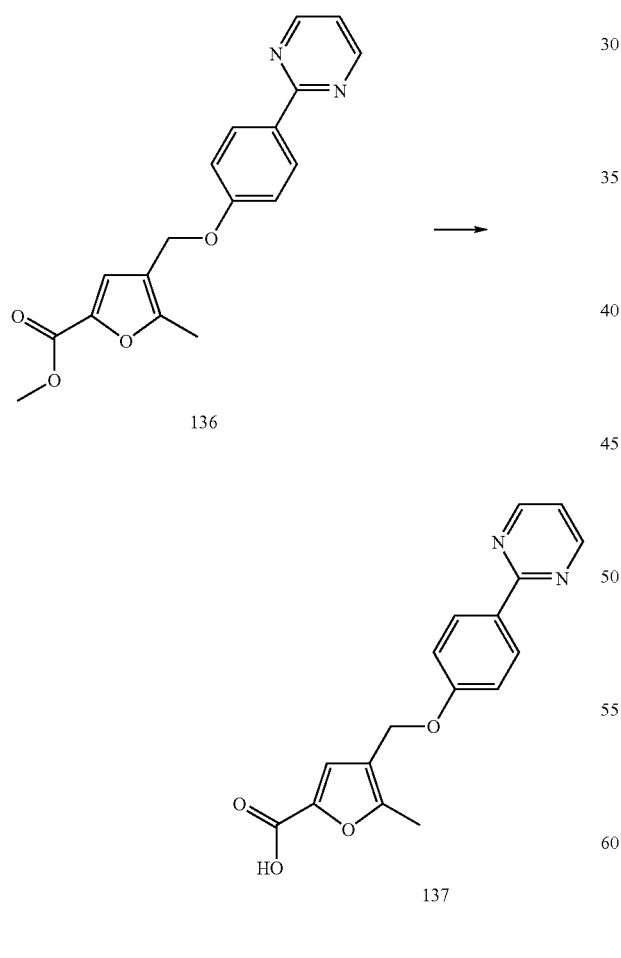

Compound (137) was prepared from compound (136) by adapting the procedure of Example 30(b). LC/MS System D; $R_t$=6.21 mins, m/z (ES$^+$)=311 (M+H for $C_{17}H_{14}N_2O_4$).

(c) N-[5-Methyl-4-(4-pyrimidin-2-yl-phenoxymethyl)-furan-2-carbonyl]-benzenesulphonamide (138)

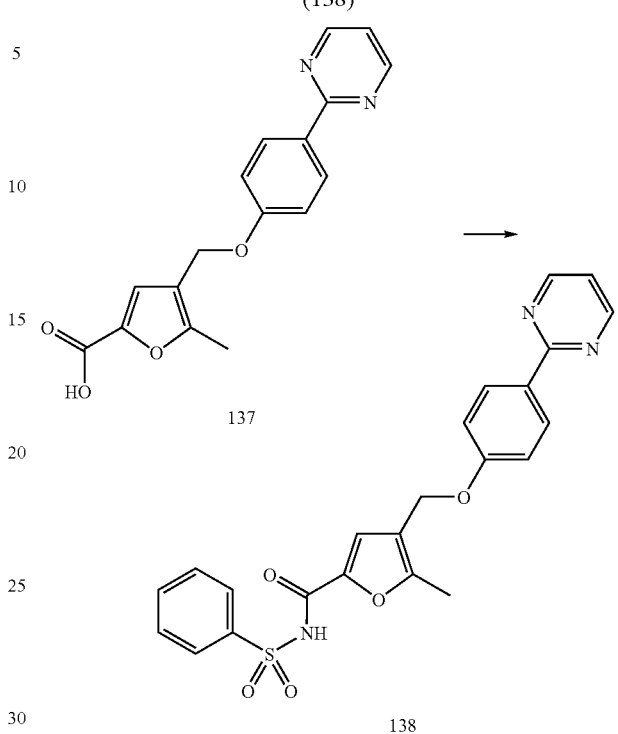

Compound (138) was prepared from compound (137) by adapting the procedure of Example 2A. LC/MS System D; $R_t$=7.50 mins, m/z (ES$^+$)=450 (M+H for $C_{23}H_{19}N_3O_5S$).

Example 34

Synthesis of 4-(2',4'-Dimethoxy-biphenyl-4-yloxymethyl)-5-methyl-furan-2-carboxylic acid (140), N-[4-(2',4'-Dimethoxy-biphenyl-4-yloxymethyl)-5-methyl-furan-2-carbonyl]-benzenesulfonamide (141) and 3,5-Dimethyl-isoxazole-4-sulfonic acid [4-(2',4'-dimethoxy-biphenyl-4-yloxymethyl)-5-methyl-furan-2-carbonyl]-amide (142).

(a) 4-(2',4'-Dimethoxy-biphenyl-4-yloxymethyl)-5-methyl-furan-2-carboxylic acid methyl ester (139)

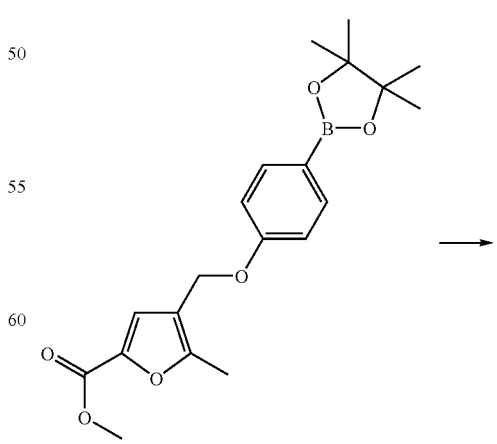

119

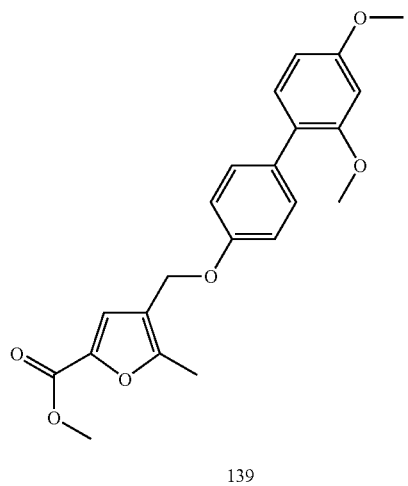

139

Compound (139) was prepared from compound (119) and 1-bromo-2,4-dimethoxy-benzene by adapting the procedure of Example 31(a). LC/MS System A; $R_t$=4.09 mins.

(b) 4-(2',4'-Dimethoxy-biphenyl-4-yloxymethyl)-5-methyl-furan-2-carboxylic acid (140)

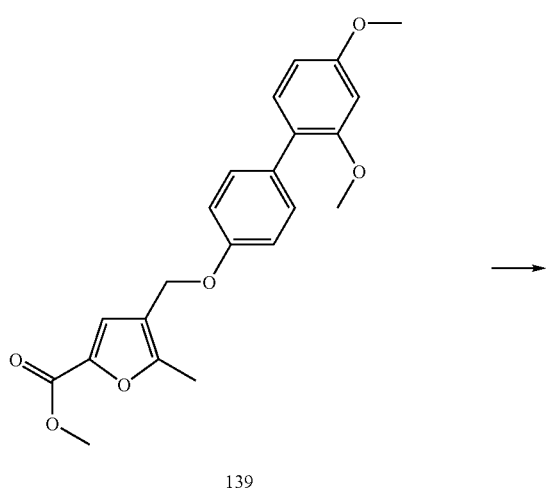

139

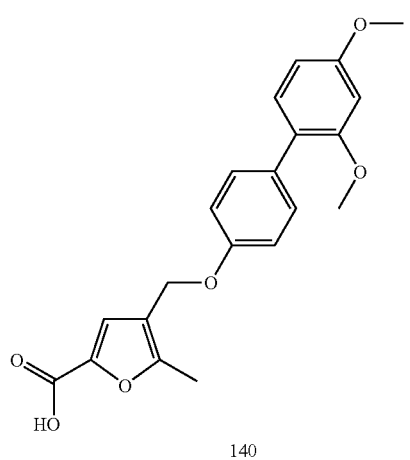

140

Compound (140) was prepared from compound (139) by adapting the procedure of Example 31(b). LC/MS System D; $R_t$=8.20 mins, m/z (ES$^+$)=369 (M+H for $C_{21}H_{20}O_6$).

(c) N-[4-(2',4'-Dimethoxy-biphenyl-4-yloxymethyl)-5-methyl-furan-2-carbonyl]-benzenesulphonamide (141)

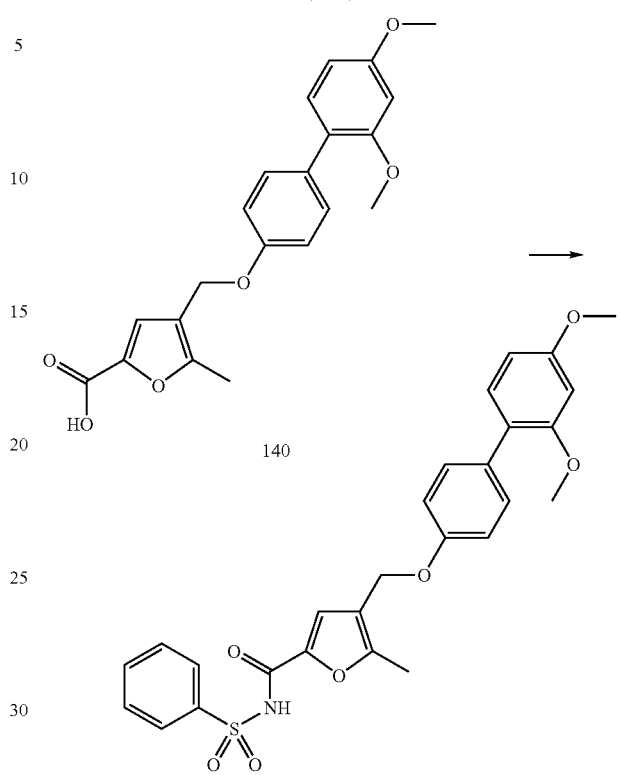

A stirred solution of 4-(2',4'-dimethoxy-biphenyl-4-yloxymethyl)-5-methyl-furan-2-carboxylic acid (140) (50 mg, 0.136 mmoles), benzenesulphonamide (32 mg, 0.204 mmoles) and 4-(N,N-dimethylamino)-pyridine (5 mg) in a mixture of tetrahydrofuran (8 ml) and acetonitrile (2 ml) was treated with 1-(3-dimethylaminopropyl)-3-ethylcarbodiimide hydrochloride (32 mg, 0.163 mmoles). The mixture was stirred at room temperature for 16 hours under an argon atmosphere. The reaction mixture was concentrated in vacuo and the residue was purified by HPLC to afford compound 141 (24 mg) as a white solid. LC/MS System C; $R_t$=8.99 mins, m/z (ES$^-$)=506 (M–H for $C_{27}H_{25}NO_7S$).

(d) 3,5-Dimethyl-isoxazole-4-sulphonic acid [4-(2',4'-dimethoxy-biphenyl-4-yloxymethyl)-5-methyl-furan-2-carbonyl]-amide (142)

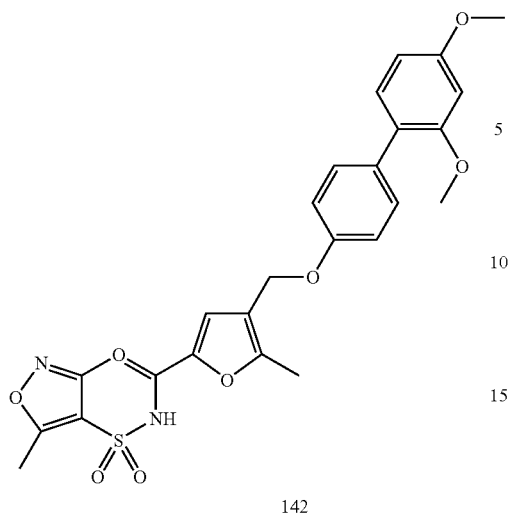

142

Compound (142) was prepared from compound (140) and 3,5-dimethyl-isoxazole-sulphonic acid amide by adapting the procedure of Example 34(c). LC/MS System C; $R_t$=9.13 mins, m/z (ES⁻)=525 (M−H for $C_{26}H_{26}N_2O_8S$).

Example 35

Synthesis of 4-(4'-Methoxy-2'-methyl-biphenyl-4-yloxymethyl)-5-methyl-furan-2-carboxylic acid (144), N-[4-(4'-Methoxy-2'-methyl-biphenyl-4-yloxymethyl)-5-methyl-furan-2-carbonyl]-benzenesulfonamide (145) and 3,5-Dimethyl-isoxazole-4-sulfonic acid [4-(4'-methoxy-2'-methyl-biphenyl-4-yloxymethyl)-5-methyl-furan-2-carbonyl]-amide (146).

(a) 4-(4'-Methoxy-2'-methyl-biphenyl-4-yloxymethyl)-5-methyl-furan-2-carboxylic acid methyl ester (143)

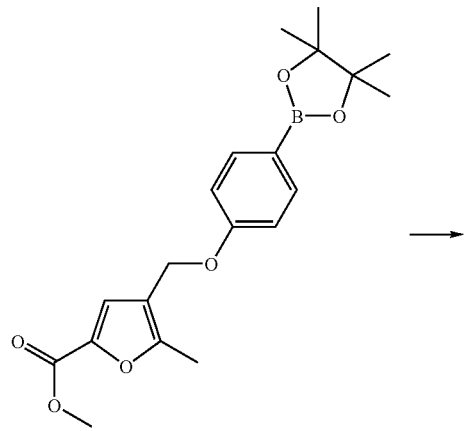

119

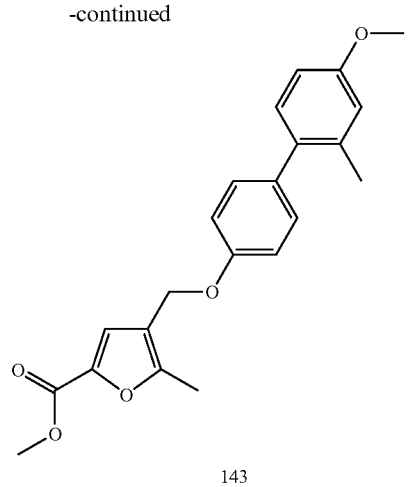

143

Compound (143) was prepared from compound (119) and 1-bromo-4-methoxy-2-methyl-benzene by adapting the procedure of Example 31(a). LC/MS System A; $R_t$=4.24 mins.

(b) 4-(4'-Methoxy-2'-methyl-biphenyl-4-yloxymethyl)-5-methyl-furan-2-carboxylic acid (144)

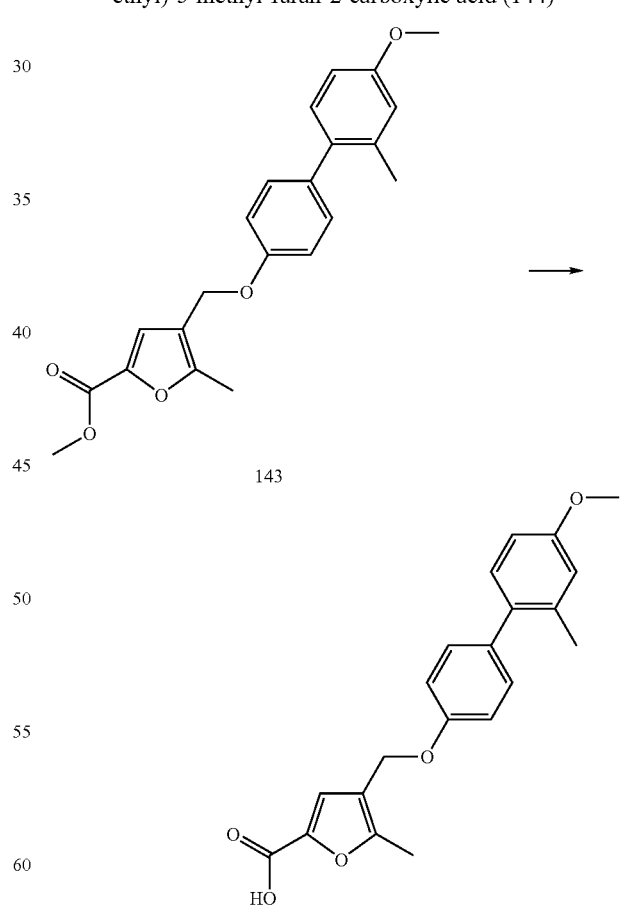

Compound (144) was prepared from compound (143) by adapting the procedure of Example 31(b). LC/MS System D; $R_t$=8.48 mins, m/z (ES⁺)=353 (M+H for $C_{21}H_{20}O_5$).

(c) N-[4-(4'-Methoxy-2'-methyl-biphenyl-4-yloxymethyl)-5-methyl-furan-2-carbonyl]-benzenesulphonamide (145)

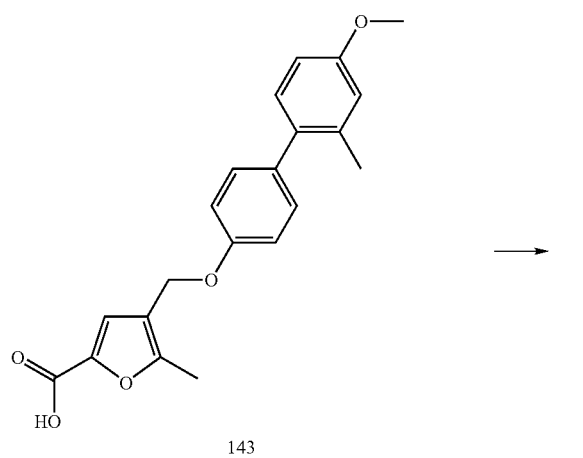

Compound (145) was prepared from compound (143) and by adapting the procedure of Example 34(c). LC/MS System C; $R_t$=9.40 mins, m/z (ES$^-$)=490 (M–H for $C_{27}H_{25}NO_6S$).

(d) 3,5-Dimethyl-isoxazole-4-sulphonic acid [4-(4'-methoxy-2'-methyl-biphenyl-4-yloxymethyl)-5-methyl-furan-2-carbonyl]-amide (146)

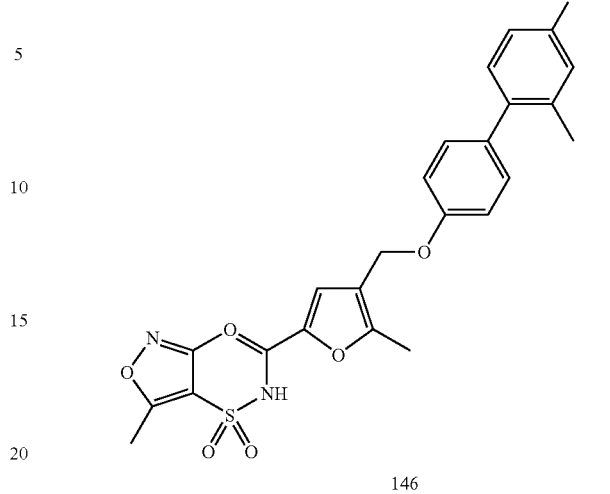

Compound (146) was prepared from compound (143) and 3,5-dimethyl-isoxazole-sulphonic acid amide by adapting the procedure of Example 34(c). LC/MS System D; $R_t$=11.29 mins, m/z (ES$^-$)=509 (M–H for $C_{26}H_{26}N_2O_7S$).

Example 36

Synthesis of 5-[4-(Biphenyl-4-yloxymethyl)-5-methyl-furan-2-yl]-1H-tetrazole (149)

(a) 4-Hydroxymethyl-5-methyl-furan-2-carbonitrile (147)

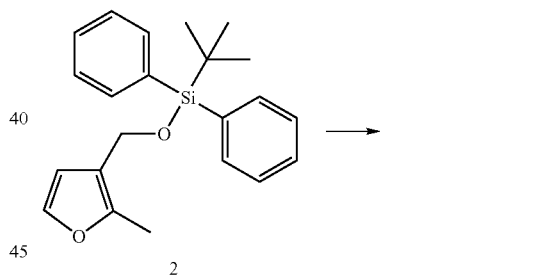

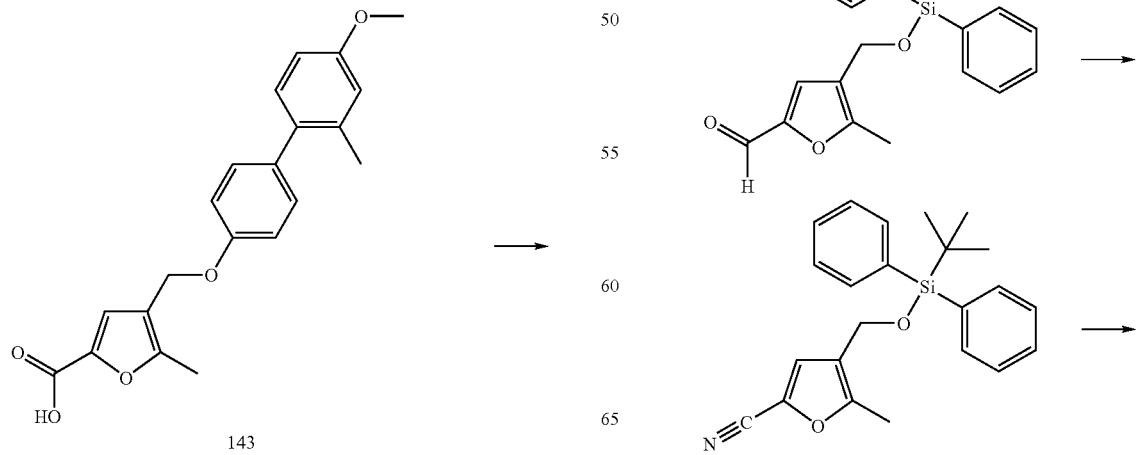

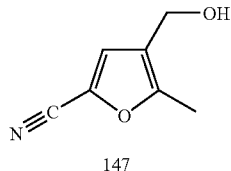

147

(i) Sec-Butyl lithium (1.3M solution in cyclohexane, 57.1 ml, 74.2 mmoles) was added, dropwise during 10 min, to a stirred solution of 4-(tert-butyl-diphenyl-silanyloxymethyl)-5-methyl-furan (reference example 2A) (20.0 g, 57.1 mmoles) under an argon atmosphere and with cooling to −78° C. After stirring for an additional 45 minutes, the cooling bath was removed for 15 minutes, and then the reaction was re-cooled to −78° C. A solution of dimethylformamide (10 ml) in tetrahydrofuran (40 ml) was added during 5 minutes, the reaction mixture stirred for 2 hours at −78° C. then allowed to warm to room temperature. The reaction was quenched by the addition of saturated aqueous ammonium chloride (200 ml). Diethyl ether (500 ml) was added the organic phase was separated, and the aqueous phase was extracted with diethyl ether (500 ml). The combined extracts were washed with water (500 ml) and brine (500 ml), and dried (MgSO$_4$). Evaporation of the solvent afforded 4-(tert-butyl-diphenyl-silanyloxymethyl)-5-methyl-furan-2-carbaldehyde (20.4 g).

(ii) Hydroxylamine hydrochloride (1.11 g, 16.0 mmoles) and triethylamine (2.22 ml) were added to a solution of 4-(tert-butyl-diphenyl-silanyloxymethyl)-5-methyl-furan-2-carbaldehyde from (i)(6.3 g, 16.0 mmoles) in dichloromethane (125 ml) and the mixture was stirred at room temperature for 17 hours. After cooling to 0° C., 2-Chloro-1,3-dimethylimidazolium chloride (2.81 g, 16.6 mmoles) and triethylamine (4.6 ml) were added and the yellow suspension was stirred at room temperature for 24 hours. The mixture was diluted with water and extracted with dichloromethane. The combined extracts were washed with 5% aqueous hydrochloric acid, saturated aqueous sodium bicarbonate and water, and finally dried (MgSO$_4$). The solvent was evaporated and the residue was purified by flash chromatography (silica, cyclohexane/diethyl ether 99:1 v/v as eluent) to afford 4-(tert-butyl-diphenyl-silanyloxymethyl)-5-methyl-furan-2-carbonitrile as a viscous oil, (3.75 g).

(iii) A solution of 4-(tert-butyl-diphenyl-silanyloxymethyl)-5-methyl-furan-2-carbonitrile from (ii) (3.75 g) in tetrahydrofuran (100 ml) was cooled to 0° C. under an argon atmosphere, and was treated with a 1M solution of tetrabutylammonium fluoride in tetrahydrofuran (22 ml). The mixture was allowed to warm to room temperature and stirred for 16 hours. The volatiles were removed and the residue was partitioned between ethyl acetate and water. The organic phase was separated and the aqueous phase was extracted with more ethyl acetate. The combined ethyl acetate extracts were washed with 1M aqueous hydrochloric acid and brine, and dried. The solvent was evaporated and the crude orange oil was purified by flash chromatography (silica, gradient elution with 0% to 40% ethyl acetate in cyclohexane) to afford compound 147 as a pale yellow oil (1.3 g).

(b) 4-(Biphenyl-4-yloxymethyl)-5-methyl-furan-2-carbonitrile (148)

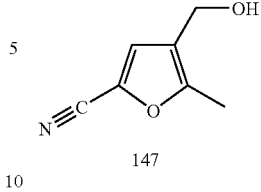

147

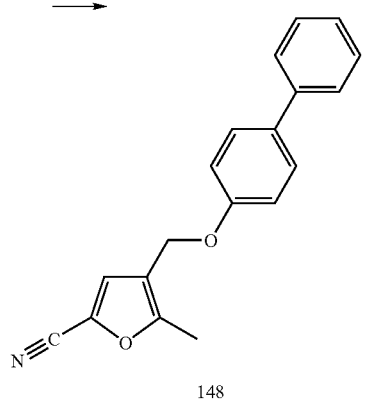

148

Diisopropylazodicarboxylate (1.84 g, 10.6 mmoles) was added to a solution of 4-hydroxymethyl-5-methyl-furan-2-carbonitrile (147) (1.32 g, 9.6 mmoles), biphenyl-4-ol (1.63 g, 9.6 mmoles) and triphenylphosphine (4.3 g, 16.35 mmoles) in tetrahydrofuran (50 mL) with stirring and cooling to 0° C. under an argon atmosphere. After 5 minutes, the cooling was removed and the mixture stirred at room temperature for 16 h. The solvent was evaporated and the residue partitioned between ethyl acetate and water. The ethyl acetate phase was washed with brine and dried. After the solvent was evaporated, the residue was purified by flash chromatography (silica, gradient elution with 5% to 10% ethyl acetate in cyclohexane) to afford compound 148 as a white solid (2.2 g). IR (powder) CN st. 2225 cm$^{-1}$.

(c) 5-[4-(Biphenyl-4-yloxymethyl)-5-methyl-furan-2-yl]-1H-tetrazole (149)

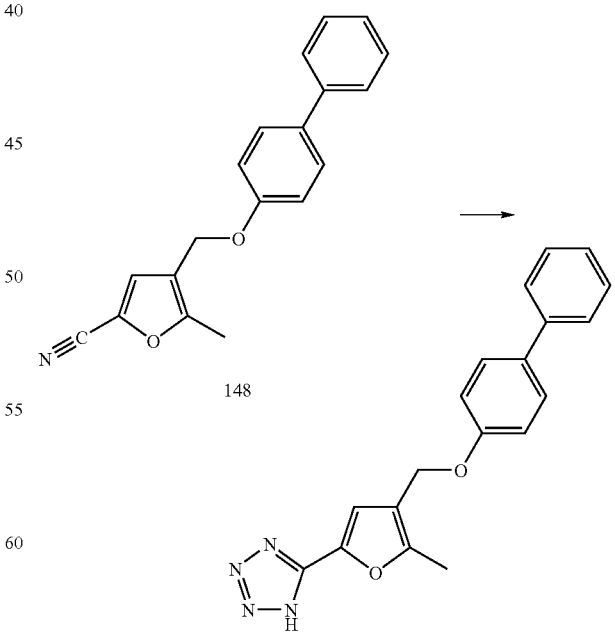

A mixture of 4-(biphenyl-4-yloxymethyl)-5-methyl-furan-2-carbonitrile (148) (100 mg, 0.35 mmoles), sodium azide (27 mg, 0.415 mmoles) and potassium carbonate (62 mg, 0.45 mmoles) in dimethylformamide (5 ml) was heated at 90° C. for 96 hours then at 120° C. for 24 hours. The mixture was evaporated and the residue purified by HPLC to afford compound 149 as a white solid (64 mg). LC/MS System D; $R_t$=9.53 mins, m/z (ES$^+$)=333 (M+H for $C_{19}H_{16}N_4O_2$).

Example 37

Synthesis of 4-(4'-Difluoromethoxy-biphenyl-4-yl-sulfanylmethyl)-5-methyl-furan-2-carboxylic acid (153), N-[4-(4'-Difluoromethoxy-biphenyl-4-ylsulfanylmethyl)-5-methyl-furan-2-carbonyl]-2-methyl-benzenesulfonamide (154), N-[4-(4'-Difluoromethoxy-biphenyl-4-ylsulfanylmethyl)-5-methyl-furan-2-carbonyl]-benzenesulfonamide (155) and N-[4-(4'-Difluoromethoxy-biphenyl-4-sulfinylmethyl)-5-methyl-furan-2-carbonyl]-2-methyl-benzenesulfonamide (156)

(a) 4-(4-Bromo-phenylsulphanylmethyl)-5-methyl-furan-2-carboxylic acid methyl ester (150)

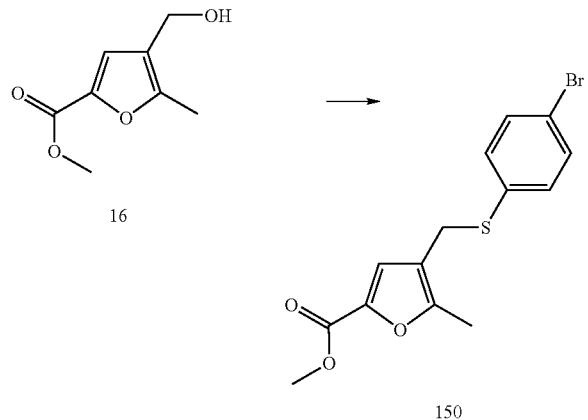

Diisopropylazodicarboxylate (1.27 g, 6.3 mmoles) was added to a solution of triphenylphosphine (1.65 g, 6.3 mmoles) in tetrahydrofuran (15 ml) with stirring and cooling in an ice/water bath. A solution of 4-hydroxymethyl-5-methyl-furan-2-carboxylic acid methyl ester (16) (536 mg, 3.15 mmoles) and 4-bromo-thiophenol (584 mg, 3.09 mmoles) in tetrahydrofuran (5 ml) was added and the mixture stirred for 30 minutes at 0° C. then 72 hours at room temperature. The solvent was evaporated and the residue extracted with heptane then diethyl ether. The extracts were combined and evaporated to give a yellow oil which was purified by flash chromatography using heptane/ethyl acetate 9:1 v/v as eluent. This gave compound 150 (600 mg) as a white solid. LC/MS System A; $R_t$=4.12 mins.

(b) 5-Methyl-4-[4-(4,4,5,5-tetramethyl-[1,3,2]dioxaborolan-2-yl)-phenylsulphanylmethyl]-furan-2-carboxylic acid methyl ester (151)

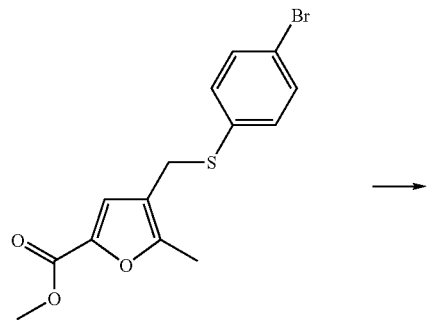

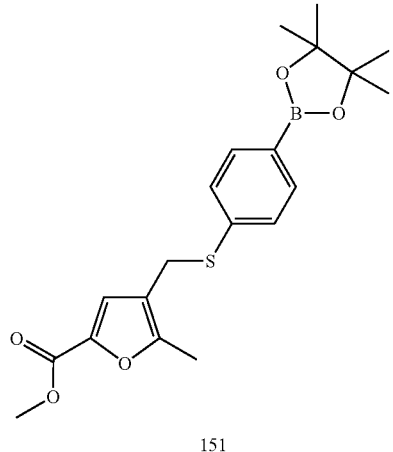

[1,1'-Bis(diphenylphosphino)ferrocene]dichloropalladium(II) complex with dichloromethane (1:1) (30 mg) and 4,4,5,5-tetramethyl-[1,3,2]dioxaborolan (2.34 ml of a 1M solution in tetrahydrofuran) were added to a degassed solution of 4-(4-bromo-phenylsulphanylmethyl)-5-methyl-furan-2-carboxylic acid methyl ester (150) (400 mg, 1.17 mmoles) in 1,4-dioxan (120 ml). The mixture was heated at 100° C., under an argon atmosphere, for 20 hours, cooled and evaporated. The residue was partitioned between ethyl acetate and water, and the organic phase washed with brine and dried (MgSO$_4$). After evaporation of the solvent the residue was purified by flash chromatography, using heptane/ethyl acetate 9:1 v/v as eluent, to afford compound 151 (212 mg) as a colourless oil.

(c) 4-(4'-difluoromethoxy-biphenyl-4-ylsulphanylmethyl)-5-methyl-furan-2-carboxylic acid methyl ester (152)

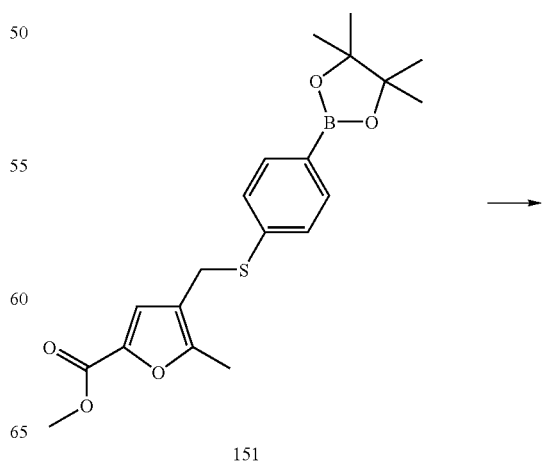

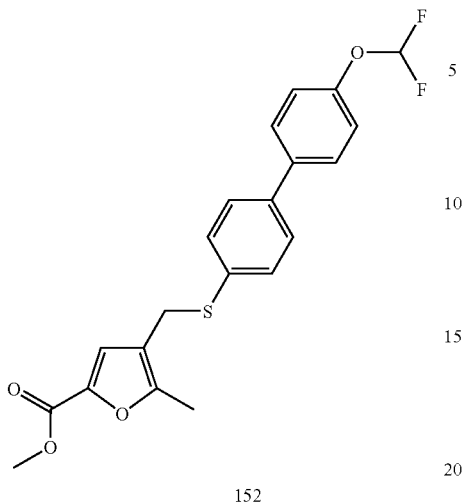

152

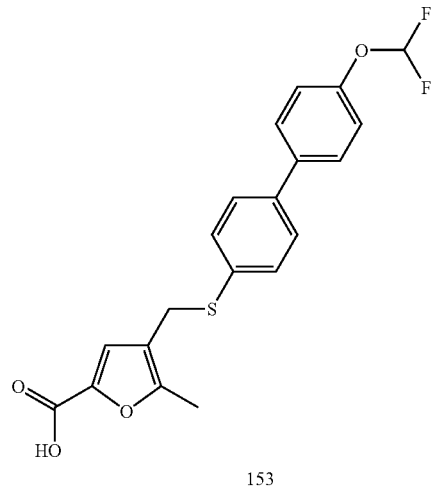

153

[1,1'-Bis(diphenylphosphino)ferrocene]dichloropalladium(II) complex with dichloromethane (1:1) (12.8 mg) was added to a degassed mixture of 5-methyl-4-[4-(4,4,5,5-tetramethyl-[1,3,2]dioxaborolan-2-yl)-phenylsulphanylmethyl]-furan-2-carboxylic acid methyl ester (151) (200 mg, 0.516 mmoles), 1-difluoromethoxy-4-iodo-benzene (153 mg, 0.568 mmoles) and 2M aqueous cesium carbonate (4.12 ml) in 1,4-dioxan (15 ml). The mixture was placed under an argon atmosphere and was heated at 100° C. for 20 hours. After cooling, the mixture was concentrated and the residue was partitioned between ethyl acetate and water, and the mixture adjusted to pH=2 with 1M aqueous hydrochloric acid. The organic phase was washed with brine and dried. After evaporation of the solvent, the residue was purified by flash chromatography, using heptane/ethyl acetate 9:1 v/v as eluent, to afford compound 152 (126 mg) as a white solid. LC/MS System A; $R_t$=4.17 mins.

(d) 4-(4'-Difluoromethoxy-biphenyl-4-ylsulphanylmethyl)-5-methyl-furan-2-carboxylic acid (153)

Compound (153) was prepared from compound (152) by adapting the procedure of Example 30(b)(127 mg) as a white solid. LC/MS System D; $R_t$=10.34 mins, m/z (ES⁻)=389 (M–H for $C_{20}H_{16}F_2O_4S$).

(e) N-[4-(4'-Difluoromethoxy-biphenyl-4-ylsulphanylmethyl)-5-methyl-furan-2-carbonyl]-2-methyl-benzenesulphonamide (154)

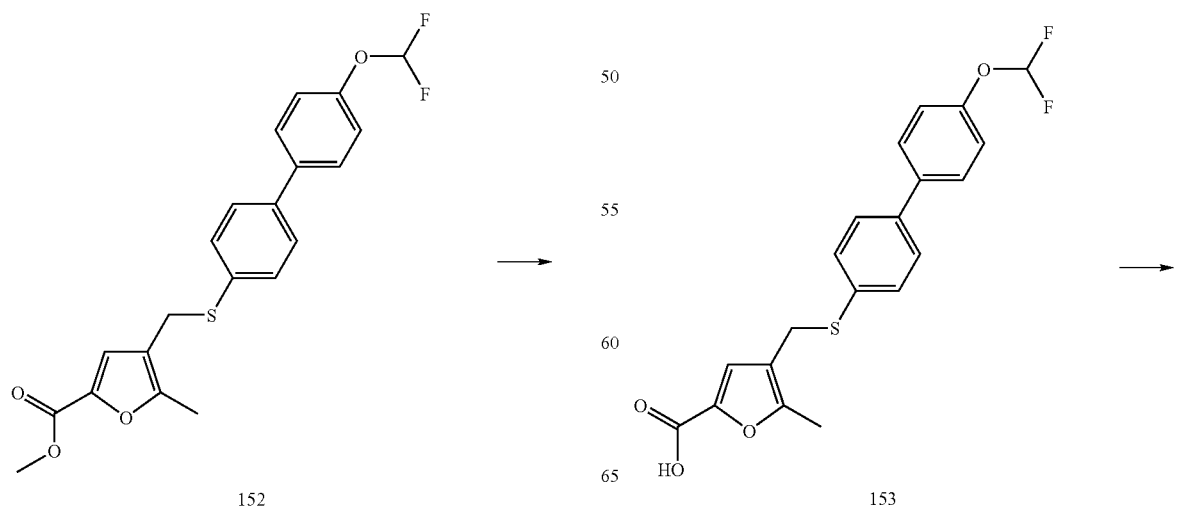

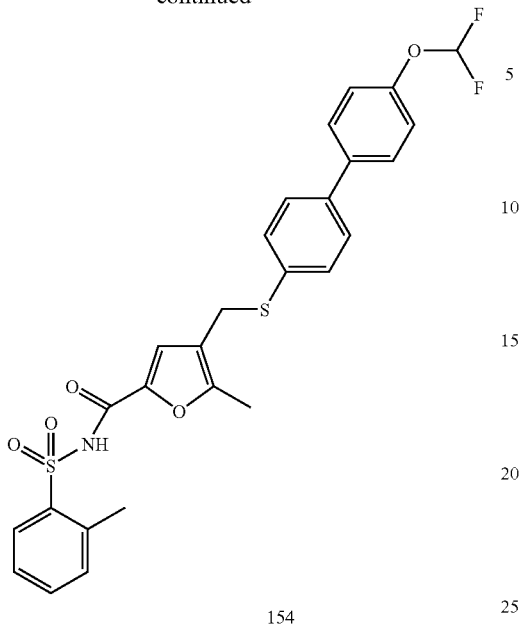

154

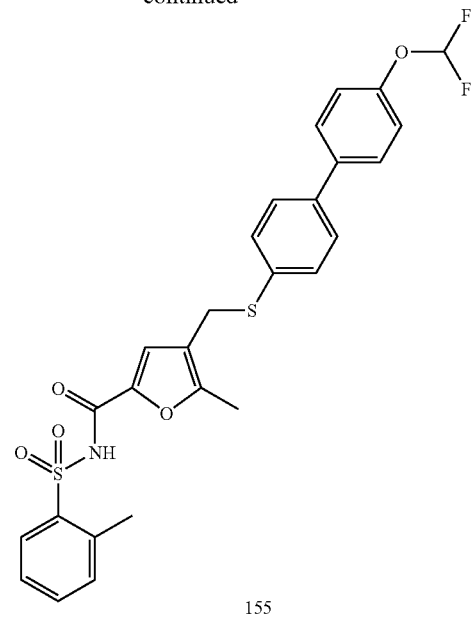

155

Compound (154) was prepared from compound (153) and 2-methyl-benzenesulphonamide by adapting the procedure of Example 34(c). LC/MS System D; $R_t$=11.61 mins, m/z (ES$^+$)=544 (M+H for $C_{27}H_{23}F_2NO_5S_2$).

Compound (155) was prepared from compound (153) by adapting the procedure of Example 2A. LC/MS System D; $R_t$=11.44 mins, m/z (ES$^+$)=530 (M+H for $C_{26}H_{21}F_2NO_5S_2$).

(f) N-[4-(4'-Difluoromethoxy-biphenyl-4-ylsulphanylmethyl)-5-methyl-furan-2-carbonyl]-benzenesulphonamide (155)

(g) N-[4-(4'-Difluoromethoxy-biphenyl-4-ylsulphinylmethyl)-5-methyl-furan-2-carbonyl]-2-methyl-benzenesulphonamide (156) and N-[4-(4'-Difluoromethoxy-biphenyl-4-sulfonylmethyl)-5-methyl-furan-2-carbonyl]-2-methyl-benzenesulfonamide (156a)

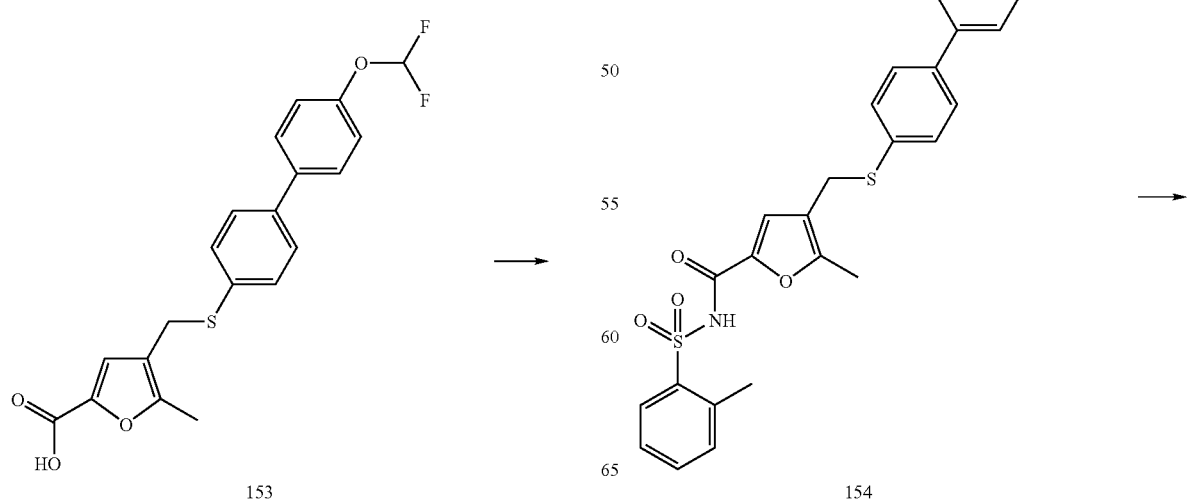

-continued

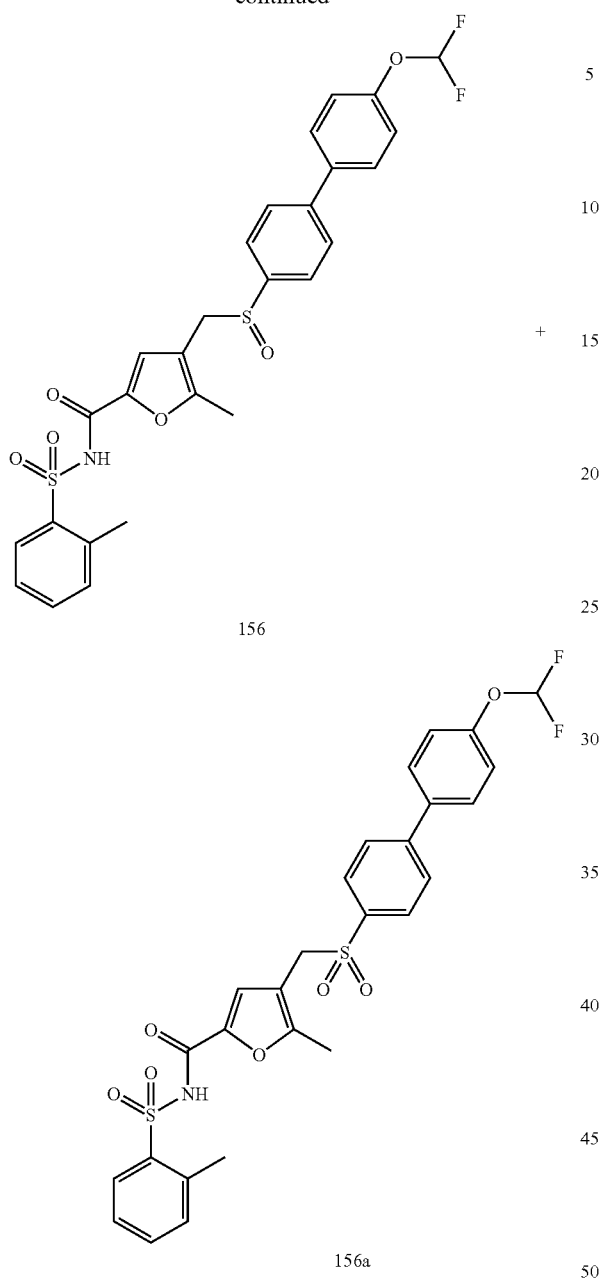

156

156a

A solution of 3-chloro-benzenecarboperoxoic acid (22 mg of 72% wt peracid) in chloroform (3 ml) was added to a solution of N-[4-(4'-difluoromethoxy-biphenyl-4-ylsulphanylmethyl)-5-methyl-furan-2-carbonyl]-2-methyl-benzenesulphonamide (154) (50 mg, 0.092 mmoles) in a mixture of methanol (1 ml) and chloroform (2 ml). After stirring for 2 hours, the solvent was evaporated and the residue was purified by HPLC (gradient: 45% acetonitrile/55% water containing 0.1% trifluoroacetic acid to 98% acetonitrile/2% water at a rate of 1%/min) to afford compound 156 (42 mg) as a white solid. LC/MS System D; $R_t$=9.61 mins, m/z (ES$^-$)=558 (M–H for $C_{27}H_{23}F_2NO_6S_2$).

Also obtained was N-[4-(4'-difluoromethoxy-biphenyl-4-ylsulphonylmethyl)-5-methyl-furan-2-carbonyl]-2-methyl-benzenesulphonamide (156a)(8 mg) as a white solid. LC/MS System D; $R_t$=10.24 mins, m/z (ES$^-$)=574 (M–H for $C_{27}H_{23}F_2NO_7S_2$).

Example 38

Synthesis of 4-(Biphenyl-4-ylaminomethyl)-5-methyl-furan-2-carboxylic acid (160), N-[4-(Biphenyl-4-ylaminomethyl)-5-methyl-furan-2-carbonyl]-benzenesulfonamide (161) and N-[4-(Biphenyl-4-ylaminomethyl)-5-methyl-furan-2-carbonyl]-2-methyl-benzenesulfonamide (162).

(a) 4-Formyl-5-methyl-furan-2-carboxylic acid methyl ester (157)

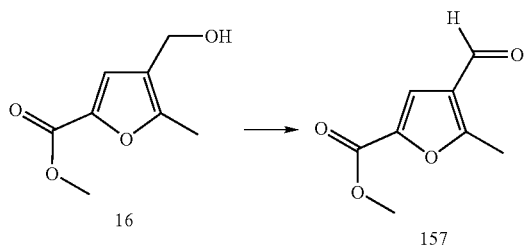

Acetic acid 1,1-diacetoxy-3-oxo-1$^{\lambda5}$-ioda-2-oxa-indan-1-yl ester (Dess-Martin reagent) (549 mg, 1.293 mmoles) in dry dichloromethane was added to a solution of 4-hydroxymethyl-5-methyl-furan-2-carboxylic acid methyl ester (16) (200 mg, 1.176 mmoles) in dry dichloromethane (9 ml) with cooling to 0° C. under an argon atmosphere. After stirring for 20 minutes, the mixture was diluted with diethyl ether (40 ml) and was poured into saturated aqueous sodium bicarbonate (30 ml) containing sodium thiosulphate pentahydrate (4 g) and agitated vigorously for 5 minutes. The organic phase was washed with saturated aqueous sodium bicarbonate (40 ml), water (50 ml) and brine (50 ml) and dried. After removal of the solvent, the residue was purified by flash chromatography, using petrol/diethyl ether 4:1 v/v as eluent, to afford compound 157 (140 mg) as a white solid.

(b) 4-(Biphenyl-4-ylaminomethyl)-5-methyl-furan-2-carboxylic acid methyl ester (158)

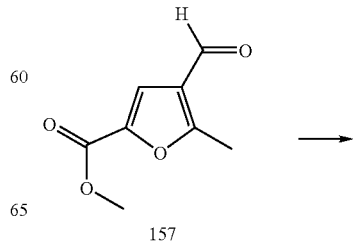

157

-continued

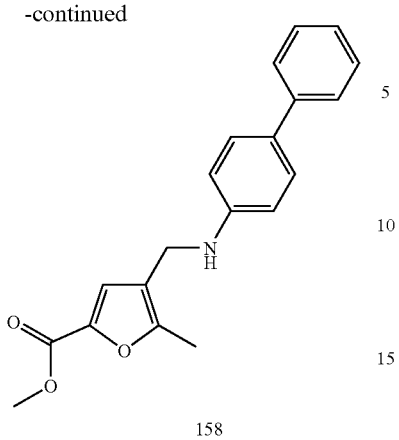
158

A solution of biphenyl-4-ylamine (150 mg, 0.883 mmoles) and 4-formyl-5-methyl-furan-2-carboxylic acid methyl ester (157) (135 mg, 0.803 mmoles) in methanol (2.0 ml) was stirred over molecular sieves (type 3 Å) for 1 hour. Sodium cyanoborohydride (55 mg, 0.883 mmoles) was added and the mixture stirred for 18 hour at room temperature. The mixture was concentrated and partitioned between ethyl acetate (25 ml) and saturated aqueous sodium bicarbonate (30 ml). The aqueous phase was re-extracted with ethyl acetate (2×25 ml) and the combined extracts were washed with brine (50 ml) and dried (MgSO$_4$). After removal of the solvent, the residue was purified by flash chromatography, using a gradient elution of petrol/diethyl ether 9:1 v/v to 4:1 v/v, to afford compound 158 (75 mg).

(c) 4-Chloromethyl-5-methyl-furan-2-carboxylic acid methyl ester (159)

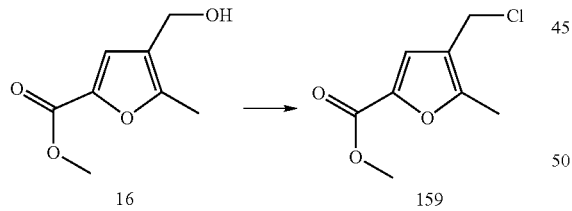

Triethylamine (196 μl, 1.41 mmoles), followed by 4-methyl-benzenesulphonyl chloride (247 mg, 1.293 mmoles) were added to a stirred solution of 4-hydroxymethyl-5-methyl-furan-2-carboxylic acid methyl ester (16) (200 mg, 1.176 mmoles) in dry dichloromethane at 0° C. under an argon atmosphere. The reaction mixture was stirred at 0° C. for 15 minutes, then allowed to warm to room temperature and was stirred for a further 4 hours. The mixture was washed with saturated aqueous sodium bicarbonate (50 ml) and brine (50 ml), and dried (MgSO$_4$). After removal of the solvent, the residue was purified by flash chromatography, using petrol/diethyl ether 19:1 v/v as eluent, to afford compound 159 (75 mg) as a white solid. LC/MS System D; R$_t$=6.34 mins, m/z (ES$^+$)=189 (M+H for C$_8$H$_9$ClO$_3$).

(d) 4-(Biphenyl-4-ylaminomethyl)-5-methyl-furan-2-carboxylic acid methyl ester (158)

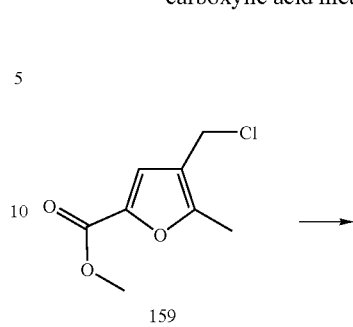
159

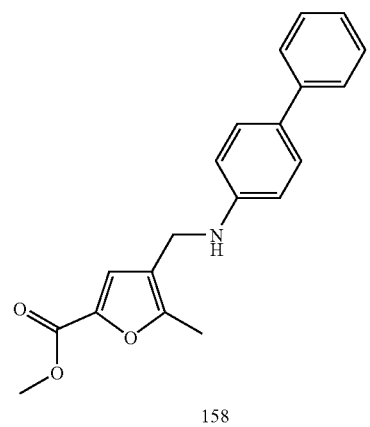
158

Potassium iodide (32 mg) and a solution of biphenyl-4-ylamine (74 mg, 0.438 mmoles) in tetrahydrofuran (1 ml) was added to a mixture of 4-chloromethyl-5-methyl-furan-2-carboxylic acid methyl ester (159)(75 mg, 0.398 mmoles) and potassium carbonate (83 mg) in tetrahydrofuran (1 ml). The mixture was stirred at room temperature under an argon atmosphere for 16 hours, and then refluxed with the exclusion of light for 16 hours. After cooling, the mixture was concentrated and the residue was purified by flash chromatography, using a gradient elution of petrol/diethyl ether 9:1 v/v to 4:1 v/v, to afford compound 158 (91 mg). LC/MS System A; R$_t$=3.93 mins, m/z (ES$^+$)=322 (M+H for C$_{20}$H$_{19}$NO$_3$).

(e) 4-(Biphenyl-4-ylaminomethyl)-5-methyl-furan-2-carboxylic acid (160)

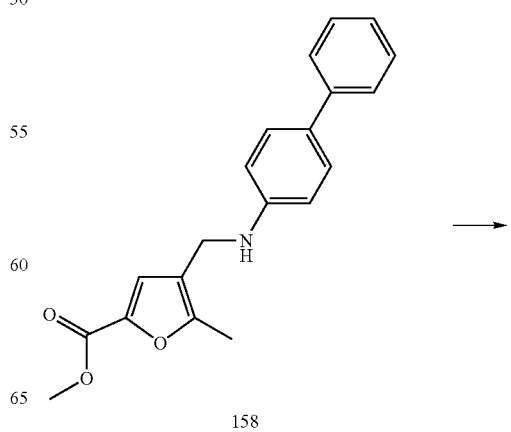
158

-continued

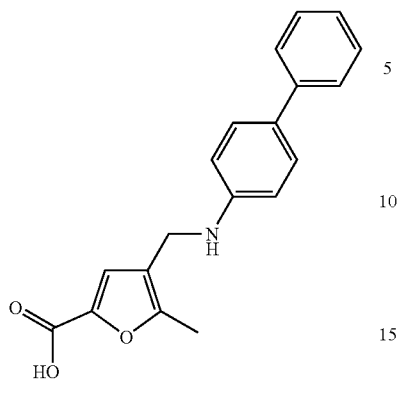

160

A solution of 4-(biphenyl-4-ylaminomethyl)-5-methyl-furan-2-carboxylic acid methyl ester (158) (91 mg, 0.283 mmoles) in dry tetrahydrofuran (5 ml) was treated with potassium trimethylsilanoate (182 mg, 1.42 mmoles) and the mixture stirred under an argon atmosphere for 3 hours. After evaporation of the solvent, the residue was purified by HPLC (gradient: 15% acetonitrile/85% water containing 0.1% trifluoroacetic acid to 55% acetonitrile/45% water at a rate of 1%/min) to afford compound 160 (35 mg) as a white solid. LC/MS System D; $R_t$=7.64 mins, m/z (ES$^+$)=308 (M+H for $C_{19}H_{17}NO_3$).

(f) N-[4-(biphenyl-4-ylaminomethyl)-5-methyl-furan-2-carbonyl]-benzenesulphonamide (161)

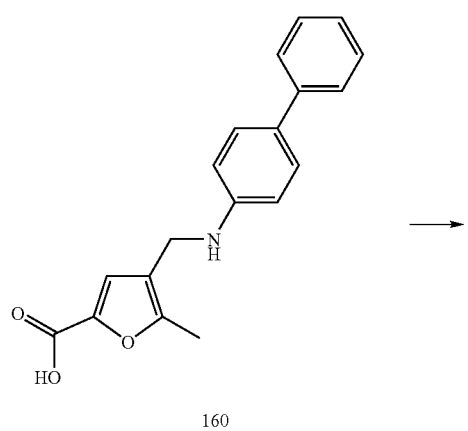

160

-continued

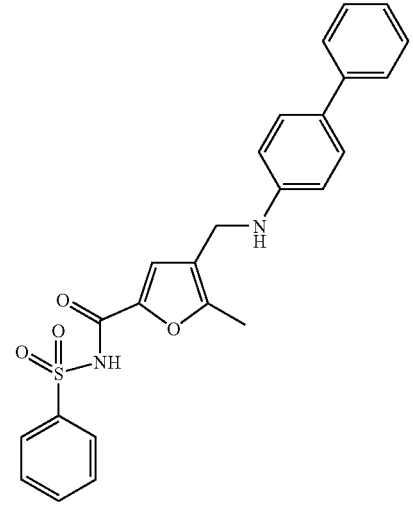

161

A stirred solution of 4-(biphenyl-4-ylaminomethyl)-5-methyl-furan-2-carboxylic acid (160) (15 mg, 0.036 mmoles), benzenesulphonamide (17 mg, 0.107 mmoles) and 4-(N,N-dimethylamino)-pyridine (1 mg) in a mixture of tetrahydrofuran (3 ml) and acetonitrile (0.5 ml) was treated with triethylamine (5.5 µl, 0.039 mmoles) and 1-(3-dimethylaminopropyl)-3-ethylcarbodiimide hydrochloride (10.5 mg, 0.053 mmoles). The mixture was stirred at room temperature for 19 hours under an argon atmosphere. The reaction mixture was concentrated in vacuo and the residue was purified by HPLC to afford compound 161 (8 mg) as a white solid. LC/MS System D; $R_t$=8.84 mins, m/z (ES$^+$)=447 (M+H for $C_{25}H_{22}N_2O_4S$).

(g) N-[4-(biphenyl-4-ylaminomethyl)-5-methyl-furan-2-carbonyl]-2-methyl-benzenesulphonamide (162)

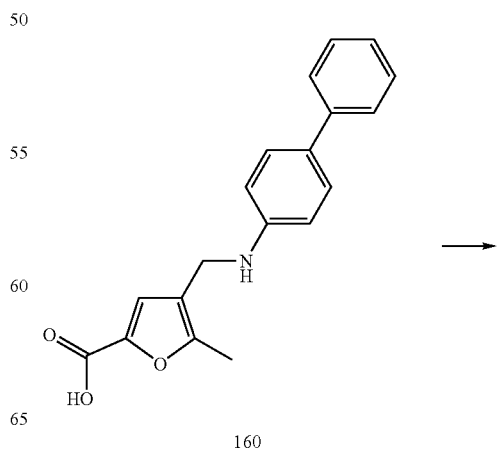

160

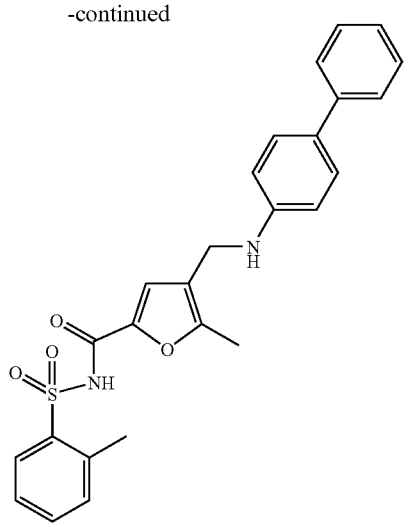

162

Compound (162) was prepared from compound (160) and 2-methyl-benzenesulphonamide by adapting the procedure of Example 38(f). LC/MS System D; $R_t$=10.39 mins, m/z (ES$^+$)=461 (M+H for $C_{26}H_{24}N_2O_4S$).

Example 39

Synthesis of N-(4-{[4-(5-Methoxy-pyridin-2-yl)-phenylamino]-methyl}-5-methyl-furan-2-carbonyl)-2-methyl-benzenesulfonamide (167)

(a) 4-[(4-Bromo-phenylamino)-methyl]-5-methyl-furan-2-carboxylic acid methyl ester (163)

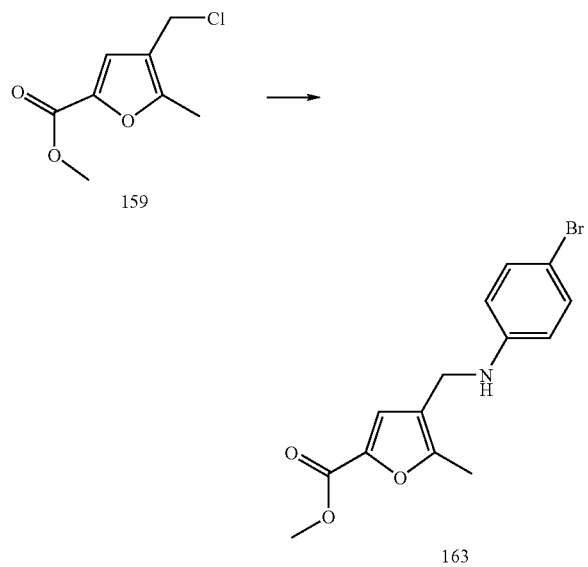

A mixture of 4-chloromethyl-5-methyl-furan-2-carboxylic acid methyl ester (159) (0.5 g, 2.65 mmoles), 4-bromoaniline (2.28 g, 13.25 mmoles) and potassium carbonate (0.55 g, 3.98 mmoles) in tetrahydrofuran (25 ml) was stirred at gentle reflux for 72 hours. The mixture was evaporated to give a yellow residue, which was purified by HPLC to afford compound 163 as a trifluoroacetic acid salt (840 mg). LC/MS System A; $R_t$=3.82 mins, m/z (ES$^+$)=324/326 (M+H for $C_{14}H_{14}BrNO_3$).

(b) 5-Methyl-4-{[4-(4,4,5,5-tetramethyl-[1,3,2]diox-aborolan-2-yl)-phenylamino]-methyl-furan-2-carboxylic acid methyl ester (164)

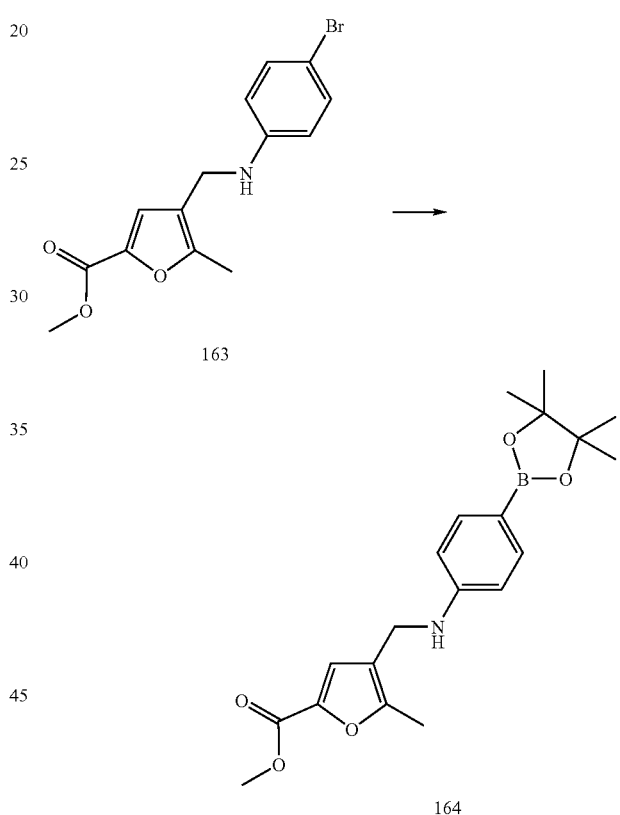

A mixture of 4-[(4-bromo-phenylamino)-methyl]-5-methyl-furan-2-carboxylic acid methyl ester (163) (280 mg, 0.864 mmoles), [1,1'-Bis(diphenylphosphino) ferrocene] dichloropalladium(II) complex with dichloromethane (1:1) (21 mg), 4,4,5,5-tetramethyl-[1,3,2]dioxaborolan (240 mg, 0.950 mmoles) and potassium acetate (250 mg, 2-59 mmoles) in dimethyl sulphoxide (6 ml) was degassed and placed under an argon atmosphere. The mixture was heated at 80° C. for 5 hours, cooled and toluene (100 ml) was added. The mixture was washed with water (50 ml) and sodium bicarbonate was added until the pH=9. The aqueous phase was discarded and the toluene layer filtered. After evaporation of the solvent the residue was purified by flash chromatography (silica, heptane/ethyl acetate 4:1 v/v as eluent) to give compound 164 as an oil, which was used directly in the next step.

(c) 4-{[4-(5-Methoxy-pyridin-2-yl)-phenylamino]-methyl}-5-methyl-furan-2-carboxylic acid methyl ester trifluoroacetic acid salt (165)

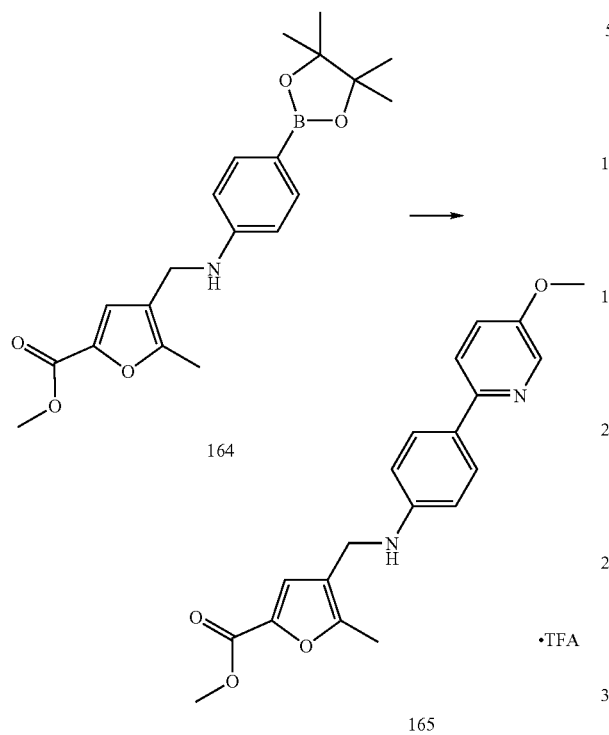

5-Methyl-4-{[4-(4,4,5,5-tetramethyl-[1,3,2]dioxaborolan-2-yl)-phenylamino]-methyl-furan-2-carboxylic acid methyl ester (164) (130 mg, 0.525 mmoles) was added to a degassed mixture of 2-bromo-5-methoxy-pyridine (99 mg, 0.350 mmoles), bis-(dibenzylidene-acetone)-palladium(0) (6 mg) and triphenyl-phosphine (11 mg) in toluene/dimethylformamide 1:1 v/v (5 ml) under an argon atmosphere. Aqueous potassium carbonate (0.23 ml of a 3M solution) was added and the mixture was heated at 100° C. for 16 hours. The reaction mixture was concentrated and the residue was purified by HPLC to afford compound 165 (38 mg). LC/MS System A; $R_t$=2.55 mins, m/z (ES$^+$)=353 (M+H for $C_{20}H_{20}N_2O_4$).

(d) 4-{[4-(5-Methoxy-pyridin-2-yl)-phenylamino]-methyl}-5-methyl-furan-2-carboxylic acid hydrochloride salt (166)

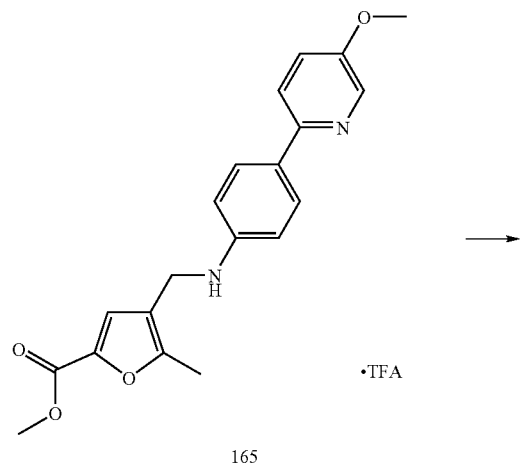

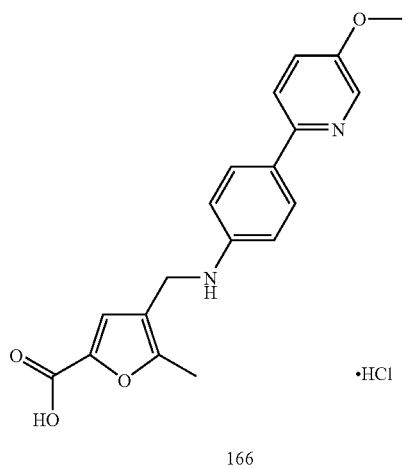

A solution of 4-{[4-(5-methoxy-pyridin-2-yl)-phenylamino]-methyl}-5-methyl-furan-2-carboxylic acid methyl ester trifluoroacetic acid salt (165) (38 mg, 0.082 mmoles) in tetrahydrofuran (4 ml) was treated with potassium trimethyl-silanoate (63 mg, 0.049 mmoles) and the mixture stirred at room temperature for 16 hours. The mixture was evaporated to dryness and pumped under high vacuum to remove silanol volatiles. The residue was purified by HPLC to afford a residue, which was dissolved in 1M aqueous hydrochloric acid. The solution was evaporated to give compound 166 as a solid (30 mg). LC/MS System A; $R_t$=2.22 mins, m/z (ES$^+$)=339 (M+H for $C_{19}H_{18}N_2O_4$) and m/z (ES$^-$)=337 (M–H for $C_{26}H_{25}N_3O_5S$).

(e) N-(4-{[4-(5-Methoxy-pyridin-2-yl)-phenylamino]-methyl}-5-methyl-furan-2-carbonyl)-2-methyl-benzenesulphonamide (167)

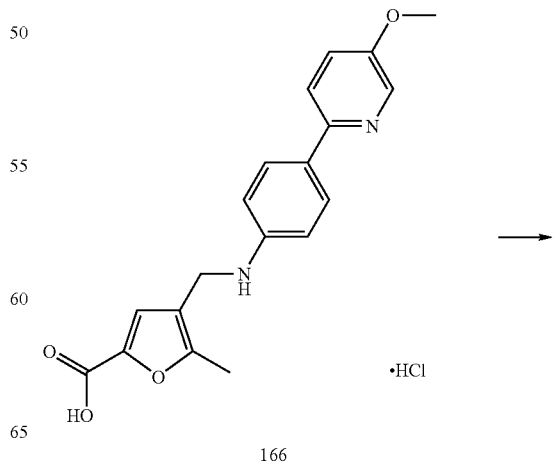

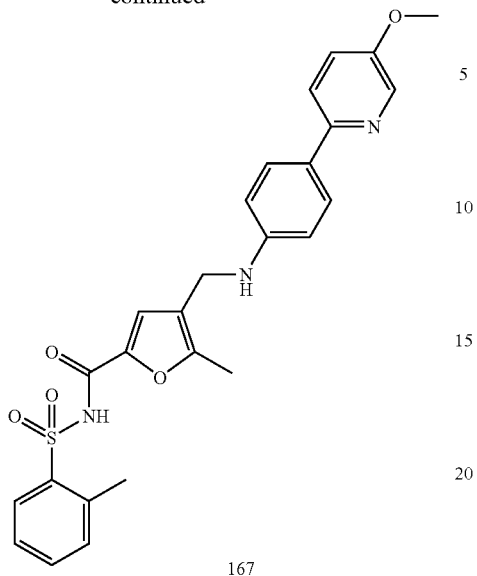

167

A suspension of 4-{[4-(5-methoxy-pyridin-2-yl)-phenylamino]-methyl}-5-methyl-furan-2-carboxylic acid hydrochloride salt (166) (30 mg, 0.08 mmoles) in tetrahydrofuran (5 ml) was treated with toluene-2-sulphonamide (41 mg, 0.24 mmoles), 1-(3-dimethylaminopropyl)-3-ethylcarbodiimide hydrochloride (34 mg, 0.176 mmoles) and 4-(N,N-dimethylamino)-pyridine (10 mg, 0.08 mmoles) and the mixture stirred at room temperature for 16 hours. Triethylamine (24.3 mg, 0.24 mmoles) was added and the mixture was stirred for a further 18 hours. The reaction mixture was concentrated and the residue was purified by HPLC to afford compound 167 as a yellow glass (1.1 mg)). LC/MS System A; $R_t$=2.72 mins, m/z (ES$^+$)=492 (M+H for $C_{26}H_{25}N_3O_5S$) and m/z (ES$^-$)=490 (M–H for $C_{26}H_{25}N_3O_5S$).

Example 40

Synthesis of 4-[(4'-Difluoromethoxy-biphenyl-4-ylamino)-methyl]-5-methyl-furan-2-carboxylic acid (171), N-{4-[(4'-Difluoromethoxy-biphenyl-4-ylamino)-methyl]-5-methyl-furan-2-carbonyl}-benzenesulfonamide (172), N-{4-[(4'-Difluoromethoxy-biphenyl-4-ylamino)-methyl]-5-methyl-furan-2-carbonyl}-2-methyl-benzenesulfonamide (173) and 3,5-Dimethyl-isoxazole-4-sulfonic acid {4-[(4'-difluoromethoxy-biphenyl-4-ylamino)-methyl]-5-methyl-furan-2-carbonyl}-amide (174)

(a) 4-Difluoromethoxy-4-nitro-biphenyl (168)

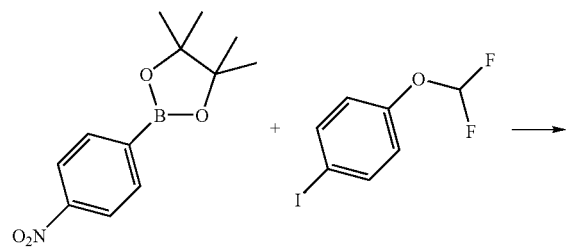

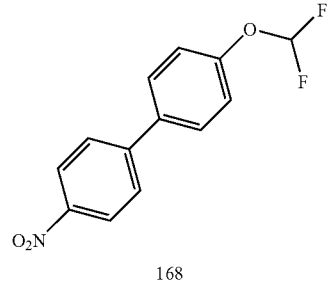

168

[1,1'-Bis(diphenylphosphino) ferrocene]dichloropalladium(II) complex with dichloromethane (1:1) (250 mg) was added to a degassed mixture of 4,4,5,5-tetramethyl-2-(4-nitro-phenyl)-[1,3,2]dioxaborolane (1.67 g, 6.70 mmoles), 1-difluoromethoxy-4-iodo-benzene (2.17 g, 8.04 mmoles) and 2M aqueous cesium carbonate (10.05 ml) in 1,4-dioxan (120 ml). The mixture was placed under an argon atmosphere and was heated at 80° C. for 20 hours. After cooling, the mixture was concentrated and the residue was partitioned between dichloromethane (2×200 ml) and water (100 ml). The combined extracts were washed with brine (150 ml) and dried (MgSO$_4$). After evaporation of the solvent, the residue was purified by flash chromatography, using petrol (60-80°)/diethyl ether 19:1 v/v as eluent, to afford compound 168 (1.15 g) as a beige coloured solid.

(b) 4'-Difluoromethoxy-biphenyl-4-ylamine (169)

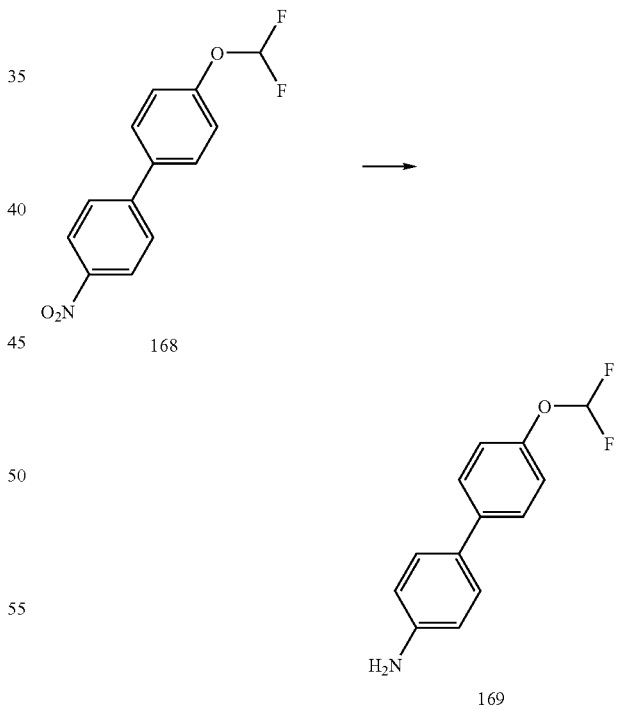

A solution of 4-difluoromethoxy-4-nitro-biphenyl (168) (1.1 g, 4.15 mmoles) in ethyl acetate (100 ml) was hydrogenated over 10% palladium on charcoal catalyst (250 mg) using a hydrogen filled balloon. After 20 hours, the mixture was filtered through a pad of diatomaceous earth and the pad rinsed with ethyl acetate. The combined filtrate and washings were evaporated to afford compound 169 (855 mg) as a solid.

LC/MS System A; $R_t$=2.87 mins, m/z (ES$^+$)=236 (M+H) and 277 (M+H acetonitrile adduct) for $C_{13}H_{11}F_2NO$.

(c) 4-(4'-Difluoromethoxy-biphenyl-4-ylaminomethyl)-5-methyl-furan-2-carboxylic acid methyl ester (170)

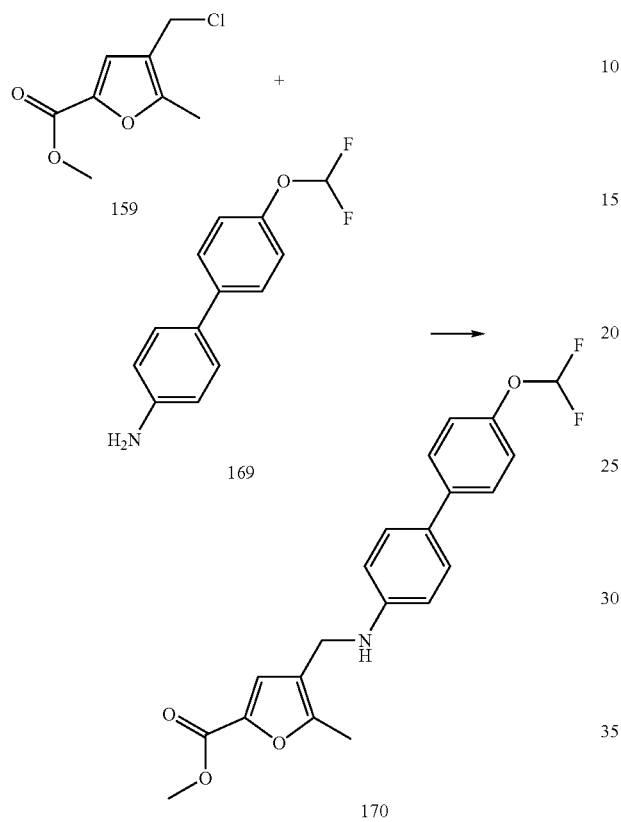

Compound (170) was prepared from compounds (159) and (169) by adapting the procedure of Example 38(d). (420 mg). LC/MS System A; $R_t$=4.00 mins, m/z (ES$^+$)=388 (M+H) and 429 (M+H acetonitrile adduct) for $C_{21}H_{19}F_2NO_3$.

(d) 4-(4'-Difluoromethoxy-biphenyl-4-ylaminomethyl)-5-methyl-furan-2-carboxylic acid (171)

-continued

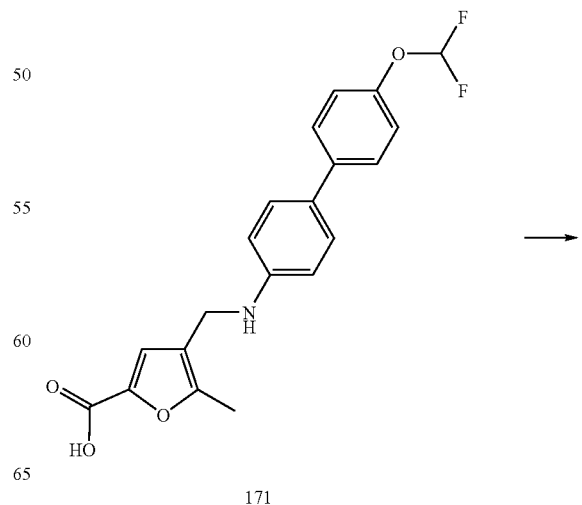

Compound (171) was prepared from compound (170) by adapting the procedure of Example 38(e). LC/MS System D; $R_t$=9.07 mins, m/z (ES$^+$)=374 (M+H for $C_{20}H_{17}F_2NO_4$).

(e) N-{4-[(4'-Difluoromethoxy-biphenyl-4-ylamino)-methyl]-5-methyl-furan-2-carbonyl}-benzenesulphonamide (172)

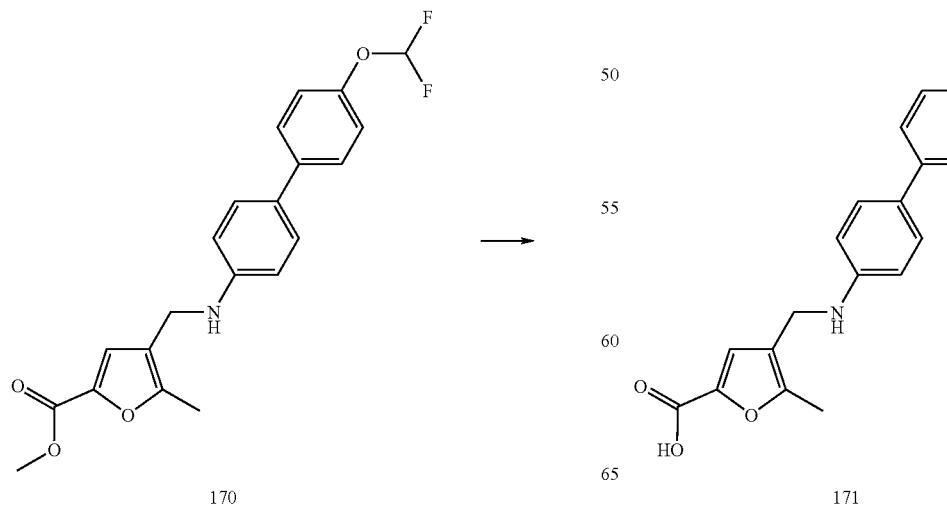

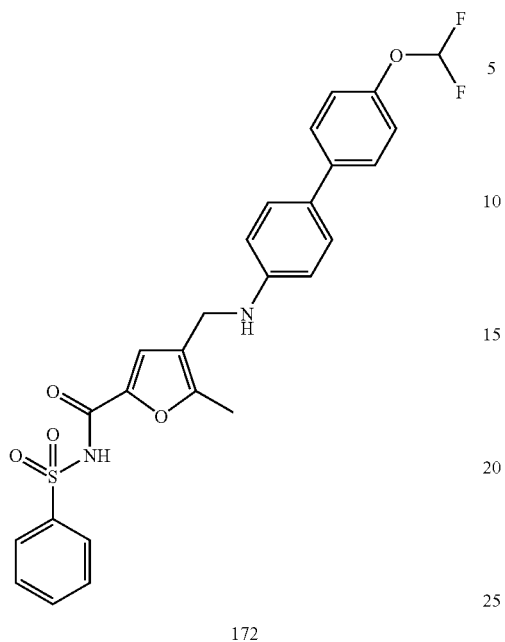

172

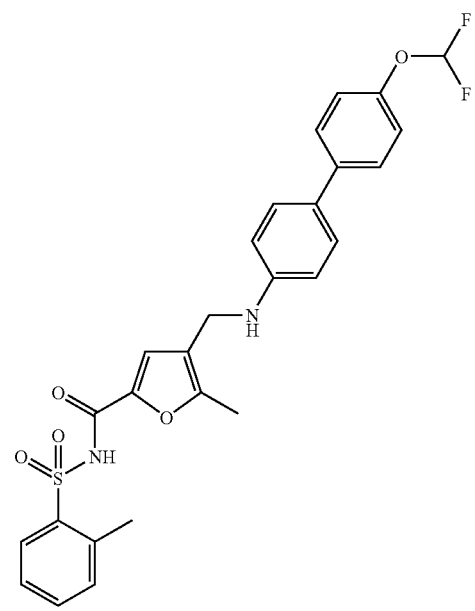

173

Compound (172) was prepared from compound (171) and benzenesulphonamide by adapting the procedure of Example 38(f). LC/MS System D; $R_t$=10.38 mins, m/z (ES$^+$)=513 (M+H for $C_{26}H_{22}F_2N_2O_5S$).

Compound (173) was prepared from compound (171) and 2-methyl-benzenesulphonamide by adapting the procedure of Example 38(f). LC/MS System D; $R_t$=10.63 mins, m/z (ES$^+$)=527 (M+H for $C_{27}H_{24}F_2N_2O_5S$).

(f) N-{4-[(4'-Difluoromethoxy-biphenyl-4-ylamino)-methyl]-5-methyl-furan-2-carbonyl}-2-methyl-benzenesulphonamide (173)

(d) 3,5-Dimethyl-isoxazole-4-sulphonic acid {4-[(4'-difluoromethoxy-biphenyl-4-ylamino)-methyl]-5-methyl-furan-2-carbonyl}-amide (174)

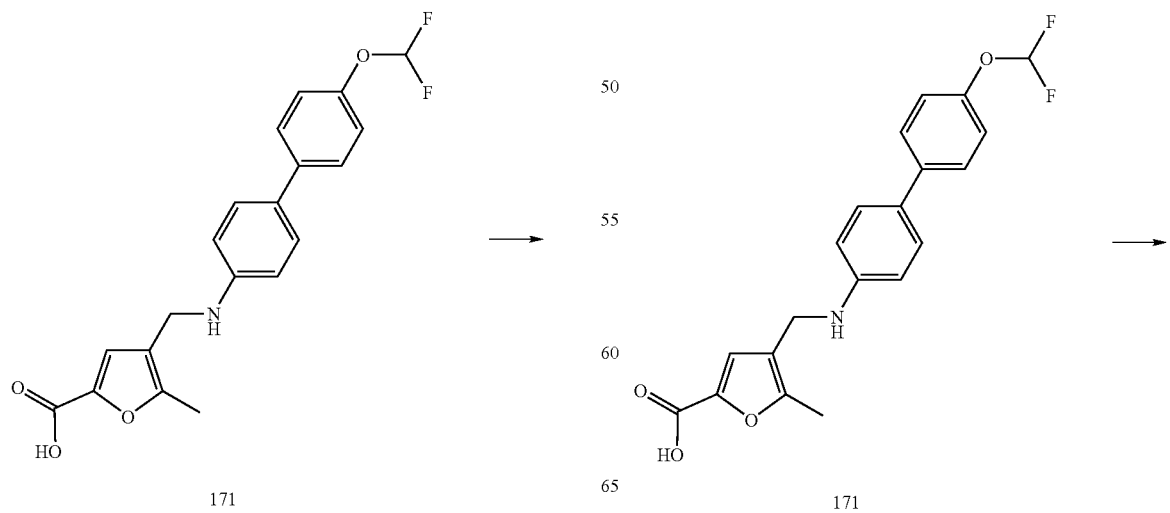

-continued

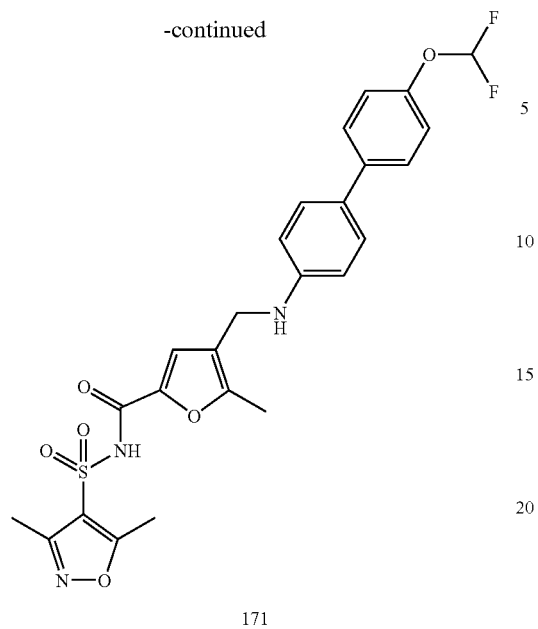

171

Diisopropylethylamine (60 μl, 0.339 mmoles) and a solution of 4-(4'-difluoromethoxy-biphenyl-4-ylaminomethyl)-5-methyl-furan-2-carboxylic acid (171) (50 mg, 0.103 mmoles) in N,N-dimethylformamide (11.0 ml) were added to a stirred solution of 3,5-dimethyl-isoxazole-4-sulphonic acid amide (55 mg, 0.308 mmoles) in N,N-dimethylformamide (5.0 ml). A solution of O-(7-azabenzotriazol-1-yl)-N,N,N',N'-tetramethyluronium hexafluorophosphate (46 mg, 0.124 mmoles) in N,N-dimethylformamide (11.0 ml) was added and the mixture was stirred at room temperature for 16 hours. The reaction mixture was concentrated in vacuo and the residue was purified by HPLC to afford compound 174 (2 mg) as a solid. LC/MS System D; $R_t$=10.35 mins, m/z (ES$^+$)=532 (M+H for $C_{25}H_{23}F_2N_3O_6S$).

Example 41

Synthesis of 4-{[(4'-Difluoromethoxy-biphenyl-4-yl)-methyl-amino]-methyl}-5-methyl-furan-2-carboxylic acid (176) and N-(4-{[(4'-Difluoromethoxy-biphenyl-4-yl)-methyl-amino]-methyl}-5-methyl-furan-2-carbonyl)-2-methyl-benzenesulfonamide (177)

(a) 4-{[(4'-Difluoromethoxy-biphenyl-4-yl)-methyl-amino]-methyl}-5-methyl-furan-2-carboxylic acid methyl ester (175)

-continued

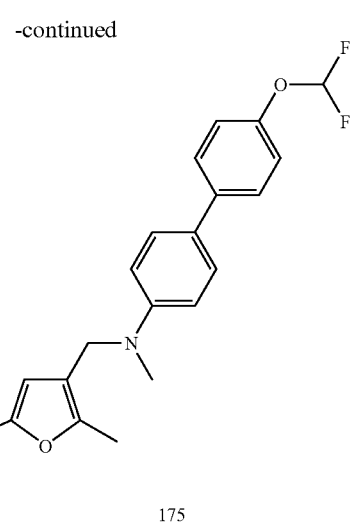

175

Iodomethane (91 mg, 0.64 mmoles) and potassium carbonate (88 mg, 0.64 mmoles) were added to a solution of 4-(4'-difluoromethoxy-biphenyl-4-yIaminomethyl)-5-methyl-furan-2-carboxylic acid methyl ester (170) (62 mg, 0.16 mmoles) in N,N-dimethylformamide (10 ml) and the mixture stirred at room temperature for 36 hours under an argon atmosphere. The mixture was then heated at 35° C. for 21 hours. The mixture was partitioned between dichloromethane and water, the organic phase separated and dried (MgSO$_4$). After evaporation of the solvent, the residue was purified by flash chromatography, using cyclohexane/ethyl acetate 99:1 v/v as eluent, to afford compound 175 (41 mg) as a brown oil. This was used directly in part (b).

(b) 4-{[(4'-Difluoromethoxy-biphenyl-4-yl)-methyl-amino]-methyl}-5-methyl-furan-2-carboxylic acid (176)

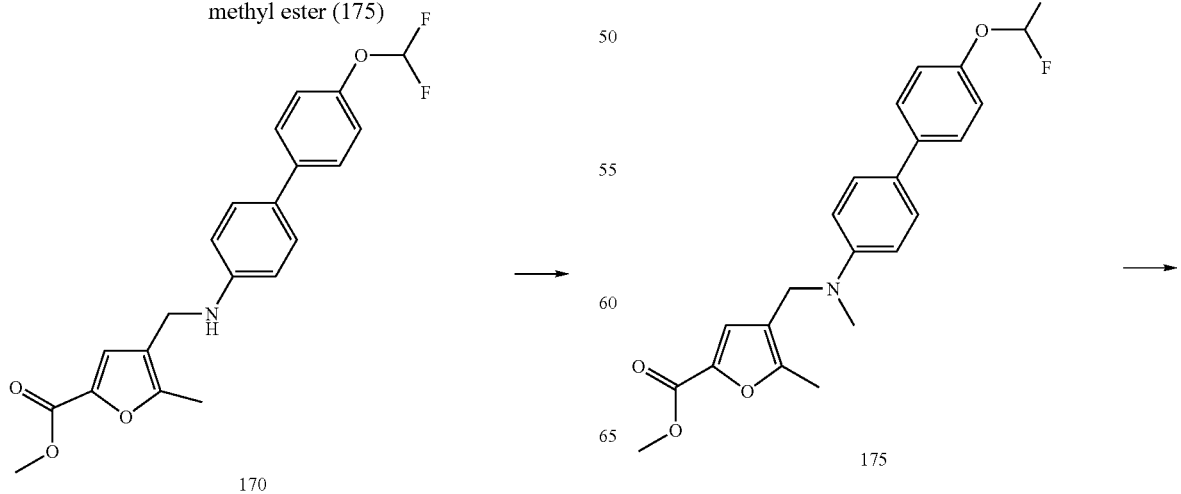

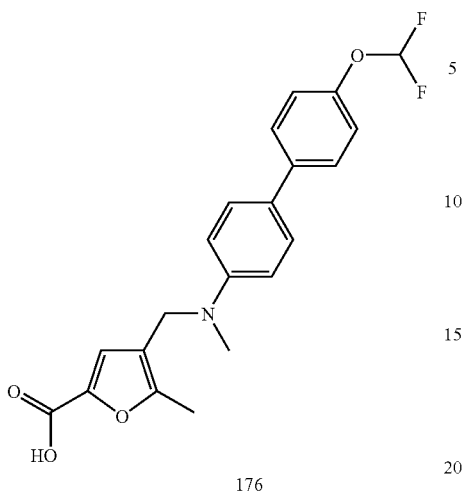

176

A solution of 4-{[(4'-difluoromethoxy-biphenyl-4-yl)-methyl-amino]-methyl}-5-methyl-furan-2-carboxylic acid methyl ester (175) (30 mg, 0.07 mmoles) in dry tetrahydrofuran (20 ml) was treated with potassium trimethylsilanoate (19 mg, 0.15 mmoles) and the mixture stirred under an argon atmosphere for 30 hours. Trifluoroacetic acid was added until the pH=2. After evaporation of the solvent, the residue was purified by HPLC to afford compound 176 (4.8 mg) as a white solid.

LC/MS System D; $R_t$=9.42 mins, m/z (ES$^+$)=388 (M+H for $C_{21}H_{19}F_2NO_4$).

(c) N-(4-{[(4'-Difluoromethoxy-biphenyl-4-yl)-methyl-amino]-methyl}-5-methyl-furan-2-carbonyl)-2-methyl-benzenesulfonamide (177)

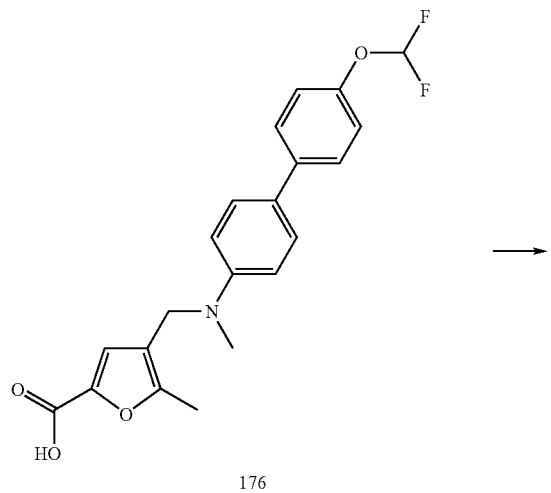

176

→

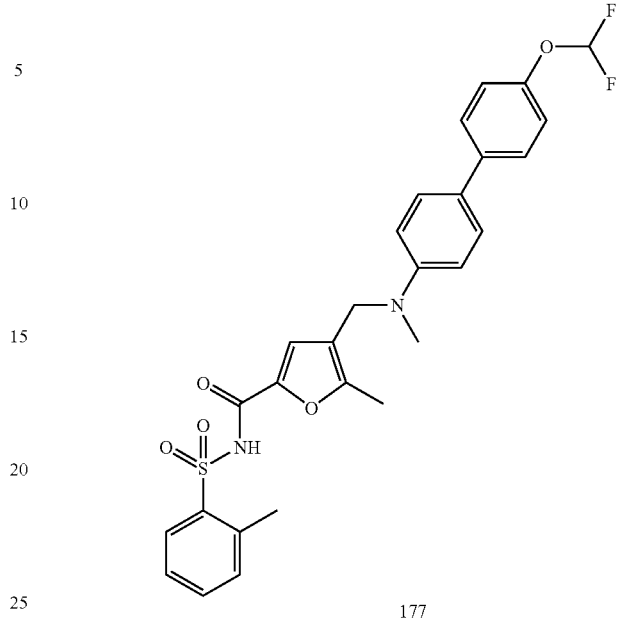

177

A stirred solution of 4-{[(4'-difluoromethoxy-biphenyl-4-yl)-methyl-amino]-methyl}-5-methyl-furan-2-carboxylic acid (176) (21 mg, 0.054 mmoles), 2-methyl-benzenesulphonamide (19 mg, 0.108 mmoles) and 4-(N,N-dimethylamino)-pyridine (1 mg) in a mixture of dichloromethane (8 ml) and acetonitrile (2 ml) was treated with 1-(3-dimethylaminopropyl)-3-ethylcarbodiimide hydrochloride (11.4 mg, 0.060 mmoles). The mixture was stirred at room temperature for 18 hours under an argon atmosphere. The reaction mixture was concentrated in vacuo and the residue was purified by HPLC to afford compound 177 (2.9 mg) as a solid. LC/MS System D; $R_t$=11.21 mins, m/z (ES$^+$)=541 (M+H for $C_{28}H_{26}F_2N_2O_5S$).

Example 42

Biological Results

Binding Ability to Human EP Receptors

Membranes were prepared from cells stably transfected with human EP receptor cDNA. In brief, cells were cultured to confluency, scraped from culture flasks, and centrifuged (800 g, 8 minutes, 4° C.). Cells were twice washed in ice cold homogenisation buffer containing 10 mM Tris-HCl, 1 mM EDTA.2Na, 250 mM sucrose, 1 mM PMSF, 0.3 mM indomethacin, pH 7.4, homogenised and re-centrifuged as before. The supernatant was stored on ice and pellets re-homogenised and re-spun. Supernatants were pooled and centrifuged at 40000 g, 10 minutes, 4° C. Resultant membrane pellets were stored at −80° C. until use.

For assay, membranes expressing human EP$_4$, EP$_3$, EP$_2$ or EP$_1$ receptors were incubated in Millipore (MHVBN45) plates containing assay buffer, radiolabelled [$^3$H]PGE$_2$ and 0.1 to 10 000 nM concentrations of compounds. Incubations were performed at suitable temperatures and for suitable times to allow equilibrium to be reached. Non-specific binding was determined in the presence of 10 uM PGE$_2$. Bound and free radiolabel was separated by vacuum manifold filtration using appropriate wash buffers, and bound radiolabel was determined by scintillation counting. Constituents of each of the buffers are included in table 1 below.

The affinity or $pK_i$ of each compound for each receptor was calculated from the concentration causing 50% radioligand displacement ($IC_{50}$) using the Cheng-Prusoff equation:

$$Ki = \frac{IC_{50}}{1 + \left(\frac{\text{radioligand concentration}}{\text{radioligand } KD}\right)}$$

This approach follows that set out in Kenakin, T. P., Pharmacologic analysis of drug receptor interaction. Raven Press, New York, $2^{nd}$ edition.

TABLE 1

| Receptor | | $EP_1$ | $EP_2$ | $EP_3$ | $EP_4$ |
|---|---|---|---|---|---|
| Protein/well | | 6.5 µg | 8 µg | 5 µg | 5 µg |
| Final [$^3$H—PGE$_2$] | | 3.6 nM | 3 nM | 2.5 nM | 1 nM |
| Buffer | Assay | 10 mM MES pH 6.0; 10 mM MgCl$_2$; 1 mM EDTA, 3 uM Indomethacin | 10 mM MES pH 6.0; 10 mM MgCl$_2$; 1 mM EDTA | 10 mM MES pH 6.0; 10 mM MgCl2; 1 mM EDTA, 100 uM GTP-gamma-S | 10 mM MES pH 6.0; 10 mM MgCl$_2$; 1 mM EDTA, 3 uM Indomethacin |
| | Wash | 10 mM MES pH 6.0; 10 mM MgCl$_2$ | 10 mM MES pH 6.0; 10 mM MgCl$_2$ | 10 mM MES pH 6.0; 10 mM MgCl$_2$ | 10 mM MES pH 6.0; 1 mM EDTA |

The results are presented as $pK_i$ values in table 2 below.

TABLE 2

| Compound | $EP_4$ | $EP_1$ | $EP_2$ | $EP_3$ |
|---|---|---|---|---|
| 4 | >6.5 | — | <5 | <5 |
| 5 | >7.5 | — | <5.5 | <5 |
| 6 | >8 | — | <5 | <5 |
| 7 | >6.5 | — | <5 | <5 |
| 8 | >8 | — | <5 | <5 |
| 9 | >8 | — | <5 | <5 |
| 10 | >8 | — | <5.5 | <5 |
| 11 | >7.5 | — | <5 | <5 |
| 12 | >7 | — | <5 | <5 |
| 13 | >8 | — | <5 | <5 |
| 19 | >6.5 | — | <5 | <5 |
| 21 | >6.5 | — | <5 | <5 |
| 22 | >8 | — | <5 | <5 |
| 24 | >6.5 | <5 | <5 | <5 |
| 25 | >6.5 | — | <5 | <5 |
| 27 | >6 | — | <5.5 | <5 |
| 28 | >6 | — | <5 | <5 |
| 37 | >6.5 | — | <5 | <5 |
| 38 | >6 | — | <5.5 | <5 |
| 39 | >7 | — | <5 | <5 |
| 40 | >7 | — | <5 | <5 |
| 42 | >7 | — | <5 | <5 |
| 43 | >7 | — | <5 | <5 |
| 46 | >7 | — | <5 | <5 |
| 49 | >8 | <5 | <5 | <5 |
| 50 | >5.5 | — | <5.5 | <5 |
| 53 | >5.5 | — | <5 | <5 |
| 56 | >5.5 | — | <4.5 | <5 |
| 57 | >5 | — | <5 | <5 |
| 59 | >5.5 | — | <5 | <5 |
| 60 | >8 | <5 | <5 | <5 |
| 61 | >6 | — | <5 | <5 |
| 62 | >7 | — | <5 | <5 |
| 63 | >6.5 | — | <5 | <5 |
| 64 | >7 | — | <5 | <5 |
| 67 | >6 | — | <5 | <5 |
| 68 | >6 | — | <5 | <5 |
| 69 | >7 | — | — | — |
| 72 | >5 | — | <5 | <5 |
| 73 | >5.5 | — | <5 | <5 |
| 74 | >5.5 | — | <5 | <5 |
| 77 | >5.5 | — | <5 | <5 |
| 78 | >5 | — | <5.5 | <5 |
| 79 | >5.5 | — | <5 | <5 |
| 80 | >6.5 | — | <5 | <5 |
| 81 | >5.5 | — | <5.5 | <5 |
| 85 | >5.5 | — | <5 | <5 |
| 86 | >6 | — | <5 | <5 |
| 87 | >5.5 | — | <5 | <5 |
| 90 | >5.5 | — | <5 | <5 |
| 91 | >5.5 | — | <5 | <5 |
| 92 | >5.5 | — | <5 | <5 |
| 93 | >5.5 | — | <5 | <5 |
| 94 | >6.5 | — | <5 | <5 |
| 95 | >5.5 | — | <5.5 | <5 |
| 96 | >5.5 | — | <5 | <5 |
| 98 | >6.5 | — | <5 | <5 |
| 99 | >6 | — | <5.5 | <5 |
| 100 | >5.5 | — | <5 | <5 |
| 102 | >5.5 | — | <5.5 | <5 |
| 104 | >6 | — | <5.5 | <5 |
| 105 | >5.5 | — | <5 | <5 |
| 108 | >5.5 | — | <5 | <5 |
| 109 | >5.5 | — | <5 | <5 |
| 110 | >5.5 | — | <5 | <5 |
| 111 | >5.5 | — | <5 | <5 |
| 112 | >5.5 | — | <5 | <5 |
| 113 | >5 | — | <5 | <5 |
| 114 | >5.5 | — | <5 | <5 |
| 115 | >5 | — | <5 | <5 |
| 116 | >6 | — | <5 | <5 |
| 117 | >5.5 | — | <5 | <5 |
| 118 | >6 | — | <5 | <5 |
| 122 | >7 | — | <5 | <5 |
| 126 | >5.5 | — | <5 | <5 |
| 127 | >7 | — | <5 | <5 |
| 129 | >7.5 | — | <5 | <5 |
| 130 | >8 | — | <5.5 | <5 |
| 131 | >8.5 | — | <5.5 | <5 |
| 132 | >7.5 | — | <5 | <5 |
| 133 | >7.5 | — | <5 | <5 |
| 134 | >7.5 | — | <5 | <5 |
| 135 | >5 | — | <5 | <5 |
| 137 | >5 | — | <5 | <5 |
| 138 | >5.5 | — | <5 | <5 |
| 140 | >5.5 | — | <5 | <5 |
| 141 | >6.5 | — | <5 | <5 |
| 142 | >7 | — | <5 | <5 |
| 144 | >6 | — | <5 | <5 |
| 145 | >7.5 | — | <5 | <5 |
| 146 | >7.5 | — | <5 | <5 |

TABLE 2-continued

| Compound | EP$_4$ | EP$_1$ | EP$_2$ | EP$_3$ |
|---|---|---|---|---|
| 149 | >7 | — | <5 | <5 |
| 153 | >6 | — | <5 | <5 |
| 154 | >7.5 | — | <5.5 | <6 |
| 155 | >6 | — | <5.5 | <5.5 |
| 156 | >5 | — | <5 | <5 |
| 156a | >5 | — | <5 | <5 |
| 160 | >5.5 | — | <5 | <5 |
| 161 | >7.5 | — | <5 | <5 |
| 162 | >8.0 | — | <5 | <5 |
| 167 | >6.5 | — | <5 | <5 |
| 171 | >6.5 | — | <5 | <5 |
| 172 | >8 | — | <5 | <5 |
| 173 | >8 | — | <5.5 | <5 |
| 174 | >8 | — | <5 | <5 |
| 176 | >6.5 | — | <5 | <5 |
| 177 | >7.5 | — | <5 | <5 |

We claim:

1. A compound of formula (I):

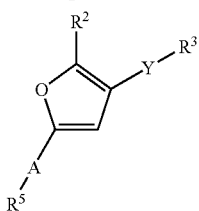

or a salt, solvate and chemically protected form thereof, wherein:

$R^2$ is H or an optionally substituted $C_{1-4}$ alkyl group;

Y is either —(CH$_2$)$_n$—X—, where n is 1 or 2 and X is NR$^{N1}$, where R$^{N1}$ is selected from H or optionally substituted $C_{1-4}$ alkyl, or Y is —C(=O)NR$^{N2}$—, where R$^{N2}$ is selected from H, and optionally substituted $C_{1-7}$ alkyl or is a $C_{5-20}$ aryl group, which $C_{5-20}$ aryl group has from 5 to 20 ring atoms, which ring atoms may be all carbon atoms or may include one or more heteroatoms;

$R^3$ is an optionally substituted $C_6$ aryl group linked to a further optionally substituted $C_6$ aryl group, wherein each optionally substituted $C_6$ aryl group has six ring atoms, which ring atoms may be all carbon atoms or may include one or more heteroatoms; and wherein if both $C_6$ aryl groups are benzene rings, there may be an oxygen bridge between the two rings, bound adjacent the link on both rings;

A is a single bond or a $C_{1-3}$ alkylene group; and $R^5$ is either:

(i) carboxy;

(ii) a group of formula (II):

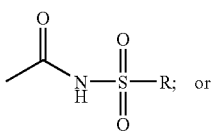

(iii) a group of formula (III):

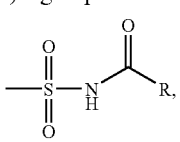

wherein R is optionally substituted $C_{1-7}$ alkyl or NR$^{N3}$R$^{N4}$, where R$^{N3}$ and R$^{N4}$ are independently selected from optionally substituted $C_{1-4}$ alkyl, or is an optionally substituted $C_{5-20}$ aryl group which $C_{5-20}$ aryl group has from 5 to 20 ring atoms, which ring atoms may be all carbon atoms or may include one or more heteroatoms, (iv) tetrazol-5-yl.

2. The compound according to claim 1, wherein $R^2$ is selected from H, methyl, CF$_3$ or iso-propyl.

3. The compound according to claim 1, wherein $R^2$ is methyl.

4. The compound according to claim 1, wherein Y is —(CH$_2$)$_n$—X—.

5. The compound according to claim 4, wherein n is 1.

6. The compound according to claim 5, wherein X is NH.

7. The compound according to claim 1, wherein Y is —C(=O)NR$^{N2}$—.

8. The compound according to claim 7, wherein R$^{N2}$ is selected from H, and optionally substituted $C_{1-4}$ alkyl.

9. The compound according to claim 1, wherein the $C_6$ aryl groups of $R^3$ are independently selected from those derived from benzene and heteroaryl groups, where the heteroatom or heteroatoms are nitrogen.

10. The compound according to claim 9, wherein the $C_6$ aryl groups of $R^3$ are independently selected from those derived from benzene, pyridine and 1,3-pyrimidine.

11. The compound according to claim 1, wherein A is a single bond.

12. The compound according to claim 1, wherein A is a $C_{1-3}$ alkylene group.

13. The compound according to claim 1, wherein $R^5$ is either:

(i) a group of formula (II):

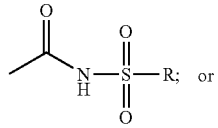

(ii) a group of formula (III):

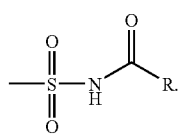

14. The compound according to claim 13, wherein R is selected from an optionally substituted $C_{5-20}$ aryl group, which $C_{5-20}$ aryl group has from 5 to 20 ring atoms, which ring atoms may be all carbon atoms or may include one or more heteroatoms, and an optionally substituted $C_{5-20}$ aryl-$C_{1-7}$ alkyl group, which $C_{5-20}$ aryl-$C_{1-7}$ alkyl group has from 5 to 20 ring atoms, which ring atoms may be all carbon atoms or may include one or more heteroatoms.

15. A pharmaceutical composition comprising a compound of formula (I):

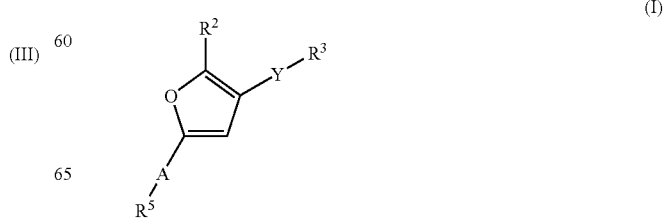

or a pharmaceutically acceptable salt thereof, together with a pharmaceutically acceptable carrier or diluent, wherein:

$R^2$ is H or an optionally substituted $C_{1-4}$ alkyl group;

Y is either —$(CH_2)_n$—X—, where n is 1 or 2 and X is $NR^{N1}$, where $R^{N1}$ is selected from H or optionally substituted $C_{1-4}$ alkyl, or Y is —C(=O)$NR^{N2}$—, where $R^{N2}$ is selected from H, and optionally substituted $C_{1-7}$ alkyl or $C_{5-20}$ aryl group which $C_{5-20}$ aryl group has from 5 to 20 ring atoms, which ring atoms may be all carbon atoms or may include one or more heteroatoms;

$R^3$ is an optionally substituted $C_6$ aryl group linked to a further optionally substituted $C_6$ aryl group, wherein each optionally substituted aryl group has six ring atoms, which ring atoms may be all carbon atoms or may include one or more heteroatoms; and wherein if both $C_6$ aryl groups are benzene rings, there may be an oxygen bridge between the two rings, bound adjacent the link on both rings;

A is a single bond or a $C_{1-3}$ alkylene group; and $R^5$ is either:

(i) carboxy;

(ii) a group of formula (II): (II)

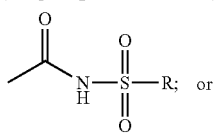

(iii) a group of formula (III): (III)

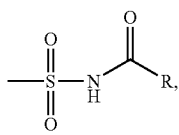

wherein R is optionally substituted $C_{1-7}$ alkyl or $NR^{N3}R^{N4}$, where $R^{N3}$ and $R^{N4}$ are independently selected from optionally substituted $C_{1-4}$ alkyl, or is an optionally substituted $C_{5-20}$ aryl group, which $C_{5-20}$ aryl group has from 5 to 20 ring atoms, which ring atoms may be all carbon atoms or may include one or more heteroatoms;

(iv) tetrazol-5-yl.

16. A method of treating a primary headache disorder by antagonism of an $EP_4$ receptor, which method comprises administering to a patient in need of treatment an effective amount of a compound of formula (I),

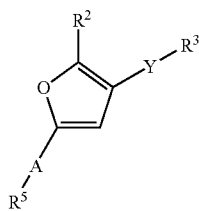
(I)

or a pharmaceutically acceptable salt thereof, wherein:

$R^2$ is H or an optionally substituted $C_{1-4}$ alkyl group;

Y is either —$(CH_2)_n$—X—, where n is 1 or 2 and X is $NR^{N1}$, where $R^{N1}$ is selected from H or optionally substituted $C_{1-4}$ alkyl, or Y is —C(=O)$NR^{N2}$—, where $R^{N2}$ is selected from H, and optionally substituted $C_{1-7}$ alkyl or a $C_{5-20}$ aryl group which $C_{5-20}$ aryl group has from 5 to 20 ring atoms, which ring atoms may be all carbon atoms or may include one or more heteroatoms;

$R^3$ is an optionally substituted $C_6$ aryl group linked to a further optionally substituted $C_6$ aryl group, wherein each optionally substituted $C_6$ aryl group has six ring atoms, which ring atoms may be all carbon atoms or may include one or more heteroatoms; and wherein if both $C_6$ aryl groups are benzene rings, there may be an oxygen bridge between the two rings, bound adjacent the link on both rings;

A is a single bond or a $C_{1-3}$ alkylene group; and $R^5$ is either:

(i) carboxy;

(ii) a group of formula (II): (II)

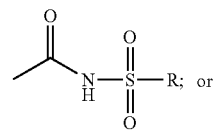

(iii) a group of formula (III): (III)

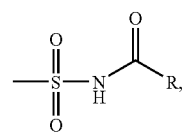

wherein R is optionally substituted $C_{1-7}$ alkyl or $NR^{N3}R^{N4}$, where $R^{N3}$ and $R^{N4}$ are independently selected from optionally substituted $C_{1-4}$ alkyl, or is an optionally substituted $C_{5-20}$ aryl group, which $C_{5-20}$ aryl group has from 5 to 20 ring atoms, which ring atoms may be all carbon atoms or may include one or more heteroatoms;

(iv) tetrazol-5-yl.

17. A method of treatment according to claim 16 in which the primary headache disorder is migraine.

18. The compound according to claim 1 wherein, of the $C_6$ aryl groups of $R^3$, only the $C_6$ aryl group of $R^3$ not bound to Y is substituted.

19. The compound according to claim 1 wherein the $C_6$ aryl groups of $R^3$ are optionally substituted by one or more groups selected from the group consisting of optionally substituted $C_{1-7}$ alkyl groups; $C_{1-7}$ alkoxy groups; $C_{1-7}$ thioether group; amino groups, optionally substituted by one or two $C_{1-4}$ alkyl groups; halo groups; cyano; alkoxylene groups and $C_{1-4}$ acyl groups.

20. The compound according to claim 1 wherein the $C_6$ aryl groups of $R^3$ are optionally substituted by one or more groups selected from the group consisting of —$CH_3$, —$CF_3$, —$CH_2OH$, —OMe, —$OCF_3$ —OEt —$OCHF_2$ —SMe, —$NH_2$, —$NMe_2$, F, Cl, —CN, —O—$CH_2$—O— and —C(=O)Me.

21. The compound according to claim 1, wherein R is an optionally substituted $C_{5-6}$ aryl or $C_{5-6}$ arylmethyl group, which $C_{5-6}$ aryl group and $C_{5-6}$ arylmethyl group have five or six ring atoms, which ring atoms may be all carbons or may contain one or more heteroatoms.

22. The compound according to claim 1, wherein R is selected from the group consisting of optionally substituted thiophen-2-yl, isoxazolyl, phenyl, benzyl, pyridinyl and pyridinylmethyl.

23. The compound according to claim 1, wherein the group R is optionally substituted by one or more groups selected from methyl and —OH.

24. A compound selected from the group consisting of
N-[4-(Biphenyl-4-ylaminomethyl)-5-methyl-furan-2-carbonyl]-benzenesulfonamide (161);
N-[4-(Biphenyl-4-ylaminomethyl)-5-methyl-furan-2-carbonyl]-2-methyl-benzenesulfonamide (162);
N-(4-{[4-(5-Methoxy-pyridin-2-yl)-phenylamino]-methyl}-5-methyl-furan-2-carbonyl)-2-methyl-benzenesulfonamide (167);
N-{4-[(4'-Difluoromethoxy-biphenyl-4-ylamino)-methyl]-5-methyl-furan-2-carbonyl}-benzenesulfonamide (172);
N-{4-[(4'-Difluoromethoxy-biphenyl-4-ylamino)-methyl]-5-methyl-furan-2-carbonyl}-2-methyl-benzenesulfonamide (173);
3,5-Dimethyl-isoxazole-4-sulfonic acid {4-[(4'-difluoromethoxy-biphenyl-4-ylamino)-methyl]-5-methyl-furan-2-carbonyl}-amide (174);and
N-(4-{[(4'-Difluoromethoxy-biphenyl-4-yl)-methyl-amino]-methyl}-5-methyl-furan-2-carbonyl)-2-methyl-benzenesulfonamide (177);
or a pharmaceutically acceptable salt thereof.

* * * * *